(12) United States Patent
Novotny et al.

(10) Patent No.: US 12,049,503 B2
(45) Date of Patent: *Jul. 30, 2024

(54) TREATMENT OF LAG-3 POSITIVE TUMORS

(71) Applicant: Bristol-Myers Squibb Company, Princeton, NJ (US)

(72) Inventors: James Novotny, Milford, NJ (US); Nils Lonberg, Woodside, CA (US); Cyrus Hedvat, New York, NY (US); Raphael Clynes, West Nyack, NY (US); Darren Locke, Bordentown, NJ (US); John P. Cogswell, Yardley, PA (US); Jeffrey Jackson, Schwenksville, PA (US); Christopher Harbison, Hamilton, NJ (US); Robin Edwards, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/451,990

(22) Filed: Aug. 18, 2023

(65) Prior Publication Data

US 2024/0092911 A1 Mar. 21, 2024

Related U.S. Application Data

(63) Continuation of application No. 16/616,574, filed as application No. PCT/US2018/035134 on May 30, 2018, now Pat. No. 11,807,686.

(60) Provisional application No. 62/582,178, filed on Nov. 6, 2017, provisional application No. 62/555,176, filed on Sep. 7, 2017, provisional application No. 62/513,813, filed on Jun. 1, 2017, provisional application No. 62/512,648, filed on May 30, 2017.

(51) Int. Cl.
| | | |
|---|---|---|
| C07K 16/28 | (2006.01) | |
| A61K 39/00 | (2006.01) | |
| A61P 35/00 | (2006.01) | |
| G01N 33/574 | (2006.01) | |

(52) U.S. Cl.
CPC .......... C07K 16/2827 (2013.01); A61P 35/00 (2018.01); C07K 16/2818 (2013.01); G01N 33/574 (2013.01); A61K 2039/507 (2013.01)

(58) Field of Classification Search
CPC . C07K 16/2827; C07K 16/2818; A61P 35/00; A61K 2039/507; G01N 33/574
See application file for complete search history.

(56) References Cited

U.S. PATENT DOCUMENTS

| | | |
|---|---|---|
| 5,545,806 A | 8/1996 | Lonberg et al. |
| 5,773,578 A | 6/1998 | Hercend et al. |
| 5,811,097 A | 9/1998 | Allison et al. |
| 5,874,250 A | 2/1999 | Hercend et al. |
| 5,976,877 A | 11/1999 | Hercend et al. |
| 6,143,273 A | 11/2000 | Faure et al. |
| 6,197,524 B1 | 3/2001 | Romagnani |
| 6,207,156 B1 | 3/2001 | Kuchroo et al. |
| 6,482,925 B1 | 11/2002 | El Tayar et al. |
| 6,500,422 B2 | 12/2002 | Biffoni |
| RE38,313 E | 11/2003 | Faure et al. |
| 6,808,710 B1 | 10/2004 | Wood et al. |
| 7,138,501 B2 | 11/2006 | Ruben et al. |
| 7,306,906 B2 | 12/2007 | Maruyama et al. |
| 7,329,737 B2 | 2/2008 | Sexton et al. |
| 7,488,802 B2 | 2/2009 | Collins et al. |
| 7,563,441 B2 | 7/2009 | Graus et al. |
| 7,595,048 B2 | 9/2009 | Honjo et al. |
| 7,605,238 B2 | 10/2009 | Korman et al. |
| 7,635,757 B2 | 12/2009 | Freeman et al. |

(Continued)

FOREIGN PATENT DOCUMENTS

| | | |
|---|---|---|
| CN | 101490085 A1 | 7/2009 |
| JP | 2006340714 A | 12/2006 |

(Continued)

OTHER PUBLICATIONS

Agrawal, S., et al., "Clinical Pharmacokinetics (PK) of BMS-936558, a Fully Human Anti-pd-1 Monoclonal Antibody," Journal of Clinical Oncology 30(15):1 (2012), ASCO Annual Meeting Website, [retrieved on Jan. 13, 2015]. Retrieved from the Internet : URL:http://www.meetinglibrary.asco.org/content/98623-114.

Anonymous: "A Phase 1 Dose Escalation and Cohort Expansion Study of the Safety, Tolerability, and Efficacy of Anti-LAG-3 (BMS-986016) in Relapsed or Refractory Chronic Lymphocytic Leukemia and Lymphomas and Multiple Myeloma," ClinicaiTrials. gov Archive Identifier NCT02061761, accessed at https://clinicaltrials.gov/archive/NCT02061761/2014_11_20, accessed on Jun. 16, 2015, 5 pages.

(Continued)

*Primary Examiner* — Mark Halvorson
*Assistant Examiner* — Dennis J Sullivan
(74) *Attorney, Agent, or Firm* — Sterne, Kessler, Goldstein & Fox P.L.L.C.

(57) ABSTRACT

The invention provides a method of treating a tumor in a human patient comprising (i) identifying a patient as having a LAG-3 positive tumor and (ii) administering to the patient a PD-1 pathway inhibitor, a combination of a PD1 pathway inhibitor and an immune checkpoint inhibitor, a combination of a LAG-3 inhibitor and a PD-1 pathway inhibitor, or an anti-CTLA4 antibody. In some embodiments, the method further comprises identifying the patient as having a LAG-3 positive PD-L1 positive tumor. In some embodiments, the LAG-3 inhibitor is an anti-LAG-3 antibody and the PD-1 pathway inhibitor is an anti-PD-1 antibody. The methods of the invention can improve response rates to treatment with a PD-1 pathway inhibitor, a combination of a PD1 pathway inhibitor and an immune checkpoint inhibitor, or a combination of a LAG-3 inhibitor and a PD-1 pathway inhibitor.

30 Claims, 33 Drawing Sheets

Specification includes a Sequence Listing.

(56) References Cited

U.S. PATENT DOCUMENTS

| | | |
|---|---|---|
| 7,790,160 B2 | 9/2010 | Von Strandmann et al. |
| 7,850,965 B2 | 12/2010 | Jensen et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,354,509 B2 | 1/2013 | Carven et al. |
| 8,383,796 B2 | 2/2013 | Korman et al. |
| 8,409,577 B2 | 4/2013 | Thompson et al. |
| 8,476,419 B2 | 7/2013 | Thielemans |
| 8,551,481 B2 | 10/2013 | Pardoll et al. |
| 8,609,089 B2 | 12/2013 | Langermann et al. |
| 8,686,119 B2 | 4/2014 | Rotem-Yehudar et al. |
| 8,728,474 B2 | 5/2014 | Honjo et al. |
| 8,779,105 B2 | 7/2014 | Korman et al. |
| 8,900,587 B2 | 12/2014 | Carven et al. |
| 9,005,614 B2 | 4/2015 | Damiano et al. |
| 9,005,629 B2 | 4/2015 | Pardoll et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,212,224 B2 | 12/2015 | Cogswell et al. |
| 9,220,776 B2 | 12/2015 | Sharma et al. |
| 9,273,135 B2 | 3/2016 | Korman et al. |
| 9,358,289 B2 | 6/2016 | Korman et al. |
| 9,387,247 B2 | 7/2016 | Korman et al. |
| 9,393,301 B2 | 7/2016 | Honjo et al. |
| 9,402,899 B2 | 8/2016 | Honjo et al. |
| 9,439,962 B2 | 9/2016 | Honjo et al. |
| 9,492,539 B2 | 11/2016 | Korman et al. |
| 9,492,540 B2 | 11/2016 | Korman et al. |
| 9,505,839 B2 | 11/2016 | Lonberg et al. |
| 9,580,505 B2 | 2/2017 | Korman et al. |
| 9,580,507 B2 | 2/2017 | Korman et al. |
| 9,856,320 B2 | 1/2018 | Cogswell |
| 10,072,082 B2 | 9/2018 | Cogswell |
| 10,081,681 B2 | 9/2018 | Korman et al. |
| 10,138,299 B2 | 11/2018 | Cogswell |
| 10,266,591 B2 | 4/2019 | Lonberg |
| 10,266,594 B1 | 4/2019 | Cogswell |
| 10,266,595 B2 | 4/2019 | Cogswell |
| 10,266,596 B1 | 4/2019 | Cogswell |
| 10,308,714 B2 | 6/2019 | Cogswell |
| 10,316,090 B2 | 6/2019 | Cogswell |
| 10,316,091 B2 | 6/2019 | Cogswell |
| 10,323,092 B2 | 6/2019 | Cogswell |
| 10,323,093 B2 | 6/2019 | Cogswell |
| 10,344,089 B2 | 7/2019 | Thudium |
| 10,358,495 B2 | 7/2019 | Ullman et al. |
| 10,377,824 B2 | 8/2019 | Lonberg et al. |
| 10,441,655 B2 | 10/2019 | Korman et al. |
| 10,577,423 B2 | 3/2020 | Cogswell et al. |
| 10,584,170 B2 | 3/2020 | Cogswell et al. |
| 10,604,575 B2 | 3/2020 | Cogswell et al. |
| 10,988,535 B2 | 4/2021 | Thudium |
| 10,988,536 B2 | 4/2021 | Thudium |
| 11,001,630 B2 | 5/2021 | Thudium |
| 11,236,163 B2 | 2/2022 | Thudium |
| 11,236,164 B2 | 2/2022 | Thudium |
| 11,236,165 B2 | 2/2022 | Thudium |
| 11,274,152 B2 | 3/2022 | Korman et al. |
| 11,345,752 B2 | 5/2022 | Lonberg et al. |
| 11,512,130 B2 | 11/2022 | Thudium et al. |
| 11,530,267 B2 | 12/2022 | Thudium et al. |
| 11,723,975 B2 | 8/2023 | Burton et al. |
| 11,807,686 B2 | 11/2023 | Novotny, Jr. et al. |
| 2002/0086014 A1 | 7/2002 | Korman et al. |
| 2002/0146753 A1 | 10/2002 | Ditzel et al. |
| 2003/0059937 A1 | 3/2003 | Ruben et al. |
| 2003/0129601 A1 | 7/2003 | Cole |
| 2004/0072164 A1 | 4/2004 | Maruyama et al. |
| 2004/0171551 A1 | 9/2004 | Triebel |
| 2005/0009136 A1 | 1/2005 | Nixon et al. |
| 2005/0226876 A1 | 10/2005 | Graus et al. |
| 2005/0276823 A1 | 12/2005 | Cini et al. |
| 2006/0110383 A1 | 5/2006 | Honjo et al. |
| 2006/0083744 A1 | 6/2006 | Chen et al. |
| 2006/0177442 A1 | 8/2006 | Von Strandmann et al. |
| 2006/0240024 A1 | 10/2006 | Pardoll et al. |
| 2007/0004910 A1 | 1/2007 | Sexton et al. |
| 2007/0160598 A1 | 7/2007 | Dennis et al. |
| 2008/0038264 A1 | 2/2008 | Bodary et al. |
| 2008/0069822 A1 | 3/2008 | Jensen et al. |
| 2008/0260641 A1 | 10/2008 | Teeling et al. |
| 2008/0279865 A1 | 11/2008 | Gomez-Navarro |
| 2009/0055944 A1 | 2/2009 | Korman et al. |
| 2009/0203538 A1 | 8/2009 | Sugioka et al. |
| 2009/0217401 A1 | 8/2009 | Korman et al. |
| 2009/0252741 A1 | 10/2009 | Liu |
| 2009/0297518 A1 | 12/2009 | Honjo et al. |
| 2009/0317368 A1 | 12/2009 | Chen |
| 2010/0055102 A1 | 3/2010 | Langermann et al. |
| 2010/0196394 A1 | 8/2010 | Pardoll et al. |
| 2010/0233183 A1 | 9/2010 | Triebel et al. |
| 2011/0007023 A1 | 1/2011 | Abrahamsson et al. |
| 2011/0081341 A1 | 4/2011 | Honjo et al. |
| 2011/0150892 A1 | 6/2011 | Thudium et al. |
| 2011/0209230 A1 | 8/2011 | Korman et al. |
| 2013/0017199 A1 | 1/2013 | Langermann et al. |
| 2013/0122014 A1 | 5/2013 | Korman et al. |
| 2013/0133091 A1 | 5/2013 | Korman et al. |
| 2013/0309250 A1 | 11/2013 | Cogswell et al. |
| 2014/0093511 A1 | 4/2014 | Lonberg et al. |
| 2014/0212422 A1 | 7/2014 | Korman et al. |
| 2014/0271684 A1 | 9/2014 | Li |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0341917 A1 | 11/2014 | Nastri et al. |
| 2014/0348743 A1 | 11/2014 | Korman et al. |
| 2015/0079109 A1 | 3/2015 | Li et al. |
| 2015/0093380 A1 | 4/2015 | Honjo et al. |
| 2015/0125463 A1 | 5/2015 | Cogswell et al. |
| 2015/0165025 A1 | 6/2015 | Korman et al. |
| 2015/0197572 A1 | 7/2015 | Honjo et al. |
| 2015/0259420 A1 | 9/2015 | Triebel et al. |
| 2015/0307609 A1 | 10/2015 | Lonberg et al. |
| 2015/0337038 A1 | 11/2015 | Korman et al. |
| 2016/0024593 A1 | 1/2016 | Zheng et al. |
| 2016/0075782 A1 | 3/2016 | Korman et al. |
| 2016/0090417 A1 | 3/2016 | Cogswell et al. |
| 2016/0108121 A1 | 4/2016 | Pardoll et al. |
| 2016/0152720 A1 | 6/2016 | Kim et al. |
| 2016/0158355 A1 | 6/2016 | Honjo et al. |
| 2016/0158356 A1 | 6/2016 | Honjo et al. |
| 2016/0222116 A1 | 8/2016 | Korman et al. |
| 2016/0272708 A1 | 9/2016 | Chen |
| 2016/0326248 A1 | 11/2016 | Gutierrez et al. |
| 2016/0362495 A1 | 12/2016 | Korman et al. |
| 2017/0051060 A1 | 2/2017 | Honjo et al. |
| 2017/0088615 A1 | 3/2017 | Korman et al. |
| 2017/0101472 A1 | 4/2017 | Ullman et al. |
| 2017/0137514 A1 | 5/2017 | Lonberg et al. |
| 2017/0143827 A1 | 5/2017 | Vikram et al. |
| 2017/0158767 A1 | 6/2017 | Korman et al. |
| 2017/0168054 A1 | 6/2017 | Balko et al. |
| 2017/0260271 A1 | 9/2017 | Igawa et al. |
| 2018/0066054 A1 | 3/2018 | Thudium |
| 2018/0086830 A1 | 3/2018 | Triebel et al. |
| 2018/0282414 A1 | 6/2018 | Cogswell |
| 2018/0244773 A1 | 8/2018 | Gutierrez et al. |
| 2018/0273624 A1 | 9/2018 | Cogswell |
| 2018/0282413 A1 | 10/2018 | Cogswell |
| 2018/0312590 A1 | 11/2018 | Cogswell |
| 2018/0319801 A1 | 11/2018 | Cogswell |
| 2018/0371087 A1 | 12/2018 | Lonberg |
| 2019/0092863 A1 | 3/2019 | Cogswell |
| 2019/0100589 A1 | 4/2019 | Cogswell |
| 2019/0100590 A1 | 4/2019 | Cogswell |
| 2019/0112376 A1 | 4/2019 | Cogswell |
| 2019/0112377 A1 | 4/2019 | Cogswell |
| 2019/0135920 A1 | 5/2019 | Cogswell |

(56) References Cited

U.S. PATENT DOCUMENTS

| | | |
|---|---|---|
| 2019/0153099 A1 | 5/2019 | Cogswell |
| 2019/0256594 A1 | 8/2019 | Lonberg et al. |
| 2019/0276538 A1 | 9/2019 | Thudium |
| 2019/0276539 A1 | 9/2019 | Thudium |
| 2020/0062845 A1 | 2/2020 | Korman et al. |
| 2020/0062846 A1 | 2/2020 | Honjo et al. |
| 2020/0062848 A1 | 2/2020 | Korman et al. |
| 2020/0138945 A1 | 5/2020 | Korman et al. |
| 2020/0231671 A1 | 7/2020 | Thudium |
| 2020/0308282 A1 | 10/2020 | Cogswell et al. |
| 2020/0385466 A1 | 12/2020 | Thudium |
| 2020/0385467 A1 | 12/2020 | Thudium |
| 2021/0009692 A1 | 1/2021 | Korman et al. |
| 2021/0122820 A1 | 4/2021 | Gutierrez et al. |
| 2021/0238287 A1 | 8/2021 | Srivastava et al. |
| 2021/0283251 A1 | 9/2021 | Burton et al. |
| 2021/0338813 A1 | 11/2021 | Maurer et al. |
| 2021/0340250 A1 | 11/2021 | Korman et al. |
| 2022/0185892 A1 | 6/2022 | Korman et al. |
| 2022/0195040 A1 | 6/2022 | Thudium et al. |
| 2022/0204612 A1 | 6/2022 | Thudium et al. |
| 2022/0348653 A1 | 11/2022 | Hedvat et al. |
| 2022/0411499 A1 | 12/2022 | Srivastava et al. |
| 2023/0061544 A1 | 3/2023 | Korman et al. |
| 2023/0077348 A1 | 3/2023 | Lonberg et al. |
| 2023/0111786 A1 | 4/2023 | Korman et al. |
| 2023/0265188 A1 | 8/2023 | Srivastava et al. |
| 2023/0272079 A1 | 8/2023 | Korman et al. |
| 2023/0322919 A1 | 10/2023 | Thudium et al. |
| 2024/0002512 A1 | 1/2024 | Cogswell et al. |

FOREIGN PATENT DOCUMENTS

| | | |
|---|---|---|
| WO | WO-9110682 A1 | 7/1991 |
| WO | WO-9530750 A2 | 11/1995 |
| WO | WO-9703695 A1 | 2/1997 |
| WO | WO-9713852 A1 | 4/1997 |
| WO | WO-9732733 A1 | 9/1997 |
| WO | WO-9842752 A1 | 10/1998 |
| WO | WO-9858059 A1 | 12/1998 |
| WO | WO-0037504 A2 | 6/2000 |
| WO | WO-0069914 A2 | 11/2000 |
| WO | WO-0114424 A2 | 3/2001 |
| WO | WO-200243478 A2 | 6/2002 |
| WO | WO-03088808 A2 | 10/2003 |
| WO | WO-03099196 A2 | 12/2003 |
| WO | WO-2004004771 A1 | 1/2004 |
| WO | WO-2004039956 A2 | 5/2004 |
| WO | WO-2004078928 A2 | 9/2004 |
| WO | WO-2005034733 A2 | 4/2005 |
| WO | WO-2005059106 A2 | 6/2005 |
| WO | WO-2005067620 A2 | 7/2005 |
| WO | WO-2006007850 A1 | 1/2006 |
| WO | WO-2006121168 A1 | 11/2006 |
| WO | WO-2006126835 A1 | 11/2006 |
| WO | WO-2006133396 A2 | 12/2006 |
| WO | WO-2007005874 A2 | 1/2007 |
| WO | WO-2008007648 A1 | 1/2008 |
| WO | WO-2008073160 A2 | 6/2008 |
| WO | WO-2008121615 A2 | 10/2008 |
| WO | WO-2008121616 A2 | 10/2008 |
| WO | WO-2008132601 A1 | 11/2008 |
| WO | WO-2008156712 A1 | 12/2008 |
| WO | WO-2009014708 A2 | 1/2009 |
| WO | WO-2009044273 A2 | 4/2009 |
| WO | WO-2009114335 A2 | 9/2009 |
| WO | WO-2010019570 A2 | 2/2010 |
| WO | WO-2011008092 A2 | 1/2011 |
| WO | WO-2011066389 A1 | 6/2011 |
| WO | WO-2011161699 A2 | 12/2011 |
| WO | WO-2012009442 A2 | 1/2012 |
| WO | WO-2012054438 A1 | 4/2012 |
| WO | WO-2012059858 A1 | 5/2012 |
| WO | WO-2012145493 A1 | 10/2012 |
| WO | WO-2013014668 A1 | 1/2013 |
| WO | WO-2013063186 A2 | 5/2013 |
| WO | WO-2013079174 A1 | 6/2013 |
| WO | WO-2013166118 A2 | 11/2013 |
| WO | WO-2013173223 A1 | 11/2013 |
| WO | WO-2013181634 A2 | 12/2013 |
| WO | WO-2014008218 A1 | 1/2014 |
| WO | WO-2014140180 A1 | 9/2014 |
| WO | WO-2014179664 A2 | 11/2014 |
| WO | WO-2014194302 A2 | 12/2014 |
| WO | WO-2014206107 A1 | 12/2014 |
| WO | WO-2015016718 A1 | 2/2015 |
| WO | WO-2015035606 A1 | 3/2015 |
| WO | WO-2015042246 A1 | 3/2015 |
| WO | WO-2015085847 A1 | 6/2015 |
| WO | WO-2015094995 A2 | 6/2015 |
| WO | WO-2015094996 A2 | 6/2015 |
| WO | WO-2015095404 A2 | 6/2015 |
| WO | WO-2015112800 A1 | 7/2015 |
| WO | WO-2015112900 A1 | 7/2015 |
| WO | WO-2015116539 A1 | 8/2015 |
| WO | WO-2015138920 A1 | 9/2015 |
| WO | WO-2015175340 A1 | 11/2015 |
| WO | WO-2015200119 A1 | 12/2015 |
| WO | WO-2016028672 A1 | 2/2016 |
| WO | WO-2016106159 A1 | 6/2016 |
| WO | WO-2016110593 A1 | 7/2016 |
| WO | WO-2016126858 A2 | 8/2016 |
| WO | WO-2016127220 A1 | 8/2016 |
| WO | WO-2016149201 A2 | 9/2016 |
| WO | WO-2016168716 A1 | 10/2016 |
| WO | WO-2016176504 A1 | 11/2016 |
| WO | WO-2016197367 A1 | 12/2016 |
| WO | WO-2016200782 A1 | 12/2016 |
| WO | WO-2016207646 A1 | 12/2016 |
| WO | WO-2017004153 A1 | 1/2017 |
| WO | WO-2017013436 A1 | 1/2017 |
| WO | WO-2017015560 A2 | 1/2017 |
| WO | WO-2017019846 A1 | 2/2017 |
| WO | WO-2017019894 A1 | 2/2017 |
| WO | WO-2017020291 A1 | 2/2017 |
| WO | WO-2017020858 A1 | 2/2017 |
| WO | WO-2017024465 A1 | 2/2017 |
| WO | WO-2017024515 A1 | 2/2017 |
| WO | WO-2017025016 A1 | 2/2017 |
| WO | WO-2017025051 A1 | 2/2017 |
| WO | WO-2017025498 A1 | 2/2017 |
| WO | WO-2017034916 A1 | 3/2017 |
| WO | WO-2017037203 A1 | 3/2017 |
| WO | WO-2017040790 A1 | 3/2017 |
| WO | WO-2007045996 A1 | 4/2017 |
| WO | WO-2017062888 A1 | 4/2017 |
| WO | WO-2017070585 A1 | 4/2017 |
| WO | WO-2017079150 A1 | 5/2017 |
| WO | WO-2017086367 A1 | 5/2017 |
| WO | WO-2017086419 A1 | 5/2017 |
| WO | WO-2017087589 A2 | 5/2017 |
| WO | WO-2017087599 A1 | 5/2017 |
| WO | WO-2017087678 A2 | 5/2017 |
| WO | WO-2017087901 A2 | 5/2017 |
| WO | WO-2017106061 A1 | 6/2017 |
| WO | WO-2017106129 A1 | 6/2017 |
| WO | WO-2017123557 A1 | 7/2017 |
| WO | WO-2017132827 A1 | 8/2017 |
| WO | WO-2017133540 A1 | 8/2017 |
| WO | WO-2017149143 A1 | 9/2017 |
| WO | WO-2017198741 A1 | 11/2017 |
| WO | WO-2017219995 A1 | 12/2017 |
| WO | WO-2017220555 A1 | 12/2017 |
| WO | WO-2017220569 A1 | 12/2017 |
| WO | WO-2018034227 A1 | 2/2018 |
| WO | WO-2018057506 A1 | 3/2018 |
| WO | WO-2018069500 A2 | 4/2018 |
| WO | WO-2018071500 A1 | 4/2018 |
| WO | WO-2018071824 A1 | 4/2018 |
| WO | WO-2018083087 A2 | 5/2018 |
| WO | WO-2018148476 A1 | 8/2018 |
| WO | WO-2018201096 A1 | 11/2018 |
| WO | WO-2018204374 A1 | 11/2018 |
| WO | WO-2018208868 A1 | 11/2018 |

(56) References Cited

FOREIGN PATENT DOCUMENTS

| WO | WO-2018218215 A1 | 11/2018 |
|---|---|---|
| WO | WO-2018222718 A1 | 12/2018 |
| WO | WO-2018222722 A2 | 12/2018 |

OTHER PUBLICATIONS

Anonymous: "A Phase 1 Dose Escalation and Cohort Expansion Study of the Safety, Tolerability, and Efficacy of Anti-LAG-3 Monoclonal Antibody (BMS-986016) Administered Alone and in Combination With Anti-PD-1 Monoclonal Antibody (Nivolumab, BMS-936558) in Advanced Solid Tumors," ClinicaiTrials.gov Archive Identifier NCT01968109, accessed at https://clinicaltrials.gov/archive/NCT01968109/2014_01_23, last accessed on Jun. 12, 2015, 5 pages.
ATCC Product Data Sheet,"A3.4H2 (ATCC® HB-12319™)," American Type Culture Collections, 2013. 2 pages.
ATCC Product Data Sheet,"A3.6B10 (ATCC® HB-12318™)," American Type Culture Collections, 2013. 2 pages.
Baixeras, E., et al., "Characterization of the Lymphocyte Activation Gene 3-encoded Protein. A New Ligand for Human Leukocyte Antigen Class II Antigens," The Journal of Experimental Medicine 176(2):327-337, Rockefeller University Press, United States (Aug. 1992).
Blackburn, S.D., et al., "Coregulation of CD8+ T cell exhaustion by multiple inhibitory receptors during chronic viral infection," Nature immunology 10(1):29-37, Nature America Inc., United States (Jan. 2009).
Casati, C., et al., "Soluble Human LAG-3 Molecule Amplifies the in Vitro Generation of Type 1 Tumor-specific Immunity," Cancer Research 66(8):4450-4460, American Association for Cancer Research, United States (Apr. 2006).
Cashion, M.P. and Long, T.E., "Biomimetic Design and Performance of Polymerizable Lipids," Accounts of Chemical Research 42(8):1016-1025, American Chemical Society, United States (Aug. 2009).
Chelius, D., et al., "Identification and Characterization of Deamidation Sites in the Conserved Regions of Human Immunoglobulin Gamma Antibodies," Analytical Chemistry 77(18):6004-6011, American Chemical Society, United States (2005).
Cleland, J,L., et al., "The Development of Stable Protein Formulations: A Close Look at Protein Aggregation, Deamidation, and Oxidation," Critical Reviews in Therapeutic Drug Carrier Systems 10(4):307-377, CRC Press, United States (1993).
Correia, I,R., et al., "Stability of IgG Isotypes in Serum," mAbs 2(3):221-232, Taylor & Francis, United States (May-Jun. 2010).
De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).
Drake, C.G., et al., "Blocking the Regulatory T Cell Molecule LAG-3 Augments in Vivo Anti-tumor Immunity in an Autochthonous Model of Prostate Cancer," Journal of Clinical Oncology 24(18):2573 (Jun. 2006).
El Mir, S. and Triebel, F., "A Soluble Lymphocyte Activation Gene-3 Molecule Used as a Vaccine Adjuvant Elicits Greater Humoral and Cellular Immune Responses to Both Particulate and Soluble Antigens," Journal of Immunology 164(11):5583-5589, American Association of Immunologists, United States (Jun. 2000).
Extended European Search Report for EP Application No. 17177885, Hague, Netherlands, mailed on Nov. 17, 2017.
Extended European Search Report mailed Feb. 23, 2017 in EP Patent Application No. 16197459.7, European Patent Office, Munich, Germany, 15 pages.
Fishwild, D.M., et al., "High-Avidity Human IgG Kappa Monoclonal Antibodies from a Novel Strain of Minilocus Transgenic Mice," Nature Biotechnology 14(7):845-851, Nature America Publishing, United States (1996).
Goding, S,R., et al., "Combination of Adoptive Cell Transfer, Anti-PD-L1 and Anti-LAG-3 Antibodies for the Treatment of Recurrent Tumors," OncoImmunology 2(8), 4 pages (May 2013).
Grosso, J.F., et al., "LAG-3 Regulates CD8+ T Cell Accumulation and Effector Function in Murine Self- and Tumor-tolerance Systems," The Journal of Clinical Investigation 117(11):3383-3392, American Society for Clinical Investigation, United States (Nov. 2007).
Harris, R.J., et al., "Identification of Multiple Sources of Charge Heterogeneity in a Recombinant Antibody," Journal of chromatography. B, Biomedical Sciences and Applications 752(2):233-245, Elsevier, Netherlands (2001).
Huang, C,T., et al., "Role of LAG-3 in Regulatory T Cells," Immunity 21(4):503-513, Cell Press, United States (Oct. 2004).
Huard, B., et al., "Characterization of the Major Histocompatibility Complex Class II Binding Site on LAG-3 Protein," Proceedings of the National Academy of Sciences of the United States of America 94(11):5744-5749, National Academy of Sciences, United States (May 1997).
Huard, B., et al., "Cellular expression and tissue distribution of the humanLAG-3-encoded protein, an MHC class II ligand," Immunogenetics 39:213-217, Springer-Verlag, Germany (1994).
Huard, B., et al., "Lymphocyte-activation Gene 3/major Histocompatibility Complex Class II Interaction Modulates the Antigenic Response of CD4+ T Lymphocytes," European Journal of Immunology 24(12):3216-3221, Wiley-VCH, Germany (Dec. 1994).
Huard, B., et al., "T Cell Major Histocompatibility Complex Class II Molecules Down-regulate CD4+ T Cell Clone Responses Following LAG-3 Binding," European Journal of Immunology 26(5):1180-1186, Wiley-VCH, Germany (May 1996).
International Preliminary Report on Patentability and Written Opinion for Application Serial No. PCT/US2013/48999, issued on Jan. 6, 2015, 7 pages.
International Preliminary Report on Patentability for Application No. PCT/US2009/053405, mailed on Feb. 15, 2011, 10 pages.
International Preliminary Report on Patentability for Application Serial No. PCT/US2014/056277, issued on Mar. 22, 2016, 10 pages.
International Search Report and written opinion for International Application No. PCT/US2009/053405, ISA/US Alexandria, Virginia, mailed on Mar. 31, 2010, 15 pages.
International Search Report and Written Opinion for International Application No. PCT/US2013/48999, European patent office, Rijswijk, mailed on Sep. 23, 2013, 11 pages.
International Search Report and Written Opinion for International Application No. PCT/US2014/056277, European patent office, Rijswijk, mailed on Feb. 4, 2015, 15 pages.
International Search Report and Written Opinion for International Application No. PCT/US2015/012916, European patent office, Rijswijk, mailed on Jun. 23, 2015, 12 pages.
Iouzalen, N., et al., "LAP, A Lymphocyte Activation Gene-3 (LAG-3)-associated Protein That Binds to a Repeated EP Motif in the Intracellular Region of LAG-3, May Participate in the Downregulation of the CD3/TCR Activation Pathway," European Journal of Immunology 31(10):2885-2891, Wiley-VCH, Germany (Oct. 2001).
Kocak, E., et al., "Combination Therapy with Anti-CTL Antigen-4 and Anti-4-1BB Antibodies Enhances Cancer Immunity and Reduces Autoimmunity," Cancer Research 66(14):7276-7284, American Association for Cancer Research, United States (Jul. 2006).
Kosky, A,A., et al., "Multivariate Analysis of the Sequence Dependence of Asparagine Deamidation Rates in Peptides," Pharmaceutical Research 26(11):2417-2428, Kluwer Academic/Plenum Publishers, United states (Nov. 2009).
Kroon, D,J., et al., "Identification of Sites of Degradation in a Therapeutic Monoclonal Antibody by Peptide Mapping," Pharmaceutical Research 9(11):1386-1393, Kluwer Academic/Plenum Publishers, United states (Nov. 1992).

(56) References Cited

OTHER PUBLICATIONS

Lonberg, N., et al., "Antigen-specific Human Antibodies from Mice Comprising Four Distinct Genetic Modifications," Nature 368(6474):856-859, Nature Publishing Group, United States (Apr. 1994).

Maccallum, R.M., et al., "Antibody-antigen Interactions: Contact Analysis and Binding Site Topography," Journal of Molecular Biology 262(5):732-745, Academic Press, England (Oct. 1996).

Macon-Lemaitre, L. and Triebel, F., "The Negative Regulatory Function of the Lymphocyte-activation Gene-3 Co-receptor (CD223) on Human T Cells," Immunology 115(2):170-178, Blackwell Scientific Publications, England (Jun. 2005).

Pardoll, D., "Chapter 14-Dendritic Cells and Coregulatory Signals: Immune Checkpoint Blockade to Stimulate Immunotherapy," Cancer Immunotherapy Immune Suppression and Tumor Growth, pp. 257-275, Elsevier Inc., United States (2007).

Prigent, P., et al., "Lymphocyte Activation Gene-3 Induces Tumor Regression and Antitumor Immune Responses," European Journal of Immunology 29(12):3867-3876, Wiley-VCH, Germany (Dec. 1999).

Reply to Communication from the Examining Division dated Nov. 25, 2016 in European Application No. 13737946.7 filed on Jul. 2, 2013, pp. 115-119.

Robinson, N,E. and Robinson, A,B., "Molecular Clocks," Proceedings of the National Academy of Sciences of the United States of America 98(3):944-949, National Academy of Sciences, United states (Jan. 2001).

Subramanyam, M., et al., "Soluble Human Lymphocyte Activation Gene-3 Modulates Allospecific T Cell Responses," International Immunology 10(5):679-689, University Press, England (May 1998).

Supplementary European Search Report for EP Application No. 09807162.4, European Patent Office, Munich, Germany, mailed on Dec. 21, 2012, 9 pages.

Third Party Observation dated Oct. 7, 2016 for European Application No. 13737946.7 filed on Jul. 2, 2013, 17 pages.

Triebel, F., et al., "LAG-3, A Novel Lymphocyte Activation Gene Closely Related to CD4," The Journal of Experimental Medicine 171(5):1393-1405, Rockefeller University Press, United States (May 1990).

Triebel, F., "LAG-3: A Regulator of T-cell and DC Responses and its Use in Therapeutic Vaccination," Trends in Immunology 24(12):619-622, Elsevier Science Ltd., England (Dec. 2003).

Tsai, P,K., et al., "Origin of the Isoelectric Heterogeneity of Monoclonal Immunoglobulin h1B4," Pharmaceutical Research 10(11):1580-1586, Kluwer Academic/Plenum Publishers, United states (Nov. 1993).

Turnis, M,E., et al., "Combinatorial Immunotherapy: PD-1 May Not Be LAG-ing Behind Any More.," Oncoimmunology 1(7):1172-1174, Taylor & Francis, United States (Oct. 2012).

Vlasak, J., et al., "Identification and Characterization of Asparagine Deamidation in the Light Chain CDR1of a Humanized IgG1 Antibody," Analytical Biochemistry 392(2):145-154, Academic Press, United states (Sep. 2009).

Woo, S,R., et al., "Immune Inhibitory Molecules LAG-3 and PD-1 Synergistically Regulate T-cell Function to Promote Tumoral Immune Escape," Cancer Research 72(4):917-927, American Association for Cancer Research, United states (Feb. 2012).

Workman, C.J. and Vignali, D.A., "Negative Regulation of T Cell Homeostasis by Lymphocyte Activation Gene-3 (CD223)," Journal of Immunology 174(2):688-695, American Association of Immunologists, United States (Jan. 2005).

Workman, C.J., et al., "Phenotypic Analysis of the Murine Cd4-related Glycoprotein, CD223 (LAG-3)," European Journal of Immunology 32(8):2255-2263, Wiley-VCH, Germany (Aug. 2002).

Nivolumab, "Guide to Pharmacology," accessed at http://www.guidetopharmacology.org/GRAC/liganddisplayforward?ligandId=7335, last accessed Sep. 28, 2018, 1 page.

Xiao Y and Freeman G.J., "The Microsatellite Instable Subset of Colorectal Cancer Is a Particularly Good Candidate for Checkpoint Blockade Immunotherapy," Cancer Discovery 5(1):16-18, American Association for Cancer Research, United States (Jan. 2015).

Zhang, F., et al., "Structural Basis of a Novel PD-L1 Nanobody for Immune Checkpoint Blockade," Cell Discovery, 3:17004, Nature Publishing Group, England (Mar. 2017).

Adib-Conquy, M., et al., "Effect of Amino Acid Substitutions in the Heavy Chain CDR3 of an Autoantibody on Its Reactivity," International Immunology 10(3):341-346, Oxford University Press, England (1998).

Beers, R., et al., "Immunotoxins With Increased Activity Against Epidermal Growth Factor Receptor vIII-expressing Cells Produced by Antibody Phage Display," Clinical Cancer Research 6(7):2835-2843, The Association, United States (2000).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (1993).

Camacho, L.H., et al., "Phase I clinical trial of anti-CTLA4 human monoclonal antibody CP-675,206 in patients (pts) with advanced solid malignancies," Journal of Clinical Oncology 22(14S): Abstract 2505, 2004 ASCO Annual Meeting Proceedings (Post-Meeting Edition), $40^{th}$ Annual Meeting, Jun. 5-8, New Orleans, LA, American Society of Clinical Oncology, United States (2004).

De Wildt, R.M.T., et al. , "Heavy Chain CDR3 Optimization of a Germline Encoded Recombinant Antibody Fragment Predisposed to Bind the ULA Protein," Protein Engineering 10(7):835-841, Oxford University Press, England (1997).

Extended European Search Report for EP Application No. 09807162. 4, European Patent Office, Netherlands, mailed on Dec. 21, 2012, 9 pages.

Greenberg, P.D. and Riddell, S.R., "Deficient Cellular Immunity-Finding and Fixing the Defects," Science 285(5427):546-551, American Association for the Advancement of Science, United States (1999).

Grosso, J.F., et al., "Functionally Distinct LAG-3 and PD-1 Subsets on Activated and Chronically Stimulated CD8 T Cells," The Journal of Immunology 182(11):6659-6669, The American Association of Immunologists, Inc., United States (Jun. 2009).

Hahne, M., et al., "Melanoma Cell Expression of Fas(Apo-1/CD95) Ligand: Implications for Tumor Immune Escape," Science 274(5291):1363-1366, American Association for the Advancement of Science, United States (1996).

Hall, B.L., et al., "A Single Amino Acid Mutation in CDR3 of the 3-14-9 L Chain Abolished Expression of the IDA 10-defined Idiotope and Antigen Binding," Journal of Immunology 149(5):1605-1612, American Association of Immunologists, United States (1992).

He, Y-F., et al., "Blocking Programmed Death-1 Ligand-PD-1 Interactions by Local Gene Therapy Results in Enhancement of Antitumor Effect of Secondary Lymphoid Tissue Chemokine," The Journal of Immunology 173(8):4919-4928, The American Association of Immunologists, United States (2004).

Holliger, P., et al., "'Diabodies': Small Bivalent and Bispecific Antibody Fragments," Proceedings of the National Academy of Sciences USA 90(14):6444-6448, National Academy of Sciences, United States (1993).

Howard, M. and Ogarra, A., "Biological Properties of Interleukin 10," Immunology Today 13(6):198-200, Elsevier Science Publishers, England (1992).

Hurwitz, A.A., et al., "CTLA-4 Blockade Synergizes With Tumor-derived Granulocyte-macrophage Colony-stimulating Factor for Treatment of an Experimental Mammary Carcinoma," Proceedings of the National Academy of Sciences of the United States of America 95(17):10067-10071, National Academy of Sciences, United States (1998).

Hutloff, A., et al., "ICOS is an Inducible T-cell Co-stimulator Structurally and Functionally Related to CD28," Nature 397(6716):263-266, Nature Publishing Group, England (1999).

Ito, D., et al., "Effective Priming of Cytotoxic T Lymphocyte Precursors by Subcutaneous Administration of Peptide Antigens in Liposomes Accompanied by Anti-CD40 and Anti-CTLA-4 Antibodies," Immunobiology 201(5):527-540, Elsevier, Netherlands (2000).

Kehrl, J.H., et al., "Production of Transforming Growth Factor ß by Human T Lymphocytes and Its Potential Role in the Regulation of

(56) References Cited

OTHER PUBLICATIONS

T Cell Growth," The Journal of Experimental Medicine 163(5):1037-1050, Rockefeller University Press, United States (1986).
Kelley, R.F. and O'connell, M.P., "Thermodynamic Analysis of an Antibody Functional Epitope," Biochemistry 32(27):6828-6835, American Chemical Society, United States (1993).
Komissarov, A.A., et al., "Site-specific Mutagenesis of a Recombinant Anti-single-stranded DNA Fab. Role of Heavy Chain Complementarity-determining Region 3 Residues in Antigen Interaction," 272(43):26864-26870, American Society for Biochemistry and Molecular Biology, United States (1997).
Melero, I., et al., "Monoclonal Antibodies Against the 4-1BB T-cell Activation Molecule Eradicate Established Tumors," Nature Medicine 3(6):682-685, Nature Publishing Company, United States (1997).
Mokyr, M.B., et al., "Realization of the Therapeutic Potential of CTLA-4 Blockade in Low-dose Chemotherapy-treated Tumor-bearing Mice," Cancer Research 58(23):5301-5304, American Association for Cancer Research, United States (1998).
Poljak, R.J., "Production and Structure of Diabodies," Structure 2(12):1121-1123, Cell Press, United States (1994).
Ridge J.P., et al., "A Conditioned Dendritic Cell Can Be a Temporal Bridge Between a CD4+ T-helper and a T-killer Cell," Nature 393(6684):474-478, Nature Publishing Group, England (1998).
Weinberg, A.D., et al., "Engagement of the OX-40 Receptor in Vivo Enhances Antitumor Immunity," Journal of Immunology 164(4):2160-2169, American Association of Immunologists, United States (2000).
Poirier, N., et al., "Antibody-mediated depletion of lymphocyte-activation gene-3 (LAG-3$^+$)-activated T lymphocytes prevents delayed-type hypersensitivity in non-human primates" Clinical and Experimental Immunology 164(2):265-274, British Society for Immunology (2011).
Kallewaard, N.L., et al., "Functional Maturation of the Human Antibody Response to Rotavirus," Journal of Immunology 180(6):3980-3989, American Association of Immunologists, United States (Mar. 2008).
Wiens, G.D., et al., "Somatic Mutation in VH complementarity-determining Region 2 and Framework Region 2: Differential Effects on Antigen Binding and Ig selection," Journal of Immunology 159(3):1293-1302, American Association of Immunologists, United States (1997).
Khan, T., et al., "Adjustable locks and flexible Keys: Plasticity of Epitope-Paratope Interactions in Germline Antibodies," J Immunol 192:5398-5405, American Association of Immunologists, United States (2014).
Torres, Marcela, et al., "The Immunoglobulin constant region contributes to affinity and specificity," Trends in Immunology 29(2): 91-97, Elsevier, Netherlands (2007).
Poosarla, V.G., et al., "Computational De Novo Design of Antibodies Binding to a Peptide With High Affinity," Biotechnology and Bioengineering 114(6):1331-1342, Wiley Online Library, United States (Jun. 2017).
Edwards, B.M., et al., "The Remarkable Flexibility of the Human Antibody Repertoire; Isolation of Over One Thousand Different Antibodies to a Single Protein," J. Mol. Biol. 334:103-118, Elsevier, Netherlands (2003).
Barber, D.L., et al., "Restoring function in exhausted CD8 T cells during chronic viral infection," Nature 439:682-687, Nature Publishing Group, United Kingdom (2006).
Declaration of Jeanette L. Fairhurst in Grounds of Opposition mailed Aug. 20, 2020 in EP Application No. 1516647.8, European Patent Office, Germany, 12 pages.
Dyrberg, T., et al., "Peptides as antigens. Importance of orientation," The Journal of Experimental Medicine 164(4):1344-1349, Rockefeller University Press, United States (1986).
Exhibit 1 in Grounds of Opposition mailed Aug. 20, 2020, in EP Application No. 15156647.8, European Patent Office, Germany, 1 page.
Extended European Search Report mailed Jul. 13, 2015, in EP Application No. 15156647.8, European Patent Office, Germany, 9 pages.
Goldberg, M.V., et al., "LAG-3 in Cancer Immunotherapy," Curr Top Microbiol Immunology 344:269-278, Springer, United States (2011).
Grounds of Opposition mailed Aug. 20, 2020, in EP Application No. 1516647.8, European Patent Office, Germany, 86 pages.
Hong, S., et al., "Progress and Application of Humanization of Monoclonal Antibodies," Chinese Journal of Biologicals 21(1):70-73, Changchun Institute of Biological Products, China (2008).
Hoogenboom, H.R., et al., "Designing and optimizing library selection strategies for generating high-affinity antibodies," TibTech Library 15:62-70, Elsevier, Netherlands (1997).
Huard, B., et al., "CD4/major histocompatibility complex class II interaction analyzed with CD4- and lymphocyte activation gene-3 (LAG-3)-Ig fusion proteins," Eur. J. Immunol.25:2718-2721, Wiley-VCH, Germany (1995).
Huard, B., et al., "LAG-3 does not define a specific mode of natural killing in human," Immunology Letters 61:109-112, Elsevier, Netherlands (1998).
Imakiire, T., et al., "Generation, immunologic characterization and antitumor effects of human monoclonal antibodies for carcinoembryonic antigen," Int J Cancer 108(4):564-570, Wiley Online Publishing, United States (2004).
Jespers, L.S., et al., "Guiding the Selection of Human Antibodies from Phage Display Reperotires to a Single Epitope of an Antigen," Biotechnology 12:899-903, Nature Publishing Group, United Kingdom (1994).
Kaufmann, D.E., et al., "Upregulation of CTLA-4 by HIV-specific CD4+ T cells correlates with disease progression and defines a reversible immune dysfunction," Nature Immunology 8(11): 1246-1254, Nature Publishing Group, United Kingdom (2007).
Response to communication in European Patent Application No. 15156647.8, dated Mar. 29, 2018, European Patent Office, Germany, 3 pages.
Response to communication in European Patent Application No. 15156647.8, dated Feb. 9, 2016, European Patent Office, Germany, 3 pages.
Perez De La Lastra, J.M., et al., "Epitope mapping of 10 monoclonal antibodies against the pig analogue of human membrane cofactor protein (MCP)," Immunology 96:663-670, Blackwell Science Ltd., United States (1999).
Shapira, M., et al., "Immunity and protection against influenza virus by synthetic peptide corresponding to antigenic sites of hemagglutinin," PNAS 81(8): 2461-2465, United States National Academy of Sciences, United States (1984).
Office Action issued Apr. 28, 2020 in CN 201710463804.9, State Intellectual Property Office of People's Republic of China, China, 8 pages.
Tanaka, T., et al., "Efficient generation of antibodies to oncoproteins by using synthetic peptide antigens," PNAS 82(10):3400-3404, United States National Academy of Sciences, United States (1985).
Workman, C.J., et al., "The CD4-related molecule, LAG-3 (CD223), regulates the expansion of activated T cells," Eur J. Immunol. 33(4):970-979, Wiley Online Library, United States (2003).
Agata, Y., et al., "Expression of the PD-1 Antigen on the Surface of Stimulated Mouse T and B lymphocytes," International Immunology 8(5):765-772, Oxford University Press, England (May 1996).
Ascierto, P.A., et al., "Initial Efficacy of Anti-lymphocyte Activation Gene-3 (Anti-LAG-3; BMS-986016) in Combination With Nivolumab (Nivo) in Pts With Melanoma (MEL) Previously Treated With Anti-PD-1/PD-L1 Therapy," Journal of Clinical Oncology 35(15_suppl): [abstract 9520], American Society of Clinical Oncology, United States (May 2017).
Bennett, F., et al., "Program Death-1 Engagement Upon TCR Activation has Distinct Effects on Costimulation and Cytokine-driven Proliferation: Attenuation of ICOS, IL-4, and IL-21, but not CD28, IL-7, and IL-15 responses," The Journal of Immunology 170(2):711-718, The American Association of Immunologists, United States (Jan. 2003).
Bettini, M., et al., "Cutting Edge: Accelerated Autoimmune Diabetes in the Absence of LAG-3," Journal of Immunology 187(7):3493-3498, American Association of Immunologists, United States (Oct. 2011).

(56) References Cited

OTHER PUBLICATIONS

Bird, R.E., et al., "Single-chain Antigen-binding Proteins," Science 242(4877):423-426, Association for the Advancement of Science, United States (Oct. 1988).
Blank, C., et al., "Interaction of PD-L1 on Tumor Cells with PD-1 on Tumor-specific T Cells as a Mechanism of Immune Evasion: Implications for Tumor Immunotherapy," Cancer Immunology Immunotherapy 54(4):307-314, Springer-Verlag, Germany (Apr. 2005).
Brown, J.A., et al., "Blockade of Programmed Death-1 Ligands on Dendritic Cells Enhances T Cell Activation and Cytokine Production," The Journal of Immunology 170(3):1257-1266, The American Association of Immunologists, United States (Feb. 2003).
Camisaschi, C., et al., "LAG-3 Expression Defines a Subset of CD4(+)CD25(High)Foxp3(+) Regulatory T Cells That Are Expanded at Tumor Sites," Journal of Immunology 184(11):6545-6551, American Association of Immunologists, United states (Jun. 2010).
Carter, L.L., et al., "PD-1:PD-L Inhibitory Pathway Affects both CD4(+) and CD8(+) T Cells and is Overcome by IL-2," European Journal of Immunology 32(3):634-643, Wiley-VCH Verlag GmbH, German (Mar. 2002).
Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).
Dong, H. and Chen, L., "B7-H1 Pathway and its Role in the Evasion of Tumor Immunity," Journal of Molecular Medicine 81(5):281-287, Springer, Germany (May 2003).
Dong, H., et al., "B7-H1, a Third Member of the B7 Family, Co-stimulates T-cell Proliferation and Interleukin-10 Secretion," Nature Medicine 5(12):1365-1369, Nature America, United States (Dec. 1999).
Dong, H., et al., "Tumor-associated B7-H1 Promotes T-cell Apoptosis: A Potential Mechanism of Immune Evasion," Nature Medicine 8(8):793-800, Nature Publishing Company, United States (Aug. 2002).
Freeman, G.J., et al., "Engagement of the PD-1 Immunoinhibitory Receptor by a Novel B7 Family Member Leads to Negative Regulation of Lymphocyte Activation," The Journal of Experimental Medicine 192(7):1027-1034, The Rockefeller University Press, United States (Oct. 2000).
Gandhi, M,K., et al., "Expression of LAG-3 by Tumor-infiltrating Lymphocytes Is Coincident With the Suppression of Latent Membrane Antigen-specific CD8+ T-cell Function in Hodgkin Lymphoma Patients," Blood 108(7):2280-2289, American Society of Hematology, United States (Oct. 2006).
GenBank, "Human hPD-1 (hPD-1) mRNA, complete cds," Accession No. U64863.1, accessed on https://www.ncbi.nlm.nih.gov/nuccore/U64863, Oct. 12, 2005.
GenBank, "lymphocyte activation gene 3 protein precursor [*Homo sapiens*]," Accession No. NP_002277.4, accessed on https://www.ncbi.nlm.nih.gov/protein/NP_002277, Oct. 6, 2016.
GenBank, "lymphocyte activation gene 3 protein precursor [Mus musculus]," Accession No. NP_032505.1, accessed on https://www.ncbi.nlm.nih.gov/protein/NP032505, Feb. 15, 2015.
GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, accessed on https://www.ncbi.nlm.nih.gov/protein/Q9NZQ7, Nov. 2, 2016.
GenBank, "RecName: Full=Programmed cell death 1 ligand 2; Short=PD-1 ligand 2; Short=PD-L2; Short=PDCD1 ligand 2; Short= Programmed death ligand 2; AltName: Full=Butyrophilin B7-DC; Short=B7-DC; AltName: CD_antigen=CD273; Flags: Precursor," Accession No. Q9BQ51.2, accessed on https://www.ncbi.nlm.nih.gov/protein/Q9BQ51, Feb. 10, 2021.
Goding, S,R., et al., "Restoring Immune Function of Tumor-specific CD4+ T Cells During Recurrence of Melanoma," Journal of Immunology 190(9):4899-4909, American Association of Immunologists, United states (May 2013).
Gorelik, L., et al., Preclinical Characterization of a Novel Fully Human IgGI anti-PD-L1 mAb CK-301, American Association for Cancer Research Annual Meeting (AACR), Abstract 4606 (Apr. 2016).
Hamid, O., et al., "Safety and Tumor Responses with Lambrolizumab (Anti-Pd-1) in Melanoma," The New England Journal of Medicine 369(2):134-144, Massachusetts Medical Society, United States of America (Jul. 2013).
Hansen, J.A., et al., "Monoclonal Antibodies Identifying a Novel T-cell Antigen and Ia Antigens of Human Lymphocytes," Immunogenetics 10:247-260, Springer-Verlag (Feb. 1980).
Herbst, R.S., et al., "A Study of MPDL3280A, an Engineered PD-L1 Antibody in Patients with Locally Advanced or Metastatic Tumors," Journal of Clinical Oncology 31(Suppl): Abstract 3000, American Society of Clinical Oncology, United States (2013).
Huston, J.S., et al., "Protein Engineering of Antibody Binding Sites: Recovery of Specific Activity in an Anti-digoxin Single-chain Fv Analogue Produced in *Escherichia Coli*," Proceedings of the National Academy of Sciences USA 85(16):5879-5883, National Academy of Sciences, United States (Aug. 1988).
International Search Report and Written Opinion for International Application No. PCT/US2018/035134, European Patent Office, Netherlands, mailed on Oct. 18, 2018.
Ishida, Y., et al., "Induced Expression of PD-1, a Novel Member of the Immunoglobulin Gene Superfamily, Upon Programmed Cell Death," The EMBO Journal 11(11):3887-3895, Oxford University Press, England (Nov. 1992).
Iwai, Y., et al., "Involvement of PD-L1 on Tumor Cells in the Escape from Host Immune System and Tumor Immunotherapy by PD-L1 Blockade," Proceedings of the National Academy of Sciences 99(19):12293-12297, The National Academy of Sciences of the United States (Sep. 2002).
Keir, M,E., et al., "PD-1 and Its Ligands in Tolerance and Immunity," Annual Review of Immunology 26:677-704, Annual Reviews Inc, United states (2008).
Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).
Konishi, J., et al., "B7-H1 Expression on Non-small Cell Lung Cancer Cells and its Relationship with Tumor-infiltrating Lymphocytes and their PD-1 Expression," Clinical Cancer Research 10(15):5094-5100, American Association for Cancer Research, United States (Aug. 2004).
European Search Report for EP Application No. 18735009, Hague, Netherlands, mailed on Feb. 16, 2021, 9 pages.
Latchman, Y., et al., "PD-L2 is a Second Ligand for PD-1 and Inhibits T Cell Activation," Nature Immunology 2(3):261-268, Nature Publishing Group, United States (Mar. 2001).
Lipson, E., et al., "Initial experience administering BMS-986016, a monoclonal antibody that targets lymphocyte activation gene (LAG)-3, alone and in combination with nivolumab to patients with hematologic and solid malignancies", Journal for Immuno Therapy of Cancer, 4(Suppl 1):P232 (Nov. 2016).
Liu, S.Y., et al., "Ongoing Clinical Trials of PD-1 and PD-L1 Inhibitors for Lung Cancer inChina," Journal of Hematology & Oncology, 10(1):136, Biomed Central, England (Jul. 2017).
Llosa, N.J., et al., "The Vigorous Immune Microenvironment of Microsatellite Instable Colon Cancer Is Balanced by Multiple Counter-inhibitory Checkpoints," Cancer Discovery 5(1):43-51, American Association for Cancer Research, United States (Jan. 2015).
Lyford-Pike, S., et al., "Evidence for a Role of the PD-1:PD-L1 Pathway in Immune Resistance of HPV-associated Head and Neck Squamous Cell Carcinoma, " Cancer Research 73(6):1733-1741, American Association for Cancer Research, United States (Mar. 2013).
Matsuzaki, J., et al., "Tumor-infiltrating NY-ESO-1-specific CD8+ T Cells Are Negatively Regulated by LAG-3 and PD-1 in Human Ovarian Cancer," Proceedings of the National Academy of Sciences

(56) References Cited

OTHER PUBLICATIONS of the United States of America 107(17):7875-7880, National Academy of Sciences, United states (Apr. 2010).
Mccabe, K.E. and Wu, A.M., "Positive Progress in ImmunoPET—not Just a Coincidence," Cancer Biotherapy & Radiopharmaceuticals 25(3):253-261, Mary Ann Liebert, Inc, United States (Jun. 2010).
NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.
NCI Drug Dictionary, anti-PD-1 monoclonal antibody MEDI0680, accessed on Dec. 1, 2016, retrieved from the Internet URL: https://www.cancer.gov/publications/dictionaries/cancer-drug?cdrid=756047.
NCI Drug Dictionary, pembrolizumab, accessed on Dec. 1, 2016, retrieved from the Internet URL: https://www.cancer.gov/drugdictionary?cancer-drug?cdrid=695789, 3 pages.
Nielsen, C., et al., "A putative regulatory polymorphism in PD-1 is associated with nephropathy in a population-based cohort of systemic lupus erythematosus patients," Lupus 13(7):510-516, SAGE, England (2004).
Nishimura, H., et al., "Autoimmune Dilated Cardiomyopathy in PD-1 Receptor-deficient Mice," Science 291(5502):319-322, American Association for the Advancement of Science, United States (Jan. 2001).
Nishimura, H., et al., "Development of Lupus-like Autoimmune Diseases by Disruption of the PD-1 Gene Encoding an ITIM Motif-carrying Immunoreceptor," Immunity 11(2):141-151, Cell Press, United States (Aug. 1999).
Okazaki, T., et al., "New Regulatory Co-receptors: Inducible co-stimulator and PD-1," Current Opinion in Immunology 14(6):779-782, Elsevier, England (Dec. 2002).
Okazaki, T., et al., "PD-1 and LAG-3 Inhibitory Co-receptors Act Synergistically to Prevent Autoimmunity in Mice," The Journal of Experimental Medicine 208(2):395-407, Rockefeller University Press, United states (Feb. 2011).
Okazaki, T., et al., "PD-1 immunoreceptor Inhibits B Cell Receptor-mediated Signaling by Recruiting src Homology 2-domain-containing Tyrosine Phosphatase 2 to Phosphotyrosine," Proceedings of the National Academy of Sciences 98(24):13866-13871, National Academy of Sciences, United States (Nov. 2001).
Olafsen, T., et al., "ImmunoPET Imaging of B-Cell Lymphoma Using 124I-Anti-CD20 scFv Dimers (Diabodies)," Protein Engineering, Design & Selection 23(4):243-249, Oxford University Press, England (Apr. 2010).
Orchard G.E and Calonje E., "The Effect of Melanin Bleaching on Immunohistochemical Staining in Heavily Pigmented Melanocytic Neoplasms," The American Journal of Dermatopathology 20(4):357-361, Lippincott Williams & Wilkins, United States (Aug. 1998).
Pardoll, D.M., "The Blockade of Immune Checkpoints in Cancer Immunotherapy," Nature Reviews Cancer 12(4):252-264, Nature Publishing Group, England (Mar. 2012).
Prokunina, L. and Alarcon-Riquelme, M., "The Genetic Basis of Systemic Lupus Erythematosus—knowledge of Today and Thoughts for Tomorrow," Human Molecular Genetics 13(1):R143-R148, Oxford University Press, England (Apr. 2004).
Salama, A.D., et al., "Critical Role of the Programmed Death-1 (PD-1) Pathway in Regulation of Experimental Autoimmune Encephalomyelitis," The Journal of Experimental Medicine 198(1):71-78, The Rockefeller University Press, United States (Jul. 2003).
Shen W and Wu W., "Study of Melanin Bleaching After Immunohistochemistry of Melanin-containing Tissues," Applied immunohistochemistry & molecular morphology : AIMM 23(4):303-307, Lippincott Williams & Wilkins, United States (Apr. 2015).
Sierro, S., et al., "The CD4-like Molecule LAG-3, Biology and Therapeutic Applications," Expert Opinion on Therapeutic Targets 15(1):91-101, Informa Healthcare, England (Jan. 2011).
Sweis R., et al., "Molecular Drivers of the Non-T Cell-Inflamed Tumor Microenvironment in Urothelial Bladder Cancer," Cancer Immunology Research 4(7): 563-568, American Association for Cancer Research, United States (Jul. 2016).

Terme, M., et al., "IL-18 Induces PD-1-dependent Immunosuppression in Cancer," Cancer Research 71(16):5393-5399, American Association for Cancer Research, United States (Aug. 2011).
Thomas, M.L., "Of ITAMs and ITIMs: Turning on and off the B Cell Antigen Receptor," The Journal of Experimental Medicine 181(6):1953-1956, The Rockefeller University Press, United States (Jun. 1995).
Topalian, S.L., et al., "Safety, Activity and Immune Correlates of Anti-PD-1 Antibody in Cancer," The New England Journal of Medicine 366(26):2443-2454, Massachusetts Medical Society, United States (Jun. 2012).
Vivier, E. and Daeron, M., "Immunoreceptor Tyrosine-based Inhibition Motifs," Immunology Today 18(6):286-291, Elsevier, England (Jun. 1997).
Wang, C., et al., "In Vitro Characterization of the Anti-PD-1 Antibody Nivolumab, BMS-936558, and in Vivo Toxicology in Non-human Primates," Cancer Immunology Research 2(9):846-856, American Association for Cancer Research, United States (Sep. 2014).
Ward, E.S., et al., "Binding Activities of a Repertoire of Single Immunoglobulin Variable Domains Secreted from *Escherichia Coli*," Nature 341(6242):544-546, Nature Publishing Group, England (Oct. 1989).
Wherry, E.J., "T Cell Exhaustion," Nature Immunology 12(6):492-499, Nature America Inc, United States (2011).
Workman, C,J., et al., "LAG-3 Regulates Plasmacytoid Dendritic Cell Homeostasis," Journal of Immunology 182(4):1885-1891, American Association of Immunologists, United states (Feb. 2009).
Monette, A., et al., "Immune-enriched NSCLC biopsy tissue microarrays demonstrate that proliferating and checkpoint expressing TIL correlate with positive outcome," Journal for immunotherapy of Cancer 4(1): 58, BMJ Journals, United Kingdom (Nov. 2016).
Burova, E., et al., "A novel anti-human LAG-3 antibody in combination with anti-human PD-1 (REGN2810) shows enhanced anti-tumor activity in PD-1 x LAG-3 dual-dehumanized mice and favorable pharmacokinetic and safety profiles in cynomolgus monkeys," Journal for Immunotherapy of Cancer 4(1):P195, BMJ Journals, United Kingdom (2016).
Liu, S-Y., et al., "Ongoing clinical trials of PD-1 and PD-L1 inhibitors for lung cancer in China," J Hematol 10:136, BMC, United Kingdom (Jul. 2017).
Daugherty, A.L. and Mrsny, R.J., "Formulation and Delivery Issues for Monoclonal Antibody Therapeutics," Advanced Drug Delivery Reviews 58(5-6):686-706, Elsevier Science Publishers, Netherlands (2006).
Freeman, G.J., et al., "Protect the Killer: CTLs Need Defenses against the Tumor," Nature Medicine 8(8):787-789, Nature Publishing Company, United States (2002).
Brahmer, J.R., et al., "Safety and Activity of Anti-PD-L1 Antibody in Patients with Advanced Cancer," The New England Journal of Medicine 366(26):2455-2465, Massachusetts Medical Society, United States (2012).
Brahmer., J.R., et al., "Phase I Study of Single-agent Anti-programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (2010).
ClinicalTrials.gov, "Safety Study of Anti-LAG-3 in CLL, HL and NHL," Identifier NCT02061761, accessed at https://clinicaltrials.gov/archive/NCT02061761/2014_08_28, last accessed on Jan. 13, 2015, 4 pages.
ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_06_20, last accessed on Jan. 13, 2015, 4 pages.
Drake, C.G., et al., "Breathing New Life into Immunotherapy: Review of Melanoma, Lung and Kidney Cancer," Nature Reviews Clinical Oncology 11(1):24-37, Nature Pub. Group, England (2014).
Gillam, W.A., et al., "A phase I study of IMP321 and Gemcitabine as the Front-Line Therapy in Patients with Advanced Pancreatic Adenocarcinoma," Investigational New Drugs 31(3):707-713, Springer, United States (2013).

(56) References Cited

OTHER PUBLICATIONS

Haycock, G.B., et al., "Geometric Method for Measuring Body Surface Area: a Height-weight Formula Validated in Infants, Children, and Adults," The Journal of Pediatrics 93(1):62-66, Mosby, United states (1978).
Hemon, P., et al., "MHC Class II Engagement by its Ligand LAG-3 (CD223) Contributes to Melanoma Resistance to Apoptosis," Journal of Immunology 86(9):5173-5183, American Association of Immunologists, United States (2011).
Lipson, E.J., et al., "Durable Cancer Regression Off-treatment and Effective Reinduction Therapy with an Anti-PD-1 Antibody," Clinical Cancer Research 19(2):462-468, The Association, United States (2013).
Ono Pharmaceutical Co., Ltd, "A full human anti-PD-1 antibody ONO-4538/BMS-936558", Results from Phase 1 Study in Cancer Patients Published in New England Journal of Medicine (NEJM) and Presented at Annual Meeting of the American Society of Clinical Oncology (ASCO), Jun. 4, 2012, [retrieved on May 24, 2018], Retrieved from the Internet: (URL:https://www.ono.co.jp/jpnw/PDF/n12_0604.pdf), Jun. 12, 2018, with translator certification statement, 8 pages.
Rosenberg, S.A., et al., "Cancer Immunotherapy in Cancer: Principles & Practice of Oncology", 332-344, Lippincott Williams & Wilkins (2011).
Sierro et al., "The CD4-Like Molecule LAG-3, Biology and Therapeutic Applications," Expert Opinion on Therapeutic Targets, 15(1):91-101, Taylor & Francis, United States (2010).
Wolchok, J.D., et al., "Guidelines for the Evaluation of Immune Therapy Activity in Solid Tumors: Immune-related Response Criteria," Clinical Cancer Research 15(23):7412-7420, The Association, United States (2009).
Wolchok, J.D., et al., "Nivolumab Plus Ipilimumab in Advanced Melanoma," The New England Journal of Medicine 369(2):122-133, Massachusetts Medical Society, United States (2013).
ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_01_23, 5 pages.
Co-Pending U.S. Appl. No. 16/108,973, inventor Korman; Alan. J., filed Aug. 22, 2018 (Unpublished).
ClinicalTrials.gov, "Safety Study of Anti-LAG-3 With and Without Anti-PD-1 in the Treatment of Solid Tumors," Identifier NCT01968109, accessed at https://clinicaltrials.gov/archive/NCT01968109/2014_05_07, last accessed on Feb. 10, 2021, 4 pages.
Anonymous: "History of Changes for Study: NCT00730639, A Phase 1b Study of MDX-1106 in Subjects With Advanced or Recurrent Malignancies (MDX1106-03)," ClinicalTrials.gov Archive, accessed at https://clinicaltrials.gov/ct2/history/NCT00730639?V_8=View, accessed on Feb. 5, 2021, 10 pages.
Ansell, S.M., et al., "Epstein-Barr Virus Infection in Richter's Transformation," American Journal of Hematology 60(2):99-104, Wiley-Blackwell, United States (1999).
Berrien-Elliott, M.M., et al., "Durable Adoptive Immunotherapy for Leukemia Produced by Manipulation of Multiple Regulatory Pathways of CD8+ T-cell Tolerance," Cancer Research 73(2):605-616, American Association for Cancer Research, United States (2013).
Cheson, B.D., et al., "Revised Response Criteria for Malignant Lymphoma," Journal of Clinical Oncology 25(5):579-586, American Society of Clinical Oncology, United States (2007).
Dickinson, J.D., et al., "11q22.3 Deletion in B-chronic Lymphocytic Leukemia is Specifically Associated with Bulky Lymphadenopathy and ZAP-70 Expression but Not Reduced Expression of Adhesion/cell Surface Receptor Molecules," Leukemia & Lymphoma 47(2):231-244, Informa Healthcare, England (2006).
Dolcetti, R. and Carbone, A., "Epstein-barr Virus Infection and Chronic Lymphocytic Leukemia: A Possible Progression Factor," Infectious Agents and Cancer 5:22, BioMed Central, England (2010).

Fujimoto, S., et al., "Studies on the Physical Surface Area of Japanese. 18. Calculation Formulas in Three Stages Over All Ages," Nihon Eiseigaku Zasshi 23(5):443-450, Nippon Eisei Gakkai,Japan (1968).
Genbank, "Predicted: Macaca mulatta lymphocyte-activation gene 3 (LAG3), transcript variant X1, mRNA," accessed at https://www.ncbi.nlm.nih.gov/nuccore/XM_001108923/, accessed on May 21, 2018.
Green, M.R., et al., "Constitutive AP-1 Activity and EBV Infection Induce PD-L1 in Hodgkin Lymphomas and Posttransplant Lymphoproliferative Disorders: Implications for Targeted Therapy," Clinical Cancer Research 18(6):1611-1618, The Association, United States (2012).
Hallek, M., et al., "Guidelines for the Diagnosis and Treatment of Chronic Lymphocytic Leukemia: a Report From the International Workshop on Chronic Lymphocytic Leukemia Updating the National Cancer Institute-working Group 1996 Guidelines," Blood 111(12):5446-5456, American Society of Hematology, United States (2008).
Kanakry, J.A., et al., "Plasma Epstein-barr Virus Dna Predicts Outcome in Advanced Hodgkin Lymphoma: Correlative Analysis From a Large North American Cooperative Group Trial," Blood 121(18):3547-3553, American Society of Hematology, United States (2013).
Kotaskova, J., et al., "High Expression of Lymphocyte-activation Gene 3 (LAG3) in Chronic Lymphocytic Leukemia Cells Is Associated With Unmutated Immunoglobulin Variable Heavy Chain Region (IGHV) Gene and Reduced Treatment-free Survival," The Journal of Molecular Diagnostics 12(3):328-334, American Society for Investigative Pathology and the Association for Molecular, United States (2010).
Manuel, M., et al., "Lymphopenia Combined With Low TCR Diversity (Divpenia) Predicts Poor Overall Survival in Metastatic Breast Cancer Patients," Oncoimmunology 1(4):432-440, Taylor & Francis, United States (2012).
Monti, S., et al., "Molecular Profiling of Diffuse Large B-cell Lymphoma Identifies Robust Subtypes Including One Characterized by Host Inflammatory Response," Blood 105(5):1851-1861, American Society of Hematology, United States (2005).
Tsimberidou, A.M., et al., "Epstein-barr Virus in Patients With Chronic Lymphocytic Leukemia: a Pilot Study," Leukemia & Lymphoma 47(5):827-836, Informa Healthcare, England (2006).
Zhang, J., et al., "Using Gene Co-expression Network Analysis to Predict Biomarkers for Chronic Lymphocytic Leukemia," BMC Bioinformatics 11(9):S5, BioMed Central, England (Oct. 2010).
Mathijssen, R.H., et al., "Flat-Fixed Dosing Versus Body Surface Area Based Dosing of Anticancer Drugs In Adults: Does It Make a Difference ?? ," Oncologist, 12(8):913-923, AlphaMed Press, United States (2007).
Huang, R.-Y., et al., "LAG3 and PD1 Co-Inhibitory Molecules Collaborate to Limit CD8+ T Cell Signaling and Dampen Antitumor Immunity in a Murine Ovarian Cancer Model," Oncotarget, 6(29):27359-27377 (2015).
Anonymous, "Relatlimab/Nivolumab Combo Active in Melanoma After PD-1/PD-L1 Therapy," Jan. 1, 2017, accessed at https://www.onclive.com/printer?url=/web-exclusives/relatlimabnivolumab-combo-active-in-melanoma-after-pd1pd11-therapy, accessed on Oct. 12, 2019, 2 pages.
Ascierto, P.A., et al., "Efficacy of BMS-986016, a monoclonal antibody that targets lymphocyte activation gene 3 (LAG-3), in combination with nivolumab in pts with melanoma who progressed during prior anti-PD-1/PD-L1 therapy (mel prior IO) in all-comer and biomarker-enriched populations," Annals of Oncology 28(S5):LBA18, Elsevier, Netherlands (Sep. 2017).
Camisachi, C., et al., "Alternative activation of human plasmacytoid DCs in vitro and in melanoma lesions: involvement of LAG-3," Journal of Investigative Dermatology 134:1893-1902, Society of Investigative Dermatology, United States (2014).
Capelle, M.A.H., et al., "High throughput screening of protein formulation stability: practical considerations," Eur. J. Pharm. Biopharm. 65:131-148, Elsevier, Netherlands (2006).

(56) References Cited

OTHER PUBLICATIONS

Dudgeon, K., et al., "General strategy for the generation of human antibody variable domains with increased aggregation resistance," Proc. Natl. Acad. Sci. USA 109:10879-10884, National Academy of Sciences, United States (2012).

Johnson, L., et al., "Development of a LAG-3 immunohistochemistry assay for melanoma," J. Clin. Pathol. 0:1-8, BMJ Publishing Group, United Kingdom (2022).

Kang, Y.K., et al., "Nivolumab in patients with advanced gastric or gastro-oesophageal junction cancer refractory to, or intolerant of, at least two previous chemotherapy regimens (ONO-4538-12, Attraction-2): a randomised, double-blind, placebo-controlled, phase 3 trial," Lancet 390: 2461-2471, Elsevier, Netherlands (Oct. 2017).

Kayser, V., et al., "A screening tool for therapeutic monoclonal antibodies: Identifying the most stable protein and its best formulation based on thioflavin T binding," Biotechnology Journal 7:127-132, Wiley, United States (2012).

Lambert, J., "2017 ASCO Annual Meeting Preview and Education Program Highlights," Connection.ASCO.org, accessed at https://connection.asco.org/magazine/features/2017-asco-annual-meeting-preview-and-education-program-highlights, published Mar. 2, 2017, accessed on Aug. 31, 2021, 10 pages.

Lunter, P. and Champ, T., email exchange, "Publication date of J. Clin. Oncol. 35, No. 15 (supplement)," Aug. 2021, 2 pages.

Taieb, J., et al., "Evolution of checkpoint inhibitors for the treatment of metastatic gastric cancers: Current status and future perspectives," Cancer Treatment Reviews 66:104-113, Elsevier, Netherlands (May 2018).

Turnis, M.E., et al., "Inhibitory receptors as targets for cancer immunotherapy," Eur. J. Immunol. 45:1892-1905, Wiley, United States (2015).

U.S. Food Drug Administration, "Highlights of Prescribing Information, OPDIVO (nivolumab) injection, for intravenous use," Reference ID: 3710966, U.S. FDA, 27 pages (2015).

Wang, X., et al., "Potential aggregation prone regions in biotherapeutics: A survey of commercial monoclonal antibodies," MAbs 1(3):254-267, Oxford Academic Press, United Kingdom (2009).

Xu-Monette, Z.Y., et al., "PD-1 expression and clinical PD-1 blockade in B-cell lymphomas," Blood 131(1):68-83, American Society of Hematology, United States (Jan. 2018).

Zhang, Y., et al., "[Novel immunotherapeutic anti-Hugh for anti-cancer targets]," BIT's 1$^{st}$ Annual International Congress of Genetics, China (2016).

English Machine Translation of Zhang, Y., et al., "[Novel immunotherapeutic anti-Hugh for anti-cancer targets]," BIT's 1$^{st}$ Annual International Congress of Genetics, China (2016).

Demeure, C.E., et al., "T Lymphocytes infiltrating various tumour types express the MHC class II ligand lymphocyte activation gene-3 (LAG-3): role of LAG-3/MHC class II interactions in cell-cell contacts," European Journal of Cancer 37:1709-1718, Elsevier Inc., Netherlands (2001).

Non-final Office Action mailed Feb. 16, 2022, in U.S. Appl. No. 16/616,574, filed Nov. 25, 2019 (15 pages).

Final Office Action mailed Aug. 12, 2022, in U.S. Appl. No. 16/616,574, filed Nov. 25, 2019 (18 pages).

Final Office Action mailed Nov. 18, 2022, in U.S. Appl. No. 16/616,574, filed Nov. 25, 2019 (19 pages).

Patel, S.P., et al., "PD-L1 Expression as a Predictive Biomarker in Cancer Immunotherapy," Molecular Cancer Therapeutics 14(4):847-856 (2015).

Huang, R.Y., et al., "Compensatory upregulation of PD-1, LAG-3, and CTLA-4 limits the efficacy of single-agent checkpoint blockade in metastatic ovarian cancer," Oncoimmunology 6(1):e1249561, Taylor & Francis, United Kingdom (Oct. 2016).

Co-Pending U.S. Appl. No. 18/052,099, inventor Cogswell; John P et al., filed Nov. 2, 2022 (not yet published).

Co-Pending U.S. Appl. No. 18/336,889, inventor Burton; Lori S. et al., filed Jun. 16, 2023 (not yet published).

Co-Pending U.S. Appl. No. 18/227,636, inventor Gutierrez; Andres A. et al., filed Jul. 28, 2023 (not yet published).

Co-Pending U.S. Appl. No. 18/033,200, inventor Toms; Laurence David et al., filed Apr. 21, 2023 (not yet published).

Notice of Opposition and Grounds of Opposition dated Jun. 13, 2024, Roth, C., in European Patent No. 3631454, European Patent Office, Germany, 47 pages.

Notice of Opposition and Grounds of Opposition dated Jun. 13, 2024, Regeneron Pharmaceuticals, Inc., in European Patent No. 3631454, European Patent Office, Germany, 28 pages.

Deng, W.-W., et al., "LAG-3 confers poor prognosis and its blockade reshapes antitumor response and neck squamous carcinoma," Oncoimmunology 5(11):e1239005, Taylor & Francis, United Kingdom (Oct. 2016).

Tawbi, H.A., et al., "Relatlimab and Nivolumab versus Nivolumab in Untreated Advanced Melanoma," The New England Journal of Medicine 386(1):24-34, Massachusetts Medical Society, United States (Jan. 2022).

Hamid, O., et al., "Significant durable response with fianlimab (anti-LAG-3) and cemiplimab (anti-PD-1) in advanced melanoma: post adjuvant PD-1 analysis," Presentation At: 2023 ASCO Annual Meeting, Chicago, Illinois, United States (Jun. 2023).

U.S. Appl. No. 62/457,287, filed Feb. 10, 2017, 297 pages.

Tassi, E., et al., "Early Effector T Lymphocytes Coexpress Multiple Inhibitory Receptors in Primary Non-Small Cell Lung Cancer," Cancer Research 77(4):8510-861, American Association for Cancer Research, United States (Feb. 2017).

Ascierto, P.A., et al., "Nivolumab and Relatlimab in Patients With Advanced Melanoma That Had Progressed on Anti-Programmed Death-1/Programmed Death Ligand 1 Therapy: Results From the Phase I/IIa Relativity-020 Trial," Journal of Clinical Oncology 41(15):2724-2735, American Society of Clinical Oncology, United States (Feb. 2023).

Andrews, L.P., et al., "LAG3 (CD223) as a Cancer Immunotherapy Target," Immunological Reviews 276(1):80-96, Blackwell, United Kingdom (Mar. 2017).

Nguyen, L.T., et al., "Clinical blockade of PD 1 and LAG3—potential mechanisms of action," Nature Reviews Immunology 15(1):45-56, Nature Publishing Group, England (Jan. 2015).

Anonymous: "History of Changes for Study: NCT02061761, Safety Study of Anti-LAG-3 in Relapsed or Refractory Hematologic Malignancies," ClinicalTrials.gov Archive, accessed at https://classic.clinicaltrials.gov/ct2/history/NCT02061761?V_48=View . . . , access date Jun. 10, 2024, 13 pages.

Chen, J., et al., "The effect of immune microenvironment on the progression and prognosis of colorectal cancer," Medical Oncology 31(8):82, Springer Science+Business Media, New York, United States (Jul. 2014).

He, Y., et al., "LAG-3 Protein Expression in Non-Small Cell Lung Cancer and Its Relationship with PD-1 /PD-L1 and Tumor-Infiltrating Lymphocytes," Journal of Thoracic Oncology 12(5):814-823, Elsevier, United States (Jan. 2017).

Opdualag: EPR—Product Information, European Medicines Agency, 40 pages, first published Sep. 20, 2022.

Robert, C., et al., "Drug of the year: Programmed Death-1 receptor/Programmed Death-1 ILigand-1 receptor monoclonal antibodies," European Journal of Cancer, 49:2968-2971, Pergamon Press, United Kingdom (Jul. 2013).

Anonymous: "History of Changes for Study: NCT02750514, An Investigational Immuno-therapy Study to Test Combination Treatments in Patients With Advanced Non-Small Cell Lung Cancer (Fraction-Lung)," ClinicalTrials.gov Archive, accessed at https://classic.clinicaltrials.gov/ct2/history/NCT02750514?V_30=View . . . , access date Jun. 12, 2024, 16 pages.

Anonymous: "History of Changes for Study: NCT02460224, Safety and Efficacy of LAG525 Single Agent and in Combination With PDR001 in Patients With Advanced Malignancies," ClinicalTrials.gov Archive, accessed at https://classic.clinicaltrials.gov/ct2/history/NCT02460224?V_11=View . . . , access date Jun. 10, 2024, 13 pages.

He, Y., et al., "Lymphocyte-activation gene-3, an important immune checkpoint in cancer," Cancer Science 107(9):1193-1197, John Wiley & Sons Australia, Ltd., Australia (Sep. 2016).

Office Action dated Sep. 8, 2021, in European Application No. 18735009.5, Bristol-Myers Squibb Company, filed May 30, 2018.

(56) References Cited

OTHER PUBLICATIONS

Anonymous: "History of Changes for Study: NCT01968109, Safety Study of Anti-LAG-3 With and Without Anti-PD-1 in the Treatment of Solid Tumors," ClinicalTrials.gov Archive, accessed at https://classic.clinicaltrials.gov/ct2/history/NCT01968109?V_51=View . . . , access date Jun. 5, 2024, 16 pages.

Woo, S.-R., et al., "Differential subcellular localization of the regulatory T-cell protein LAG-3 and the coreceptor CD4," European Journal of Immunology 40(6):1768-1777, Wiley-VCH, Germany (Jun. 2010).

Ulase, D., et al., "LAG3 in gastric cancer:it's complicated," Journal of Cancer Research and Clinical Oncology 149:10797-10811, Springer-Verlag, Germany (Jun. 2023).

Saleh, R.R., et al., "Prognostic Value of Lymphocyte-Activation Gene 3 (LAG3) in Cancer: A Meta-Analysis," Frontiers in Oncology 9:Article 1040, Frontiers Research Foundation, Switzerland (Oct. 2019).

McDermott, D.F., et al., "PD-1 as a potential target in cancer therapy," Cancer Medicine 2(5):662-673, John Wiley & Sons Ltd., United States (Oct. 2013).

Luke, J.J., et al., "The PD-I-and LAG-3-targeting bispecific molecule tebotelimab in solid tumors and hematologic cancers: a phase 1 trial," Nature Medicine 29:2814-2824, Nature Publishing Company, United States (Oct. 2023).

Budczies, J., et al., "Cutoff Finder: A Comprehensive and Straightforward Web Application Enabling Rapid Biomarker Cutoff Optimization," PLOS One 7(12):e51862, 7 pages, Public Library of Sciences, United States (Dec. 2012).

Figure 4

Table 1. Baseline Demographics and Disease Characteristics

| | Mel Prior IO (n = 55) |
|---|---|
| Median age (range), years | 59 (25-80) |
| ≤ 65 years, n (%) | 36 (65) |
| Male, n (%) | 39 (71) |
| Race, n (%) | |
| White | 52 (95) |
| Black | 1 (1.8) |
| Asian | 1 (1.8) |
| Other | 1 (1.8) |
| ECOG PS, n (%) | |
| 0 | 38 (69) |
| 1 | 17 (31) |
| M stage at study entry, n (%) | |
| M0 | 7 (13) |
| M1A | 6 (11) |
| M1B | 4 (7.3) |
| M1C with brain metastasis | 1 (1.8) |
| M1C without brain metastasis | 37 (67) |
| LDH, n (%) | |
| Normal | 25 (45) |
| Normal to < 2 × ULN | 13 (24) |
| ≥ 2 × ULN | 8 (15) |
| Unknown | 9 (16) |
| Liver metastases, n (%) | |
| Yes | 11 (20) |
| No | 44 (80) |
| BRAF status, n (%) | |
| Mutation | 21 (38) |
| No mutation | 31 (56) |
| Unknown | 3 (5.5) |

M, metastasis.

Figure 5

Table 2. Prior Therapy

| Patients, n (%) | Mel Prior IO (n = 55) |
|---|---|
| Prior radiotherapy | 16 (29) |
| Prior systemic therapy | 54 (98) |
| Immunotherapy | 54 (98) |
| Anti-CTLA-4* | 32 (58) |
| Anti-PD-1/PD-L1* | 52 (95) |
| Best response to prior anti-PD-1/PD-L1* | |
| CR | 1 (1.8) |
| PR | 12 (22) |
| SD | 16 (29) |
| PD | 22 (40) |
| BRAF inhibitors | 16 (29) |
| MEK inhibitors | 11 (20) |
| Number of systemic regimens | |
| 1 | 12 (22) |
| 2 | 17 (31) |
| ≥3 | 25 (45) |
| Median (range) | 2 (1-6) |

CR, complete response; PR, partial response; SD, stable disease. *Two patients received anti-PD-1/PD-L1 + anti-CTLA-4. 5 patients received anti-PD-1/PD-L1 after anti-CTLA-4, and 29 patients received anti-CTLA-4 before anti-PD-1/PD-L1; prior anti-CTLA-4 therapy was not reported in 4 patients. *Seventy-five patients received nivolumab, 29 patients received pembrolizumab, and 2 patients received other therapies; 2 patients did not receive prior anti-PD-1/PD-L1; prior anti-PD-1/PD-L1 was unknown in 1 patient. Response in 1 patient was reported as not applicable.

Figure 7

Table 3. Preliminary Evidence of Antitumor Activity

| Patients, n (%) | Mel Prior IO (n = 48ª) |
|---|---|
| BOR | |
| CR | 0 |
| PR[b] | 6 (13) |
| SD | 20 (42) |
| PD | 16 (33) |
| Clinical progression[c] | 6 (13) |
| ORR, 95% CI[b] | |
| LAG-3 ≥ 1% (n = 25) | 6 (13), 4, 7, 25 |
| LAG-3 < 1% (n = 14) | 5 (20), 6, 8, 41 |
| | 1 (7.1), 0.2, 34 |
| DCR (CR + PR + SD)[b] | 26 (54) |
| LAG-3 ≥ 1% (n = 25) | 16 (64) |
| LAG-3 < 1% (n = 14) | 5 (36) |

BOR, best overall response; DCR, disease control rate. ªAll response-evaluable patients; all progressed on prior anti–PD-1/PD-L1 therapy. [b]Four responses were unconfirmed. [c]Occurred prior to first radiographic scan.

Figure 11

Table 4. Response by Baseline Characteristics (investigator assessed)

| | | Mel Prior IO (n = 48*) | |
|---|---|---|---|
| | | ORR | |
| | n | n (%) | 95% CI |
| LAG-3 expression | | | |
| ≥ 1% | 25 | 5 (20) | 6.8, 41 |
| < 1% | 14 | 1 (7.1) | 0.2, 34 |
| PD-L1 expression | | | |
| ≥ 1% | 16 | 2 (13) | 1.6, 38 |
| < 1% | 19 | 4 (21) | 6.1, 46 |
| Response based upon prior BOR to anti–PD-1/PD-L1 only | | | |
| CR | 1 | 0 | — |
| PR | 12 | 2 (17) | — |
| SD | 14 | 1 (7.1) | — |
| CR + PR + SD | 27 | 3 (11) | 2.4, 29 |
| PD | 20 | 2 (10) | 1.2, 32 |
| M stage at study entry | | | |
| M1A | 6 | 1 (17) | 0.4, 64 |
| M1B | 3 | 0 | 0, 71 |
| M1C with brain metastasis | 1 | 0 | 0, 97.5 |
| M1C without brain metastasis | 32 | 4 (13) | 3.5, 29 |
| Liver metastases | | | |
| Yes | 11 | 1 (9.1) | 0.2, 41 |
| No | 37 | 5 (14) | 4.5, 29 |
| BRAF status | | | |
| Mutation | 19 | 0 | 0, 18 |
| No mutation | 28 | 6 (21) | 8.3, 41 |

*48 response-evaluable patients; all progressed on prior anti–PD-1/PD-L1 therapy.

Figure 15A
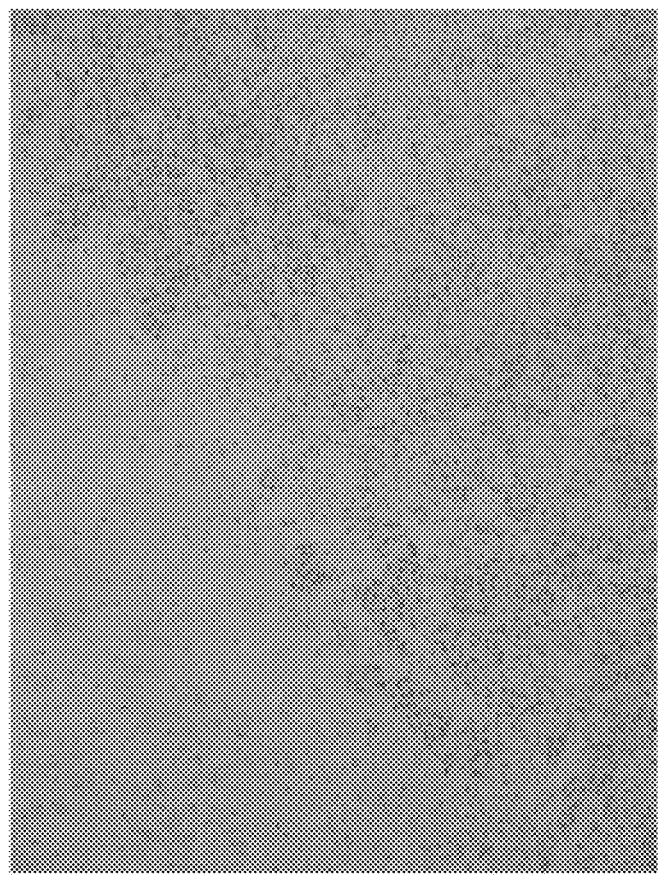
Pigmented melanoma following bleaching (nuclei counterstained with hematoxylin)
Pigmented melanoma without bleaching (nuclei counterstained with hematoxylin)

Figure 15B
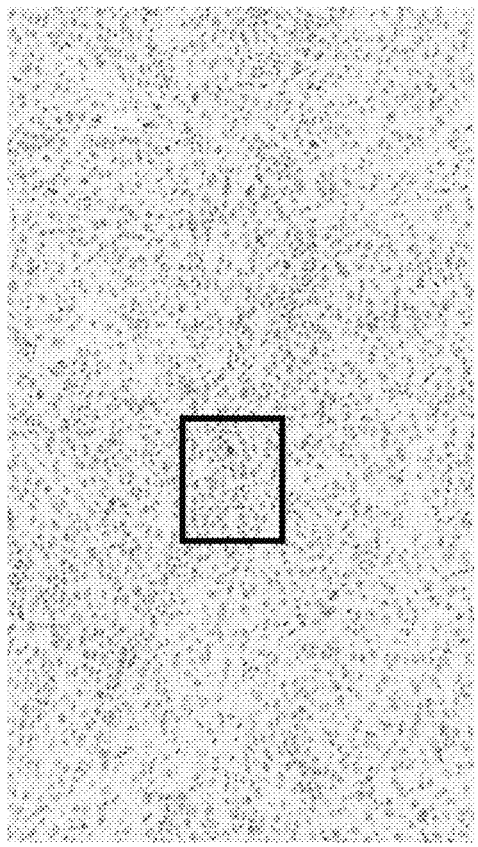
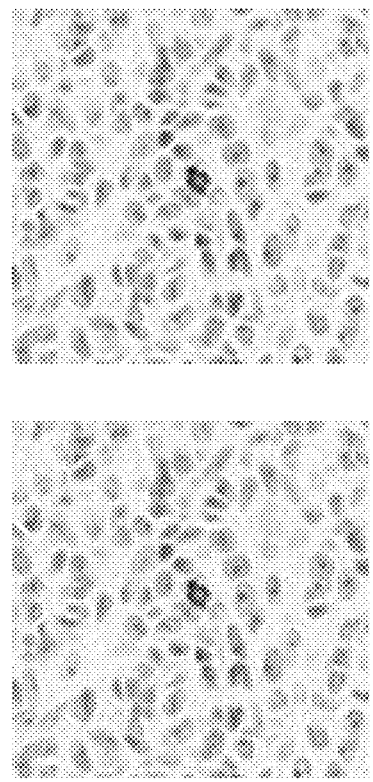
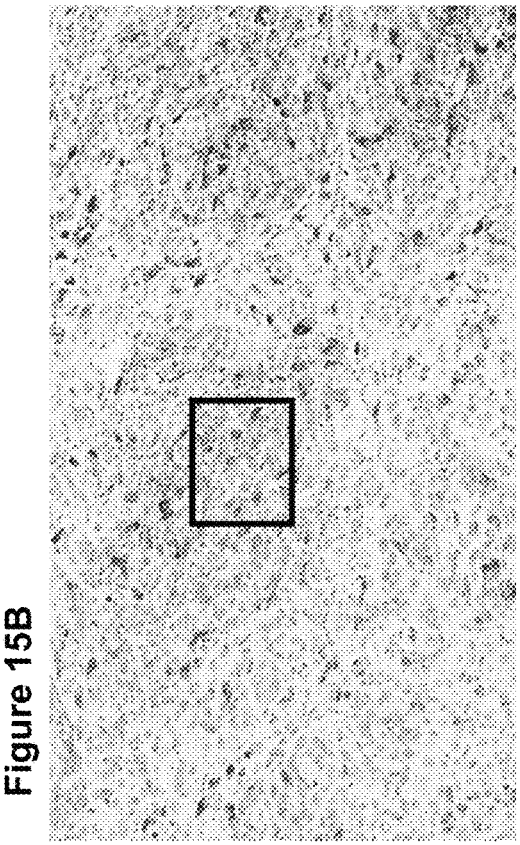
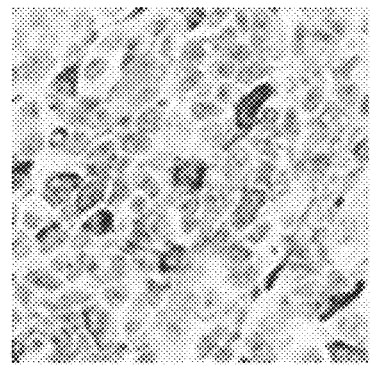
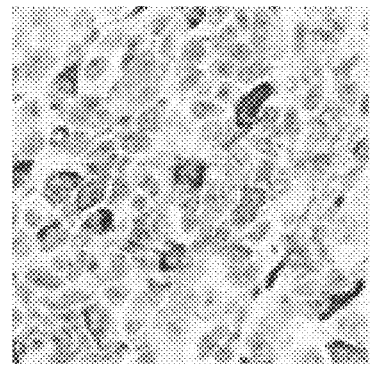
Pigmented melanoma - LAG-3 by IHC without bleaching (nuclei counterstained with hematoxylin)
LAG-3 IHC following bleaching
LAG-3 IHC indistinguishable from melanin Figure 17    Baseline Demographics and Disease Characteristics

| | Mel Prior PD-(L)1 n = 68 | | Mel Prior PD-(L)1 n = 68 |
|---|---|---|---|
| Median age (range), years | 60 (25–81) | LDH, n (%) | |
| < 65 years, n (%) | 44 (65) | Normal | 35 (51) |
| Male, n (%) | 46 (68) | Normal to < 2 × ULN | 15 (22) |
| Race, n (%) | | ≥ 2 × ULN | 9 (13) |
| White | 65 (96) | Unknown | 9 (13) |
| Other | 3 (4.4) | Liver metastases, n (%) | |
| ECOG PS, n (%) | | No | 51 (75) |
| 0 | 44 (65) | Yes | 17 (25) |
| 1 | 24 (35) | BRAF status, n (%) | |
| M stage at study entry, n (%) | | No mutation | 43 (63) |
| M0 | 6 (8.8) | Mutation | 23 (34) |
| M1A | 7 (10) | Unknown | 2 (2.9) |
| M1B | 8 (12) | | |
| M1C with brain metastasis | 1 (1.5) | | |
| M1C without brain metastasis | 46 (68) | | |

ECOG PS, Eastern Cooperative Oncology Group performance status; LDH, lactate dehydrogenase; M, metastasis; Mel Prior PD-(L)1, patients with melanoma who progressed during prior anti–PD-1/PD-L1 therapy; ULN, upper limit of normal.

Figure 18

Prior Therapies

| | N=68 n (%) |
|---|---|
| Prior radiotherapy, n (%) | 19 (28) |
| Prior systemic therapy, n (%) | 68 (100) |
| Immunotherapy | 68 (100) |
| Anti–CTLA-4[a] | 39 (57) |
| Anti–PD-1/PD-L1[b] | 68 (100) |
| Best response to prior anti–PD-1/PD-L1[c] | |
| CR | 1 (1.5) |
| PR | 12 (18) |
| SD | 20 (29) |
| PD | 31 (46) |
| BRAF inhibitors | 19 (28) |
| MEK inhibitors | 13 (19) |
| Number of systemic regimens | |
| 1 | 16 (24) |
| 2 | 21 (31) |
| ≥3 | 31 (46) |
| Median (range) | 2 (1–5) |

CR, complete response; CTLA-4, cytotoxic T lymphocyte antigen-4; PD, progressive disease; PR, partial response; SD, stable disease.
[a]Four patients received anti–PD-1/PD-L1 + anti–CTLA-4, 8 patients received anti–CTLA-4 after anti–PD-1/PD-L1, and 33 patients received anti–CTLA-4 before anti–PD-1/PD-L1; prior anti–CTLA-4 therapy was not reported in 2 patients. [b]Thirty-three patients received nivolumab, 33 patients received pembrolizumab, and 2 patients received other therapies. [c]Response in 1 patient was reported as not applicable.

Figure 19

Antitumor Activity of BMS-986016 + Nivolumab

| | Mel Prior PD-(L)1ª | |
|---|---|---|
| | All n = 61 | LAG-3 ≥1%ᵇ n = 33 |
| ORR,ᶜ n (%) | 7 (11.5)ᵈ | 6 (18)ᵈ |
| 95% CI | 4.7, 22 | 7, 36 |
| BOR,ᶜ n (%) | | |
| CR | 1 (1.6) | 1 (3.0) |
| PR | 6 (9.8)ᵈ | 5 (15)ᵈ |
| SD | 23 (38) | 15 (45) |
| PD | 25 (41) | 8 (24) |
| Clinical progressionᵉ | 6 (9.8) | 4 (12) |
| DCR (CR + PR + SD),ᶜ n (%) | 30 (49) | 21 (64) |
| 95% CI | 36, 62 | 45, 80 |

BOR, best overall response.
ªResponse-evaluable patients; all progressed during prior anti–PD-1/PD-L1 therapy. ᵇImmune-cell LAG-3 expression (percent of positive cells within invasive margin, tumor, and stroma) evaluated by IHC in tumor sections with antibody clone 17B4. ᶜTumor response evaluated by investigator per Response Evaluation Criteria in Solid Tumors v1.1. ᵈOne response was unconfirmed. ᵉOccurred prior to first radiographic scan.

Figure 20   Response by Baseline Characteristics and LAG-3 Expression

| | Melanoma PD-L1 LAG-3 Expression (N=53) | | | |
|---|---|---|---|---|
| | LAG-3 ≥ 1% | | LAG-3 < 1% | |
| | N | ORR n (%) | N | ORR n (%) |
| PD-L1 expression[b] (N = 44) | | | | |
| ≥ 1% | 16 | 1 (6.3) | 4 | 0 |
| < 1% | 11 | 3 (27) | 13 | 1 (7.7) |
| BRAF status (N = 52) | | | | |
| No mutation | 21 | 5 (24) | 11 | 1 (9.1) |
| Mutation | 11 | 1 (9.1) | 9 | 0 |
| Prior anti–CTLA-4 (N = 53) | | | | |
| No | 12 | 1 (8.3) | 7 | 1 (14) |
| Yes | 21 | 5 (24) | 13 | 0 |

[a]Response-evaluable patients; all progressed during prior anti–PD-1/PD-L1 therapy. [b]Tumor-cell PD-L1 expression (percent of positive cells within invasive margin, tumor, and stroma) evaluated by IHC in tumor sections with the Dako PD-L1 IHC 28-8 kit.

Role of LAG-3 and PD-1 in T-cell exhaustion and proposed clinical utility of BMS-986016 combined with nivolumab CD = cluster of differentiation; LAG-3 = lymphocyte-activation gene 3; MHC II = major histocompatibility complex class II; PD-1 = programmed death-1; PD-L1 = programmed death-1 ligand 1.

LAG-3 patterns of expression by IHC staining of total nucleated cells in a melanoma tumor specimen IHC = immunohistochemistry; LAG-3 = lymphocyte-activation gene 3.

Figures 26A-F. Association of LAG-3 with immune and inflammatory biomarkers

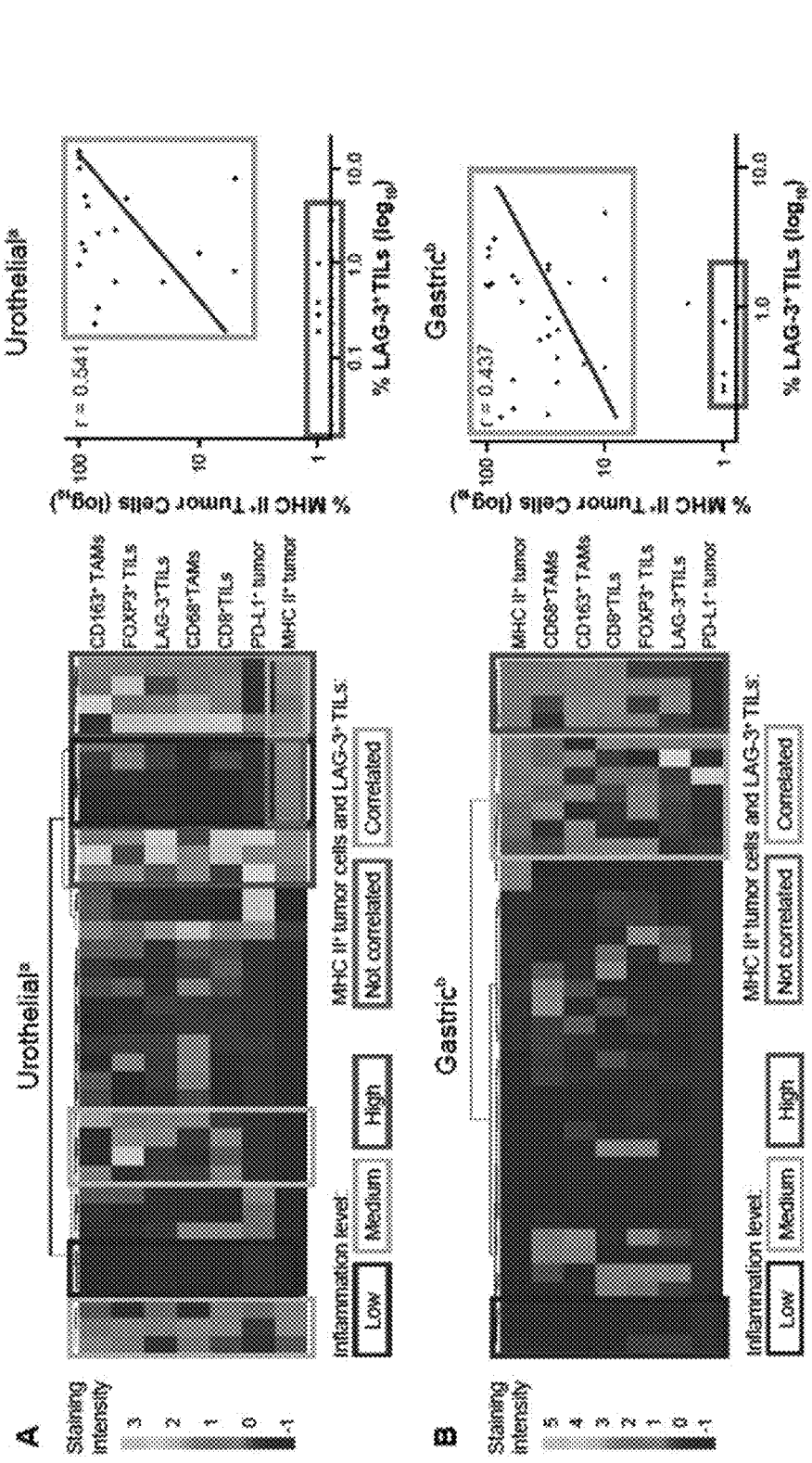
Figures 28A-B. Relationship between inflammation clusters and biomarker expression Figures 29A-C. Heterogeneous MHC II tumor cell expression and LAG-3+ TILs
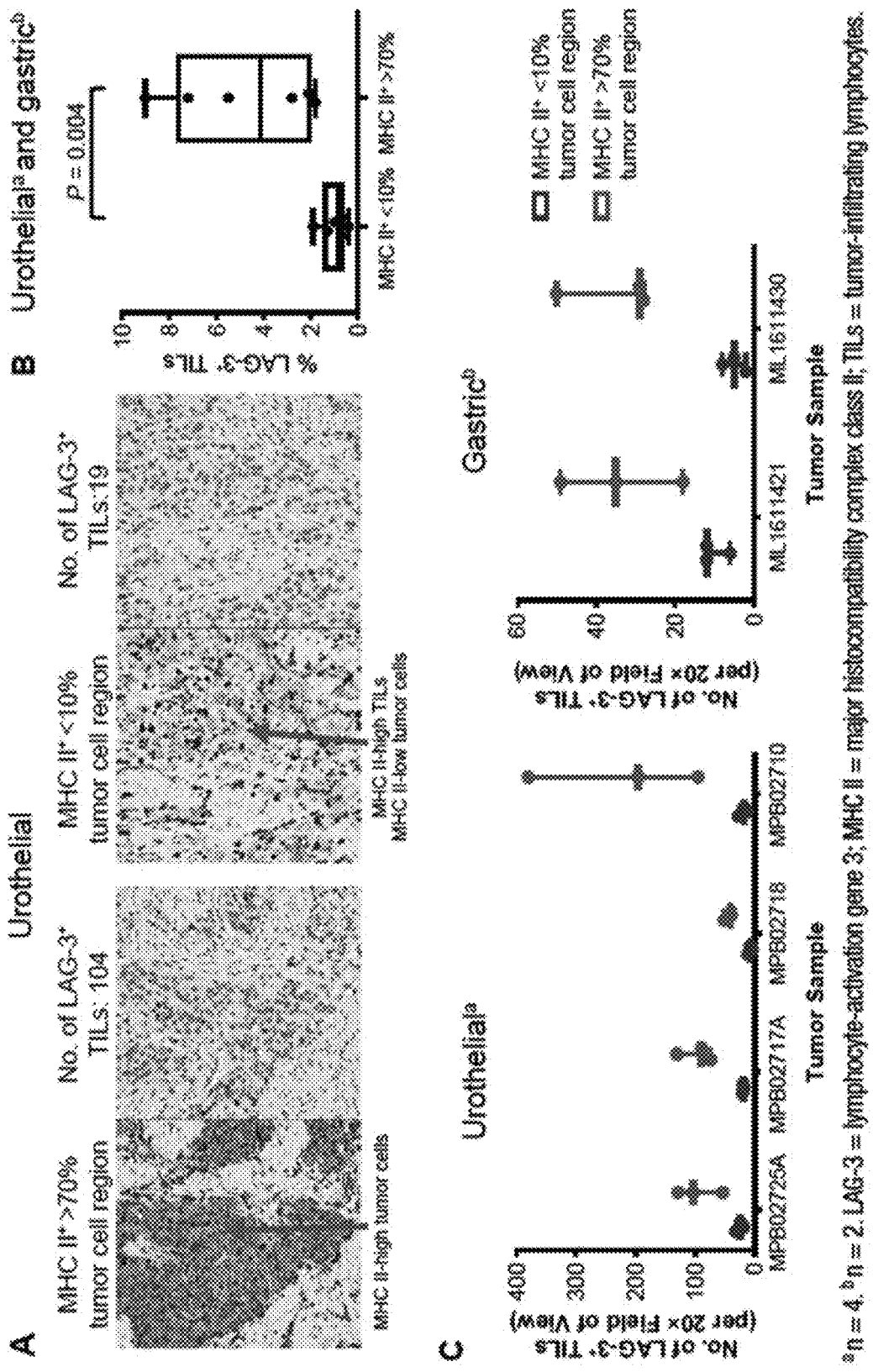

Figures 30B.

LAG-3 mRNA levels at screening and at week 2–4 of nivolumab monotherapy

| Changes in LAG-3 mRNA levels | RCC | Melanoma |
|---|---|---|
| n: pretreatment, posttreatment | 59, 55 | 61, 62 |
| P value | 0.0479 | 0.00002 |
| Mean fold increase from pretreatment baseline | 1.2 | 3.1 |

Dashed lines represent samples from the same patient. CPM = counts per million; LAG-3 = lymphocyte-activation gene 3; RCC = renal cell carcinoma.

TREATMENT OF LAG-3 POSITIVE TUMORS

CROSS-REFERENCE TO RELATED APPLICATIONS

This application is a continuation of U.S. application Ser. No. 16/616,574, 371(c) date of Nov. 25, 2019, now U.S. Pat. No. 11,807,686, issued Nov. 7, 2023, which is the National Stage of International Application No. PCT/US2018/035134, filed May 30, 2018, which claims the priority benefit of U.S. Provisional Application Nos. 62/512,648, filed May 30, 2017; 62/513,813, filed Jun. 1, 2017; 62/555,176, filed Sep. 7, 2017; and 62/582,178, filed Nov. 6, 2017, which are incorporated herein by reference in their entireties.

REFERENCE TO SEQUENCE LISTING SUBMITTED ELECTRONICALLY

The content of the electronically submitted sequence listing (Name: 3338_0700005_SequenceListing_ST26; Size: 49,787 bytes; and Date of Creation: Aug. 17, 2023) filed with the application is herein incorporated by reference in its entirety.

FIELD OF THE INVENTION

The invention disclosed herein relates to methods of treating a LAG-3 positive malignant tumor in a human patient with a PD-1 pathway inhibitor, a combination of a PD1 pathway inhibitor and an immune checkpoint inhibitor, a combination of a LAG-3 inhibitor and a PD-1 pathway inhibitor, or an anti-CTLA-4 antibody.

BACKGROUND OF THE INVENTION

Lymphocyte activation gene-3 (LAG-3; CD223) is a type I transmembrane protein that is expressed on the cell surface of activated CD4+ and CD8+ T cells and subsets of NK and dendritic cells (Triebel F, et al., J. Exp. Med. 1990; 171: 1393-1405; Workman C J, et al., J. Immunol. 2009; 182(4): 1885-91). LAG-3 is closely related to CD4, which is a co-receptor for T helper cell activation. Both molecules have 4 extracellular Ig-like domains and require binding to their ligand, major histocompatibility complex (MHC) class II, for their functional activity. In contrast to CD4, LAG-3 is only expressed on the cell surface of activated T cells and its cleavage from the cell surface terminates LAG-3 signaling. LAG-3 can also be found as a soluble protein but it does not bind to MHC class II and the function of soluble LAG-3 is unknown.

It has been reported that LAG-3 plays an important role in promoting regulatory T cell (Treg) activity and in negatively regulating T cell activation and proliferation (Workman C J, et al., J. Immunol. 2005; 174:688-695). Both natural and induced Treg express increased LAG-3, which is required for their maximal suppressive function (Camisaschi C, et al., J. Immunol. 2010; 184:6545-6551 and Huang C T, et al., Immunity. 2004; 21:503-513). Furthermore, ectopic expression of LAG-3 on CD4+ effector T cells reduced their proliferative capacity and conferred on them regulatory potential against third party T cells (Huang C T, et al., Immunity. 2004; 21:503-513). Recent studies have also shown that high LAG-3 expression on exhausted lymphocytic choriomeningitis virus (LCMV)-specific CD8+ T cells contributes to their unresponsive state and limits CD8+ T cell antitumor responses (Blackburn S D, et al., Nat. Immunol. 2009; 10:29-37 and Grosso J F, et al., J. Clin. Invest. 2007; 117:3383-3392). In fact, LAG-3 maintained tolerance to self and tumor antigens via direct effects on CD8+ T cells in 2 murine models (Grosso J F, et al., J. Clin. Invest. 2007; 117:3383-3392).

Immune tolerance observed in the setting of tumor development and tumor recurrence, however, seems to be mediated by the co-expression of various T cell negative regulatory receptors, not solely from LAG-3. Data from chronic viral infection models (Blackburn S D, et al., Nat. Immunol. 2009; 10:29-37, Grosso J F, et al., J. Clin. Invest. 2007; 117:3383-3392, and Lyford-Pike S, et al., Cancer Res. 2013; 73(6):1733-41), knock-out mice (Woo S R, et al., Cancer Res. 2012; 72:917-927; Okazaki T, et al., J. Exp Med. 2011; 208:395-407, and Bettini M. et al., J. Immunol. 2011; 187:3493-3498), tumor recurrence models (Goding S R, et al., J. Immunol. 2013; 190(9):4899-4909) and, to a more limited extent, human cancer patients (Goding S R, et al., J. Immunol. 2013; 190(9):4899-4909, Matsuzaki J, et al., Proc. Natl. Acad. Sci., USA. 2010; 107:7875-7880, and Gandhi M K, et al., Blood. 2006; 108:2280-2289) support a model wherein T cells that are continuously exposed to antigen become progressively inactivated through a process termed "exhaustion." Exhausted T cells are characterized by the expression of T cell negative regulatory receptors, predominantly Cytotoxic T-Lymphocyte Antigen-4 (CTLA-4), Programmed Cell Death 1 (PD-1), and LAG-3, whose action is to limit the cell's ability to proliferate, produce cytokines, and kill target cells and/or to increase Treg activity. However, the timing and sequence of expression of these molecules in the development and recurrence of tumors have not been fully characterized.

PD-1 is a cell surface signaling receptor that plays a critical role in the regulation of T cell activation and tolerance (Keir M E, et al., Annu Rev Immunol 2008; 26:677-704). It is a type I transmembrane protein and together with BTLA, CTLA-4, ICOS and CD28, comprise the CD28 family of T cell co-stimulatory receptors. PD-1 is primarily expressed on activated T cells, B cells, and myeloid cells (Dong H, et al., Nat Med. 1999; 5:1365-1369). It is also expressed on natural killer (NK) cells (Terme M, et al., Cancer Res 2011; 71:5393-5399). Binding of PD-1 by its ligands, PD-L1 and PD-L2, results in phosphorylation of the tyrosine residue in the proximal intracellular immune receptor tyrosine inhibitory domain, followed by recruitment of the phosphatase SHP-2, eventually resulting in down-regulation of T cell activation. One important role of PD-1 is to limit the activity of T cells in peripheral tissues at the time of an inflammatory response to infection, thus limiting the development of autoimmunity (Pardoll D M., Nat Rev Cancer 2012; 12:252-264). Evidence of this negative regulatory role comes from the finding that PD-1-deficient mice develop lupus-like autoimmune diseases including arthritis and nephritis, along with cardiomyopathy (Nishimura H, et al., Immunity, 1999; 11:141-151; and Nishimura H, et al., Science, 2001; 291:319-322). In the tumor setting, the consequence is the development of immune resistance within the tumor microenvironment. PD-1 is highly expressed on tumor-infiltrating lymphocytes, and its ligands are up-regulated on the cell surface of many different tumors (Dong H, et al., Nat Med 2002; 8:793-800). Multiple murine cancer models have demonstrated that binding of ligand to PD-1 results in immune evasion. In addition, blockade of this interaction results in anti-tumor activity (Topalian S L, et al. NEJM 2012; 366(26):2443-2454; Hamid 0, et al., NEJM 2013; 369:134-144). Moreover, it has been shown that inhibition of the PD-1/PD-L1 interaction mediates potent antitumor activity in preclinical models (U.S. Pat. Nos. 8,008,449 and 7,943,743).

Recently, several immune checkpoint pathway inhibitors have begun to provide new immunotherapeutic approaches for treating cancer, including the development of an antibody (Ab), ipilimumab (YERVOY®), that binds to and inhibits Cytotoxic T-Lymphocyte Antigen-4 (CTLA-4) for the treatment of patients with advanced melanoma, the development of antibodies such as nivolumab and pembrolizumab (formerly lambrolizumab; USAN Council Statement, (2013) Pembrolizumab: Statement on a nonproprietary name adopted by the USAN Council (ZZ-165), Nov. 27, 2013) that bind specifically to the Programmed Death-1 (PD-1) receptor and block the inhibitory PD-1/PD-1 ligand pathway, and the development of an antibody, BMS-986016 (as described in U.S. Pat. No. 9,505,839) that specifically binds LAG-3 and is capable of stimulating immune responses.

The promise of the emerging field of personalized medicine is that advances in pharmacogenomics will increasingly be used to tailor therapeutics to defined subpopulations, and ultimately, individual patients in order to enhance efficacy and minimize adverse effects. Recent successes include, for example, the development of imatinib mesylate (GLEEVEC®), a protein tyrosine kinase inhibitor that inhibits the bcr-abl tyrosine kinase, to treat Philadelphia chromosome-positive chronic myelogenous leukemia (CVL); crizotinib (XALKORI®) to treat the 5% of patients with late-stage non-small cell lung cancers who express a mutant anaplastic lymphoma kinase (ALK) gene; and vemurafenib (ZELBORAF®), an inhibitor of mutated BRAF protein (V600E-BRAF) which is expressed in around half of melanoma tumors. However, unlike the clinical development of small molecule agents that target discrete activating mutations found in select cancer populations, a particular challenge in cancer immunotherapy has been the identification of predictive biomarkers to enable patient selection and guide on-treatment management. Accordingly, it is an object of the present invention to provide improved methods for treating tumors.

SUMMARY OF THE INVENTION

One aspect of the invention disclosed herein relates to a method of selecting a malignant tumor in a human patient for treating with a PD-1 pathway inhibitor, a LAG-3 inhibitor, a combination of a PD1 pathway inhibitor and an immune checkpoint inhibitor, or a combination of a LAG-3 inhibitor and a PD-1 pathway inhibitor. In some embodiments, the method comprises detecting LAG-3 expression in the tumor. In some embodiments, the method comprises detecting LAG-3 expression and PD-L1 expression in the tumor. Also disclosed herein are methods of treating LAG-3 positive tumors in a human patient comprising administering a LAG-3 inhibitor and a PD-1 pathway inhibitor.

One aspect of the invention disclosed herein relates to a method of selecting a malignant tumor in a human patient for immunotherapy, comprising: determining the level of LAG-3 expression in a tumor sample; and selecting the tumor for immunotherapy if the tumor is a LAG-3 positive tumor. Another aspect of the invention disclosed herein relates to a method of identifying a malignant tumor in a human patient as eligible for immunotherapy, comprising: determining the level of LAG-3 expression in a tumor sample; and identifying the tumor as eligible for immunotherapy if the tumor is a LAG-3 positive tumor. Another aspect of the invention disclosed herein relates to a method of identifying a malignant tumor in a human patient that is likely to be responsive to an immunotherapy, the method comprising: determining the level of LAG-3 expression in a tumor sample; and identifying the tumor as likely to be responsive to treatment if the tumor is a LAG-3 positive tumor. Another aspect of the invention disclosed herein relates to a method of classifying a malignant tumor in a human patient as likely to be responsive to an immunotherapy, the method comprising: determining the level of LAG-3 expression in a tumor sample; and classifying the tumor as likely to be responsive to immunotherapy if the tumor is a LAG-3 positive tumor. In some embodiments, a method disclosed herein further comprises determining the level of PD-L1 expression in the tumor sample. In some embodiments, the immunotherapy comprises contacting the tumor with a therapeutically effective amount of a LAG-3 inhibitor and a PD-1 pathway inhibitor. In some embodiments, the immunotherapy comprises contacting the tumor with a therapeutically effective amount of a LAG-3 inhibitor. In some embodiments, the immunotherapy comprises contacting the tumor with a therapeutically effective amount of a PD-1 pathway inhibitor. In some embodiments, the immunotherapy comprises contacting the tumor with a therapeutically effective amount of a PD-1 pathway inhibitor and an immune checkpoint inhibitor. In some embodiments, a method disclosed herein comprises contacting the tumor with a therapeutically effective amount of a LAG-3 inhibitor and a PD-1 pathway inhibitor. In some embodiments, a method disclosed herein comprises contacting the tumor with a therapeutically effective amount of a LAG-3 inhibitor. In some embodiments, a method disclosed herein comprises contacting the tumor with a therapeutically effective amount of a PD-1 pathway inhibitor. In some embodiments, a method disclosed herein comprises contacting the tumor with a therapeutically effective amount of a PD-1 pathway inhibitor and an immune checkpoint inhibitor. In some embodiments, a method disclosed herein comprises administering to the patient a therapeutically effective amount of a LAG-3 inhibitor and a PD-1 pathway inhibitor. In some embodiments, a method disclosed herein comprises administering to the patient a therapeutically effective amount of a LAG-3 inhibitor. In some embodiments, a method disclosed herein comprises administering to the patient a therapeutically effective amount of a PD-1 pathway inhibitor. In some embodiments, a method disclosed herein comprises administering to the patient a therapeutically effective amount of a PD-1 pathway inhibitor and an immune checkpoint inhibitor.

Another aspect of the invention disclosed herein relates to a method of identifying a patient with a malignant tumor who is likely to respond to an immunotherapy, the method comprising: determining the level of LAG-3 expression in a tumor sample; and identifying the patient who is likely to respond to treatment if the tumor is a LAG-3 positive tumor. Another aspect of the invention disclosed herein relates to a method of selecting a patient with a malignant tumor for immunotherapy, the method comprising: determining the level of LAG-3 expression in a tumor sample; and selecting the patient for immunotherapy if the tumor is a LAG-3 positive tumor. In some embodiments, a method disclosed herein further comprises determining the level of PD-L1 expression in the tumor sample. In some embodiments, a method disclosed herein comprises administering to the patient a therapeutically effective amount of a LAG-3 inhibitor and a PD-1 pathway inhibitor. In some embodiments, a method disclosed herein comprises administering to the patient a therapeutically effective amount of a LAG-3 inhibitor. In some embodiments, a method disclosed herein comprises administering to the patient a therapeutically effective amount of a PD-1 pathway inhibitor. In some embodiments, a method disclosed herein comprises administering to the patient a therapeutically effective amount of a PD-1 pathway inhibitor and an immune checkpoint inhibitor.

Another aspect of the invention disclosed herein relates to a method of treating a malignant tumor in a human patient, comprising: administering to the patient a therapeutically effective amount of a LAG-3 inhibitor and a PD-1 pathway inhibitor; wherein the patient is predicted to respond to treatment with the LAG-3 inhibitor and PD-1 pathway inhibitor based upon LAG-3 expression in a sample of the patient's tumor. Another aspect of the invention disclosed herein relates to a method of treating a malignant tumor in a human patient, comprising: administering to the patient a therapeutically effective amount of a LAG-3 inhibitor; wherein the patient is predicted to respond to treatment with the LAG-3 inhibitor based upon LAG-3 expression in a sample of the patient's tumor. Another aspect of the invention disclosed herein relates to a method of treating a malignant tumor in a human patient, comprising: administering to the patient a therapeutically effective amount of a PD-1 pathway inhibitor; wherein the patient is predicted to respond to treatment with the PD-1 pathway inhibitor based upon LAG-3 expression in a sample of the patient's tumor. Another aspect of the invention disclosed herein relates to a method of treating a malignant tumor in a human patient, comprising: administering to the patient a therapeutically effective amount of a PD-1 pathway inhibitor and an immune checkpoint inhibitor; wherein the patient is predicted to respond to treatment with the PD-1 pathway inhibitor and an immune checkpoint inhibitor based upon LAG-3 expression in a sample of the patient's tumor. In some embodiments, the patient is predicted to respond to the treatment based upon LAG-3 and PD-L1 expression in a sample of the patient's tumor.

Another aspect of the invention disclosed herein relates to a method of treating a malignant tumor in a human patient in need thereof, comprising: determining the level of LAG-3 expression in a tumor sample; and administering to the patient a therapeutically effective amount of a LAG-3 inhibitor and a PD-1 pathway inhibitor if the tumor is a LAG-3 positive tumor. Another aspect of the invention disclosed herein relates to a method of treating a malignant tumor in a human patient in need thereof, comprising: determining the level of LAG-3 expression in a tumor sample; and administering to the patient a therapeutically effective amount of a LAG-3 inhibitor if the tumor is a LAG-3 positive tumor. Another aspect of the invention disclosed herein relates to a method of treating a malignant tumor in a human patient in need thereof, comprising: determining the level of LAG-3 expression in a tumor sample; and administering to the patient a therapeutically effective amount of a PD-1 pathway inhibitor if the tumor is a LAG-3 positive tumor. Another aspect of the invention disclosed herein relates to a method of treating a malignant tumor in a human patient in need thereof, comprising: determining the level of LAG-3 expression in a tumor sample; and administering to the patient a therapeutically effective amount of a PD-1 pathway inhibitor and an immune checkpoint inhibitor if the tumor is a LAG-3 positive tumor. In some embodiments, a method disclosed herein further comprises determining the level of PD-L1 expression in the tumor sample.

Another aspect of the invention disclosed herein relates to a method for treating a malignant tumor in a human patient in need thereof comprising administering to the patient a therapeutically effective amount of a LAG-3 inhibitor and a PD-1 pathway inhibitor, wherein the patient is identified as having a LAG-3 positive malignant tumor prior to the administration. Another aspect of the invention disclosed herein relates to a method for treating a malignant tumor in a human patient in need thereof comprising administering to the patient a therapeutically effective amount of a LAG-3 inhibitor, wherein the patient is identified as having a LAG-3 positive malignant tumor prior to the administration. Another aspect of the invention disclosed herein relates to a method for treating a malignant tumor in a human patient in need thereof comprising administering to the patient a therapeutically effective amount of a PD-1 pathway inhibitor, wherein the patient is identified as having a LAG-3 positive malignant tumor prior to the administration. Another aspect of the invention disclosed herein relates to a method for treating a malignant tumor in a human patient in need thereof comprising administering to the patient a therapeutically effective amount of a PD-1 pathway inhibitor and an immune checkpoint inhibitor, wherein the patient is identified as having a LAG-3 positive malignant tumor prior to the administration. In some embodiments, the patient is identified as having a LAG-3 positive PD-L1 positive malignant tumor prior to the administration. In some embodiments, the patient is identified as having a LAG-3 positive PD-L1 negative malignant tumor prior to the administration.

Another aspect of the invention disclosed herein relates to a method for treating a malignant tumor in a human patient in need thereof, comprising: identifying the patient as having a LAG-3 positive malignant tumor; and administering to the patient a therapeutically effective amount of a LAG-3 inhibitor and a PD-1 pathway inhibitor. Another aspect of the invention disclosed herein relates to a method for treating a malignant tumor in a human patient in need thereof, comprising: identifying the patient as having a LAG-3 positive malignant tumor; and administering to the patient a therapeutically effective amount of a LAG-3 inhibitor. Another aspect of the invention disclosed herein relates to a method for treating a malignant tumor in a human patient in need thereof, comprising: identifying the patient as having a LAG-3 positive malignant tumor; and administering to the patient a therapeutically effective amount of a PD-1 pathway inhibitor. Another aspect of the invention disclosed herein relates to a method for treating a malignant tumor in a human patient in need thereof, comprising: identifying the patient as having a LAG-3 positive malignant tumor; and administering to the patient a therapeutically effective amount of a PD-1 pathway inhibitor and an immune checkpoint inhibitor. In some embodiments, a method disclosed herein further comprises identifying the patient as having a LAG-3 positive PD-L1 positive malignant tumor. In some embodiments, a method disclosed herein further comprises identifying the patient as having a LAG-3 positive PD-L1 negative malignant tumor.

Another aspect of the invention disclosed herein relates to a method for extending a progression-free survival period for over 12 months in a human patient afflicted with a malignant tumor comprising administering to the patient a LAG-3 inhibitor and a PD-1 pathway inhibitor, wherein the patient is identified as having a LAG-3 positive malignant tumor prior to the administration and wherein the patient demonstrates progression-free survival for over 12 months. Another aspect of the invention disclosed herein relates to a method for extending a progression-free survival period for over 12 months in a human patient afflicted with a malignant tumor comprising administering to the patient a LAG-3 inhibitor, wherein the patient is identified as having a LAG-3 positive malignant tumor prior to the administration and wherein the patient demonstrates progression-free survival for over 12 months. Another aspect of the invention disclosed herein relates to a method for extending a progression-free survival period for over 12 months in a human patient afflicted with a malignant tumor comprising administering to the patient a PD-1 pathway inhibitor, wherein the patient is identified as having a LAG-3 positive malignant tumor prior to the administration and wherein the patient demonstrates progression-free survival for over 12 months. Another aspect of the invention disclosed herein relates to a method for extending a progression-free survival period for over 12 months in a human patient afflicted with a malignant tumor comprising administering to the patient a PD-1 pathway inhibitor and an immune checkpoint inhibitor, wherein the patient is identified as having a LAG-3 positive malignant tumor prior to the administration and wherein the patient demonstrates progression-free survival for over 12 months. In some embodiments, the patient is identified as having a LAG-3 positive PD-L1 positive malignant tumor prior to the administration. In some embodiments, the patient is identified as having a LAG-3 positive PD-L1 negative malignant tumor prior to the administration. In some embodiments, the progression-free survival of the patient is extended after the administration for over about 13 months, about 14 months, about 15 months, about 16 months, about 17 months, about 18 months, about 2 years, about 3 years, about 4 years, about 5 years, about 6 years, about 7 years, about 8 years, about 9 years, or about 10 years. In certain embodiments, the progression-free survival of the patient is extended for over 14 months.

Another aspect of the invention disclosed herein relates to a method for reducing a tumor size at least by 10% in a human patient afflicted with a malignant tumor comprising administering to the patient a therapeutically effective amount of a LAG-3 inhibitor and a PD-1 pathway inhibitor, wherein the patient is identified as having a LAG-3 positive malignant tumor prior to the administration and wherein the administration reduces the tumor size at least about 10%, about 20%, about 30%, about 40%, about 50%, about 60%, about 70%, about 80%, about 90%, or 100% compared to the tumor size prior to the administration. Another aspect of the invention disclosed herein relates to a method for reducing a tumor size at least by 10% in a human patient afflicted with a malignant tumor comprising administering to the patient a therapeutically effective amount of a LAG-3 inhibitor, wherein the patient is identified as having a LAG-3 positive malignant tumor prior to the administration and wherein the administration reduces the tumor size at least about 10%, about 20%, about 30%, about 40%, about 50%, about 60%, about 70%, about 80%, about 90%, or 100% compared to the tumor size prior to the administration. Another aspect of the invention disclosed herein relates to a method for reducing a tumor size at least by 10% in a human patient afflicted with a malignant tumor comprising administering to the patient a therapeutically effective amount of a PD-1 pathway inhibitor, wherein the patient is identified as having a LAG-3 positive malignant tumor prior to the administration and wherein the administration reduces the tumor size at least about 10%, about 20%, about 30%, about 40%, about 50%, about 60%, about 70%, about 80%, about 90%, or 100% compared to the tumor size prior to the administration. Another aspect of the invention disclosed herein relates to a method for reducing a tumor size at least by 10% in a human patient afflicted with a malignant tumor comprising administering to the patient a therapeutically effective amount of a PD-1 pathway inhibitor and an immune checkpoint inhibitor, wherein the patient is identified as having a LAG-3 positive malignant tumor prior to the administration and wherein the administration reduces the tumor size at least about 10%, about 20%, about 30%, about 40%, about 50%, about 60%, about 70%, about 80%, about 90%, or 100% compared to the tumor size prior to the administration. In some embodiments, the patient is identified as having a LAG-3 positive PD-L1 positive malignant tumor prior to the administration. In some embodiments, the patient is identified as having a LAG-3 positive PD-L1 negative malignant tumor prior to the administration. In some embodiments, a method disclosed herein further comprises identifying the patient as having a LAG-3 positive malignant tumor prior to the administration. In some embodiments, a method disclosed herein further comprises identifying the patient as having a LAG-3 positive PD-L1 positive malignant tumor prior to the administration. In some embodiments, a method disclosed herein further comprises identifying the patient as having a LAG-3 positive PD-L1 negative malignant tumor prior to the administration. In some embodiments, the patient experiences (i) extended progression-free survival for over 12 months, (ii) tumor size reduction at least about 10%, about 20%, about 30%, about 40%, or about 50% compared to the tumor size prior to the administration, or (iii) both.

Another aspect of the invention disclosed herein relates to a method for increasing an objective response rate to a cancer treatment to be higher than 50% in a human patient population, each of whom is afflicted with a malignant tumor, to a cancer treatment comprising administering to the patient a therapeutically effective amount of a LAG-3 inhibitor and a PD-1 pathway inhibitor, wherein each patient is identified as having a LAG-3 positive malignant tumor prior to the administration and wherein the objective response rate is higher than 55%, 60%, 65%, 70%, or 75%. Another aspect of the invention disclosed herein relates to a method for increasing an objective response rate to a cancer treatment to be higher than 50% in a human patient population, each of whom is afflicted with a malignant tumor, to a cancer treatment comprising administering to the patient a therapeutically effective amount of a LAG-3 inhibitor, wherein each patient is identified as having a LAG-3 positive malignant tumor prior to the administration and wherein the objective response rate is higher than 55%, 60%, 65%, 70%, or 75%. Another aspect of the invention disclosed herein relates to a method for increasing an objective response rate to a cancer treatment to be higher than 50% in a human patient population, each of whom is afflicted with a malignant tumor, to a cancer treatment comprising administering to the patient a therapeutically effective amount of a PD-1 pathway inhibitor, wherein each patient is identified as having a LAG-3 positive malignant tumor prior to the administration and wherein the objective response rate is higher than 55%, 60%, 65%, 70%, or 75%. Another aspect of the invention disclosed herein relates to a method for increasing an objective response rate to a cancer treatment to be higher than 50% in a human patient population, each of whom is afflicted with a malignant tumor, to a cancer treatment comprising administering to the patient a therapeutically effective amount of a PD-1 pathway inhibitor and an immune checkpoint inhibitor, wherein each patient is identified as having a LAG-3 positive malignant tumor prior to the administration and wherein the objective response rate is higher than 55%, 60%, 65%, 70%, or 75%. In some embodiments, each patient is identified as having a LAG-3 positive PD-L1 positive malignant tumor prior to the administration. In some embodiments, each patient is identified as having a LAG-3 positive PD-L1 negative malignant tumor prior to the administration.

Another aspect of the invention disclosed herein relates to a method for increasing a disease control rate to be higher than 50% in a human patient population, each of whom is afflicted with a malignant tumor, to a cancer treatment comprising administering to the patient a therapeutically effective amount of a LAG-3 inhibitor and a PD-1 pathway inhibitor, wherein each patient is identified as having a LAG-3 positive malignant tumor prior to the administration and wherein the objective response rate is higher than 55%, 60%, 65%, 70%, or 75%. Another aspect of the invention disclosed herein relates to a method for increasing a disease control rate to be higher than 50% in a human patient population, each of whom is afflicted with a malignant tumor, to a cancer treatment comprising administering to the patient a therapeutically effective amount of a LAG-3 inhibitor, wherein each patient is identified as having a LAG-3 positive malignant tumor prior to the administration and wherein the objective response rate is higher than 55%, 60%, 65%, 70%, or 75%. Another aspect of the invention disclosed herein relates to a method for increasing a disease control rate to be higher than 50% in a human patient population, each of whom is afflicted with a malignant tumor, to a cancer treatment comprising administering to the patient a therapeutically effective amount of a PD-1 pathway inhibitor, wherein each patient is identified as having a LAG-3 positive malignant tumor prior to the administration and wherein the objective response rate is higher than 55%, 60%, 65%, 70%, or 75%. Another aspect of the invention disclosed herein relates to a method for increasing a disease control rate to be higher than 50% in a human patient population, each of whom is afflicted with a malignant tumor, to a cancer treatment comprising administering to the patient a therapeutically effective amount of a PD-1 pathway inhibitor and an immune checkpoint inhibitor, wherein each patient is identified as having a LAG-3 positive malignant tumor prior to the administration and wherein the objective response rate is higher than 55%, 60%, 65%, 70%, or 75%. In some embodiments, each patient is identified as having a LAG-3 positive PD-L1 positive malignant tumor prior to the administration. In some embodiments, each patient is identified as having a LAG-3 positive PD-L1 negative malignant tumor prior to the administration. In some embodiments, the median duration of response is ≥3 month, ≥6 month, ≥12 month, or ≥18 month.

In some embodiments, a method disclosed herein further comprises identifying each patient of the patient population as having a LAG-3 positive malignant tumor prior to the administration. In some embodiments, a method disclosed herein further comprises identifying each patient of the patient population as having a LAG-3 positive PD-L1 positive malignant tumor prior to the administration. In some embodiments, a method disclosed herein further comprises identifying each patient of the patient population as having a LAG-3 positive PD-L1 negative malignant tumor prior to the administration. In some embodiments, each patient of the patient population is further characterized by (i) extended progression-free survival for over 12 months, (ii) tumor size reduction at least about 10%, about 20%, about 30%, about 40%, or about 50% compared to the tumor size prior to the administration, or (iii) both. In some embodiments, the patient population comprises at least about 100, 200, 300, 400, 500, 600, 700, 800, 900, or 1000 patients having a LAG-3 positive malignant tumor.

Another aspect of the invention disclosed herein relates to a method for selecting a human patient suitable for a combination therapy comprising: identifying a patient as having a LAG-3 positive malignant tumor; and instructing a healthcare provider to administer to the patient a therapeutically effective amount of a LAG-3 inhibitor and a PD-1 pathway inhibitor. Another aspect of the invention disclosed herein relates to a method for selecting a human patient suitable for a combination therapy comprising: identifying a patient as having a LAG-3 positive malignant tumor; and instructing a healthcare provider to administer to the patient a therapeutically effective amount of a LAG-3 inhibitor. Another aspect of the invention disclosed herein relates to a method for selecting a human patient suitable for a combination therapy comprising: identifying a patient as having a LAG-3 positive malignant tumor; and instructing a healthcare provider to administer to the patient a therapeutically effective amount of a PD-1 pathway inhibitor. Another aspect of the invention disclosed herein relates to a method for selecting a human patient suitable for a combination therapy comprising: identifying a patient as having a LAG-3 positive malignant tumor; and instructing a healthcare provider to administer to the patient a therapeutically effective amount of a PD-1 pathway inhibitor and an immune checkpoint inhibitor. In some embodiments, a method disclosed herein further comprises identifying the patient as having a LAG-3 positive PD-L1 positive malignant tumor. In some embodiments, a method disclosed herein further comprises identifying the patient as having a LAG-3 positive PD-L1 negative malignant tumor. In some embodiments, the administration treats the malignant tumor.

In some embodiments, identifying the patient as having a LAG-3 positive malignant tumor comprises determining LAG-3 expression in the malignant tumor. In some embodiments, identifying the patient as having a LAG-3 positive PD-L1 positive malignant tumor comprises determining PD-L1 expression in the malignant tumor. In some embodiments, identifying the patient as having a LAG-3 positive PD-L1 negative malignant tumor comprises determining PD-L1 expression in the malignant tumor. In some embodiments, LAG-3 expression is determined by reviewing the results of an assay capable of determining LAG-3 expression. In some embodiments, LAG-3 expression is determined by reviewing the results of an immunohistochemistry assay capable of detecting LAG-3 expression. In some embodiments, PD-L1 expression is determined by reviewing the results of an assay capable of determining PD-L1 expression. In some embodiments, PD-L1 expression is determined by reviewing the results of an immunohistochemistry assay capable of detecting PD-L1 expression.

In certain embodiments, a LAG-3 positive tumor comprises at least about 1%, at least about 2%, at least about 3%, at least about 4%, at least about 5%, at least about 7%, at least about 10%, at least about 15%, at least about 20%, at least about 25%, at least about 30%, at least about 40%, at least about 50%, at least about 60%, at least about 70%, at least about 80%, at least about 90%, or 100% cells expressing LAG-3. In certain embodiments, a LAG-3 positive tumor comprises at least about 1% cells expressing LAG-3. In certain embodiments, a LAG-3 positive tumor comprises at least about 5% cells expressing LAG-3. In some embodiments, the cells expressing LAG-3 comprise tumor infiltrating lymphocytes. In certain embodiments, the cells expressing LAG-3 are the total number of cells. In other embodiments, the cells express LAG-3 on the cell surface.

In some embodiments, the malignant tumor is selected from the group consisting of a liver cancer, bone cancer, pancreatic cancer, skin cancer, oral cancer, cancer of the head or neck, breast cancer, lung cancer, including small cell and non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, cancers of the childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combination thereof.

In some embodiments, the malignant tumor is chosen from melanoma, non-small cell lung cancer (NSCLC), human papilloma virus (HPV)-related tumor, and gastric adenocarcinoma.

In some embodiments, the malignant tumor is NSCLC, a virally-related cancer related tumor, or gastric adenocarcinoma.

In some embodiments, the malignant tumor is melanoma, gastric cancer, gastroesophageal junction cancer, non-small cell lung cancer, bladder cancer, head and neck squamous cell carcinoma, or renal cell cancer.

In some embodiments, the malignant tumor is lung cancer, melanoma, squamous cell carcinoma of the head and neck, renal cancer, gastric cancer, or hepatocellular carcinoma.

In some embodiments, the LAG-3 positive malignant tumor is a melanoma tumor comprising about 1% or more cells expressing LAG-3.

In some embodiments, the LAG-3 positive malignant tumor is a gastric cancer tumor comprising about 1% or more cells expressing LAG-3.

In some embodiments, the malignant tumor is refractory to treatment with an immune checkpoint inhibitor. In some embodiments, the malignant tumor is refractory to treatment with an anti-PD-1 antibody. In some embodiments, the malignant tumor is refractory to treatment with an anti-PD-L1 antibody.

Another aspect of the invention disclosed herein relates to a method for treating melanoma in a human patient, comprising: identifying the patient as having a LAG-3 positive melanoma; and administering to the patient a therapeutically effective amount of a LAG-3 inhibitor and a PD-1 pathway inhibitor. In some embodiments, identifying the patient as having a LAG-3 positive melanoma comprises determining LAG-3 expression in the melanoma tumor. In some embodiments, LAG-3 expression is determined by reviewing the results of an assay capable of determining LAG-3 expression. In some embodiments, LAG-3 expression is determined by an immunohistochemistry assay capable of detecting LAG-3 expression. In some embodiments, a method disclosed herein further comprises identifying the patient as having a LAG-3 positive PD-L1 positive malignant tumor. In some embodiments, a method disclosed herein further comprises identifying the patient as having a LAG-3 positive PD-L1 negative malignant tumor.

Another aspect of the invention disclosed herein relates to a method for treating a melanoma in a human patient in need thereof comprising administering to the patient a therapeutically effective amount of a LAG-3 inhibitor and a PD-1 pathway inhibitor, wherein the patient is identified as having a LAG-3 positive melanoma prior to the administration. Another aspect of the invention disclosed herein relates to a method for extending a progression-free survival period for over 12 months in a human patient afflicted with a melanoma comprising administering to the patient a LAG-3 inhibitor and a PD-1 pathway inhibitor, wherein the patient is identified as having a LAG-3 positive melanoma prior to the administration and wherein the patient demonstrates progression-free survival for over 12 months. In some embodiments, the patient is identified as having a LAG-3 positive PD-L1 positive melanoma prior to the administration. In some embodiments, the patient is identified as having a LAG-3 positive PD-L1 negative melanoma prior to the administration.

Another aspect of the invention disclosed herein relates to a method for increasing an objective response rate to a cancer treatment to be higher than 15% in a human patient population, each of whom is afflicted with melanoma, comprising administering to the patient a therapeutically effective amount of a LAG-3 inhibitor and a PD-1 pathway inhibitor, wherein each patient is identified as having a LAG-3 positive malignant tumor prior to the administration and wherein the objective response rate is higher than 15%. Another aspect of the invention disclosed herein relates to a method for increasing a disease control rate to a cancer treatment to be higher than 70% in a human patient population, each of whom is afflicted with melanoma, comprising administering to the patient a therapeutically effective amount of a LAG-3 inhibitor and a PD-1 pathway inhibitor, wherein each patient is identified as having a LAG-3 positive melanoma prior to the administration and wherein the objective response rate is higher than 70%. In some embodiments, a method disclosed herein further comprises identifying each patient of the patient population as having a LAG-3 positive melanoma prior to the administration. In some embodiments, the median duration of response is ≥3 month, ≥6 month, ≥12 month, or ≥18 month. In some embodiments, each patient is identified as having a LAG-3 positive PD-L1 positive melanoma prior to the administration. In some embodiments, each patient is identified as having a LAG-3 positive PD-L1 negative melanoma prior to the administration.

In some embodiments, the melanoma is refractory to treatment with an immune checkpoint inhibitor. In some embodiments, the melanoma is refractory to treatment with an anti-PD-1 antibody or an anti-PD-L1 antibody.

In some embodiments, determining the level of LAG-3 and/or PD-L1 expression comprises providing a test tissue sample obtained from the patient, the test tissue sample comprising tumor cells and/or tumor-infiltrating immune cells. In some embodiments, the test tissue sample is a tumor biopsy. In some embodiments, the test tissue sample is a formalin-fixed paraffin embedded (FFPE) sample.

In some embodiments, determining comprises detecting LAG-3 and/or PD-L1 protein or RNA expression in the test tissue sample.

In some embodiments, LAG-3 and/or PD-L1 expression is detected by an assay capable of detecting the level of LAG-3 and/or PD-L1 protein, respectively, in the test tissue sample.

In some embodiments, LAG-3 and/or PD-L1 expression is detected by an immunohistochemistry assay. In some embodiments, the immunohistochemistry assay is a monoplex assay (assay designed to detect/measure the presence of a single analyte, e.g., antigen/antibody pair). In some embodiments, the immunohistochemistry assay is a multiplex assay (assay designed to detect/measure multiple analytes, either simultaneously or sequentially). In some embodiments, the immunohistochemistry assay comprises contacting the tumor sample with the 17B4, SP346, 11E3, 874501, or EPR4392(2) anti-human LAG-3 monoclonal antibody. In some embodiments, the immunohistochemistry assay comprises contacting the tumor sample with an anti-LAG-3 antibody comprising heavy and light chain variable regions comprising the sequences set forth in SEQ ID NOs:3 and 5, respectively.

In some embodiments, the immunohistochemistry assay uses a black or brown chromogen. In some embodiments, the immunohistochemistry assay uses a red chromogen. In some embodiments, the immunohistochemistry assay uses a blue chromogen. In some embodiments, the immunohistochemistry assay uses a green chromogen. In some embodiments, the immunohistochemistry assay uses a purple chromogen. In certain embodiments, the immunohistochemistry assay uses a yellow chromogen.

In some embodiments, the immunohistochemistry assay is scored at a low magnification (e.g., 4× or 10×). In some embodiments, low magnification is about 20×.

In some embodiments, the immunohistochemistry assay is scored at high magnification. In some embodiments, high magnification is about 40×, or greater (60×, 100×).

In some embodiments, the immunohistochemistry assay is scored by an image analysis software. In some embodiments, the immunohistochemistry assay is scored manually by a pathologist.

In some embodiments, scoring the immunohistochemistry assay comprises assessing the proportion of cells in the test tissue sample that express LAG-3 and/or assessing the proportion of cells in the test tissue sample that express PD-L1. In some embodiments, scoring the immunohistochemistry assay comprises assessing the proportion of tumor cells in the test tissue sample that express LAG-3 and/or assessing the proportion of tumor cells in the test tissue sample that express PD-L1. In some embodiments, scoring the immunohistochemistry assay comprises assessing the proportion of immune cells in the test tissue sample that express LAG-3 and/or assessing the proportion of immune cells in the test tissue sample that express PD-L1. In some embodiments, scoring the immunohistochemistry assay comprises assessing the proportion of T cells in the test tissue sample that express LAG-3 and/or assessing the proportion of T cells in the test tissue sample that express PD-L1. In some embodiments, scoring the immunohistochemistry assay comprises assessing the proportion of CD8+ T cells in the test tissue sample that express LAG-3 and/or assessing the proportion of CD8+ T cells in the test tissue sample that express PD-L1. In some embodiments, scoring the immunohistochemistry assay comprises assessing the proportion of CD4+ T cells in the test tissue sample that express LAG-3 and/or assessing the proportion of CD4+ T cells in the test tissue sample that express PD-L1. In some embodiments, scoring the immunohistochemistry assay comprises assessing the proportion of FOXP3+ T cells in the test tissue sample that express LAG-3 and/or assessing the proportion of FOXP3+ T cells in the test tissue sample that express PD-L1.

In some embodiments, cells with partial membrane/cytoplasmic LAG-3 localization are scored as LAG-3 expressing cells. In some embodiments, cells with dot-like LAG-3 localization are scored as LAG-3 expressing cells. In some embodiments, cells with complete membrane/cytoplasmic LAG-3 localization are scored as LAG-3 expressing cells. In some embodiments, cells with any LAG-3 localization pattern are scored as LAG-3 expressing cells.

In some embodiments, the immunohistochemistry assay is a multiplex assay that further comprises detecting the expression of MHC Class II by the tumor cells. In some embodiments, scoring the immunohistochemistry assay comprises assessing the proportion of cells in the test tissue sample that expresses MHC Class II. In some embodiments, scoring the immunohistochemistry assay comprises assessing the proportion of non-immune cells in the test tissue sample that expresses MHC II.

In some embodiments, LAG-3 and/or PD-L1 protein expression is detected by flow cytometry. In some embodiments, the test tissue sample obtained from the patient comprises tumor infiltrating immune cells. In some embodiments, the malignant tumor is a hematological malignancy and the tissue sample comprises circulating lymphocytes. In some embodiments, the flow cytometry is a multiplex assay. In some embodiments, the flow cytometry comprises detecting the expression of markers comprising LAG-3, PD-L1, CD4, CD8, FOXP3, MHC Class II and any combination thereof.

In some embodiments, scoring the flow cytometry comprises assessing the proportion of T cells in the test tissue sample that express LAG-3. In some embodiments, scoring the flow cytometry comprises assessing the proportion of CD8+ T cells in the test tissue sample that express LAG-3. In some embodiments, scoring the flow cytometry comprises assessing the proportion of CD4+ T cells in the test tissue sample that express LAG-3. In some embodiments, scoring the flow cytometry comprises assessing the proportion of FOXP3+ T cells in the test tissue sample that express LAG-3.

In some embodiments, LAG-3 and/or PD-L1 expression is detected by an assay capable of detecting the level of LAG-3 and/or PD-L1, respectively, RNA in the tumor sample. In some embodiments, LAG-3 and/or PD-L1 expression is detected by an RT-PCR based assay. In some embodiments, scoring the RT-PCR based assay comprises assessing the level of LAG-3 and/or PD-L1 RNA expression in the test tissue sample relative to a predetermined level.

In some embodiments, the LAG-3 inhibitor is an anti-LAG-3 antibody or antigen-binding fragment thereof. In some embodiments, the anti-LAG-3 antibody is a bispecific antibody.

In some embodiments, the anti-LAG-3 antibody or antigen-binding fragment thereof comprises (a) a heavy chain variable region CDR1 comprising the sequence set forth in SEQ ID NO:7; (b) a heavy chain variable region CDR2 comprising the sequence set forth in SEQ ID NO:8; (c) a heavy chain variable region CDR3 comprising the sequence set forth in SEQ ID NO:9; (d) a light chain variable region CDR1 comprising the sequence set forth in SEQ ID NO:10;

(e) a light chain variable region CDR2 comprising the sequence set forth in SEQ ID NO:11; and (f) a light chain variable region CDR3 comprising the sequence set forth in SEQ ID NO:12.

In some embodiments, the anti-LAG-3 antibody or antigen-binding fragment thereof comprises heavy and light chain variable regions comprising the sequences set forth in SEQ ID NOs:3 and 5, respectively.

In some embodiments, the anti-LAG-3 antibody is MK-4280 (28G-10), REGN3767, GSK2837781, IMP731 (H5L7BW), BAP050, IMP-701 (LAG-525), IMIP321, FS-118, Sym022, TSR-033, MGD013, FS118, or GSK2831781.

In some embodiments, the PD-1 pathway inhibitor is an anti-PD-1 antibody or antigen-binding fragment thereof. In some embodiments, the anti-PD-1 antibody or antigen-binding fragment thereof comprises (a) a heavy chain variable region CDR1 comprising the sequence set forth in SEQ ID NO:23; (b) a heavy chain variable region CDR2 comprising the sequence set forth in SEQ ID NO:24; (c) a heavy chain variable region CDR3 comprising the sequence set forth in SEQ ID NO:25; (d) a light chain variable region CDR1 comprising the sequence set forth in SEQ ID NO:26; (e) a light chain variable region CDR2 comprising the sequence set forth in SEQ ID NO:27; and (f) a light chain variable region CDR3 comprising the sequence set forth in SEQ ID NO:28.

In some embodiments, the anti-PD-1 antibody or antigen-binding fragment thereof comprises heavy and light chain variable regions comprising the sequences set forth in SEQ ID NOs:19 and 21, respectively.

In some embodiments, the anti-PD-1 antibody or antigen-binding fragment thereof comprises heavy and light chains comprising the sequences set forth in SEQ ID NOs:17 and 18, respectively.

In some embodiments, the anti-PD-1 antibody is pembrolizumab (KEYTRUDA; MK-3475), pidilizumab (CT-011), or nivolumab (OPDIVO; BMS-936558).

In some embodiments, the PD-1 pathway inhibitor is an anti-PD-L1 antibody or antigen-binding fragment thereof. In some embodiments, the anti-PD-L1 antibody is atezolizumab (Tecentriq or RG7446), durvalumab (Imfinzi or MEDI4736), avelumab (Bavencio) or BMS-936559.

In some embodiments, the PD-1 pathway inhibitor is an anti-PD-L2 antibody or antigen-binding fragment thereof.

In some embodiments, the immune checkpoint inhibitor is a CTLA-4 antagonist, a CD80 antagonist, a CD86 antagonist, a Tim-3 antagonist, a TIGIT antagonist, a CD20 antagonist, a CD96 antagonist, a IDO1 antagonist, a STING antagonist, a GARP antagonist, a CD40 antagonist, A2aR antagonist, a CEACAM1 (CD66a) antagonist, a CEA antagonist, a CD47 antagonist a PVRIG antagonist, a TDO antagonist, a VISTA antagonist, or a KIR antagonist.

In some embodiments, the method comprises at least one administration cycle, wherein the cycle is a period of eight weeks, wherein for each of the at least one cycles, four doses of the anti-LAG-3 antibody are administered at a dose of 3, 20, 80, 160, or 240 mg.

In some embodiments, the method comprises at least one administration cycle, wherein the cycle is a period of eight weeks, wherein for each of the at least one cycles, four doses of the anti-PD-1 antibody are administered at a dose of 80 or 240 mg.

In some embodiments, the method comprises at least one administration cycle, wherein the cycle is a period of eight weeks, wherein for each of the at least one cycles, four doses of the anti-PD-L1 antibody are administered at a dose of 3, 20, 80, 160, or 240 mg.

In some embodiments, the method comprises at least one administration cycle, wherein the cycle is a period of eight weeks, wherein for each of the at least one cycles, four doses of the anti-LAG-3 antibody are administered at a dose of 3, 20, 80, 160, or 240 mg and four doses of the anti-PD-1 antibody are administered at a dose of 80 or 240 mg.

In some embodiments, the anti-LAG-3 antibody and anti-PD-1 antibody are administered at the following doses: (a) 3 mg of anti-LAG-3 antibody and 80 mg of anti-PD-1 antibody; (b) 3 mg of anti-LAG-3 antibody and 240 mg of anti-PD-1 antibody; (c) 20 mg of anti-LAG-3 antibody and 240 mg of anti-PD-1 antibody; (d) 80 mg of anti-LAG-3 antibody and 160 mg of anti-PD-1 antibody; (e) 80 mg of anti-LAG-3 antibody and 240 mg of anti-PD-1 antibody; (f) 160 mg of anti-LAG-3 antibody and 240 mg of anti-PD-1 antibody, or (g) 240 mg of anti-LAG-3 antibody and 240 mg of anti-PD-1 antibody.

In some embodiments, the anti-LAG-3 antibody and anti-PD-1 antibody are administered at the dose of 80 mg of anti-LAG-3 antibody and 160 mg of anti-PD-1 antibody.

In some embodiments, the anti-LAG-3 antibody and anti-PD-1 antibody are administered at the dose of 80 mg of anti-LAG-3 antibody and 240 mg of anti-PD-1 antibody.

In some embodiments, the anti-LAG-3 antibody and anti-PD-1 antibody are administered at the dose of 160 mg of anti-LAG-3 antibody and 240 mg of anti-PD-1 antibody.

In some embodiments, the anti-PD-1 and anti-LAG-3 antibodies or antigen-binding fragments thereof are formulated for intravenous administration.

In some embodiments, the anti-PD-1 and anti-LAG-3 antibodies or antigen-binding fragments thereof are formulated together. In some embodiments, the anti-PD-1 and anti-LAG-3 antibodies or antigen-binding fragments thereof are formulated separately.

In some embodiments, the treatment consists of up to 12 cycles.

In some embodiments, anti-PD-1 antibody or antigen-binding fragment thereof is administered on Days 1, 15, 29, and 43 of each cycle.

In some embodiments, anti-LAG-3 antibody or antigen-binding fragment thereof is administered on Days 1, 15, 29, and 43 of each cycle.

In some embodiments, the anti-PD-1 antibody or antigen-binding fragment thereof is administered prior to administration of the anti-LAG-3 antibody or antigen-binding fragment thereof. In some embodiments, the anti-LAG-3 antibody or antigen-binding fragment thereof is administered within about 30 minutes prior to administration of the anti-PD-1 antibody or antigen-binding fragment thereof. In some embodiments, the anti-PD-1 antibody or antigen-binding fragment thereof is administered after administration of the anti-LAG-3 antibody or antigen-binding fragment thereof. In some embodiments, the anti-PD-1 antibody or antigen-binding fragment thereof is administered before administration of the anti-LAG-3 antibody or antigen-binding fragment thereof. In some embodiments, the anti-PD-1 antibody or antigen-binding fragment thereof is administered concurrently with the anti-LAG-3 antibody or antigen-binding fragment thereof.

In some embodiments, the anti-LAG-3 antibody or antigen-binding fragment thereof and PD-1 pathway inhibitor are administered as a first line of treatment. In some embodiments, the anti-LAG-3 antibody or antigen-binding fragment thereof and PD-1 pathway inhibitor are administered as a second line of treatment.

In some embodiments, a method disclosed herein further comprises the administration of at least one additional therapeutic agent. In some embodiments, the at least one additional therapeutic agent is a chemotherapeutic agent. In some embodiments, the at least one additional therapeutic agent is an immune checkpoint inhibitor.

In some embodiments, the method produces at least one therapeutic effect chosen from a reduction in size of a tumor, reduction in number of metastatic lesions over time, complete response, partial response, and stable disease.

In some embodiments, administering the anti-LAG-3 antibody or antigen-binding fragment thereof and PD-1 pathway inhibitor activates the patient's T cells. In some embodiments, administering the anti-LAG-3 antibody or antigen-binding fragment thereof and PD-1 pathway inhibitor induces the expression activation markers by the patient's T cells.

In some embodiments, administering the anti-LAG-3 antibody or antigen-binding fragment thereof results in the occupancy of at least about 10%, at least about 20%, at least about 30%, at least about 40%, at least about 50%, at least about 60%, at least about 70%, at least about 80%, at least about 90%, at least about 95%, or about 100% of the LAG-3 receptors on the patient's T cells. In some embodiments, the T cells are CD8+ T cells. In some embodiments, the T cells are tumor infiltrating T cells.

In some embodiments, the PD-1 pathway inhibitor comprises an anti-PD-1 antibody or antigen-binding fragment thereof.

Another aspect of the invention disclosed herein relates to a kit for treating a patient afflicted with a malignant tumor, the kit comprising: a dosage ranging from about 0.1 to about 10 mg/kg body weight of an anti-LAG-3 antibody or an antigen-binding fragment thereof; a dosage ranging from about 0.1 to about 10 mg/kg body weight of an anti-PD-1 antibody or an antigen-binding fragment thereof; and instructions for using the anti-LAG-3 antibody and anti-PD-1 antibody or the antigen-binding fragments thereof in any of the methods disclosed herein.

Another aspect of the invention disclosed herein relates to a kit for treating a patient afflicted with a malignant tumor, the kit comprising: a dosage ranging from about 0.1 to about 10 mg/kg body weight of an anti-PD1 antibody or an antigen-binding fragment thereof; a dosage an immune checkpoint inhibitor; and instructions for using the anti-PD-1 antibody or antigen-binding fragment thereof and immune checkpoint inhibitor in any of the methods disclosed herein.

Another aspect of the invention disclosed herein relates to a kit for treating a patient afflicted with a malignant tumor, the kit comprising: a dosage ranging from about 0.1 to about 10 mg/kg body weight of an anti-LAG-3 antibody or an antigen-binding fragment thereof; and instructions for using the anti-LAG-3 antibody or the antigen-binding fragment thereof in any of the methods disclosed herein.

Another aspect of the invention disclosed herein relates to a kit for treating a patient afflicted with a malignant tumor, the kit comprising: a dosage ranging from 0.1 to 10 mg/kg body weight of an anti-PD-1 antibody or an antigen-binding fragment; and instructions for using the anti-PD-1 antibody or the antigen-binding fragment thereof in any of the methods disclosed herein.

An aspect of the invention relates to a method of identifying a patient that is refractory to treatment with a PD-1 antagonist, the method comprising determining the level of LAG-3 expression, wherein an increased level of LAG-3 expression following treatment with the PD-1 antagonist, relative to the level of LAG-3 expression prior to treatment with the PD-1 antagonist, indicates that a patient is refractory to PD-1 antagonist therapy. Another aspect of the invention relates to a method of identifying a patient that is at risk of becoming refractory to treatment with a PD-1 antagonist, the method comprising determining the level of LAG-3 expression, wherein an increased level of LAG-3 expression following treatment with the PD-1 antagonist, relative to the level of LAG-3 expression prior to treatment with the PD-1 antagonist, indicates that a patient is at risk of becoming refractory to PD-1 antagonist therapy. Some aspects of the invention relate to a method of identifying a patient who is likely to respond to a LAG-3 therapy, the method comprising determining the level of LAG-3 expression in the patient, wherein an increased level of LAG-3 expression following treatment with a PD-1 antagonist, relative to the level of LAG-3 expression prior to treatment with the PD-1 antagonist, indicates that a patient is likely to respond to a LAG-3 therapy. Certain aspects of the invention relate to a method of selecting a patient for treatment with a LAG-3 therapy, the method comprising determining the level of LAG-3 expression in the patient, wherein an increased level of LAG-3 expression following treatment with a PD-1 antagonist, relative to the level of LAG-3 expression prior to treatment with the PD-1 antagonist, indicates that a patient is likely to respond to a LAG-3 therapy. In one embodiment, the PD-1 antagonist is a PD-1 inhibitor. In certain embodiments, the PD-1 antagonist is a PD-1 antibody. In some embodiments, the LAG-3 therapy is a LAG-3 inhibitor. In particular embodiments, the LAG-3 therapy is an anti-LAG-3 antibody. In one embodiment, wherein the LAG-3 therapy is a combination therapy. In an embodiment, the LAG-3 combination therapy is a combination of an anti-LAG-3 antibody and an anti-PD-1 antibody.

BRIEF DESCRIPTION OF THE FIGURES

(FIG. 3A) Study design and endpoints. (FIG. 3B) Key eligibility criteria for patients in the melanoma prior IO expansion cohort.

FIG. 4. Baseline demographics and disease characteristics.

FIG. 5. Prior therapy.

FIG. 7. Response by investigator assessment of patients with melanoma who progressed on prior anti-PD1/PD-L1 therapy.

FIG. 11. Response by baseline characteristics (investigator assessed).

FIGS. 15A and B. FIG. 15A. Pigmented melanoma sections. Nuclei were counterstained with hematoxylin with or without bleaching. FIG. 15B. Pigmented melanoma LAG-3 IHC with or without prior bleaching. Nuclei were counterstained with hematoxylin.

FIG. 17. Updated baseline demographics and disease characteristics.

FIG. 18. Updated prior therapies.

FIG. 19. Updated antitumor activity of BMS-986016 and Nivolumab combination therapy.

FIG. 20. Updated response by baseline characteristics and LAG-3 expression.

FIGS. 28A-C. Relationship between inflammation clusters and biomarker expression in (A) urothelial cancer, (B) NSCLC, and (C) all tumor types.

FIGS. 29A-C. Heterogeneous MHC II tumor cell expression and LAG-3+ TILs. (A) LAG-3+ TIL numbers in MHC II high and MHC II low tumor cell regions in urothelial carcinoma. (B-C) Ratio of LAG-3+ TIL cells in MHC II high and MHC II low tumor cell regions in urothelial and gastric carcinoma samples.

DETAILED DESCRIPTION OF THE INVENTION

Figure 1:
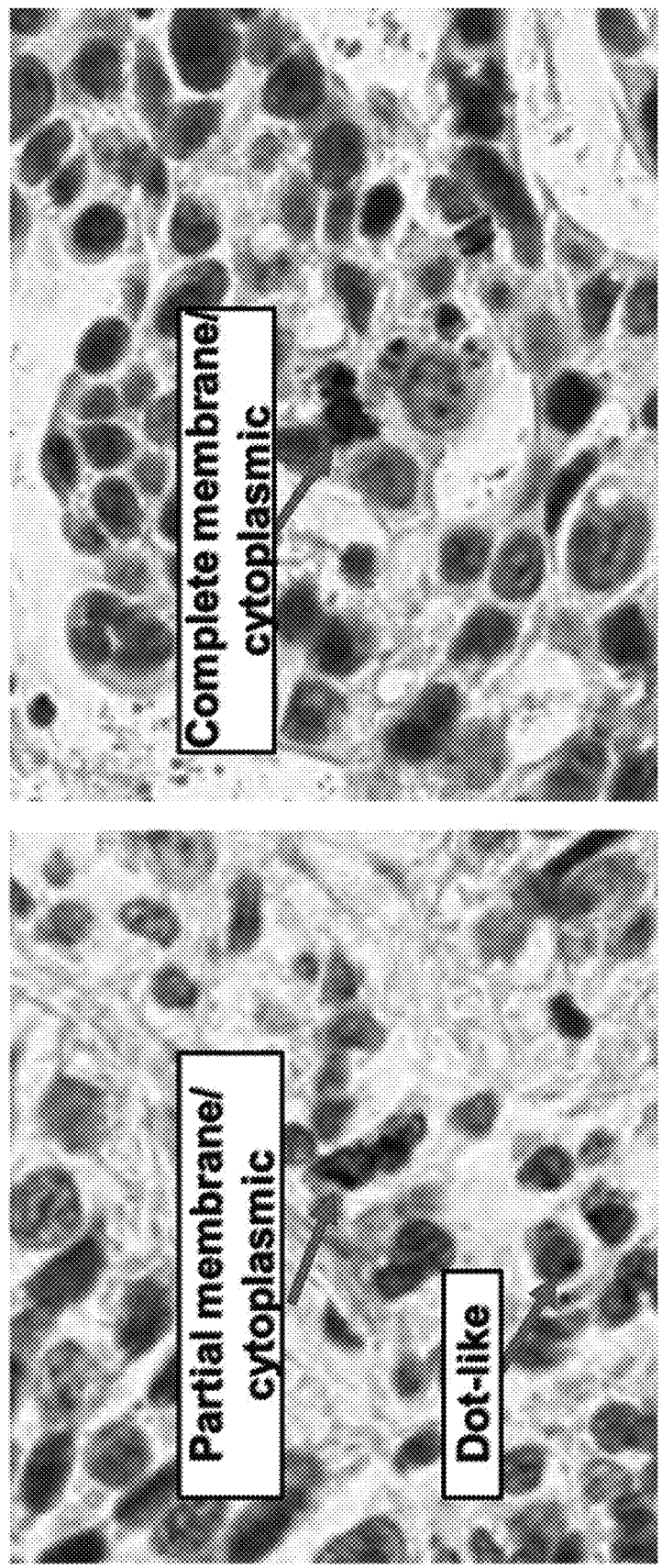
FIG. 1. Staining patterns observed in monoplex LAG-3 immunohistochemistry (IHC) samples.

In one aspect, the present invention relates to an improved method of treatment for malignant tumors in a human patient. In particular, the present invention shows that the administration of an anti-LAG-3 antibody in combination with an anti-PD-1 antibody achieves surprisingly improved treatment outcomes in a patient population having a LAG-3 positive malignant tumor compared to a population comprising patients having both LAG-3 positive and LAG-3 negative tumors. Accordingly, in one aspect, the invention described herein relates to a method for identifying patents having a LAG-3 positive tumor, e.g., melanoma. In another aspect, the invention described herein relates to a method of treating a LAG-3 positive malignant tumor by administering a combination of a LAG-3 inhibitor (e.g., anti-LAG-3 antibody) and a PD-1 pathway inhibitor (e.g., an anti-PD-1 antibody).

In another aspect, the invention described herein relates to a method of treating a LAG-3 positive malignant tumor by administering a PD-1 pathway inhibitor (e.g., an anti-PD-1 antibody) or a combination of a PD-1 pathway inhibitor and an immune checkpoint inhibitor.

In another aspect, the invention described herein relates to a method of treating a LAG-3 positive malignant tumor by administering an anti-CTLA4 antibody.

1. Definitions

In order that the present disclosure may be more readily understood, certain terms are first defined. As used in this application, except as otherwise expressly provided herein, each of the following terms shall have the meaning set forth below. Additional definitions are set forth throughout the application.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. A heavy chain may have the C-terminal lysine or not. Unless specified otherwise herein, the amino acids in the variable regions are numbered using the Kabat numbering system and those in the constant regions are numbered using the EU system.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Where not expressly stated, and unless the context indicates otherwise, the term "antibody" includes monospecific, bispecific, or multi-specific antibodies, as well as a single chain antibody. In embodiments, the antibody is a bispecific antibody. In other embodiments, the antibody is a monospecific antibody.

As used herein, an "IgG antibody" has the structure of a naturally occurring IgG antibody, i.e., it has the same number of heavy and light chains and disulfide bonds as a naturally occurring IgG antibody of the same subclass. For example, an anti-ICOS IgG1, IgG2, IgG3 or IgG4 antibody consists of two heavy chains (HCs) and two light chains (LCs), wherein the two heavy chains and light chains are linked by the same number and location of disulfide bridges that occur in naturally occurring IgG1, IgG2, IgG3 and IgG4 antibodies, respectively (unless the antibody has been mutated to modify the disulfide bonds).

An "isolated antibody" refers to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 may, however, have cross-reactivity to other antigens, such as PD-1 molecules from different species. Moreover, an isolated antibody may be substantially free of other cellular material and/or chemicals.

The antibody may be an antibody that has been altered (e.g., by mutation, deletion, substitution, conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term antibody also includes artificial polypeptide constructs which comprise at least one antibody-derived antigen binding site.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. MAbs may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-LAG-3 antibody binds specifically to LAG-3.

An "antigen-binding portion" of an antibody (also called an "antigen-binding fragment") refers to one or more fragments of an antibody that retain the ability to bind specifically to the antigen bound by the whole antibody. It has been shown that the antigen-binding function of an antibody can be performed by fragments or portions of a full-length antibody. Examples of binding fragments encompassed within the term "antigen-binding portion" or "antigen-binding fragment" of an antibody, e.g., an anti-LAG-3 antibody described herein, include:

(1) a Fab fragment (fragment from papain cleavage) or a similar monovalent fragment consisting of the VL, VH, LC and CH1 domains;
(2) a F(ab')2 fragment (fragment from pepsin cleavage) or a similar bivalent fragment comprising two Fab fragments linked by a disulfide bridge at the hinge region;
(3) a Fd fragment consisting of the VH and CH1 domains;
(4) a Fv fragment consisting of the VL and VH domains of a single arm of an antibody,
(5) a single domain antibody (dAb) fragment (Ward et al., (1989) Nature 341:544-46), which consists of a VH domain;
(6) a bi-single domain antibody which consists of two VH domains linked by a hinge (dual-affinity re-targeting antibodies (DARTs));
(7) a dual variable domain immunoglobulin;
(8) an isolated complementarity determining region (CDR); and
(9) a combination of two or more isolated CDRs, which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" or "antigen-binding fragment" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "LAG-3", "LAG3", or "Lymphocyte Activation Gene-3" refers to Lymphocyte Activation Gene-3. The term LAG-3 as used herein includes human LAG-3 (hLAG-3), variants, isoforms, and species homologs of hLAG-3, and analogs having at least one common epitope with hLAG-3.

The term LAG-3 as used herein includes variants, isoforms, homologs, orthologs and paralogs. For example, antibodies specific for a human LAG-3 protein may, in certain cases, cross-react with a LAG-3 protein from a species other than human. In other embodiments, the antibodies specific for a human LAG-3 protein may be completely specific for the human LAG-3 protein and may not exhibit species or other types of cross-reactivity, or may cross-react with LAG-3 from certain other species, but not all other species (e.g., cross-react with monkey LAG-3 but not mouse LAG-3). The term "human LAG-3" refers to human sequence LAG-3, such as the complete amino acid sequence of human LAG-3 having GenBank Accession No. NP_002277 (SEQ ID NO:13). The term "mouse LAG-3" refers to mouse sequence LAG-3, such as the complete amino acid sequence of mouse LAG-3 having GenBank Accession No. NP_032505. LAG-3 is also known in the art as, for example, CD223. The human LAG-3 sequence may differ from human LAG-3 of GenBank Accession No. NP_002277 by having, e.g., conserved mutations or mutations in non-conserved regions and the LAG-3 has substantially the same biological function as the human LAG-3 of GenBank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules.

A particular human LAG-3 sequence will generally be at least 90% identical in amino acid sequence to human LAG-3 of GenBank Accession No. NP_002277 and contains amino acid residues that identify the amino acid sequence as being human when compared to LAG-3 amino acid sequences of other species (e.g., murine). In certain cases, a human LAG-3 can be at least 95%, or even at least 96%, 97%, 98%, or 99% identical in amino acid sequence to LAG-3 of GenBank Accession No. NP_002277. In certain embodiments, a human LAG-3 sequence will display no more than 10 amino acid differences from the LAG-3 sequence of GenBank Accession No. NP_002277. In certain embodiments, the human LAG-3 can display no more than 5, or even no more than 4, 3, 2, or 1 amino acid difference from the LAG-3 sequence of GenBank Accession No. NP_002277. Percent identity can be determined as described herein.

As used herein, the terms "Programmed Death 1," "Programmed Cell Death 1," "Protein PD-1," "PD-1," "PD1," "PDCD1," "hPD-1" and "hPD-1" are used interchangeably, and include variants, isoforms, species homologs of human PD-1, and analogs having at least one common epitope with PD-1. The complete PD-1 sequence can be found under GenBank Accession No. U64863 (SEQ ID NO:29).

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al. (2002) Curr. Opin. Immunol. 14: 391779-82; Bennett et al. (2003) J Immunol 170:711-8). The initial members of the family, CD28 and ICOS, were discovered by functional effects on augmenting T cell proliferation following the addition of monoclonal antibodies (Hutloff et al. Nature (1999); 397:263-266; Hansen et al. Immunogenics (1980); 10:247-260). PD-1 was discovered through screening for differential expression in apoptotic cells (Ishida et al. EMBO J (1992); 11:3887-95). The other members of the family, CTLA-4 and BTLA, were discovered through screening for differential expression in cytotoxic T lymphocytes and TH1 cells, respectively. CD28, ICOS and CTLA-4 all have an unpaired cysteine residue allowing for homodimerization. In contrast, PD-1 is suggested to exist as a monomer, lacking the unpaired cysteine residue characteristic in other CD28 family members.

The PD-1 gene is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E and Daeron, M (1997) Immunol Today 18:286-91). Although structurally similar to CTLA-4, PD-1 lacks the MYPPPY motif (SEQ ID NO: 32) that is critical for B7-1 and B7-2 binding. Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other CD28 family members. PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

Consistent with PD-1 being an inhibitory member of the CD28 family, PD-1 deficient animals develop various autoimmune phenotypes, including autoimmune cardiomyopathy and a lupus-like syndrome with arthritis and nephritis (Nishimura et al. (1999) Immunity 11:141-51; Nishimura et al. (2001) Science 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) J Exp Med 198:71-78; Prokunina and Alarcon-Riquelme (2004) Hum Mol Genet 13:R143; Nielsen et al. (2004) Lupus 13:510). In a murine B cell tumor line, the ITSM of PD-1 was shown to be essential to block BCR-mediated Ca.sup.2+-flux and tyrosine phosphorylation of downstream effector molecules (Okazaki et al. (2001) PNAS 98:13866-71).

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and 5 analogs having at least one common epitope with hPD-L1. The complete hPD-L1 sequence can be found under GenBank Accession No. Q9NZQ7.

The terms "Programmed Death Ligand-2" and "PD-L2" as used herein include human PD-L2 (hPD-L2), variants, isoforms, and species homologs of hPD-L2, and analogs having at least one common epitope with hPD-L2. The complete hPD-L2 sequence can be found under GenBank Accession No. Q9BQ51.

A "patient" as used herein includes any patient who is afflicted with a cancer (e.g., melanoma). The terms "subject" and "patient" are used interchangeably herein.

"Administering" refers to the physical introduction of a composition comprising a therapeutic agent to a subject, using any of the various methods and delivery systems known to those skilled in the art. Routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, in some embodiments, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

As used herein, "effective treatment" refers to treatment producing a beneficial effect, e.g., amelioration of at least one symptom of a disease or disorder. A beneficial effect can take the form of an improvement over baseline, i.e., an improvement over a measurement or observation made prior to initiation of therapy according to the method. A beneficial effect can also take the form of arresting, slowing, retarding, or stabilizing of a deleterious progression of a marker of solid tumor. Effective treatment may refer to alleviation of at least one symptom of a solid tumor. Such effective treatment may, e.g., reduce patient pain, reduce the size and/or number of lesions, may reduce or prevent metastasis of a tumor, and/or may slow tumor growth.

The term "effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to solid tumors, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay tumor development. In some embodiments, an effective amount is an amount sufficient to prevent or delay tumor recurrence. An effective amount can be administered in one or more administrations. The effective amount of the drug or composition may: (i) reduce the number of cancer cells; (ii) reduce tumor size; (iii) inhibit, retard, slow to some extent and may stop cancer cell infiltration into peripheral organs; (iv) inhibit (i.e., slow to some extent and may stop tumor metastasis; (v) inhibit tumor growth; (vi) prevent or delay occurrence and/or recurrence of tumor; and/or (vii) relieve to some extent one or more of the symptoms associated with the cancer. In one example, an "effective amount" is the amount of anti-LAG-3 antibody and the amount of anti-PD-1 antibody, in combination, clinically proven to affect a significant decrease in cancer or slowing of progression of cancer, such as an advanced solid tumor. As used herein, the terms "fixed dose", "flat dose" and "flat-fixed dose" are used interchangeably and refer to a dose that is administered to a patient without regard for the weight or body surface area (BSA) of the patient. The fixed or flat dose is therefore not provided as a mg/kg dose, but rather as an absolute amount of the agent (e.g., the anti-LAG-3 antibody and/or anti-PD-1 antibody).

The term "progression-free survival," which can be abbreviated as PFS, as used herein refers to the length of time during and after the treatment of a solid tumor (i.e., melanoma) that a patient lives with the disease but it does not get worse.

"Dosing interval," as used herein, means the amount of time that elapses between multiple doses of a formulation disclosed herein being administered to a subject. Dosing interval can thus be indicated as ranges.

The term "dosing frequency" as used herein refers to the frequency of administering doses of a formulation disclosed herein in a given time. Dosing frequency can be indicated as the number of doses per a given time, e.g., once a week or once in two weeks.

The use of the term "fixed dose" with regard to a composition of the invention means that two or more different antibodies in a single composition are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody to mg second antibody. For example, the 3:1 ratio of a first antibody and a second antibody can mean that a vial can contain about 240 mg of the first antibody and 80 mg of the second antibody or about 3 mg/ml of the first antibody and 1 mg/ml of the second antibody.

The use of the term "flat dose" with regard to the composition of the invention means a dose that is administered to a patient without regard for the weight or body surface area (BSA) of the patient. The flat dose is therefore not provided as a mg/kg dose, but rather as an absolute amount of the agent (e.g., the anti-LAG-3 antibody and/or anti-PD-1 antibody). For example, a 60 kg person and a 100 kg person would receive the same dose of the composition (e.g., 240 mg of an anti-PD-1 antibody and 80 mg of an anti-LAG-3 antibody in a single fixed dosing formulation vial containing both 240 mg of an anti-PD-1 antibody and 80 mg of an anti-LAG-3 antibody (or two fixed dosing formulation vials containing 120 mg of an anti-PD-1 antibody and 40 mg of an anti-LAG-3 antibody, etc.)).

The term "weight based dose" as referred to herein means that a dose that is administered to a patient is calculated based on the weight of the patient. For example, when a patient with 60 kg body weight requires 3 mg/kg of an anti-LAG-3 antibody in combination with 3 mg/kg of an anti-PD-1 antibody, one can draw the appropriate amounts of the anti-LAG-3 antibody (i.e., 180 mg) and the anti-PD-1 antibody (i.e., 180 mg) at once from a 1.1 ratio fixed dosing formulation of an anti-LAG3 antibody and an anti-PD-1 antibody.

The terms "about once a week," "once about every week," "once about every two weeks," or any other similar dosing interval terms as used herein means approximate number, and "about once a week" or "once about every week" can include every seven days±two days, i.e., every five days to every nine days. The dosing frequency of "once a week" thus can be every five days, every six days, every seven days, every eight days, or every nine days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

A "cancer" refers a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

The term "tumor" as used herein refers to any mass of tissue that results from excessive cell growth or proliferation, either benign (non-cancerous) or malignant (cancerous), including pre-cancerous lesions.

The term "LAG-3 positive" or "LAG-3 expression positive," relating to LAG-3 expression, refers to the proportion of cells in a test tissue sample comprising tumor cells and tumor-infiltrating inflammatory cells above which the tissue sample is scored as expressing LAG-3. In some embodiments, for LAG-3 expression assayed by immunohistochemistry (IHC), the LAG-3 positive tumor or LAG-3 expression positive tumor means that at least about 0.01%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, or 100% of the total number of cells express LAG-3. In other embodiments, for LAG-3 expression assayed by immunohistochemistry (IHC) or flow cytometry, the LAG-3 positive tumor or LAG-3 expression positive tumor means that at least about 0.01%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, or 100% of the total number of tumor-infiltrating inflammatory cells (e.g., T cells, CD8+ T cells, CD4+ T cells, FOXP3+ cells) express LAG-3. LAG-3 positive tumor or LAG-3 expression positive tumor can also be expressed herein as tumor expressing LAG-3. In some embodiments, the LAG-3 positive tumor or LAG-3 expression positive tumor means that at least about 0.1% to at least about 20% of the total number of cells express LAG-3. In some embodiments, a LAG-3 positive tumor or LAG-3 expression positive tumor means that at least about 0.1% to at least about 20% of the total number of tumor-infiltrating inflammatory cells (e.g., T cells, CD8+ T cells, CD4+ T cells, FOXP3+ cells) express LAG-3. In certain embodiments, a LAG-3 positive tumor or LAG-3 expression positive tumor means that at least about 0.1% to at least about 10% of the total number of cells express LAG-3. In certain embodiments, a LAG-3 positive tumor or LAG-3 expression positive tumor means that at least about 0.1% to at least about 10% of the total number of tumor-infiltrating inflammatory cells (e.g., T cells, CD8+ T cells, CD4+ T cells, FOXP3+ cells) express LAG-3. In some embodiments, a LAG-3 positive or LAG-3 expression positive tumor means that at least about 1% of the total number of cells express LAG-3 on the cell surface. In some embodiments, a LAG-3 positive or LAG-3 expression positive tumor means that at least about 1% of the total number of tumor-infiltrating inflammatory cells (e.g., T cells, CD8+ T cells, CD4+ T cells, FOXP3+ cells) express LAG-3 on the cell surface. In other embodiments, a LAG-3 positive or LAG-3 expression positive tumor means that at least about 5% of the total number of cells express LAG-3 on the cell surface. In other embodiments, a LAG-3 positive or LAG-3 expression positive tumor means that at least about 5% of the total number of tumor-infiltrating inflammatory cells (e.g., T cells, CD8+ T cells, CD4+ T cells, FOXP3+ cells) express LAG-3 on the cell surface. In one particular embodiment, LAG-3 positive or LAG-3 expression positive tumor means that at least about 1%, or in the range of 1-5% of the total number of cells express LAG-3 on the cell surface. In one particular embodiment, LAG-3 positive or LAG-3 expression positive tumor means that at least about 1%, or in the range of 1-5% of the total number of tumor-infiltrating inflammatory cells (e.g., T cells, CD8+ T cells, CD4+ T cells, FOXP3+ cells) express LAG-3 on the cell surface.

"LAG-3 negative" or "LAG-3 expression negative," refers to the lack of a detectable amount of LAG-3 expression. In some embodiments, for LAG-3 expression assayed by IHC, a LAG-3 negative tumor or LAG-3 expression negative tumor means that less than 0.01% of the total number of cells express a detectable level of LAG-3. In some embodiments, for LAG-3 expression assayed by IHC or flow cytometry, a LAG-3 negative tumor or LAG-3 expression negative tumor means that less than 0.01% of the total number of tumor-infiltrating inflammatory cells (e.g., T cells, CD8+ T cells, CD4+ T cells, FOXP3+ cells) express a detectable level of LAG-3. In some embodiments, for LAG-3 expression assayed by IHC, a LAG-3 negative tumor or LAG-3 expression negative tumor means that less than 1% of the total number of cells express a detectable level of LAG-3. In some embodiments, for LAG-3 expression assayed by IHC or flow cytometry, a LAG-3 negative tumor or LAG-3 expression negative tumor means that less than 1% of the total number of tumor-infiltrating inflammatory cells (e.g., T cells, CD8+ T cells, CD4+ T cells, FOXP3+ cells) express a detectable level of LAG-3. In some embodiments, a LAG-3 negative tumor or LAG-3 expression negative tumor means that zero (0) cells express a detectable level of LAG-3. In some embodiments, a LAG-3 negative or a LAG-3 expression negative tumor is any tumor other than a LAG-3 positive or a LAG-3 expression positive tumor.

The term "PD-L1 positive" or "PD-L1 expression positive," relating to cell surface PD-L1 expression, refers to the proportion of cells in a test tissue sample comprising tumor cells and tumor-infiltrating inflammatory cells above which the sample is scored as expressing cell surface PD-L1. For cell surface expression assayed by immunohistochemistry (IHC), e.g., with the mAb 28-8, the PD-L1 positive tumor or PD-L1 expression positive tumor means that at least about 0.01%, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, or at least about 30% of the total number of cells express PD-L1. PD-L1 positive tumor or PD-L1 expression positive tumor can also be expressed herein as tumor expressing PD-L1. In other embodiments, the PD-L1 positive tumor or PD-L1 expression positive tumor means that at least about 0.1% to at least about 20% of the total number of cells express PD-L1. In certain embodiments, the PD-L1 positive tumor or PD-L1 expression positive tumor means that at least about 0.1% to at least about 10% of the total number of cells express PD-L1. In some embodiments, the PD-L1 positive or PD-L1 expression positive tumor means that at least about 1% of the total number of cells express PD-L1 on the cell surface. In other embodiments, the PD-L1 positive or PD-L1 expression positive tumor means that at least about 5% of the total number of cells express PD-L1 on the cell surface. In one particular embodiment, PD-L1 positive or PD-L1 expression positive tumor means that at least about 1%, or in the range of 1-5% of the total number of cells express PD-L1 on the cell surface.

The term "PD-L1 negative" or "PD-L1 expression negative," relating to cell surface PD-L1 expression, refers to the proportion of cells in a test tissue sample comprising tumor cells and tumor-infiltrating inflammatory cells that are not PD-L1 positive or PD-L1 expression positive.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including antibodies, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

A "tumor-infiltrating inflammatory cell" is any type of cell that typically participates in an inflammatory response in a subject and which infiltrates tumor tissue. Such cells include tumor-infiltrating lymphocytes (TILs), macrophages, monocytes, eosinophils, histiocytes and dendritic cells.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 5th ed., 2013, Academic Press; and the Oxford Dictionary Of Biochemistry And Molecular Biology, 2006, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

Various aspects of the invention are described in further detail in the following subsections.

2. Methods of the Invention

In one aspect, the present invention is directed to a method for treating a LAG-3-positive malignant tumor (e.g., melanoma) in a subject in need thereof. A combination therapy of a LAG-3 inhibitor (e.g., anti-LAG-3 antibody) and a PD-1 pathway inhibitor (e.g., anti-PD-1 antibody) results in better therapeutic outcomes (e.g., objective response rate and disease control rate) in a patient population with LAG-3 positive malignant tumors (e.g., melanoma) than in a general patient population having a mix of LAG-3-negative malignant tumors and LAG-3-positive malignant tumors. In order to improve the treatment of malignant tumors, in one aspect, the present invention provides identifying a patient as having a LAG-3-positive tumor and providing an immunotherapy of a LAG-3 inhibitor (e.g., anti-LAG-3 antibody) and a PD-1 pathway inhibitor (e.g., anti-PD-1 antibody).

In another aspect, the present invention is directed to identifying a patient as having a LAG-3-positive tumor and treating the LAG-3 positive tumor by administering a PD-1 pathway inhibitor (e.g., an anti-PD-1 antibody) or a combination of a PD-1 pathway inhibitor and an immune checkpoint inhibitor. In one embodiment, the invention includes a method of identifying a patient as having a LAG-3-positive tumor and treating the LAG-3 positive tumor by administering an anti-PD-1 antibody. In one embodiment, the invention includes a method of identifying a patient as having a LAG-3-positive tumor and treating the LAG-3 positive tumor by administering an anti-PD-L1 antibody.

In another aspect, the present invention is directed to identifying a patient as having a LAG-3-positive tumor and treating the LAG-3 positive tumor by administering an anti-CTLA-4 antibody.

In one embodiment, the invention includes a method of selecting a malignant tumor in a human patient for immunotherapy, comprising: (a) determining the level of LAG-3 expression in a tumor sample; and (b) selecting the tumor for immunotherapy if the tumor is a LAG-3 positive tumor. In one embodiment, the invention includes a method of identifying a malignant tumor in a human patient as eligible for immunotherapy, comprising: (a) determining the level of LAG-3 expression in a tumor sample; and (b) identifying the tumor as eligible for immunotherapy if the tumor is a LAG-3 positive tumor. In one embodiment, the invention includes a method of identifying a malignant tumor in a human patient that is likely to be responsive to a immunotherapy, the method comprising: (a) determining the level of LAG-3 expression in a tumor sample; and (b) identifying the tumor as likely to be responsive to treatment if the tumor is a LAG-3 positive tumor. In one embodiment, the invention includes a method of identifying a malignant tumor in a human patient that is likely to be responsive to a immunotherapy, the method comprising: (a) determining the level of LAG-3 expression in a tumor sample; and (b) identifying the tumor as likely to be responsive to treatment if the tumor is a LAG-3 positive tumor. In one embodiment, the invention includes a method of classifying a malignant tumor in a human patient as likely to be responsive to a immunotherapy, the method comprising: (a) determining the level of LAG-3 expression in a tumor sample; and (b) classifying the tumor as likely to be responsive to immunotherapy if the tumor is a LAG-3 positive tumor. In some embodiments, the immunotherapy comprises contacting the tumor with a therapeutically effective amount of a LAG-3 inhibitor and a PD-1 pathway inhibitor. In some embodiments, the immunotherapy comprises contacting the tumor with a therapeutically effective amount of a LAG-3 inhibitor. In some embodiments, the immunotherapy comprises contacting the tumor with a therapeutically effective amount of a PD-1 pathway inhibitor. In some embodiments, the immunotherapy comprises contacting the tumor with a therapeutically effective amount of an anti-PD-1 antibody. In some embodiments, the immunotherapy comprises contacting the tumor with a therapeutically effective amount of an anti-PD-L1 antibody. In some embodiments, the immunotherapy comprises contacting the tumor with a therapeutically effective amount of an anti-CTLA-4 antibody. In some embodiments, the immunotherapy comprises contacting the tumor with a therapeutically effective amount of a PD-1 pathway inhibitor and an immune checkpoint inhibitor. In some embodiments, the method comprises contacting the tumor with a therapeutically effective amount of a LAG-3 inhibitor and a PD-1 pathway inhibitor. In some embodiments, the method comprises contacting the tumor with a therapeutically effective amount of a LAG-3 inhibitor. In some embodiments, the method comprises contacting the tumor with a therapeutically effective amount of a PD-1 pathway inhibitor. In some embodiments, the method comprises contacting the tumor with a therapeutically effective amount of an anti-PD-1 antibody. In some embodiments, the method comprises contacting the tumor with a therapeutically effective amount of an anti-PD-L1 antibody. In some embodiments, the method comprises contacting the tumor with a therapeutically effective amount of an anti-CTLA-4 antibody. In some embodiments, the method comprises contacting the tumor with a therapeutically effective amount of a PD-1 pathway inhibitor and an immune checkpoint inhibitor. In some embodiments, the method comprises administering to the patient a therapeutically effective amount of a LAG-3 inhibitor and a PD-1 pathway inhibitor. In some embodiments, the method comprises administering to the patient a therapeutically effective amount of a LAG-3 inhibitor. In some embodiments, the method comprises administering to the patient a therapeutically effective amount of a PD-1 pathway inhibitor. In some embodiments, the method comprises administering to the patient a therapeutically effective amount of an anti-CTLA-4 antibody. In some embodiments, the method comprises administering to the patient a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In certain embodiments, any of the present methods further comprise determining PD-L1 expression in the tumor sample.

In one embodiment, the invention includes a method of identifying a patient with a malignant tumor who is likely to respond to a immunotherapy, the method comprising: (a) determining the level of LAG-3 expression in a tumor sample; and (b) identifying the patient who is likely to respond to treatment if the tumor is a LAG-3 positive tumor. In one embodiment, the invention includes a method of selecting a patient with a malignant tumor for immunotherapy, the method comprising: (a) determining the level of LAG-3 expression in a tumor sample; and (b) selecting the patient for immunotherapy if the tumor is a LAG-3 positive tumor. In some embodiments, the immunotherapy comprises contacting the tumor with a therapeutically effective amount of a LAG-3 inhibitor and a PD-1 pathway inhibitor. In some embodiments, the immunotherapy comprises contacting the tumor with a therapeutically effective amount of a LAG-3 inhibitor. In some embodiments, the immunotherapy comprises contacting the tumor with a therapeutically effective amount of a PD-1 pathway inhibitor. In some embodiments, the immunotherapy comprises contacting the tumor with a therapeutically effective amount of an anti-PD-1 antibody. In some embodiments, the immunotherapy comprises contacting the tumor with a therapeutically effective amount of an anti-PD-L1 antibody. In some embodiments, the immunotherapy comprises contacting the tumor with a therapeutically effective amount of an anti-CTLA-4 antibody. In some embodiments, the immunotherapy comprises contacting the tumor with a therapeutically effective amount of a PD-1 pathway inhibitor and an immune checkpoint inhibitor. In some embodiments, the method comprises contacting the tumor with a therapeutically effective amount of a LAG-3 inhibitor and a PD-1 pathway inhibitor. In some embodiments, the method comprises contacting the tumor with a therapeutically effective amount of a LAG-3 inhibitor.

In some embodiments, the method comprises contacting the tumor with a therapeutically effective amount of a PD-1 pathway inhibitor. In some embodiments, the method comprises contacting the tumor with a therapeutically effective amount of an anti-PD-1 antibody. In some embodiments, the method comprises contacting the tumor with a therapeutically effective amount of an anti-PD-L1 antibody. In some embodiments, the method comprises contacting the tumor with a therapeutically effective amount of an anti-CTLA-4 antibody. In some embodiments, the method comprises contacting the tumor with a therapeutically effective amount of a PD-1 pathway inhibitor and an immune checkpoint inhibitor. In some embodiments, the method comprises administering to the patient a therapeutically effective amount of a LAG-3 inhibitor and a PD-1 pathway inhibitor. In some embodiments, the method comprises administering to the patient a therapeutically effective amount of a LAG-3 inhibitor. In some embodiments, the method comprises administering to the patient a therapeutically effective amount of a PD-1 pathway inhibitor. In some embodiments, the method comprises administering to the patient a therapeutically effective amount of an anti-CTLA-4 antibody. In some embodiments, the method comprises administering to the patient a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In certain embodiments, any of the present methods further comprise determining PD-L1 expression in the tumor sample.

In one embodiment, the invention includes a method of treating a malignant tumor in a human patient, comprising: administering to the patient an immunotherapy disclosed herein; wherein the patient is predicted to respond to treatment with the LAG-3 inhibitor and PD-1 pathway inhibitor based upon LAG-3 expression or based upon LAG-3 and PD-L1 expression in a sample of the patient's tumor. In some embodiments, the LAG-3 inhibitor is an anti-LAG-3 antibody and the PD-1 pathway inhibitor is an anti-PD-1 antibody.

In one embodiment, the invention includes a method of treating a malignant tumor in a human patient in need thereof, comprising: (a) determining the level of LAG-3 expression or the level of LAG-3 and PD-L1 expression in a tumor sample; and (b) administering to the patient a therapeutically effective amount of a LAG-3 inhibitor if the tumor is a LAG-3 positive tumor or a LAG-3 positive PD-L1 positive tumor. In one embodiment, the invention includes a method for treating a malignant tumor in a human patient in need thereof, comprising: (a) identifying the patient as having a LAG-3 positive malignant tumor or a LAG-3 positive PD-L1 positive malignant tumor; and (b) administering to the patient a therapeutically effective amount of a LAG-3 inhibitor. In one embodiment, the invention includes a method for treating a malignant tumor in a human patient in need thereof comprising administering to the patient a therapeutically effective amount of a LAG-3 inhibitor, wherein the patient is identified as having a LAG-3 positive malignant tumor or a LAG-3 positive PD-L1 positive malignant tumor prior to the administration. In some embodiments, the LAG-3 positive tumor is a LAG-3 positive PD-L1 negative tumor. In some embodiments, the LAG-3 positive malignant tumor is a LAG-3 positive PD-L1 negative malignant tumor. In some embodiments, the LAG-3 inhibitor is an anti-LAG-3 antibody.

In one embodiment, the invention includes a method of treating a malignant tumor in a human patient in need thereof, comprising: (a) determining the level of LAG-3 expression or the level of LAG-3 and PD-L1 expression in a tumor sample; and (b) administering to the patient a therapeutically effective amount of a PD-1 pathway inhibitor if the tumor is a LAG-3 positive tumor or a LAG-3 positive PD-L1 positive tumor. In one embodiment, the invention includes a method for treating a malignant tumor in a human patient in need thereof, comprising: (a) identifying the patient as having a LAG-3 positive malignant tumor or a LAG-3 positive PD-L1 positive malignant tumor; and (b) administering to the patient a therapeutically effective amount of a PD-1 pathway inhibitor. In one embodiment, the invention includes a method for treating a malignant tumor in a human patient in need thereof comprising administering to the patient a therapeutically effective amount of a PD-1 pathway inhibitor, wherein the patient is identified as having a LAG-3 positive malignant tumor or a LAG-3 positive PD-L1 positive malignant tumor prior to the administration. In some embodiments, the PD-1 pathway inhibitor is an anti-PD-1 antibody. In some embodiments, the PD-1 pathway inhibitor is an anti-PD-L1 antibody. In some embodiments, the LAG-3 positive tumor is a LAG-3 positive PD-L1 negative tumor. In some embodiments, the LAG-3 positive malignant tumor is a LAG-3 positive PD-L1 negative malignant tumor.

In one embodiment, the invention includes a method of treating a malignant tumor in a human patient in need thereof, comprising: (a) determining the level of LAG-3 expression or the level of LAG-3 and PD-L1 expression in a tumor sample; and (b) administering to the patient a therapeutically effective amount of an anti-CTLA-4 antibody if the tumor is a LAG-3 positive tumor or a LAG-3 positive PD-L1 positive tumor. In one embodiment, the invention includes a method for treating a malignant tumor in a human patient in need thereof, comprising: (a) identifying the patient as having a LAG-3 positive malignant tumor or a LAG-3 positive PD-L1 positive malignant tumor; and (b) administering to the patient a therapeutically effective amount of an anti-CTLA-4 antibody. In one embodiment, the invention includes a method for treating a malignant tumor in a human patient in need thereof comprising administering to the patient a therapeutically effective amount of an anti-CTLA-4 antibody, wherein the patient is identified as having a LAG-3 positive malignant tumor or a LAG-3 positive PD-L1 positive malignant tumor prior to the administration. In some embodiments, the LAG-3 positive tumor is a LAG-3 positive PD-L1 negative tumor. In some embodiments, the LAG-3 positive malignant tumor is a LAG-3 positive PD-L1 negative malignant tumor.

In one embodiment, the invention includes a method of treating a malignant tumor in a human patient in need thereof, comprising: (a) determining the level of LAG-3 expression or the level of LAG-3 and PD-L1 expression in a tumor sample; and (b) administering to the patient a therapeutically effective amount of a LAG-3 inhibitor and PD-1 pathway inhibitor if the tumor is a LAG-3 positive tumor or a LAG-3 positive PD-L1 positive tumor. In one embodiment, the invention includes a method for treating a malignant tumor in a human patient in need thereof, comprising: (a) identifying the patient as having a LAG-3 positive malignant tumor or a LAG-3 positive PD-L1 positive malignant tumor; and (b) administering to the patient a therapeutically effective amount of a LAG-3 inhibitor and a PD-1 pathway inhibitor. In one embodiment, the invention includes a method for treating a malignant tumor in a human patient in need thereof comprising administering to the patient a therapeutically effective amount of a LAG-3 inhibitor and a PD-1 pathway inhibitor, wherein the patient is identified as having a LAG-3 positive malignant tumor or a LAG-3 positive PD-L1 positive malignant tumor prior to the administration. In some embodiments, the LAG-3 positive tumor is a LAG-3 positive PD-L1 negative tumor. In some embodiments, the LAG-3 positive malignant tumor is a LAG-3 positive PD-L1 negative malignant tumor. In some embodiments, the LAG-3 inhibitor is an anti-LAG-3 antibody and the PD-1 pathway inhibitor is an anti-PD-L1 antibody. In some embodiments, the LAG-3 inhibitor is an anti-LAG-3 antibody and the PD-1 pathway inhibitor is an anti-PD-1 antibody.

In one embodiment, the invention includes a method of treating a malignant tumor in a human patient in need thereof, comprising: (a) determining the level of LAG-3 expression or the level of LAG-3 and PD-L1 expression in a tumor sample; and (b) administering to the patient a therapeutically effective amount of a PD1 pathway inhibitor and an immune checkpoint inhibitor if the tumor is a LAG-3 positive tumor or a LAG-3 positive PD-L1 positive tumor. In one embodiment, the invention includes a method for treating a malignant tumor in a human patient in need thereof, comprising: (a) identifying the patient as having a LAG-3 positive malignant tumor or a LAG-3 positive PD-L1 positive malignant tumor; and (b) administering to the patient a therapeutically effective amount of a PD1 pathway inhibitor and an immune checkpoint inhibitor. In one embodiment, the invention includes a method for treating a malignant tumor in a human patient in need thereof comprising administering to the patient a therapeutically effective amount of a PD1 pathway inhibitor and an immune checkpoint inhibitor, wherein the patient is identified as having a LAG-3 positive malignant tumor or a LAG-3 positive PD-L1 positive malignant tumor prior to the administration. In some embodiments, the LAG-3 positive tumor is a LAG-3 positive PD-L1 negative tumor. In some embodiments, the LAG-3 positive malignant tumor is a LAG-3 positive PD-L1 negative malignant tumor. In some embodiments, the PD-1 pathway inhibitor is an anti-PD-L1 antibody. In some embodiments, the PD-1 pathway inhibitor is an anti-PD-1 antibody.

In another embodiment, the invention includes a method for treating a malignant tumor in a human patient in need thereof comprising administering to the patient an immunotherapy disclosed herein, wherein the patient is identified as having a LAG-3 positive malignant tumor or a LAG-3 positive PD-L1 positive malignant tumor prior to the administration. In some embodiments, the LAG-3 positive malignant tumor is a LAG-3 positive PD-L1 negative malignant tumor. In some embodiments, the immunotherapy comprises administering a therapeutically effective amount of a LAG-3 inhibitor and a PD-1 pathway inhibitor. In some embodiments, the immunotherapy comprises administering a therapeutically effective amount of a LAG-3 inhibitor. In some embodiments, the immunotherapy comprises administering a therapeutically effective amount of a PD-1 pathway inhibitor. In some embodiments, the immunotherapy comprises administering a therapeutically effective amount of an anti-CTLA-4 antibody. In some embodiments, the immunotherapy comprises administering a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-L1 antibody. In some embodiments, the LAG-3 inhibitor is an anti-LAG-3 antibody and the PD-1 pathway inhibitor is an anti-PD-1 antibody.

In certain embodiments, the invention includes method for extending a progression-free survival period for over 12 months in a human patient afflicted with a malignant tumor comprising administering to the patient an immunotherapy disclosed herein, wherein the patient is identified as having a LAG-3 positive malignant tumor or a LAG-3 positive PD-L1 positive malignant tumor prior to the administration and wherein the patient demonstrates progression-free survival for over 12 months. In some embodiments, the LAG-3 positive malignant tumor is a LAG-3 positive PD-L1 negative malignant tumor. In some embodiments, the progression-free survival of the patient can be extended, after the administration, for over about 13 months, about 14 months, about 15 months, about 16 months, about 17 months, about 18 months, about 2 years, about 3 years, about 4 years, about 5 years, about 6 years, about 7 years, about 8 years, about 9 years, or about 10 years. In some embodiments, the immunotherapy comprises administering a therapeutically effective amount of a LAG-3 inhibitor and a PD-1 pathway inhibitor. In some embodiments, the immunotherapy comprises administering a therapeutically effective amount of a LAG-3 inhibitor. In some embodiments, the immunotherapy comprises administering a therapeutically effective amount of a PD-1 pathway inhibitor. In some embodiments, the immunotherapy comprises administering a therapeutically effective amount of an anti-CTLA-4 antibody. In some embodiments, the immunotherapy comprises administering a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In some embodiments, the LAG-3 inhibitor is an anti-LAG-3 antibody and the PD-1 pathway inhibitor is an anti-PD-L1 antibody.

In still other embodiments, the invention is includes a method for reducing a tumor size at least by 10% in a human patient afflicted with a malignant tumor comprising administering to the patient an immunotherapy disclosed herein, wherein the patient is identified as having a LAG-3 positive malignant tumor (e.g., melanoma) or a LAG-3 positive PD-L1 positive malignant tumor prior to the administration and wherein the administration reduces the tumor size at least about 10%, about 20%, about 30%, about 40%, about 50%, about 60%, about 70%, about 80%, about 90%, or 100% compared to the tumor size prior to the administration. In some embodiments, the method comprises identifying the patient as having a LAG-3 positive malignant tumor or a LAG-3 positive PD-L1 positive malignant tumor prior to the administration. In some embodiments, the LAG-3 positive malignant tumor is a LAG-3 positive PD-L1 negative malignant tumor. In some embodiments, the immunotherapy comprises administering a therapeutically effective amount of a LAG-3 inhibitor and a PD-1 pathway inhibitor. In some embodiments, the immunotherapy comprises administering a therapeutically effective amount of a LAG-3 inhibitor. In some embodiments, the immunotherapy comprises administering a therapeutically effective amount of a PD-1 pathway inhibitor. In some embodiments, the immunotherapy comprises administering a therapeutically effective amount of an anti-PD-1 antibody. In some embodiments, the immunotherapy comprises administering a therapeutically effective amount of an anti-PD-L1 antibody. In some embodiments, the immunotherapy comprises administering a therapeutically effective amount of an anti-CTLA-4 antibody. In some embodiments, the immunotherapy comprises administering a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In some embodiments, the LAG-3 inhibitor is an anti-LAG-3 antibody and the PD-1 pathway inhibitor is an anti-PD-L1 antibody.

The invention can also include a method of preventing a relapse and/or inducing a remission in a patient comprising administering to the patient an immunotherapy disclosed herein, wherein the patient is identified as having a LAG-3-positive malignant tumor (e.g., melanoma) or a LAG-3 positive PD-L1 positive malignant tumor prior to the administration. In some embodiments, the method of the invention comprises (i) identifying a patient as having a LAG-3-positive malignant tumor or a LAG-3 positive PD-L1 positive malignant tumor; (ii) administering to the patient an immunotherapy disclosed herein. In some embodiments, the immunotherapy comprises administering a therapeutically effective amount of a LAG-3 inhibitor and a PD-1 pathway inhibitor. In some embodiments, the LAG-3 positive malignant tumor is a LAG-3 positive PD-L1 negative malignant tumor. In some embodiments, the immunotherapy comprises administering a therapeutically effective amount of a LAG-3 inhibitor. In some embodiments, the immunotherapy comprises administering a therapeutically effective amount of a PD-1 pathway inhibitor. In some embodiments, the immunotherapy comprises administering a therapeutically effective amount of an anti-PD-1 antibody. In some embodiments, the immunotherapy comprises administering a therapeutically effective amount of an anti-PD-L1 antibody. In some embodiments, the immunotherapy comprises administering a therapeutically effective amount of an anti-CTLA-4 antibody. In some embodiments, the immunotherapy comprises administering a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In some embodiments, the LAG-3 inhibitor is an anti-LAG-3 antibody and the PD-1 pathway inhibitor is an anti-PD-L1 antibody.

In certain embodiments, the invention includes a method for increasing an objective response rate to be higher than 55% in a patient population, wherein each patient of the patient population is afflicted with a malignant tumor, in a cancer treatment comprising administering to the patient an immunotherapy disclosed herein, wherein each patient is identified as having a LAG-3 positive malignant tumor (e.g., melanoma) or a LAG-3 positive PD-L1 positive malignant tumor prior to the administration and wherein the objective response rate is higher than 55%, 60%, 65%, 70%, or 75%. In some embodiments, the method comprises identifying the patient as having a LAG-3 positive malignant tumor or a LAG-3 positive PD-L1 positive malignant tumor prior to the administration. In some embodiments, the LAG-3 positive malignant tumor is a LAG-3 positive PD-L1 negative malignant tumor. In some embodiments, the immunotherapy comprises administering a therapeutically effective amount of a LAG-3 inhibitor and a PD-1 pathway inhibitor. In some embodiments, the immunotherapy comprises administering a therapeutically effective amount of a LAG-3 inhibitor and an anti-PD-1 antibody. In some embodiments, the immunotherapy comprises administering a therapeutically effective amount of a LAG-3 inhibitor and an anti-PD-L1 antibody. In some embodiments, the immunotherapy comprises administering a therapeutically effective amount of a LAG-3 inhibitor. In some embodiments, the immunotherapy comprises administering a therapeutically effective amount of a PD-1 pathway inhibitor. In some embodiments, the immunotherapy comprises administering a therapeutically effective amount of an anti-CTLA-4 antibody. In some embodiments, the immunotherapy comprises administering a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In some embodiments, the LAG-3 inhibitor is an anti-LAG-3 antibody and the PD-1 pathway inhibitor is an anti-PD-L1 antibody.

In certain embodiments, the invention includes a method for increasing a disease control rate to be higher than 55% in a patient population, wherein each patient of the patient population is afflicted with a malignant tumor, in a cancer treatment comprising administering to the patient an immunotherapy disclosed herein, wherein each patient is identified as having a LAG-3 positive malignant tumor (e.g., melanoma) or a LAG-3 positive PD-L1 positive malignant tumor prior to the administration and wherein the disease control rate is higher than 55%, 60%, 65%, 70%, or 75%. In some embodiments, the method comprises identifying the patient as having a LAG-3 positive malignant tumor or a LAG-3 positive PD-L1 positive malignant tumor prior to the administration. In some embodiments, the LAG-3 positive malignant tumor is a LAG-3 positive PD-L1 negative malignant tumor. In some embodiments, the immunotherapy comprises administering a therapeutically effective amount of a LAG-3 inhibitor and a PD-1 pathway inhibitor. In some embodiments, the immunotherapy comprises administering a therapeutically effective amount of a LAG-3 inhibitor. In some embodiments, the immunotherapy comprises administering a therapeutically effective amount of a PD-1 pathway inhibitor. In some embodiments, the immunotherapy comprises administering a therapeutically effective amount of an anti-PD-1 antibody. In some embodiments, the immunotherapy comprises administering a therapeutically effective amount of an anti-PD-L1 antibody. In some embodiments, the immunotherapy comprises administering a therapeutically effective amount of an anti-CTLA-4 antibody. In some embodiments, the immunotherapy comprises administering a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In some embodiments, the LAG-3 inhibitor is an anti-LAG-3 antibody and the PD-1 pathway inhibitor is an anti-PD-L1 antibody.

In other embodiments, each patient in the methods experiences (i) extended progression-free survival for over 12 months, (ii) tumor size reduction at least about 10%, about 20%, about 30%, about 40%, or about 50% compared to the tumor size prior to the administration, or (iii) both. In some embodiments, the patient population can be at least 100 patients having a LAG-3 positive malignant tumor (e.g., melanoma) or a LAG-3 positive PD-L1 positive malignant tumor. In some embodiments, the patient population can be at least 200, 300, 400, 500, 600, 700, 800, 900, or 1000 patients having a LAG-3 positive malignant tumor or a LAG-3 positive PD-L1 positive malignant tumor. In some embodiments, the LAG-3 positive malignant tumor is a LAG-3 positive PD-L1 negative malignant tumor.

In further embodiments, the invention provides a method for selecting a human patient suitable for a combination therapy comprising: (a) identifying a patient as having a LAG-3 positive malignant tumor or a LAG-3 positive PD-L1 positive malignant tumor; and (b) instructing a healthcare provider to administer to the patient an immunotherapy disclosed herein. In some embodiments, the LAG-3 positive malignant tumor is a LAG-3 positive PD-L1 negative malignant tumor. The method can further comprise administering an immunotherapy disclosed herein. In some embodiments, the immunotherapy comprises administering a therapeutically effective amount of a LAG-3 inhibitor and a PD-1 pathway inhibitor. In some embodiments, the immunotherapy comprises administering a therapeutically effective amount of a LAG-3 inhibitor. In some embodiments, the immunotherapy comprises administering a therapeutically effective amount of a PD-1 pathway inhibitor. In some embodiments, the immunotherapy comprises administering to the patient a therapeutically effective amount of an anti-PD-1 antibody. In some embodiments, the immunotherapy comprises administering to the patient a therapeutically effective amount of an anti-PD-L1 antibody. In some embodiments, the immunotherapy comprises administering a therapeutically effective amount of an anti-CTLA-4 antibody. In some embodiments, the immunotherapy comprises administering a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In some embodiments, the LAG-3 inhibitor is an anti-LAG-3 antibody and the PD-1 pathway inhibitor is an anti-PD-L1 antibody. In some embodiments, the administration treats the malignant tumor.

The methods of the invention, as a result of the administration of an immunotherapy disclosed herein, can treat the malignant tumor, reduce the tumor size, prevent growth of the tumor, eliminate the tumor from the patient, prevent a relapse of a tumor, induce a remission in a patient, or any combination thereof. In certain embodiments, the administration of an immunotherapy disclosed herein induces a complete response. In other embodiments, the administration of the immunotherapy disclosed herein induces a partial response. In some embodiments, the immunotherapy comprises administering a therapeutically effective amount of a LAG-3 inhibitor and a PD-1 pathway inhibitor. In some embodiments, the immunotherapy comprises administering a therapeutically effective amount of a LAG-3 inhibitor. In some embodiments, the immunotherapy comprises administering a therapeutically effective amount of a PD-1 pathway inhibitor. In some embodiments, the immunotherapy comprises administering to the patient a therapeutically effective amount of an anti-PD-1 antibody. In some embodiments, the immunotherapy comprises administering to the patient a therapeutically effective amount of an anti-PD-L1 antibody. In some embodiments, the immunotherapy comprises administering to the patient a therapeutically effective amount of an anti-CTLA-4 antibody. In some embodiments, the immunotherapy comprises administering a therapeutically effective amount of a PD-1 pathway inhibitor and an immune checkpoint inhibitor. In some embodiments, the LAG-3 inhibitor is an anti-LAG-3 antibody and the PD-1 pathway inhibitor is an anti-PD-1 antibody. In some embodiments, the LAG-3 inhibitor is an anti-LAG-3 antibody and the PD-1 pathway inhibitor is an anti-PD-L1 antibody.

In some embodiments, the LAG-3 positive tumor comprises at least about 1%, at least about 2%, at least about 3%, at least about 4%, at least about 5%, at least about 7%, at least about 10%, at least about 15%, at least about 20%, at least about 25%, at least about 30%, at least about 40%, at least about 50%, at least about 60%, at least about 70%, at least about 80%, at least about 90%, or 100% cells expressing LAG-3. In some embodiments, the cells expressing LAG-3 comprise tumor infiltrating lymphocytes.

In some embodiments, the identifying comprises determining LAG-3 expression in a malignant tumor.

In some embodiments, LAG-3 expression is determined by receiving the results of an assay capable of determining LAG-3 expression.

In certain embodiments, any of the present methods further comprise determining PD-L1 expression in the tumor sample.

In certain embodiments, any of the present methods further comprise identifying the patient as having a PD-L1 positive malignant tumor prior to the administration. In certain embodiments, any of the present methods further comprise identifying the patient as having a PD-L1 negative malignant tumor prior to the administration.

In certain embodiments, any of the present methods further comprise determining PD-L1 expression in the malignant tumor.

In certain embodiments of any of the present methods, the patient is identified as having a PD-L1 positive malignant tumor prior to the administration. In certain embodiments of any of the present methods, the patient is identified as having a PD-L1 negative malignant tumor prior to the administration.

Method for determining PD-L1 expression in a tumor sample, methods for identifying the patient as having a PD-L1 positive malignant tumor, and methods for determining PD-L1 expression in a malignant tumor have been disclosed in PCT/US2016/029878.

In certain embodiments, the methods of the invention include methods of treating a human patient with unresectable or metastatic melanoma in need thereof with a combination of a PD-1 pathway inhibitor and a LAG-3 inhibitor, wherein the patient was previously treated with an anti-PD-1 inhibitor and/or an anti-PD-L1 inhibitor. In certain embodiments, the PD-1 pathway inhibitor is an anti-PD-1 antibody. In particular embodiments, the anti-PD-1 antibody is nivolumab. In some embodiments, the LAG-3 inhibitor is an anti-LAG-3 antibody. In certain embodiments, the LAG-3 antibody is BMS-986016. In embodiments, the melanoma is a LAG-3 expressing tumor. In particular embodiments, the melanoma is a LAG-3 expression tumor, with LAG-3 expression ≥1%.

Measurement of LAG-3 Expression

In certain embodiments, identifying a patient suitable for a LAG-3 inhibitor/PD-1 pathway inhibitor combination therapy, a PD-1 pathway inhibitor (e.g., an anti-PD-1 antibody) therapy, or an anti-CTLA-4 antibody therapy for the present methods includes measuring or assessing a LAG-3 expression in a sample, for example, a malignant tumor test tissue sample comprising tumor cells and tumor infiltrating inflammatory cells. The phrases "tumors expressing LAG-3," "LAG-3 expressing tumor," "LAG-3 positive tumor," and "LAG-3 expression positive tumor" are used interchangeably herein and encompass tumors comprising LAG-3 expressing tumor-infiltrating lymphocytes. The meaning of the phrases is provided elsewhere herein. The methods of measuring or assessing the LAG-3 expression can be achieved by any methods applicable.

In order to assess the LAG-3 expression, in one embodiment, a test tissue sample is obtained from the patient who is in need of the therapy. In some embodiments, a test tissue sample includes, but is not limited to, any clinically relevant tissue sample, such as a tumor biopsy, a core biopsy tissue sample, a fine needle aspirate, or a sample of bodily fluid, such as blood, plasma, serum, lymph, ascites fluid, cystic fluid, or urine. In some embodiments, the test tissue sample is from a primary tumor. In some embodiments, the test tissue sample is from a metastasis. In some embodiments, test tissue samples are taken from a subject at multiple time points, for example, before treatment, during treatment, and/or after treatment. In some embodiments, test tissue samples are taken from different locations in the subject, for example, a sample from a primary tumor and a sample from a metastasis in a distant location.

In some embodiments, the test tissue sample is a paraffin-embedded fixed tissue sample. In some embodiments, the test tissue sample is a formalin-fixed paraffin embedded (FFPE) tissue sample. In some embodiments, the test tissue sample is a fresh tissue (e.g., tumor) sample. In some embodiments, the test tissue sample is a frozen tissue sample. In some embodiments, the test tissue sample is a fresh frozen (FF) tissue (e.g., tumor) sample. In some embodiments, the test tissue sample is a cell isolated from a fluid. In some embodiments, the test tissue sample comprises circulating tumor cells (CTCs). In some embodiments, the test tissue sample comprises tumor-infiltrating lymphocytes (TILs). In some embodiments, the test tissue sample comprises tumor cells and tumor-infiltrating lymphocytes (TILs). In some embodiments, the test tissue sample comprises circulating lymphocytes. In some embodiments, the test tissue sample is an archival tissue sample. In some embodiments, the test tissue sample is an archival tissue sample with known diagnosis, treatment, and/or outcome history. In some embodiments, the sample is a block of tissue. In some embodiments, the test tissue sample is dispersed cells. In some embodiments, the sample size is from about 1 cell to about $1\times10^6$ cells or more. In some embodiments, the sample size is about 1 cell to about $1\times10^5$ cells. In some embodiments, the sample size is about 1 cell to about 10,000 cells. In some embodiments, the sample size is about 1 cell to about 1,000 cells. In some embodiments, the sample size is about 1 cells to about 100 cells. In some embodiments, the sample size is about 1 cell to about 10 cells. In some embodiments, the sample size is a single cell.

In another embodiment, the assessment of LAG-3 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express LAG-3 on the surface of the cells based on an assessment that the proportion of cells in the test tissue sample that express LAG-3 on the cell surface is higher than a predetermined threshold level.

In any of the methods comprising the measurement of LAG-3 expression in a test tissue sample, however, it should be understood that the step comprising the provision of a test tissue sample obtained from a patient is an optional step. That is, in certain embodiments the method includes this step, and in other embodiments, this step is not included in the method. It should also be understood that in certain embodiments the "measuring" or "assessing" step to identify, or determine the number or proportion of, cells in the test tissue sample that express LAG-3 is performed by a transformative method of assaying for LAG-3 expression, for example by performing a reverse transcriptase-polymerase chain reaction (RT-PCR) assay or an IHC assay. In certain other embodiments, no transformative step is involved and LAG-3 expression is assessed by, for example, reviewing a report of test results from a laboratory. In some embodiments, LAG-3 expression is assessed by reviewing the results of an immunohistochemistry assay from a laboratory. In certain embodiments, the steps of the methods up to, and including, assessing LAG-3 expression provides an intermediate result that may be provided to a physician or other healthcare provider for use in selecting a suitable candidate for the combination therapy of a LAG-3 inhibitor and a PD-1 pathway inhibitor. In certain embodiments, the steps of the methods up to, and including, assessing LAG-3 expression provides an intermediate result that may be provided to a physician or other healthcare provider for use in selecting a suitable candidate for PD-1 pathway inhibitor (e.g., anti-PD-1 antibody) therapy. In certain embodiments, the steps of the methods up to, and including, assessing LAG-3 expression provides an intermediate result that may be provided to a physician or other healthcare provider for use in selecting a suitable candidate for anti-CTLA-4 antibody therapy. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express LAG-3 is assessed by performing an assay to detect the presence of LAG-3 RNA. In further embodiments, the presence of LAG-3 RNA is detected by RT-PCR, in situ hybridization or RNase protection. In some embodiments, the presence of LAG-3 RNA is detected by an RT-PCR based assay. In some embodiments, scoring the RT-PCR based assay comprises assessing the level of LAG-3 RNA expression in the test tissue sample relative to a predetermined level.

In other embodiments, the proportion of cells that express LAG-3 is assessed by performing an assay to detect the presence of LAG-3 polypeptide. In further embodiments, the presence of LAG-3 polypeptide is detected by IHC, enzyme-linked immunosorbent assay (ELISA), in vivo imaging, or flow cytometry. In some embodiments, LAG-3 expression is assayed by IHC. In other embodiments of all of these methods, cell surface expression of LAG-3 is assayed using, e.g., IHC or in vivo imaging.

In embodiments, the biomarker measured is LAG-3, CD4, CD8, FOXP3, CD163 CD68, and any combination thereof. In embodiments, the biomarker is measured using any detection method disclosed herein. In other embodiments, the proportion of cells that express LAG-3 in the test tissue sample is assessed by flow cytometry. In some embodiments, the test tissue sample assayed by flow cytometry comprises tumor infiltrating immune cells. In some embodiments, the malignant tumor is a hematological malignancy and the tissue sample assayed by flow cytometry comprises peripheral blood cells. In some embodiments, the flow cytometry is a multiplex assay. In some embodiments, scoring the flow cytometry comprises detecting the expression of markers comprising LAG-3, CD4, CD8, FOXP3, and any combination thereof. In some embodiments, LAG-3, CD4, CD8, and FOXP3 are detected as single markers. In some embodiments, scoring the flow cytometry comprises assessing the proportion of T cells in the test tissue sample that express LAG-3. In some embodiments, scoring the flow cytometry comprises assessing the proportion of CD8+ T cells in the test tissue sample that express LAG-3. In some embodiments, scoring the flow cytometry comprises assessing the proportion of CD4+ T cells in the test tissue sample that express LAG-3. In some embodiments, scoring the flow cytometry comprises assessing the proportion of FOXP3+ T cells in the test tissue sample that express LAG-3. In some embodiments, scoring the flow cytometry comprises detecting the expression of markers comprising CD163 and/or CD68. In some embodiments, scoring the flow cytometry comprises assessing the proportion of cells in the test tissue sample that express CD163 and/or CD68.

In certain embodiments of any of the present methods, the proportion of cells that express LAG-3 in the test tissue sample is assessed by performing an assay to detect the presence of LAG-3 polypeptide. In some embodiments, the presence of LAG-3 polypeptide is detected by an immunohistochemistry assay. In some embodiments, the test tissue sample is a tumor biopsy. In some embodiments, the test tissue sample is a formalin-fixed paraffin embedded (FFPE) sample.

In some embodiments, the immunohistochemistry assay is a monoplex assay. In some embodiments, the immunohistochemistry assay is a multiplex assay. In some embodiments, the multiplex immunohistochemistry assay is capable of detecting the presence of CD4, CD8, FOXP3, CD163, CD68, or any combination thereof.

In some embodiments, the immunohistochemistry assay comprises contacting the tumor sample with the 17B4 mouse anti-human LAG-3 IgG1 monoclonal antibody. In some embodiments, the immunohistochemistry assay comprises contacting the tumor sample with an anti-LAG-3 antibody comprising heavy and light chain variable regions comprising the sequences set forth in SEQ ID NOs: 3 and 5, respectively. In some embodiments, the immunohistochemistry assay comprises contacting the tumor sample with the SP346 rabbit anti-human LAG-3 IgG monoclonal antibody. In some embodiments, the immunohistochemistry assay comprises contacting the tumor sample with the 11E3 (Novusbio), 874501 (Novusbio), or EPR4392(2) (Abcam) anti-human LAG-3 monoclonal antibody.

Melanin, for example, in melanoma tumor samples, can interfere with histological analysis by obscuring histological features, and by interfering with and/or masking staining during immunohistochemistry (IHC). Melanin can be removed by bleaching the samples. See, e.g., Shen & Wu, Appl Immunohistochem Mol Morphol, 23(4): 303-307 (2015); Orchard & Calonje, Am J Dermatopathol, 20(4): 357-61 (1998). In some embodiments, the immunohistochemistry assay comprises melanin bleaching prior to contacting the sample with an anti-LAG-3 antibody. See, e.g., FIG. 15. In some embodiments, the melanin bleaching comprises contacting the sample with dilute hydrogen peroxide (0.1 to 30% v/v), trichloroisocyanuric acid (TCCA), potassium permanganate/oxalic acid, or other traditional oxidation methods for depigmenting (i.e., removing melanin from) tissue samples.

In some embodiments, the immunohistochemistry assay uses a black or brown chromogen. In some embodiments, the immunohistochemistry assay uses a red chromogen. In some embodiments, the immunohistochemistry assay uses a blue chromogen. In some embodiments, the immunohistochemistry assay uses a green chromogen. In some embodiments, the immunohistochemistry assay uses a purple chromogen. In some embodiments, the immunohistochemistry assay uses a yellow chromogen.

In some embodiments, the immunohistochemistry assay is scored at a low magnification. In some embodiments, low magnification is about 20×. In some embodiments, the immunohistochemistry assay is scored at high magnification. In some embodiments, high magnification is about 40×.

In some embodiments, the immunohistochemistry assay is scored by an image analysis software. In some embodiments, the immunohistochemistry assay is scored by a pathologist visual immune score. In some embodiments, the immunohistochemistry assay is scored manually.

In some embodiments, scoring the immunohistochemistry assay comprises assessing the proportion of cells in the test tissue sample that express LAG-3. In some embodiments, scoring the immunohistochemistry assay comprises assessing the proportion of immune cells in the test tissue sample that express LAG-3. In some embodiments, scoring the immunohistochemistry assay comprises assessing the proportion of T cells in the test tissue sample that express LAG-3. In some embodiments, scoring the immunohistochemistry assay comprises assessing the proportion of CD8+ T cells in the test tissue sample that express LAG-3. In some embodiments, scoring the immunohistochemistry assay comprises assessing the proportion of CD4+ T cells in the test tissue sample that express LAG-3. In some embodiments, scoring the immunohistochemistry assay comprises assessing the proportion of FOXP3+ T cells in the test tissue sample that express LAG-3.

LAG-3 polypeptide localization includes partial membrane/cytoplasmic localization, dot like localization, perinuclear, and complete membrane/cytoplasmic localization. In some embodiments, cells with partial membrane/cytoplasmic LAG-3 localization are scored. In some embodiments, cells with dot-like LAG-3 localization are scored. In some embodiments, cells with complete membrane/cytoplasmic LAG-3 localization are scored. In some embodiments, cells with perinuclear LAG-3 localization are scored. In some embodiments, cells with any LAG-3 localization pattern are scored.

In some embodiments, the immunohistochemistry assay is a multiplex assay that further comprises detecting the expression of MHC Class II by the tumor cells. In some embodiments, scoring the immunohistochemistry assay comprises assessing the proportion of cells in the test tissue sample that expresses MHC Class II. In some embodiments, scoring the immunohistochemistry assay comprises assessing the proportion of non-immune cells in the test tissue sample that expresses MHC Class IL In some embodiments, the distribution of MHC II expressing cells is heterogenous in the tumor sample. In some embodiments, scoring the immunohistochemistry assay comprises assessing the proportion of cells that expresses MHC Class II in regions of the tumor sample comprising a high density of MHC Class II expressing cells.

In some embodiments, the immunohistochemistry assay is a multiplex assay that further comprises detecting the expression of CD163 and/or CD68 by tumor infiltrating lymphocytes (TIL). In some embodiments, scoring the immunohistochemistry assay comprises assessing the proportion of TILs in the test tissue sample that expresses CD163 and/or CD68.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, *Cold Spring Harb. Perspect. Biol.* 2(12):a003848 (2010)). Antibody specificity, coupled with the sensitivity and resolution of PET, makes immunoPET imaging particularly attractive for monitoring and assaying expression of antigens in tissue samples (McCabe and Wu, *Cancer Biother. Radiopharm.* 25(3):253-61 (2010); Olafsen et al., *Protein Eng. Des. Sel.* 23(4):243-9 (2010)). In certain embodiments of any of the present methods, LAG-3 expression is assayed by immunoPET imaging. In certain embodiments immunoPET is performed using a zirconium-89 radiolabeled anti-LAG-3 antibody. In certain embodiments of any of the present methods, the proportion of cells in a test tissue sample that express LAG-3 is assessed by performing an assay to determine the presence of LAG-3 polypeptide on the surface of cells in the test tissue sample. In certain embodiments, the test tissue sample is a FFPE tissue sample. In other embodiments, the presence of LAG-3 polypeptide is determined by IHC assay. In further embodiments, the IHC assay is performed using an automated process. In some embodiments, the IHC assay is performed using an anti-LAG-3 mAb to bind to the LAG-3 polypeptide.

Assaying LAG-3 Expression by Automated IHC

In one embodiment of the present methods, an automated IHC method is used to assay the expression of LAG-3 in FFPE tissue specimens. This disclosure provides methods for detecting the presence of human LAG-3 antigen in a test tissue sample, or quantifying the level of human LAG-3 antigen or the proportion of cells in the sample that express the antigen, which methods comprise contacting the test sample, and a negative control sample, with a mAb that specifically binds to human LAG-3, under conditions that allow for formation of a complex between the antibody or portion thereof and human LAG-3. In certain embodiments, the test and control tissue samples are FFPE samples. The formation of a complex is then detected, wherein a difference in complex formation between the test sample and the negative control sample is indicative of the presence of human LAG-3 antigen in the sample. Various methods are used to quantify LAG-3 expression.

In a particular embodiment, the automated IHC method comprises: (a) deparaffinizing and rehydrating mounted tissue sections in an autostainer; (b) retrieving antigen in an autostainer; (c) setting up reagents on an autostainer; and (d) running the autostainer to include steps of neutralizing endogenous peroxidase in the tissue specimen; blocking non-specific protein-binding sites on the slides; incubating the slides with primary Ab; incubating with a postprimary blocking agent; incubating with a postprimary antibody detection agent, such as another antibody that may or may not be conjugated to a detection enzyme; incubating with a polymeric-enzyme detection reagent; adding a chromogen substrate and developing; and counterstaining with hematoxylin. In some embodiments, the retrieving antigen comprises using any heat based antigen retrieval device.

In some embodiments, for assessing LAG-3 expression in tumor tissue samples, a pathologist examines the number of LAG-3+ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%.

In some embodiments, staining is also assessed in tumor-infiltrating inflammatory cells such as macrophages and lymphocytes. Macrophages and lymphocytes are assessed for LAG-3 staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two or more pathologists operating independently, and the scores are subsequently consolidated. In certain other embodiments, the identification of positive and negative cells is scored using appropriate software.

A histoscore (H-score) is used as a more quantitative measure of the IHC data. The histoscore is calculated as follows:

$$\text{Histoscore}=[(\% \text{ tumor}\times 1(\text{low intensity}))+(\% \text{ tumor}\times 2(\text{medium intensity}))+(\% \text{ tumor}\times 3(\text{high intensity}))]$$

To determine the histoscore, the pathologist estimates the percentage of stained cells in each intensity category within a specimen. Because expression of most biomarkers is heterogeneous the histoscore is a truer representation of the overall expression. The final histoscore range is 0 (minimum score, no expression) to 300 (maximum score, strong and inclusive expression).

3. Lag-3 Inhibitors

In one aspect, the invention features methods of using a LAG-3 inhibitor in the treatment of malignant tumors. As used herein LAG-3 inhibitor includes, but is not limited to, LAG-3 binding agents and soluble LAG-3 polypeptides. LAG-3 binding agents include antibodies that specifically bind to LAG-3.

In some embodiments, a LAG-3 inhibitor is a LAG-3-binding agent, for example an anti-LAG-3 antibody. In some embodiments, the LAG-3 inhibitor is a soluble LAG-3 polypeptide, for example, a LAG-3-Fc fusion polypeptide capable of binding to MHC Class II.

Anti-human-LAG-3 antibodies (or VH/VL domains derived therefrom) suitable for use in the invention can be generated using methods well known in the art. Alternatively, art recognized anti-LAG-3 antibodies can be used. In certain embodiments, LAG-3 inhibitors include an anti-LAG-3 bispecific antibody. In some embodiments, the anti-LAG-3 antibody binds LAG-3 and PD-1.

In some embodiments, the anti-LAG-3 antibody is BMS-986016 comprising heavy and light chains comprising the sequences shown in SEQ ID NOs:1 and 2, respectively, or antigen binding fragments and variants thereof, as described in PCT/US13/48999.

In other embodiments, the antibody has the heavy and light chain CDRs or variable regions of BMS-986016. Accordingly, in one embodiment, the antibody comprises CDR1, CDR2, and CDR3 domains of the VH region of BMS-986016 having the sequence set forth in SEQ ID NO:3, and CDR1, CDR2 and CDR3 domains of the VL region of BMS-986016 having the sequence set forth in SEQ ID NO:5. In another embodiment, the antibody comprises CDR1, CDR2 and CDR3 domains comprising the sequences set forth in SEQ ID NOs:7, 8, and 9, respectively, and CDR1, CDR2 and CDR3 domains comprising the sequences set forth in SEQ ID NOs:10, 11, and 12, respectively. In another embodiment, the antibody comprises VH and/or VL regions comprising the amino acid sequences set forth in SEQ ID NO:3 and/or SEQ ID NO: 5, respectively. In another embodiment, the antibody comprises heavy chain variable (VH) and/or light chain variable (VL) regions encoded by the nucleic acid sequences set forth in SEQ ID NO:4 and/or SEQ ID NO:6, respectively. In another embodiment, the antibody competes for binding with and/or binds to the same epitope on LAG-3 as the above-mentioned antibodies. In another embodiment, the antibody binds an epitope of human LAG-3 comprising the amino acid sequence PGHPLAPG (SEQ ID NO:14). In another embodiment, the antibody binds an epitope of human LAG-3 comprising the amino acid sequence HPAAPSSW (SEQ ID NO:15) or PAAPSSWG (SEQ ID NO:16).

In another embodiment, the antibody has at least about 90% variable region amino acid sequence identity with the above-mentioned antibodies (e.g., at least about 90%, 95% or 99% variable region identity with SEQ ID NO:3 or SEQ ID NO:5).

In some embodiments, art recognized anti-LAG-3 antibodies can be used in the therapeutic methods of the invention. For example, the anti-human LAG-3 antibody described in US2011/0150892 A1, and referred to as monoclonal antibody 25F7 (also known as "25F7" and "LAG-3.1") can be used. Other art recognized anti-LAG-3 antibodies that can be used include IMP731 (H5L7BW) described in US 2011/007023, MK-4280 (28G-10) described in WO2016028672, REGN3767 described in Journal for ImmunoTherapy of Cancer, (2016) Vol. 4, Supp. Supplement 1 Abstract Number: P195, BAP050 described in WO2017/019894, IMP-701 (LAG-525), Sym022, TSR-033, MGD013, BI754111, FS118, AVA-017 and GSK2831781. These and other anti-LAG-3 antibodies useful in the claimed invention can be found in, for example: WO2016/028672, WO2017/106129, WO2017/062888, WO2009/044273, WO2018/069500, WO2016/126858, WO2014/179664, WO2016/200782, WO2015/200119, WO2017/019846, WO2017/198741, WO2017/220555, WO2017/220569, WO2018/071500, WO2017/015560, WO2017/025498, WO2017/087589, WO2017/087901, WO2018/083087, WO2017/149143, WO2017/219995, US2017/0260271, WO2017/086367, WO2017/086419, WO2018/034227, and WO2014/140180. In one embodiment, the LAG-3 inhibitor is IMP321 (eftilagimod alpha). The contents of each of these references are incorporated by reference herein in their entirety.

Antibodies that compete with any of the above-referenced art-recognized antibodies for binding to LAG-3 also can be used.

In certain embodiments, an anti-LAG-3 antibody is used to determine LAG-3 expression. In some embodiments, an anti-LAG-3 antibody is selected for its ability to bind to LAG-3 in formalin-fixed, paraffin-embedded (FFPE) tissue specimens. In other embodiments, an anti-LAG-3 antibody is capable of binding to LAG-3 in frozen tissues. In further embodiments, an anti-LAG-3 antibody is capable of distinguishing membrane bound, cytoplasmic, and/or soluble forms of LAG-3.

In some embodiments, an anti-LAG-3 antibody useful for assaying, detecting, and/or quantifying LAG-3 expression in accordance with the methods described herein is the 17B4 mouse IgG1 anti-human LAG-3 monoclonal antibody, or an antigen binding fragment thereof. See, e.g., J. Matsuzaki, et al.; PNAS 107, 7875 (2010).

4. Pd-1 Pathway Inhibitors

In one aspect, the invention features methods of using a PD-1 inhibitor in the treatment of malignant tumors. As used herein "PD-1 pathway inhibitor" includes, but is not limited to, PD-1 binding agents, PD-L1 binding agent and PD-L2 binding agents. PD-1 binding agents include antibodies that specifically bind to PD-1. PD-L1 and PD-L2 binding agents include antibodies that specifically bind to PD-L1 and/or PD-L2, as well as soluble PD-1 polypeptides that bind to PD-L1 and/or PD-L2.

In some embodiments, PD-1 pathway inhibitor is a PD-1-binding agent, for example an anti-PD-1 antibody. In some embodiments, the PD-1 pathway inhibitor is a PD-L1-binding agent, for example, an anti-PD-L1 antibody. In some embodiments, the PD-1 pathway inhibitor is a PD-L2-binding agent, for example an anti-PD-L2 antibody. In further embodiments, the PD-L1-binding agent is a soluble PD-1 polypeptide, for example, a PD-1-Fc fusion polypeptide capable of binding to PD-L1. In further embodiments, the PD-L2-binding agent is a soluble PD-1 polypeptide, for example, a PD-1-Fc fusion polypeptide capable of binding to PD-L2.

Anti-human-PD-1 antibodies (or VH and/or VL domains derived therefrom) suitable for use in the invention can be generated using methods well known in the art. Alternatively, art recognized anti-PD-1 antibodies can be used. For example, monoclonal antibodies 5C4 (referred to herein as Nivolumab or BMS-936558), 17D8, 2D3, 4H1, 4A11, 7D3, and 5F4, described in WO 2006/121168 can be used. Other known PD-1 antibodies include lambrolizumab (MK-3475) described in WO 2008/156712, and AMP-514 described in WO 2012/145493. Further known PD-1 antibodies and other PD-1 inhibitors include those described in, for example, WO 2009/014708, WO 03/099196, WO 2009/114335 and WO 2011/161699, which are herein incorporated by reference. In one embodiment, the anti-PD-1 antibody is REGN2810. In one embodiment, the anti-PD-1 antibody is PDR001. Another known anti-PD-1 antibody is pidilizumab (CT-011).

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., Cancer Immunol Res. 2(9):846-56 (2014)). In another embodiment, the anti-PD-1 antibody or fragment thereof cross-competes with nivolumab. In other embodiments, the anti-PD-1 antibody or fragment thereof binds to the same epitope as nivolumab. In certain embodiments, the anti-PD-1 antibody has the same CDRs as nivolumab.

In some embodiments, the anti-PD-1 antibody comprises heavy and light chains comprising the sequences shown in SEQ ID NOs:17 and 18, respectively, or antigen binding fragments and variants thereof.

In other embodiments, the antibody has heavy and light chain CDRs or variable regions of nivolumab. Accordingly, in one embodiment, the antibody comprises CDR1, CDR2, and CDR3 domains of the VH of nivolumab having the sequence set forth in SEQ ID NO:19, and CDR1, CDR2 and CDR3 domains of the VL of nivolumab having the sequence set forth in SEQ ID NO:21. In another embodiment, the antibody comprises CDR1, CDR2 and CDR3 domains comprising the sequences set forth in SEQ ID NOs:23, 24, and 25, respectively, and CDR1, CDR2 and CDR3 domains comprising the sequences set forth in SEQ ID NOs:26, 27, and 28, respectively. In another embodiment, the antibody comprises VH and/or VL regions comprising the amino acid sequences set forth in SEQ ID NO: 19 and/or SEQ ID NO: 21, respectively. In another embodiment, the antibody comprises heavy chain variable (VH) and/or light chain variable (VL) regions encoded by the nucleic acid sequences set forth in SEQ ID NO:20 and/or SEQ ID NO:22, respectively. In another embodiment, the antibody competes for binding with and/or binds to the same epitope on PD-1 as the above-mentioned antibodies. In another embodiment, the antibody has at least about 90% variable region amino acid sequence identity with the above-mentioned antibodies (e.g., at least about 90%, 95% or 99% variable region identity with SEQ ID NO:19 or SEQ ID NO:21).

Human monoclonal antibodies (HuMAbs) that bind specifically to PD-1 with high affinity have been disclosed in U.S. Pat. Nos. 8,008,449 and 8,779,105. Other anti-PD-1 mAbs have been described in, for example, U.S. Pat. Nos. 6,808,710, 7,488,802, 8,168,757 and 8,354,509, and PCT Publication No. WO 2012/145493, which are herein incorporated by reference. In some embodiments, the anti-PD-1 antibody has been demonstrated to exhibit one or more of the following characteristics: (a) binds to human PD-1 with a $K_D$ of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies useful for the present invention include mAbs that bind specifically to human PD-1 and exhibit at least one, at least two, at least three, at least four, or at least five of the preceding characteristics. Anti-PD-1 antibodies that exhibit one or more of these characteristics have been disclosed in U.S. Pat. Nos. 8,008,449, 8,779,105, 6,808,710, 7,488,802, 8,168,757 and 8,354,509, and PCT Publication No. WO 2012/145493, which are herein incorporated by reference. In another embodiment, the anti-PD-1 antibody is pembrolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587, which are herein incorporated by reference.

In some embodiments, the anti-PD-1 antibody or fragment thereof cross-competes with pembrolizumab. In some embodiments, the anti-PD-1 antibody or fragment thereof binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also http://www.cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody or fragment thereof cross-competes with MEDI0608. In still other embodiments, the anti-PD-1 antibody or fragment thereof binds to the same epitope as MEDI0608. In certain embodiments, the anti-PD-1 antibody has the same CDRs as MEDI0608. In other embodiments, the anti-PD-1 antibody is MEDI0608 (formerly AMP-514), which is a monoclonal antibody. MEDI0608 is described, for example, in U.S. Pat. No. 8,609,089B2 or in http://www.cancer.gov/drugdictionary?cdrid=756047 (last accessed Dec. 14, 2014).

In certain embodiments, the first antibody is an anti-PD-1 antagonist. One example of the anti-PD-1 antagonist is AMP-224, which is a B7-DC Fc fusion protein. AMP-224 is discussed in U.S. Publ. No. 2013/0017199 or in http://www.cancer.gov/publications/dictionaries/cancer-drug?cdrid=700595 (last accessed Jul. 8, 2015).

In other embodiments, the anti-PD-1 antibody or fragment thereof cross-competes with BGB-A317. In some embodiments, the anti-PD-1 antibody or fragment thereof binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

In some embodiments, the antibody is pidilizumab (CT-011), which is an antibody previously reported to bind to PD-1 but which is believed to bind to a different target. pidilizumab is described in U.S. Pat. No. 8,686,119 B2 or WO 2013/014668 A1.

In certain embodiments, the antibodies that cross-compete for binding to human PD-1 with, or bind to the same epitope region of human PD-1 as, nivolumab are mAbs. For administration to human subjects, these cross-competing antibodies can be chimeric antibodies, or humanized or human antibodies. Such chimeric, humanized or human mAbs can be prepared and isolated by methods well known in the art.

Other anti-PD-1 monoclonal antibodies have been described in, for example, U.S. Pat. Nos. 6,808,710, 7,488, 802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

In some embodiments, the anti-PD-1 antibody is selected from the group consisting of nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (Jiangsu Hengrui Medicine; also known as SHR-1210; see WO 2015/085847; Si-Yang Liu et al., *J. Hematol. Oncol.*

10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), and IBI308 (Innovent; see WO 2017/024465, WO 2017/025016, WO 2017/132825, and WO 2017/133540).

Anti-PD-1 antibodies useful for the compositions of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Anti-PD-1 antibodies usable in the disclosed methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some embodiments, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

Anti-PD-1 antibodies suitable for use in the disclosed methods are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized or human monoclonal antibody or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014 *Cancer Immunol Res.* 2(9):846-56). In yet other embodiments, the antibody comprises a light chain constant region which is a human kappa or lambda constant region. In other embodiments, the anti-PD-1 antibody or antigen-binding portion thereof is a mAb or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or BGB-A317.

In embodiments, the anti-PD-1 antibody is a bispecific antibody. In embodiments, the anti-PD-1 antibody is a bispecific antibody that binds both PD-1 and LAG-3.

5. Anti-Pd-L1 Antibodies

In certain embodiments, the present application encompasses use of an anti-PD-L1 antibody as the PD-1 pathway inhibitor. In one embodiment, the anti-PD-L1 antibody inhibits the binding of PD-L1 receptor, i.e., PD-1 to its ligand PD-L1.

Anti-human-PD-L1 antibodies (or $V_H$ and/or $V_L$ domains derived therefrom) suitable for use in the invention can be generated using methods well known in the art. Alternatively, art recognized anti-PD-L1 antibodies can be used. For example, human anti-PD-L1 antibodies disclosed in U.S. Pat. No. 7,943,743 can be used. Such anti-PD-L1 antibodies include 3G10, 12A4 (also referred to as BMS-936559), 10A5, 5F8, 10H10, 1B12, 7H1, 11E6, 12B7, and 13G4.

In some embodiments, the anti-PD-L1 antibody is atezolizumab (Tecentriq or RG7446) (see, e.g., Herbst et al. (2013) J Clin Oncol 31(suppl):3000. Abstract; U.S. Pat. No. 8,217,149), durvalumab (Imfinzi or MEDI4736) (Khleif (2013) In: Proceedings from the European Cancer Congress 2013; Sep. 27-Oct. 1, 2013; Amsterdam, The Netherlands. Abstract 802), avelumab (Bavencio). Other art recognized anti-PD-L1 antibodies which can be used include those described in, for example, U.S. Pat. Nos. 7,635,757 and 8,217,149, U.S. Publication No. 2009/0317368, and PCT Publication Nos. WO 2011/066389 and WO 2012/145493, which are herein incorporated by reference. Antibodies that compete with any of these art-recognized antibodies or inhibitors for binding to PD-L1 also can be used. Examples of anti-PD-L1 antibodies useful in the methods of the present disclosure include the antibodies disclosed in U.S. Pat. No. 9,580,507. Anti-PD-L1 human monoclonal antibodies disclosed in U.S. Pat. No. 9,580,507 have been demonstrated to exhibit one or more of the following characteristics: (a) bind to human PD-L1 with a $K_D$ of $1\times10-7$ M or less, as determined by surface plasmon resonance using a Biacore biosensor system; (b) increase T-cell proliferation in a Mixed Lymphocyte Reaction (MLR) assay; (c) increase interferon-γ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present invention include monoclonal antibodies that bind specifically to human PD-L1 and exhibit at least one, in some embodiments, at least five, of the preceding characteristics.

In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446 and atezolizumab) (see, e.g., Herbst et al. 2013 J Clin Oncol 31(suppl):3000; U.S. Pat. No. 8,217,149), MEDI4736 (Khleif, 2013, In: Proceedings from the European Cancer Congress 2013; Sep. 27-Oct. 1, 2013; Amsterdam, The Netherlands. Abstract 802), or MSB0010718C (also called Avelumab; see US 2014/0341917). In certain embodiments, antibodies that cross-compete for binding to human PD-L1 with, or bind to the same epitope region of human PD-L1 as the above-references PD-L1 antibodies are mAbs. For administration to human subjects, these cross-competing antibodies can be chimeric antibodies, or can be humanized or human antibodies. Such chimeric, humanized or human mAbs can be prepared and isolated by methods well known in the art. In certain embodiments, the anti-PD-L1 antibody is selected from the group consisting of BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) J Clin Oncol 31(suppl):3000), durvalumab (AstraZeneca; also known as IMFINZI™, MEDI-4736; see WO 2011/066389), avelumab (Pfizer; also known as BAVENCIO®, MSB-0010718C; see WO 2013/079174), STI-1014 (Sorrento; see WO2013/181634), CX-072 (Cytomx; see WO2016/149201), KN035 (3D Med/Alphamab; see Zhang et al., Cell Discov. 7:3 (March 2017), LY3300054 (Eli Lilly Co.; see, e.g., WO 2017/034916), and CK-301 (Checkpoint Therapeutics; see Gorelik et al., AACR: Abstract 4606 (April 2016)).

In certain embodiments, the PD-L1 antibody is atezolizumab (TECENTRIQ®). Atezolizumab is a fully humanized IgG1 monoclonal anti-PD-L1 antibody.

In certain embodiments, the PD-L1 antibody is durvalumab (IMFINZI™) Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

In other embodiments, the anti-PD-L1 monoclonal antibody is selected from the group consisting of 28-8, 28-1, 28-12, 29-8, 5H1, and any combination thereof.

Anti-PD-L1 antibodies usable in the disclosed methods also include isolated antibodies that bind specifically to human PD-L1 and cross-compete for binding to human PD-L1 with any anti-PD-L1 antibody disclosed herein, e.g., atezolizumab, durvalumab, and/or avelumab. In some embodiments, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the methods of the disclosed invention also include antigen-binding portions of the above antibodies. It has been amply demonstrated that the antigen-binding function of an antibody can be performed by fragments of a full-length antibody.

Anti-PD-L1 antibodies suitable for use in the disclosed methods or compositions are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab, durvalumab, and/or avelumab for binding to human PD-L1.

Anti-PD-L1 antibodies useful for the invention include antibodies engineered starting from antibodies having one or more of the $V_H$ and/or $V_L$ sequences disclosed herein, which engineered antibodies can have altered properties from the starting antibodies. An anti-PD-L1 antibody can be engineered by a variety of modifications as described above for the engineering of modified anti-PD-1 antibodies of the invention.

6. Anti-Ctla-4 Antibodies

In certain embodiments, the present application encompasses use of an anti-CTLA-4 antibody. In one embodiment, the anti-CTLA-4 antibody binds to and inhibits CTLA-4. In some embodiments, the anti-CTLA-4 antibody is ipilimumab (YERVOY), tremelimumab (ticilimumab; CP-675, 206), AGEN-1884, or ATOR-1015.

7. Immune Checkpoint Inhibitors

In one aspect, the invention features methods of using a PD-1 inhibitor in combination with an immune checkpoint inhibitor in the treatment of malignant tumors. Any art recognized immune checkpoint inhibitor can be used.

In certain embodiments, the immune checkpoint inhibitor is a CTLA-4 antagonist, a CD80 antagonist, a CD86 antagonist, a Tim-3 antagonist, a TIGIT antagonist, a CD20 antagonist, a CD96 antagonist, a IDO1 antagonist, a STING antagonist, a GARP antagonist, a CD40 antagonist, A2aR antagonist, a CEACAM1 (CD66a) antagonist, a CEA antagonist, a CD47 antagonist a PVRIG antagonist, a TDO antagonist, a VISTA antagonist, or a KIR antagonist.

In one embodiment, the immune checkpoint inhibitor is a CTLA-4 antagonist. In certain embodiments, the CTLA-4 antagonist is an anti-CTLA-4 antibody or antigen binding fragment thereof. In some embodiments, the anti-CTLA-4 antibody is ipilimumab (YERVOY), tremelimumab (ticilimumab; CP-675,206), AGEN-1884, or ATOR-1015.

In one embodiment, the CTLA-4 antagonist is a soluble CTLA-4 polypeptide. In one embodiment, the soluble CTLA-4 polypeptide is abatacept (Orencia), belatacept (Nulojix), RG2077, or RG-1046. In another embodiment, the CTLA-4 antagonist is a cell based therapy. In some embodiments, the CTLA-4 antagonist is an anti-CTLA-4 mAb RNA/GITRL RNA-transfected autologous dendritic cell vaccine or an anti-CTLA-4 mAb RNA-transfected autologous dendritic cell vaccine.

In one embodiment, the immune checkpoint inhibitor is a KIR antagonist. In certain embodiments, the KIR antagonist is an anti-KIR antibody or antigen binding fragment thereof. In some embodiments, the anti-KIR antibody is lirilumab (1-7F9, BMS-986015, IPH 2101) or IPH4102.

In one embodiment, the immune checkpoint inhibitor is TIGIT antagonist. In one embodiment, the TIGIT antagonist is an anti-TIGIT antibody or antigen binding fragment thereof. In certain embodiments, the anti-TIGIT antibody is BMS-986207, AB 154, COM902 (CGEN-15137), or OMP-313M32.

In one embodiment, the immune checkpoint inhibitor is Tim-3 antagonist. In certain embodiments, the Tim-3 antagonist is an anti-Tim-3 antibody or antigen binding fragment thereof. In some embodiments, the anti-Tim-3 antibody is TSR-022 or LY3321367.

In one embodiment, the immune checkpoint inhibitor is a IDO1 antagonist. In another embodiment, the IDO1 antagonist is indoximod (NLG8189; 1-methyl-D-TRP), epacadostat (INCB-024360, INCB-24360), KHK2455, PF-06840003, navoximod (RG6078, GDC-0919, NLG919), BMS-986205 (F001287), or pyrrolidine-2,5-dione derivatives.

In one embodiment, the immune checkpoint inhibitor is a STING antagonist. In certain embodiments, the STING antagonist is 2' or 3'-mono-fluoro substituted cyclic-di-nucleotides; 2'3'-di-fluoro substituted mixed linkage 2',5'-3', 5' cyclic-di-nucleotides; 2'-fluoro substituted, bis-3',5' cyclic-di-nucleotides; 2',2''-diF-Rp,Rp,bis-3',5' cyclic-di-nucleotides; or fluorinated cyclic-di-nucleotides.

In one embodiment, the immune checkpoint inhibitor is CD20 antagonist. In some embodiments, the CD20 antagonist is an anti-CD20 antibody or antigen binding fragment thereof. In one embodiment, the anti-CD20 antibody is rituximab (RITUXAN; IDEC-102; IDEC-C2B8), ABP 798, ofatumumab, or obinutuzumab.

In one embodiment, the immune checkpoint inhibitor is CD80 antagonist. In certain embodiments, the CD80 antagonist is an anti-CD80 antibody or antigen binding fragment thereof. In one embodiment, the anti-CD80 antibody is galiximab or AV 1142742.

In one embodiment, the immune checkpoint inhibitor is a GARP antagonist. In some embodiments, the GARP antagonist is an anti-GARP antibody or antigen binding fragment thereof. In certain embodiments, the anti-GARP antibody is ARGX-115.

In one embodiment, the immune checkpoint inhibitor is a CD40 antagonist. In certain embodiments, the CD40 antagonist is an anti-CD40 antibody for antigen binding fragment thereof. In some embodiments, the anti-CD40 antibody is BMS3h-56, lucatumumab (HCD122 and CHIR-12.12), CHIR-5.9, or dacetuzumab (huS2C6, PRO 64553, RG 3636, SGN 14, SGN-40). In another embodiment, the CD40 antagonist is a soluble CD40 ligand (CD40-L). In one embodiment, the soluble CD40 ligand is a fusion polypeptide. In one embodiment, the soluble CD40 ligand is a CD40-L/FC2 or a monomeric CD40-L.

In one embodiment, the immune checkpoint inhibitor is an A2aR antagonist. In some embodiments, the A2aR antagonist is a small molecule. In certain embodiments, the A2aR antagonist is CPI-444, PBF-509, istradefylline (KW-6002), preladenant (SCH420814), tozadenant (SYN115), vipadenant (BIIB014), HTL-1071, ST1535, SCH412348, SCH442416, SCH58261, ZM241385, or AZD4635.

In one embodiment, the immune checkpoint inhibitor is a CEACAM1 antagonist. In some embodiments, the CEACAM1 antagonist is an anti-CEACAM1 antibody or antigen binding fragment thereof. In one embodiment, the anti-CEACAM1 antibody is CM-24 (MK-6018).

In one embodiment, the immune checkpoint inhibitor is a CEA antagonist. In one embodiment, the CEA antagonist is an anti-CEA antibody or antigen binding fragment thereof. In certain embodiments, the anti-CEA antibody is cerguzumab amunaleukin (RG7813, RO-6895882) or RG7802 (RO6958688).

In one embodiment, the immune checkpoint inhibitor is a CD47 antagonist. In some embodiments, the CD47 antagonist is an anti-CD47 antibody or antigen binding fragment thereof. In certain embodiments, the anti-CD47 antibody is HuF9-G4, CC-90002, TTI-621, ALX148, NI-1701, NI-1801, SRF231, or Effi-DEM.

In one embodiment, the immune checkpoint inhibitor is a PVRIG antagonist. In certain embodiments, the PVRIG antagonist is an anti-PVRIG antibody or antigen binding fragment thereof. In one embodiment, the anti-PVRIG antibody is COM701 (CGEN-15029).

In one embodiment, the immune checkpoint inhibitor is a TDO antagonist. In one embodiment, the TDO antagonist is a 4-(indol-3-yl)-pyrazole derivative, a 3-indol substituted derivative, or a 3-(indol-3-yl)-pyridine derivative. In another embodiment, the immune checkpoint inhibitor is a dual IDO and TDO antagonist. In one embodiment, the dual IDO and TDO antagonist is a small molecule.

In one embodiment, the immune checkpoint inhibitor is a VISTA antagonist. In some embodiments, the VISTA antagonist is CA-170 or JNJ-61610588.

8. Pharmaceutical Compositions

Pharmaceutical compositions suitable for administration to human patients are typically formulated for parenteral administration, e.g., in a liquid carrier, or suitable for reconstitution into liquid solution or suspension for intravenous administration.

In general, such compositions typically comprise a pharmaceutically acceptable carrier. As used herein, the term "pharmaceutically acceptable" means approved by a government regulatory agency or listed in the U.S. Pharmacopeia or another generally recognized pharmacopeia for use in animals, particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil, glycerol polyethylene glycol ricinoleate, and the like. Water or aqueous solution saline and aqueous dextrose and glycerol solutions may be employed as carriers, particularly for injectable solutions (e.g., comprising an anti-LAG-3 and/or anti-PD-1 antibody). Liquid compositions for parenteral administration can be formulated for administration by injection or continuous infusion. Routes of administration by injection or infusion include intravenous, intraperitoneal, intramuscular, intrathecal and subcutaneous. In one embodiment, the anti-LAG-3 and/or anti-PD-1 antibodies are administered intravenously (e.g., in separate formulations or together (in the same formulation or in separate formulations)).

9. Patient Populations

Provided herein are clinical methods for treating malignant tumors (e.g., advanced refractory solid tumors and hematological malignancies) in human patients using an immunotherapy disclosed herein, for example, a LAG-3 inhibitor (e.g., an anti-LAG-3 antibody), a PD-1 pathway inhibitor (e.g., an anti-PD-1 antibody), an anti-CTLA-4 antibody, or a combination of a LAG-3 inhibitor (e.g., an anti-LAG-3 antibody) and a PD-1 pathway inhibitor (e.g., an anti-PD-1 antibody).

Examples of cancers and/or malignant tumors that may be treated using the methods of the invention, include liver cancer, hepatocellular carcinoma (HCC), bone cancer, pancreatic cancer, skin cancer, oral cancer, cancer of the head or neck, breast cancer, lung cancer, small cell lung cancer, NSCLC, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, squamous cell carcinoma of the head and neck (SCCHN), non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present invention is also applicable to treatment of metastatic cancers. In embodiments, the cancer is renal cell carcinoma (RCC), gastric/gastoesophogeal junction carcinoma, non-small cell lung carcinoma (NSCLC), melanoma, squamous cell carcinoma of the head and neck (SCCHN), hepatocellular carcinoma, or urothelial carcinoma.

In certain embodiments, the melanoma is unresectable or metastatic melanoma. In embodiments, the patient was previously treated with an anti-PD-1 or an anti-PD-L1 antibody. In certain embodiments, the tumor is a LAG-3 expressing tumor. In particular embodiments, the tumor is a LAG-3 expressing tumor with LAG-3 expression ≥1%.

In one embodiment, the human patient suffers from unresectable metastatic melanoma and was previously treated with an anti-PD-1 or anti-PD-L1 metastatic inhibitor. In a particular embodiment, the human patient suffers from unresectable metastatic melanoma and was previously treated with an anti-PD-1 or anti-PD-L1 metastatic inhibitor and the tumor is a LAG-3 expressing tumor. In one embodiment, the human patient suffers from unresectable metastatic melanoma and was previously treated with an anti-PD-1 or anti-PD-L1 metastatic inhibitor and the tumor is a LAG-3 expressing tumor. In a certain embodiment, the human patient suffers from unresectable metastatic melanoma and was previously treated with an anti-PD-1 or anti-PD-L1 metastatic inhibitor and the tumor is a LAG-3 expressing tumor with LAG-3 expression ≥1%.

In one embodiment, the human patient suffers from a malignant tumor that is refractory to treatment with an immune checkpoint inhibitor. In another embodiment, the patient suffers from a malignant tumor that is refractory to treatment with a PD-1 inhibitor. In another embodiment, the patient suffers from a malignant tumor that is refractory to treatment with an anti-PD-1 antibody. In another embodiment, the patient suffers from a malignant tumor that is refractory to treatment with an anti-PD-L1 antibody. In some embodiments, the malignant tumor is gastric cancer, renal cancer, HCC, SCCHN, or NSCLC.

In one embodiment, the human patient suffers from melanoma. In another embodiment, the patient suffers from melanoma that is refractory to treatment with an immune checkpoint inhibitor. In another embodiment, the patient suffers from melanoma that is refractory to treatment with a PD-1 inhibitor. In another embodiment, the patient suffers from melanoma that is refractory to treatment with an anti-PD-1 antibody. In another embodiment, the patient suffers from melanoma that is refractory to treatment with an anti-PD-L1 antibody.

In one embodiment, the human patient suffers from melanoma, gastric cancer, renal cancer, HCC, SCCHN, or NSCLC. In one embodiment, the human patient suffers from melanoma.

In one embodiment, the human patient suffers from NSCLC or a virally-related cancer (e.g., a human papilloma virus (HPV)-related tumor) or gastric adenocarcinoma. In a particular embodiment, the HPV-related tumor is HPV+ head and neck cancer (HNC). In another particular embodiment, the gastric adenocarcinoma is associated with Epstein-Barr virus (EBV) infection.

Patients can be tested or selected for one or more of the above described clinical attributes prior to, during or after treatment.

In accordance with the methods described herein, the malignant tumors can be tested to determine LAG-3 expression. In some embodiments, the malignant tumors treated in accordance with the methods disclosed herein are LAG-3 positive tumors. In some embodiments, the malignant tumor is a LAG-3 positive melanoma. In another embodiment, the malignant tumor is a LAG-3 positive gastric cancer, renal cancer, HCC, SCCHN, or NSCLC.

In some embodiments, at least about 0.5%, at least about 0.75%, at least about 1%, at least about 1.25%, at least about 1.5%, at least about 1.75%, at least about 2%, at least about 3% cells of the total number of cells in a LAG-3 positive melanoma tumor express LAG-3.

In some embodiments, at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, or at least about 30% of the total number of cells of a malignant tumor express LAG-3. In some embodiments, the malignant tumor is melanoma, gastric cancer, renal cancer, HCC, SCCHN, or NSCLC.

In accordance with the methods described herein, the malignant tumors can be tested to determine LAG-3 and PD-L1 expression. In some embodiments, the malignant tumors treated in accordance with the methods disclosed herein are LAG-3 positive PD-L1 positive tumors. In some embodiments, the malignant tumor is a LAG-3 positive PD-L1 positive melanoma. In another embodiment, the malignant tumor is a LAG-3 positive PD-L1 positive gastric cancer, renal cancer, HCC, SCCHN, or NSCLC.

In some embodiments, the malignant tumors treated in accordance with the methods disclosed herein are LAG-3 positive PD-L1 negative tumors. In some embodiments, the malignant tumor is a LAG-3 positive PD-L1 negative melanoma. In another embodiment, the malignant tumor is a LAG-3 positive PD-L1 negative gastric cancer, renal cancer, HCC, SCCHN, or NSCLC.

10. Immunotherapies

In one aspect, immunotherapies provided herein involve administration of a LAG-3 inhibitor (e.g., an anti-LAG-3 antibody) and another antibody that blocks an inhibitory immune receptor (e.g., a receptor, which upon binding to its natural ligand, inhibits/neutralizes activity, such as cytotoxic activity), particularly an anti-PD-1 antibody or an anti-PD-L1 antibody, to treat subjects having malignant tumors (e.g., advanced refractory solid tumors or hematological malignancies). In another aspect, immunotherapies provided herein involve administration of an anti-PD-1 antibody or an anti-PD-L1 antibody to treat subjects having malignant tumors (e.g., advanced refractory solid tumors or hematological malignancies). In another aspect, immunotherapies provided herein involve administration of an anti-CTLA-4 antibody to treat subjects having malignant tumors (e.g., advanced refractory solid tumors or hematological malignancies).

In one embodiment, the invention provides an anti-LAG-3 antibody and an anti-PD-1 antibody in combination according to a defined clinical dosage regimen, to treat subjects having a malignant tumor (e.g., an advanced refractory solid tumor). In a particular embodiment, the anti-LAG-3 antibody is BMS-986016. In another embodiment, the anti-PD-1 antibody is BMS-936558. In another embodiment, dosage regimens are adjusted to provide the optimum desired response (e.g., an effective response).

In another embodiment, the invention provides an anti-LAG-3 antibody and an anti-PD-L1 antibody in combination according to a defined clinical dosage regimen, to treat subjects having a malignant tumor (e.g., an advanced refractory solid tumor). In a particular embodiment, the anti-LAG-3 antibody is BMS-986016. In another embodiment, the anti-PD-L1 antibody is BMS-936559. In another embodiment, dosage regimens are adjusted to provide the optimum desired response (e.g., an effective response).

In another aspect, the invention provides an anti-LAG-3 antibody according to a defined clinical dosage regimen, to treat subjects having a malignant tumor (e.g., an advanced refractory solid tumor). In a particular embodiment, the anti-LAG-3 antibody is BMS-986016. In another embodiment, dosage regimens are adjusted to provide the optimum desired response (e.g., an effective response).

In another aspect, the invention provides an anti-PD-1 antibody according to a defined clinical dosage regimen, to treat subjects having a malignant tumor (e.g., an advanced refractory solid tumor). In a particular embodiment, the anti-PD-1 antibody is BMS-936558. In another embodiment, dosage regimens are adjusted to provide the optimum desired response (e.g., an effective response).

In another aspect, the invention provides an anti-PD-L1 antibody according to a defined clinical dosage regimen, to treat subjects having a malignant tumor (e.g., an advanced refractory solid tumor). In a particular embodiment, the anti-PD-L1 antibody is BMS-936559. In another embodiment, dosage regimens are adjusted to provide the optimum desired response (e.g., an effective response).

In another aspect, the invention provides an anti-CTLA-4 antibody according to a defined clinical dosage regimen, to treat subjects having a malignant tumor (e.g., an advanced refractory solid tumor). In a particular embodiment, the anti-CTLA4 antibody is ipilimumab (YERVOY). In a particular embodiment, the anti-CTLA4 antibody is tremelimumab (ticilimumab; CP-675,206), AGEN-1884, or ATOR-1015. In another embodiment, dosage regimens are adjusted to provide the optimum desired response (e.g., an effective response).

In another aspect, immunotherapies provided herein involve administration of an anti-PD-1 antibody and an immune checkpoint inhibitor to treat subjects having malignant tumors (e.g., advanced refractory solid tumors or hematological malignancies). In one embodiment, the anti-PD-1 antibody is BMS-936558. In one embodiment, the immune checkpoint inhibitor is a CTLA-4 antagonist, a CD80 antagonist, a CD86 antagonist, a Tim-3 antagonist, a TIGIT antagonist, a CD20 antagonist, a CD96 antagonist, a IDO1 antagonist, a STING antagonist, a GARP antagonist, a CD40 antagonist, A2aR antagonist, a CEACAM1 (CD66a) antagonist, a CEA antagonist, a CD47 antagonist a PVRIG antagonist, a TDO antagonist, a VISTA antagonist, or a KIR antagonist.

In another aspect, immunotherapies provided herein involve administration of an anti-PD-L1 antibody and an immune checkpoint inhibitor to treat subjects having malignant tumors (e.g., advanced refractory solid tumors or hematological malignancies). In one embodiment, the anti-PD-L1 antibody is BMS-936559. In one embodiment, the immune checkpoint inhibitor is a CTLA-4 antagonist, a CD80 antagonist, a CD86 antagonist, a Tim-3 antagonist, a TIGIT antagonist, a CD20 antagonist, a CD96 antagonist, a IDO1 antagonist, a STING antagonist, a GARP antagonist, a CD40 antagonist, A2aR antagonist, a CEACAM1 (CD66a) antagonist, a CEA antagonist, a CD47 antagonist a PVRIG antagonist, a TDO antagonist, a VISTA antagonist, or a KIR antagonist.

As used herein, adjunctive or combined administration (coadministration) includes simultaneous administration of the compounds in the same or different dosage form, or separate administration of the compounds (e.g., sequential administration). Thus, for example, the anti-LAG-3 and anti-PD-1 antibodies can be simultaneously administered in a single formulation. Alternatively, the anti-LAG-3 and anti-PD-1 antibodies can be formulated for separate administration and are administered concurrently or sequentially (e.g., one antibody is administered within about 30 minutes prior to administration of the second antibody).

For example, the anti-PD-1 antibody can be administered first followed by (e.g., immediately followed by) the administration of the anti-LAG-3 antibody, or vice versa. In one embodiment, the anti-PD-1 antibody is administered prior to administration of the anti-LAG-3 antibody. In another embodiment, the anti-PD-1 antibody is administered after administration of the anti-LAG-3 antibody. In another embodiment, the anti-LAG-3 antibody and anti-PD-1 antibody are administered concurrently. Such concurrent or sequential administration preferably results in both antibodies being simultaneously present in treated patients.

11. Treatment Protocols

In one aspect, suitable treatment protocols for treating a malignant tumor in a human patient include administering to the patient an effective amount of a LAG3 inhibitor (e.g., an anti-LAG-3 antibody).

In some embodiments, a suitable treatment protocol for treating a malignant tumor in a human patient include, for example, administering to the patient an effective amount of an anti-LAG-3 antibody, such as one comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5, wherein the method comprises at least one administration cycle, wherein the cycle is a period of eight weeks, wherein for each of the at least one cycles, at least four doses of the anti-LAG-3 antibody are administered at a flat dose of about 1, 3, 10, 20, 50, 80, 100, 130, 150, 16, 180, 200, 240 or 280 mg. In another embodiment, four doses of the anti-LAG-3 antibody are administered at a dose of 0.01, 0.03, 0.25, 0.1, 0.3, 1 or 3, 5, 8 or 10 mg/kg body weight.

In one aspect, suitable treatment protocols for treating a malignant tumor in a human patient include administering to the patient an effective amount of a PD1 pathway inhibitor (e.g., an anti-PD1 antibody).

In some embodiments, a suitable treatment protocol for treating a malignant tumor in a human patient include, for example, administering to the patient an effective amount of an anti-PD-1 antibody, such as one comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21, wherein the method comprises at least one administration cycle, wherein the cycle is a period of eight weeks, wherein for each of the at least one cycles, at least four doses of the anti-PD-1 antibody are administered at flat dose of about 50, 80, 100, 130, 150, 180, 200, 240 or 280 mg. In another embodiment, four doses of the anti-PD-1 antibody are administered at a dose of 0.1, 0.3, 1, 3, 5, 8 or 10 mg/kg body weight.

In one aspect, suitable treatment protocols for treating a malignant tumor in a human patient include administering to the patient an effective amount of an anti-CTLA-4 antibody.

In some embodiments, a suitable treatment protocol for treating a malignant tumor in a human patient include, for example, administering to the patient an effective amount of an anti-CTLA-4 antibody, wherein the method comprises at least one administration cycle, wherein the cycle is a period of eight weeks, wherein for each of the at least one cycles, at least four doses of the anti-CTLA-4 antibody are administered at flat dose of about 50, 80, 100, 130, 150, 180, 200, 240 or 280 mg. In another embodiment, four doses of the anti-CTLA-4 antibody are administered at a dose of 0.1, 0.3, 1, 3, 5, 8 or 10 mg/kg body weight.

In one aspect, suitable treatment protocols for treating a malignant tumor in a human patient include administering to the patient an effective amount of each of a LAG3 inhibitor (e.g., an anti-LAG-3 antibody) and a PD-1 pathway inhibitor (e.g., an anti-PD-1 antibody).

In some embodiments, a suitable treatment protocol for treating a malignant tumor in a human patient include, for example, administering to the patient an effective amount of each of:
(a) an anti-LAG-3 antibody, such as one comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5,
(b) an anti-PD-1 antibody, such as one comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21, wherein the method comprises at least one administration cycle, wherein the cycle is a period of eight weeks, wherein for each of the at least one cycles, at least four doses of the anti-LAG-3 antibody are administered at a flat dose of about 1, 3, 10, 20, 50, 80, 100, 130, 150, 16, 180, 200, 240 or 280 mg and at least four doses of the anti-PD-1 antibody are administered at flat dose of about 50, 80, 100, 130, 150, 180, 200, 240 or 280 mg. In another embodiment, four doses of the anti-LAG-3 antibody are administered at a dose of 0.01, 0.03, 0.25, 0.1, 0.3, 1 or 3, 5, 8 or 10 mg/kg body weight and four doses of the anti-PD-1 antibody are administered at a dose of 0.1, 0.3, 1, 3, 5, 8 or 10 mg/kg body weight.

In one embodiment, the anti-LAG-3 antibody and anti-PD-1 antibody are administered at the following doses:
(a) 3 mg of anti-LAG-3 antibody and 80 mg of anti-PD-1 antibody;
(b) 3 mg of anti-LAG-3 antibody and 240 mg of anti-PD-1 antibody;
(c) 20 mg of anti-LAG-3 antibody and 240 mg of anti-PD-1 antibody;
(d) 80 mg of anti-LAG-3 antibody and 160 mg of anti-PD-1 antibody;
(e) 80 mg of anti-LAG-3 antibody and 240 mg of anti-PD-1 antibody;
(f) 160 mg of anti-LAG-3 antibody and 240 mg of anti-PD-1 antibody; or
(g) 240 mg of anti-LAG-3 antibody and 240 mg of anti-PD-1 antibody.

In one embodiment, the anti-LAG-3 antibody and anti-PD-1 antibody are administered at a dose of 20 mg of anti-LAG-3 antibody and 80 mg of anti-PD-1 antibody. In one embodiment, the tumor is lung cancer.

In one embodiment, the anti-LAG-3 antibody and anti-PD-1 antibody are administered at a dose of 20 mg of anti-LAG-3 antibody and 240 mg of anti-PD-1 antibody.

In one embodiment, the anti-LAG-3 antibody and anti-PD-1 antibody are administered at a dose of 80 mg of anti-LAG-3 antibody and 240 mg of anti-PD-1 antibody. In one embodiment, the tumor is melanoma (e.g., anti-PD1/PD-L1 antibody experienced melanoma or first line melanoma treatment), RCC (e.g., IO naïve RCC), NSCLC (e.g., anti-PD1/PD-L1 antibody experienced NSCLC), gastric cancer (e.g., IO naïve gastric cancer), HCC (e.g., IO naïve HCC), NSCLC (e.g., first line treatment of NSCLC), or SCCHN (e.g., IO naïve SCCHN).

In one embodiment, the anti-LAG-3 antibody and anti-PD-1 antibody are administered at a dose of 240 mg of anti-LAG-3 antibody and 240 mg of anti-PD-1 antibody.

In one embodiment, the anti-LAG-3 antibody and anti-PD-1 antibody are administered at a dose of 160 mg of anti-LAG-3 antibody and 240 mg of anti-PD-1 antibody. In one embodiment, the tumor is melanoma (e.g., anti-PD1/PD-L1 antibody experienced melanoma or first line melanoma treatment), RCC (e.g., IO naïve RCC), NSCLC (e.g., anti-PD1/PD-L1 antibody experienced NSCLC), gastric cancer (e.g., IO naïve gastric cancer), HCC (e.g., IO naïve HCC), NSCLC (e.g., first line treatment of NSCLC), or SCCHN (e.g., IO naïve SCCHN). In another embodiment, the tumor is Hodgkin's lymphoma (e.g., prior IO treated Hodgkin's lymphoma); DLBCL, PD-1/PD-L1 naïve Hodgkin's lymphoma, or PD-1/PD-L1 progressed/refractory Hodgkin's lymphoma.

In another embodiment, the anti-LAG-3 antibody and anti-PD-1 antibody are administered at the following doses:
(a) 0.3 mg/kg of anti-LAG-3 antibody and 1 mg/kg of anti-PD-1 antibody;
(b) 0.3 mg/kg of anti-LAG-3 antibody and 3 mg/kg of anti-PD-1 antibody;
(c) 0.25 mg/kg of anti-LAG-3 antibody and 3 mg/kg of anti-PD-1 antibody;
(d) 1 mg/kg of anti-LAG-3 antibody and 3 mg/kg of anti-PD-1 antibody; or
(e) 3 mg/kg of anti-LAG-3 antibody and 3 mg/kg of anti-PD-1 antibody.

In one embodiment, the dose of the anti-LAG-3 and/or anti-PD-1 antibody is calculated per body weight, e.g., mg/kg body weight. In another embodiment, the dose of the anti-LAG-3 and/or anti-PD-1 antibody is a flat-fixed dose. In another embodiment, the dose of the anti-LAG-3 and/or anti-PD-1 antibody is varied over time. For example, the anti-LAG-3 antibody and/or anti-PD-1 antibody may be initially administered at a high dose and may be lowered over time. In another embodiment, the anti-LAG-3 antibody and/or anti-PD-1 antibody is initially administered at a low dose and increased over time.

In another embodiment, the amount of the anti-LAG-3 and/or anti-PD-1 antibodies administered is constant for each dose. In another embodiment, the amount of antibody administered varies with each dose. For example, the maintenance (or follow-on) dose of the antibody can be higher or the same as the loading dose which is first administered. In another embodiment, the maintenance dose of the antibody can be lower or the same as the loading dose.

In another embodiment, the anti-LAG-3 and/or anti-PD-1 antibodies are formulated for intravenous administration. In one embodiment, the anti-PD-1 antibody is administered on Days 1, 15, 29, and 43 of each cycle. In another embodiment, the anti-LAG-3 antibody is administered on Days 1, 15, 29, and 43 of each cycle.

In other embodiments, the anti-LAG-3 and/or anti-PD-1 antibodies are administered about once per week, once about every or three two weeks, about once per month or as long as a clinical benefit is observed or until there is a complete response, confirmed progressive disease or unmanageable toxicity.

In another embodiment, a cycle of administration is eight weeks, which can be repeated, as necessary. In another embodiment, the treatment consists of up to 12 cycles.

In another embodiment, 4 doses of the anti-PD-1 antibody are administered per eight week cycle. In another embodiment, 4 doses of the anti-LAG-3 antibody are administered per eight week cycle.

In another embodiment, the anti-PD-1 antibody and anti-LAG-3 antibody are administered as a first line of treatment (e.g., the initial or first treatment). In another embodiment, the anti-PD-1 antibody and anti-LAG-3 antibody are administered as a second line of treatment (e.g., after the initial or first treatment, including after relapse and/or where the first treatment has failed).

In one embodiment, the invention provides a method of treating a human patient with unresectable or metastatic melanoma, comprising: administering to the patient a therapeutically effective amount of a LAG-3 inhibitor and a PD-1 pathway inhibitor; wherein the patient has previously been treated with a PD-1 inhibitor. In some embodiments, the invention provides a method of treating a human patient with unresectable or metastatic melanoma, comprising: administering to the patient a therapeutically effective amount of a LAG-3 inhibitor and a PD-1 pathway inhibitor; wherein the patient has previously been treated with a PD-L1 inhibitor. In certain embodiments, the invention is directed to a method of treating a human patient with unresectable or metastatic melanoma, comprising: administering to the patient a therapeutically effective amount of a LAG-3 inhibitor and a PD-1 pathway inhibitor; wherein the patient has previously been treated with a PD-1 inhibitor, and wherein the melanoma expresses LAG-3. In one embodiment, the invention is directed to a method of treating a human patient with unresectable or metastatic melanoma, comprising: administering to the patient a therapeutically effective amount of a LAG-3 inhibitor and a PD-1 pathway inhibitor; wherein the patient has previously been treated with a PD-L1 inhibitor, and wherein the melanoma expresses LAG-3. In one embodiment, the invention provides a method of treating a human patient with melanoma that progressed while-on or after treatment with a PD-1 pathway inhibitor or a PD-L1 pathway inhibitor, comprising: administering to the patient a therapeutically effective amount of a LAG-3 inhibitor and a PD-1 pathway inhibitor; wherein the patient has previously been treated with an anti-PD-1 inhibitor. In some embodiments, the invention provides a method of treating a human patient with melanoma that progressed while-on or after treatment with a PD-1 pathway inhibitor or a PD-L1 pathway inhibitor, comprising: administering to the patient a therapeutically effective amount of a LAG-3 inhibitor and a PD-1 pathway inhibitor; wherein the patient has previously been treated with an anti-PD-L1 inhibitor. In certain embodiments, the invention provides a method of treating a human patient with melanoma that progressed while-on or after treatment with a PD-1 pathway inhibitor or a PD-L1 pathway inhibitor, comprising: administering to the patient a therapeutically effective amount of a LAG-3 inhibitor and a PD-1 pathway inhibitor; wherein the patient has previously been treated with an anti-PD-1 inhibitor, and wherein the melanoma expresses LAG-3. In one embodiment, the invention provides a method of treating a human patient with melanoma that progressed while-on or after treatment with a PD-1 pathway inhibitor or a PD-L1 pathway inhibitor, comprising: administering to the patient a therapeutically effective amount of a LAG-3 inhibitor and a PD-1 pathway inhibitor; wherein the patient has previously been treated with an anti-PD-L1 inhibitor, and wherein the melanoma expresses LAG-3. In some embodiments, the LAG-3 expression of the melanoma is ≥1%. In particular embodiments, the PD-1 pathway inhibitor administered is an anti-PD-1 antibody. In one embodiment, the PD-1 antibody is nivolumab. In certain embodiments, the LAG-3 inhibitor is a LAG-3 antibody. In one embodiment, the LAG-3 antibody is BMS-986016. In an embodiment, the PD-1 pathway inhibitor administered is an anti-PD-L1 antibody.

In one embodiment, the anti-LAG-3 antibody is BMS-986016 and the anti-PD-1 antibody is nivolumab. In one embodiment, the anti-LAG-3 antibody is MK-4280 and the anti-PD-1 antibody is pembrolizumab. In one embodiment, the anti-LAG-3 antibody is REGN3767 and the anti-PD-1 antibody is REGN2810. In one embodiment, the anti-LAG-3 antibody is LAG525 (Int'l Publ. No. WO2015/138920) and the anti-PD-1 antibody is PDR001.

In another aspect, the invention features any of the aforementioned embodiments, wherein the anti-PD-1 antibody is replaced by, or combined with, an anti-PD-L1 or anti-PD-L2 antibody.

In another aspect, the invention features any of the aforementioned embodiments, wherein administering the anti-LAG-3 antibody or antigen-binding fragment thereof and PD-1 pathway inhibitor (e.g., anti-PD-1 antibody) activates the patient's T cells. In some embodiments, administering the anti-LAG-3 antibody or antigen-binding fragment thereof and PD-1 pathway inhibitor (e.g., anti-PD-1 antibody) induces the expression of activation markers by the patient's T cells. Expression of activation markers by the patient's T cells can be detected by analyzing a patient sample, for example, peripheral lymphocytes or tumor-infiltrating lymphocytes using flow cytometry.

In another aspect, the invention features any of the aforementioned embodiments, wherein administering the anti-LAG-3 antibody or antigen-binding fragment thereof results in the occupancy of at least about 10%, at least about 20%, at least about 30%, at least about 40%, at least about 50%, at least about 60%, at least about 70%, at least about 80%, at least about 90%, at least about 95%, or about 100% of the LAG-3 receptors on the patient's T cells. In some embodiments, the T cells are CD8+ T cells. In some embodiments, the T cells are tumor infiltrating T cells.

In another aspect, the invention features any of the aforementioned embodiments, wherein the treatment protocol further comprises the administration of at least one additional therapeutic agent. In some embodiments, the at least one additional therapeutic agent is a chemotherapeutic agent. In some embodiments, the at least one additional therapeutic agent is an immune checkpoint inhibitor.

12. Outcomes

With Respect to Target Lesions, Responses to Therapy May Include:

| | |
|---|---|
| Complete Response (CR) (RECIST V1.1) | Disappearance of all target lesions. Any pathological lymph nodes (whether target or non-target) must have reduction in short axis to <10 mm. |
| Partial Response (PR) (RECIST V1.1) | At least a 30% decrease in the sum of the diameters of target lesions, taking as reference the baseline sum diameters. |
| Progressive Disease (PD) (RECIST V1.1) | At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) (RECIST V1.1) | Neither sufficient shrinkage to qualify for PR nor sufficient increase to qualify for PD, taking as reference the smallest sum diameters while on study. |
| Immune-related Complete Response (irCR) (irRECIST) | Disappearance of all target lesions. Any pathological lymph nodes (whether target or non-target) must have reduction in short axis to <10 mm. |
| Immune-related Partial Response (irPR) (irRECIST) | At least a 30% decrease in the sum of diameters of target lesions and all new measurable lesions (i.e., Percentage Change in Tumor Burden), taking as reference the baseline sum diameters. Note: the appearance of new measurable lesions is factored into the overall Tumor Burden, but does not automatically qualify as progressive disease until the sum of the diameters increases by ≥20% when compared to nadir. |
| Immune-related Progressive Disease (irPD) (irRECIST) | At least a 20% increase in Tumor Burden (ie the sum of diameters of target lesions, and any new measurable lesions) taking as reference the smallest sum on study (this includes the baseline sum if that is the smallest on study). In addition to the relative increase of 20%, the sum must also demonstrate an absolute increase of at least 5 mm. Tumor assessments using immune-related criteria for progressive disease incorporates the contribution of new measurable lesions. Each net percentage change in tumor burden per assessment accounts for the size and growth kinetics of both old and new lesions as they appear. |
| Immune-related Stable Disease (irSD) (irRECIST) | Neither sufficient shrinkage to qualify for irPR nor sufficient increase to qualify for irPD, taking as reference the smallest sum diameters while on study. |

With respect to non-target lesions, responses to therapy may include:

| | |
|---|---|
| Complete Response (CR) (RECIST V1.1) | Disappearance of all non-target lesions. All lymph nodes must be non-pathological in size (<10 mm short axis). |
| Non-CR/Non-PD (RECIST V1.1) | Persistence of one or more non-target lesion(s). |
| Progressive Disease (PD) (RECIST V1.1) | Unequivocal progression of existing non-target lesions. The appearance of one or more new lesions is also considered progression. |
| Immune-related Complete Response (irCR) (irRECIST) | Disappearance of all non-target lesions. All lymph nodes must be non-pathological in size (<10 mm short axis). |
| Immune-related Progressive Disease (irPD) (irRECIST) | Increases in number or size of non-target lesion(s) does not constitute progressive disease unless/until Tumor Burden increases by 20% (ie the sum of the diameters at nadir of target lesions and any new measurable lesions increases by the required amount). Non-target lesions are not considered in the definition of Stable Disease and Partial Response. |

Patients treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a complete response (CR), a partial response (PR), stable disease (SD), immune-related complete disease (irCR), immune-related partial response (irPR), or immune-related stable disease (irSD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, administration of effective amounts of the anti-LAG-3 antibody, anti-PD-1 antibody, anti-PD-L1 antibody, anti-CTLA-4 antibody, a combination of the anti-LAG-3 antibody and anti-PD-1 antibody, or a combination of the anti-PD-1 antibody and an immune checkpoint inhibitor according to any of the methods provided herein produces at least one therapeutic effect selected from the group consisting of reduction in size of a tumor, reduction in number of metastatic lesions appearing over time, complete remission, partial remission, or stable disease.

In still other embodiments, the methods of treatment produce a clinical benefit rate (CBR=CR+PR+SD≥6 months) better than that achieved by a method of treatment that does not comprise a step of (i) determining the level of LAG-3 expression in a tumor sample prior to treatment, (ii) selecting a LAG-3 positive tumor for treatment, (iii) treating a tumor that has been identified as LAG-3 positive prior to treatment, or (iv) any combinations thereof. In other embodiments, the improvement of clinical benefit rate is about 20% 20%, 30%, 40%, 50%, 60%, 70%, 80% or more compared to a method of treatment that does not comprise a step of (i) determining the level of LAG-3 expression in a tumor sample prior to treatment, (ii) selecting a LAG-3 positive tumor for treatment, (iii) treating a tumor that has been identified as LAG-3 positive prior to treatment, or (iv) any combinations thereof.

In still other embodiments, the methods of treatment produce an objective response rate (ORR=CR+PR) of at least about 15%, at least about 20%, at least about 25%, at least about 30%, at least about 40%, at least about 50%, at least about 60%, at least about 70%, at least about 80%, at least about 90%, or about 100%. In one embodiment, the methods of treatment produce an objective response rate of at least about 15%, wherein the malignant tumor is a LAG-3 positive melanoma that is resistant to treatment with an anti-PD-1 or anti-PD-L1 antibody. In some embodiments, the median duration of response is ≥3 month, ≥6 month, ≥12 month, or ≥18 month. In one embodiment, the median duration of response is ≥6 month. In some embodiments, the frequency of patients with duration of response ≥6 month is at least about 30%, at least about 40%, at least about 50%, at least about 60%, at least about 70%, at least about 80%, at least about 90%, or 100%.

In still other embodiments, the methods of treatment produce an objective response rate (ORR=CR+PR) better than that achieved by a method of treatment that does not comprise a step of (i) determining the level of LAG-3 expression in a tumor sample prior to treatment, (ii) selecting a LAG-3 positive tumor for treatment, (iii) treating a tumor that has been identified as LAG-3 positive prior to treatment, or (iv) any combinations thereof. In other embodiments, the improvement of objective response rate is about 20% 20%, 30%, 40%, 50%, 60%, 70%, 80% or more compared to a method of treatment that does not comprise a step of (i) determining the level of LAG-3 expression in a tumor sample prior to treatment, (ii) selecting a LAG-3 positive tumor for treatment, (iii) treating a tumor that has been identified as LAG-3 positive prior to treatment, or (iv) any combinations thereof. In some embodiments, the median duration of response is ≥3 month, ≥6 month, ≥12 month, or ≥18 month. In one embodiment, the median duration of response is ≥6 month.

In still other embodiments, the methods of treatment produce a disease control rate (DRR=CR+PR+SD) of at least about 20%, at least about 30%, at least about 40%, at least about 50%, at least about 60%, at least about 70%, at least about 80%, at least about 90%, or about 100%. In one embodiment, the methods of treatment produce a disease control rate of at least about 70%, wherein the malignant tumor is a LAG-3 positive melanoma that is resistant to treatment with an anti-PD-1 or anti-PD-L1 antibody. In some embodiments, the median duration of response is ≥3 month, ≥6 month, ≥12 month, or ≥18 month. In one embodiment, the median duration of response is ≥6 month. In some embodiments, the frequency of patients with duration of response ≥6 month is at least about 30%, at least about 40%, at least about 50%, at least about 60%, at least about 70%, at least about 80%, at least about 90%, or 100%.

In still other embodiments, the methods of treatment produce a disease control rate (DRR=CR+PR+SD) better than that achieved by a method of treatment that does not comprise a step of (i) determining the level of LAG-3 expression in a tumor sample prior to treatment, (ii) selecting a LAG-3 positive tumor for treatment, (iii) treating a tumor that has been identified as LAG-3 positive prior to treatment, or (iv) any combinations thereof. In other embodiments, the improvement of disease control rate is about 20% 20%, 30%, 40%, 50%, 60%, 70%, 80% or more compared to a method of treatment that does not comprise a step of (i) determining the level of LAG-3 expression in a tumor sample prior to treatment, (ii) selecting a LAG-3 positive tumor for treatment, (iii) treating a tumor that has been identified as LAG-3 positive prior to treatment, or (iv) any combinations thereof. In some embodiments, the median duration of response is ≥3 month, ≥6 month, ≥12 month, or ≥18 month. In one embodiment, the median duration of response is ≥6 month.

13. Kits and Unit Dosage Forms

Also within the scope of the present invention are diagnostic kits comprising an anti-LAG-3 antibody for assaying LAG-3 expression as a biomarker for screening patients for the immunotherapy or for predicting the efficacy of the immunotherapy. Kits typically include a label indicating the intended use of the contents of the kit and instructions for use. The term "label" includes any writing, or recorded material supplied on or with the kit, or which otherwise accompanies the kit. In certain embodiments of a diagnostic kit, a first anti-LAG-3 antibody for assaying, detecting, and/or quantifying LAG-3 expression is co-packaged with at least one therapeutic antibody (e.g., a second anti-LAG-3 antibody, an anti-PD-1 antibody, an anti-PD-L1 antibody, and/or an anti-CTLA-4 antibody) for the treatment of a LAG-3 positive tumor. In some embodiments, the kit further comprises an anti-PD-L1 antibody for assaying, detecting, and/or quantifying PD-L1 expression as a biomarker for predicting the efficacy of the immunotherapy. In one embodiment, the immunotherapy comprises administering to the patient a therapeutically effective amount of a LAG-3 inhibitor (e.g., anti-LAG-3 antibody) and a PD-1 pathway inhibitor (e.g., anti-PD1 antibody or anti-PD-L1 antibody). In one embodiment, the immunotherapy comprises administering to the patient a therapeutically effective amount of a LAG-3 inhibitor (e.g., anti-LAG-3 antibody). In one embodiment, the immunotherapy comprises administering to the patient a therapeutically effective amount of a PD-1 pathway inhibitor (e.g., anti-PD1 antibody or anti-PD-L1 antibody). In one embodiment, the immunotherapy comprises administering to the patient a therapeutically effective amount of an anti-PD1 antibody. In one embodiment, the immunotherapy comprises administering to the patient a therapeutically effective amount of an anti-CTLA-4 antibody. In one embodiment, the immunotherapy comprises administering to the patient a therapeutically effective amount of a PD-1 pathway inhibitor (e.g., anti-PD1 antibody or anti-PD-L1 antibody) and an immune checkpoint inhibitor.

In certain embodiments, the diagnostic kit comprises an anti-human LAG-3 monoclonal antibody for assaying, detecting, and/or quantifying LAG-3 expression. See, e.g., J. Matsuzaki, et al.; PNAS 107, 7875 (2010).

Also provided herein are therapeutic kits which include a pharmaceutical composition containing an anti-LAG-3 antibody, such as BMS-986016, and an anti-PD-1 antibody, such as nivolumab, and a pharmaceutically-acceptable carrier, in a therapeutically effective amount adapted for use in the preceding methods. In certain embodiments of a therapeutic kit, the anti-LAG-3 antibody is co-packaged with an anti-PD-1 antibody in unit dosage form. The kits optionally also can include instructions, e.g., comprising administration schedules, to allow a practitioner (e.g., a physician, nurse, or patient) to administer the composition contained therein to administer the composition to a patient having cancer (e.g., a solid tumor). The kit also can include a syringe.

Optionally, the diagnostic and/or therapeutic kits include multiple packages of the single-dose pharmaceutical compositions each containing an effective amount of the anti-LAG-3 or anti-PD-1 antibody for a single administration in accordance with the methods provided above. Instruments or devices necessary for administering the pharmaceutical composition(s) also may be included in the kits. For instance, a kit may provide one or more pre-filled syringes containing an amount of the anti-LAG-3 or anti-PD-1 antibody.

In one embodiment, the present invention provides a kit for treating a patient afflicted with a malignant tumor, the kit, for example, comprising:
  (a) a dose of an anti-LAG-3 antibody, such as one comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5;
  (b) a dose of an anti-PD-1 antibody, such as one comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21; and
  (c) instructions for using the anti-LAG-3 antibody and anti-PD-1 antibody in the methods described herein.

In one embodiment, the present invention provides a kit for treating a patient afflicted with a malignant tumor, the kit, for example, comprising:
  (a) a dose of an anti-LAG-3 antibody, such as one comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5; and
  (b) instructions for using the anti-LAG-3 antibody in the methods described herein.

In one embodiment, the present invention provides a kit for treating a patient afflicted with a malignant tumor, the kit, for example, comprising:
  (a) a dose of an anti-PD-1 antibody, such as one comprising CDR1, CDR2 and CDR3 domains of the heavy chain variable region having the sequence set forth in SEQ ID NO:19, and CDR1, CDR2 and CDR3 domains of the light chain variable region having the sequence set forth in SEQ ID NO:21; and
  (b) instructions for using the anti-PD-1 antibody in the methods described herein.

In one embodiment, the present invention provides a kit for treating a patient afflicted with a malignant tumor, the kit, for example, comprising:
  (a) a dose of an anti-PD-L1 antibody, such as BMS-936559; and
  (b) instructions for using the anti-PD-L1 antibody in the methods described herein.

In one embodiment, the present invention provides a kit for treating a patient afflicted with a malignant tumor, the kit, for example, comprising:
  (a) a dose of an anti-CTLA-4 antibody, such as ipilimumab (YERVOY); and
  (b) instructions for using the anti-CTLA-4 antibody in the methods described herein.

In one embodiment, the present invention provides a kit for treating a patient afflicted with a malignant tumor, the kit, for example, comprising:
  (a) a dose of an anti-LAG-3 antibody, such as one comprising CDR1, CDR2 and CDR3 domains of the heavy chain variable region having the sequence set forth in SEQ ID NO:3, and CDR1, CDR2 and CDR3 domains of the light chain variable region having the sequence set forth in SEQ ID NO:5;
  (b) a dose of an immune checkpoint inhibitor; and
  (c) instructions for using the anti-PD-1 antibody and the immune checkpoint inhibitor in the methods described herein.

In some embodiments, the malignant tumor is a LAG-3 positive tumor. In some embodiments, the malignant tumor is a LAG-3/PD-L1 positive tumor. In some embodiments, the malignant tumor is a LAG-3 positive/PD-L1 negative tumor.

In some embodiments, the malignant tumor is melanoma.

The present invention is further illustrated by the following examples which should not be construed as further limiting.

EXAMPLES

Example 1

Optimization and Validation of an Assay for the Automated Detection of LAG3 (Mouse Clone 17B4) by Single Stain Immunohistochemistry with DAB Chromogen and Evaluation by Image Analysis in Formalin-Fixed, Paraffin Embedded Human Tissue The purpose of this study was to validate an immunohistochemical assay for lymphocyte activation gene-3 (LAG3) using a commercially available antibody (mouse clone 17B4) from LS Biosciences, for use in formalin fixed, paraffin embedded (FFPE) human tissue.

Immunohistochemistry (IHC) refers to the process of localizing proteins or other molecules in cells of a tissue section. Immunohistochemical staining is widely used in the diagnosis of cancer and has recently been used to help predict whether patients are likely to respond to a targeted chemotherapeutic agent. As opposed to many other analytical techniques such as the Western blot or ELISA, IHC retains the spatial localization of protein expression within a tissue specimen. This technique involves using an antibody (primary antibody) to specifically bind a target within the cellular context and then using the bound antibody to deposit a dye in the region of the target.

Test System. FFPE validation were performed on remnant, de-identified, or anonymized human samples. Tissues used for sensitivity testing and analysis included 40 bladder urothelial cancer, 41 gastric/GEJ cancer, 41 HNSCC, 41 melanoma, 41 NSCLC, and 43 RCC. The positive and negative control selected for LAG3 IHC was a tonsil tissue. Tonsil tissue contains cellular features that are positive and negative for LAG3.

Test Articles. The LAG3 mouse clone 17B4 antibody was purchased from LS Biosciences (Seattle, WA) and stored at −20° C. A mouse IgG isotype control antibody was purchased from BD Pharmingen (San Jose, CA) and stored at 2-8° C.

Immunohistochemistry. Immunohistochemistry was performed in accordance with standard laboratory techniques.

Pre-Processing. The procedure for IHC analysis of LAG3 (mouse clone 17B4) was performed using automated detection at room temperature (RT) on the Leica Bond Rx (Leica Biosystems, Buffalo Grove, IL) using commercially available reagents. Specimens were sectioned at 4-micron thickness, mounted onto positive-charged glass slides, dried, baked, deparaffinized, and rehydrated offline. Tissues were then placed onto the autostainer and underwent pretreatment using Epitope Retrieval Solution 1 (Catalog #AR9961, Leica) for 20 minutes at 100° C. followed by a rinse with Bond Wash Buffer (Catalog #AR9590, Leica) at RT.

DAB Chromogen Assay Tissues were incubated with Peroxide Block (Catalog #DS9800, Leica) for 5 minutes followed by 3 rinses in Bond Wash Buffer. Tissues were incubated with Protein Block, Serum Free (Catalog #X0909, Dako, Carpinteria, CA) for 5 minutes followed by incubation with the primary antibody or isotype negative control reagent diluted in Bond Primary Antibody Diluent (Catalog #AR9352, Leica) for 30 minutes and 3 rinses in Bond Wash Buffer. Tissues were incubated with Post Primary (Bond Polymer Refine Detection Kit, Catalog #DS9800, Leica) for 8 minutes followed by 3 rinses in Bond Wash buffer for 2 minutes each. Tissues were incubated with Polymer (Bond Polymer Refine Detection Kit) for 8 minutes followed by 3 rinses in Bond Wash buffer for 2 minutes each and 2 rinses in distilled water. Tissues were incubated with DAB (Bond Polymer Refine Detection Kit) for 10 minutes followed by 4 rinses in distilled water.

Red Chromogen Assay Tissues were then incubated with 3% hydrogen peroxide for 5 minutes followed by 3 rinses in Bond Wash Buffer. Tissues were incubated with Protein Block, Serum Free for 5 minutes followed by incubation with the primary antibody or isotype negative control reagent diluted in Bond Primary Antibody Diluent for 30 minutes and 3 rinses in Bond Wash Buffer. Tissues were incubated with Post Primary AP (Catalog #DS9390, Bond Polymer Refine Red Detection Kit, Leica) for 20 minutes followed by 3 rinses in Bond Wash buffer for 2 minutes each. Tissues were incubated with Polymer AP (Bond Polymer Refine Red Detection Kit) for 30 minutes followed by 3 rinses in Bond Wash buffer for 2 minutes each and 2 rinses in distilled water. Tissues were incubated with Red Refine (Bond Polymer Refine Red Detection Kit) for 10 minutes followed by 4 rinses in distilled water.

Post-Processing Tissues were incubated with Hematoxylin (Bond Polymer Refine Detection Kit) for 5 minutes followed by a rinse in distilled water and a rinse in Bond Wash Buffer. Coverslip mounting occurred offline using an automated glass coverslipper (Leica) in accordance with standard procedures.

Slides were scanned using an Aperio Turbo AT system (Aperio, Vista, CA) to produce whole slide images. A 20×JPEG image of each stain is provided for this report.

Image Analysis Tissues stained with LAG3 (mouse clone 17B4) using DAB chromogen or red chromogen were evaluated by image analysis with a Nuclear v9 algorithm from Aperio The ROI includes the area of tumor tissue with intervening stroma. Areas excluded from analysis include normal tissue, larger stromal areas, necrotic tissue, tar (if possible), and staining artifact.

A nuclear algorithm was selected because heavy cytoplasmic stains in small cells, such as immune cells, often obscure the hematoxylin in the nucleus. The cytoplasmic and membrane algorithm require visualization of hematoxylin in the nucleus to quantify a cell. The nuclear algorithm has a featured called "fill holes" that will fill the central portion of a lymphocyte if there is hematoxylin present and record it as one cell.

Pathologist Visual Immune Score A subset of samples within the dynamic range were also scored by a pathologist during QC of image analysis. The purpose of the pathologist visual immune score is to provide a back-up result in the event of an image analysis score that does not produce an accurate result as deemed by a board-certified pathologist. Reasons for image analysis failure may include but not limited to: 1) light counterstain; 2) crushed tissue; 3) presence of tar in NSCLC tissues; 4) staining of hemosiderin; or 5) presence of melanin that precludes evaluation. The pathologist visual immune score is the percentage of positive immune cells within the annotated region (to mimic the algorithm).

LAG3 IHC Assay Validation—Sensitivity A sensitivity analysis was performed using the optimized LAG3 (mouse clone 17B4) IHC assay on 247 FFPE human tissues (40 bladder urothelial cancer, 41 gastric/GEJ cancer, 41 HNSCC, 41 melanoma, 41 NSCLC, 43 RCC) tissues to demonstrate the dynamic range of the assay within the 6 indications. All specimens were evaluated by image analysis of 1 ROI (tumor+intervening stroma) and a subset of the tissues (10 each within the 6 indications) were also evaluated by pathologist visual immune score.

On average, LAG-3 (mouse clone 17B4) expression was highest in melanoma (3.54%), followed by bladder urothelial cancer (2.58%), NSCLC (1.68%), HNSCC (1.47%), Gastric/GEJ cancer (1.27%), and RCC (1.24%). Positivity ranged from 0.01% to 25.57% with an average of 1.95% and a median of 0.84%. Using a threshold of 2% demonstrated 192 negative and 55 positive tissues (12 bladder urothelial, 6 gastric/GEJ cancer, 7 HNSCC, 18 melanoma, 8 NSCLC, and 4 RCC).

FIG. 1 shows anti-LAG-3 staining patterns observed in the tumor samples using monoplex IHC. The staining patterns observed included partial membrane/cytoplasmic localization, dot like localization, and complete membrane/cytoplasmic localization.

Figure 2:
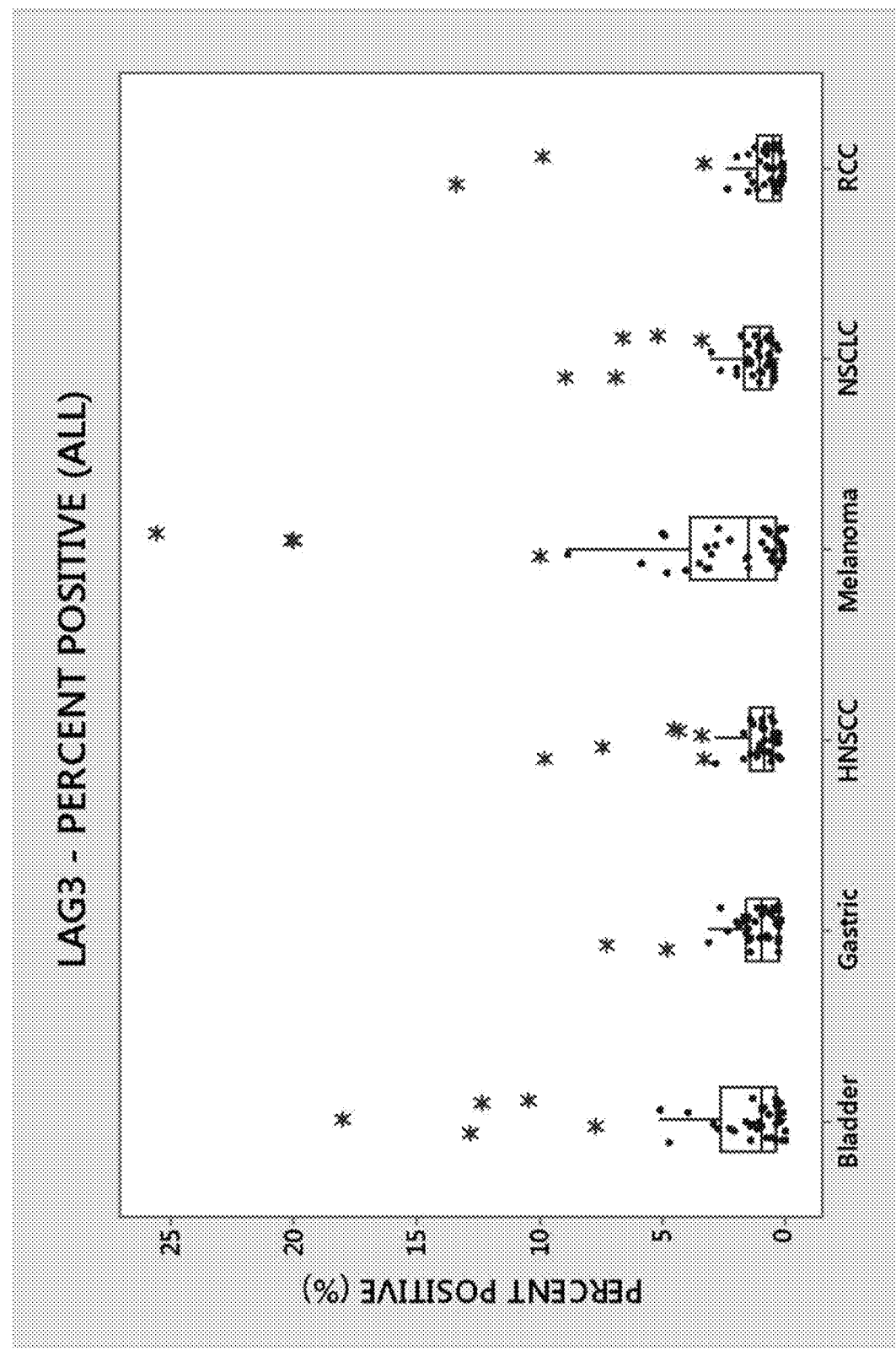
FIG. 2. Frequency distribution of LAG-3+ cells as a ratio of total tumor cells in a sample analyzed with monoplex LAG-3 IHC.

FIG. 2 shows the frequency distribution of LAG-3 positive cell as a ratio of total tumor cells across various tumors as detected by monoplex LAG-3 IHC.

Example 2

Initial Efficacy of Anti-Lymphocyte Activation Gene-3 (Anti-LAG-3: BMS-986016) in Combination with Nivolumab in Patients with Melanoma Previously Treated with Anti-PD1/PD-L1 Therapy Simultaneous blockade of the negative T-cell regulators LAG-3 and PD-1 may function synergistically to restore T-cell activation and enhance antitumor immunity. Data from a phase 1/2a study of BMS-986016 (fully human IgG4 mAb that targets LAG-3)±nivolumab (fully human IgG4 mAb that targets PD-1) demonstrated that the combination was well tolerated and showed promising antitumor activity in patients with melanoma who were refractory to or relapsed during prior anti-PD-1/PD-L1 therapy (NCT01968109; Ascierto et al. *J Clin Oncol.* 2017; 35(suppl) [abstract 9520]). Below is efficacy data in patients with advanced melanoma who progressed on prior anti-PD-1/PD-L1 therapy.

This was a phase I/IIa, open label, dose escalation and cohort expansion study evaluating the safety, tolerability, and efficacy of BMS-986016 administered alone or in combination with nivolumab in patients with advanced solid tumors. Patients received study therapy intravenously once every two weeks for up to twelve 8-week treatment cycles. Combination dose for expansion was BMS-986016 80 mg+nivolumab 240 mg.

Figures 3A, 3B:
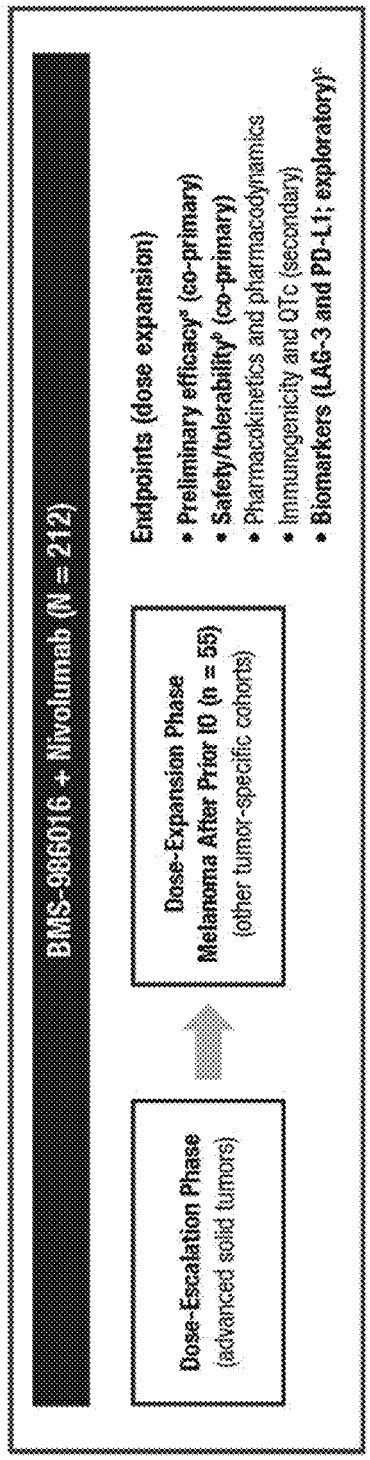
FIGS. 3A-B.

Study design and endpoints are shown in FIGS. 3 and 17.

Key eligibility criteria for patients in the melanoma prior IO expansion cohort are shown in FIG. 3.

Results. As of the Apr. 7, 2017 data cut-off, 212 patients were treated, including 55 patients with melanoma who progressed on prior anti-PD1/PD-L1 therapy (mel prior IO). Of the 212 patients, 61% were still on treatment at data cut-off. Of the 83 patients that discontinued treatment, the primary reason was disease progression (86%). Of the mel prior IO cohort, 67% of patients had M1C disease without brain metastasis, 15% had lactate dehydrogenase (LDH)≥2× upper limit of normal (ULN), and 20% had liver metastasis. FIG. 4.

Patients in the mel prior IO cohort were heavily pretreated. FIG. 5. Of 55 patients, 76% had ≥2 prior therapies; 40% of patients had progressive disease (PD) as best response to prior anti-PD1/PD-L1 therapy.

Figure 6:
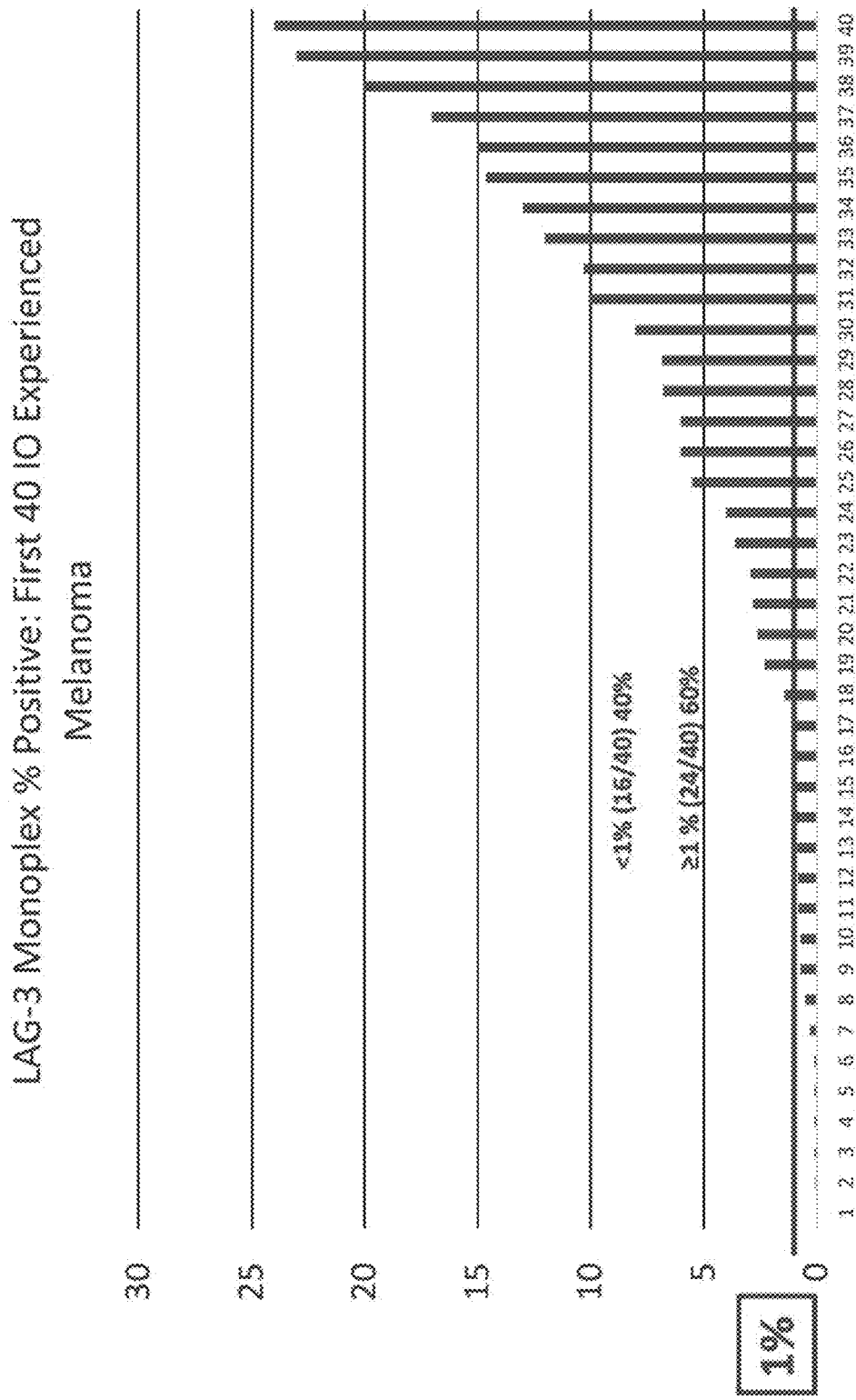
FIG. 6. LAG-3 expression status of first 40 IO experienced melanomas.

FIG. 6 shows the LAG-3 expression status of the first 40 IO experienced melanoma samples. 40% (16/40) of the samples were scored as LAG-3 positive using ≥1% cut-off in a monoplex IHC assay.

Figure 8:
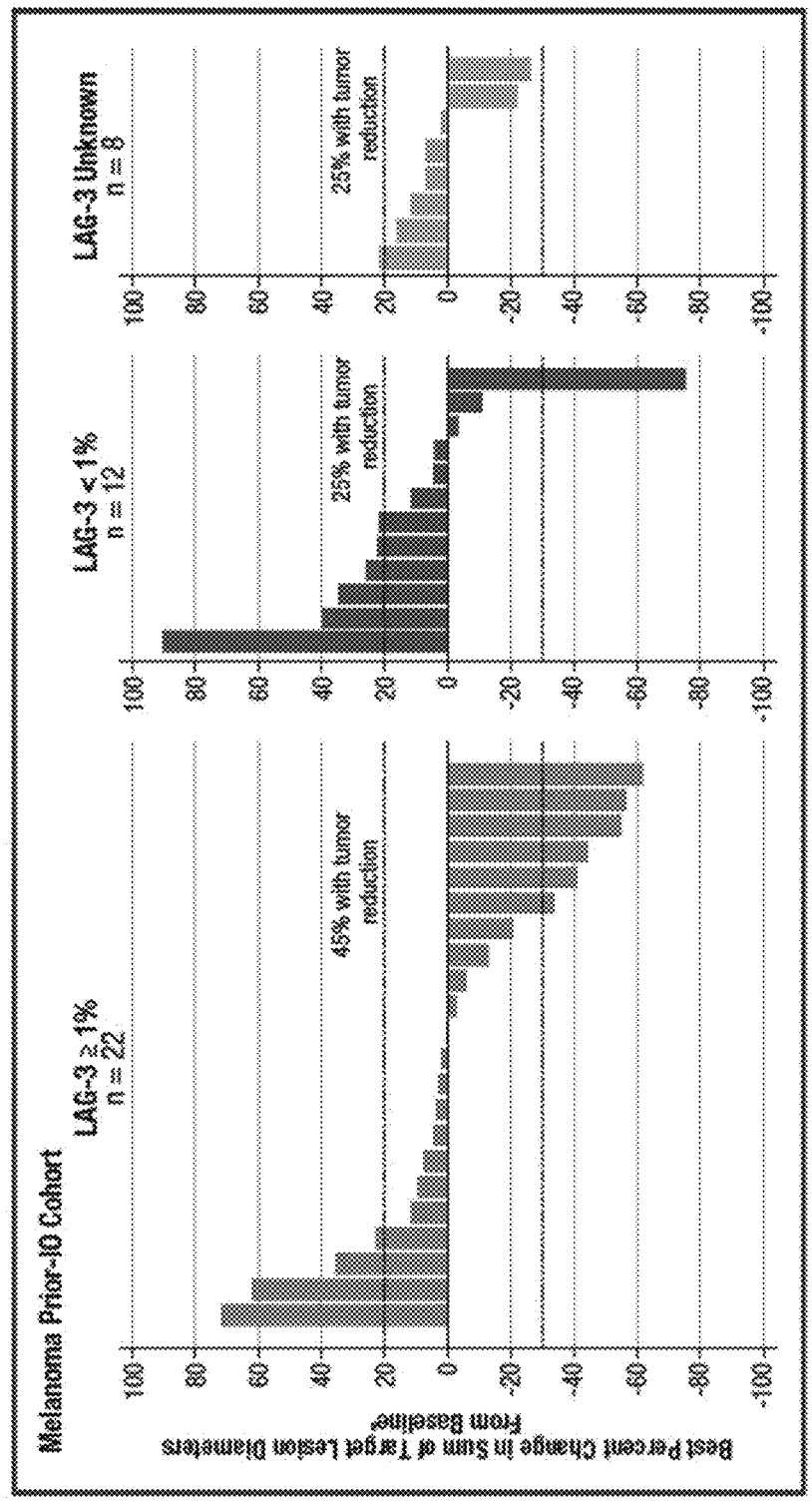
FIG. 8. LAG-3 expression enriches for response.
Figure 9:
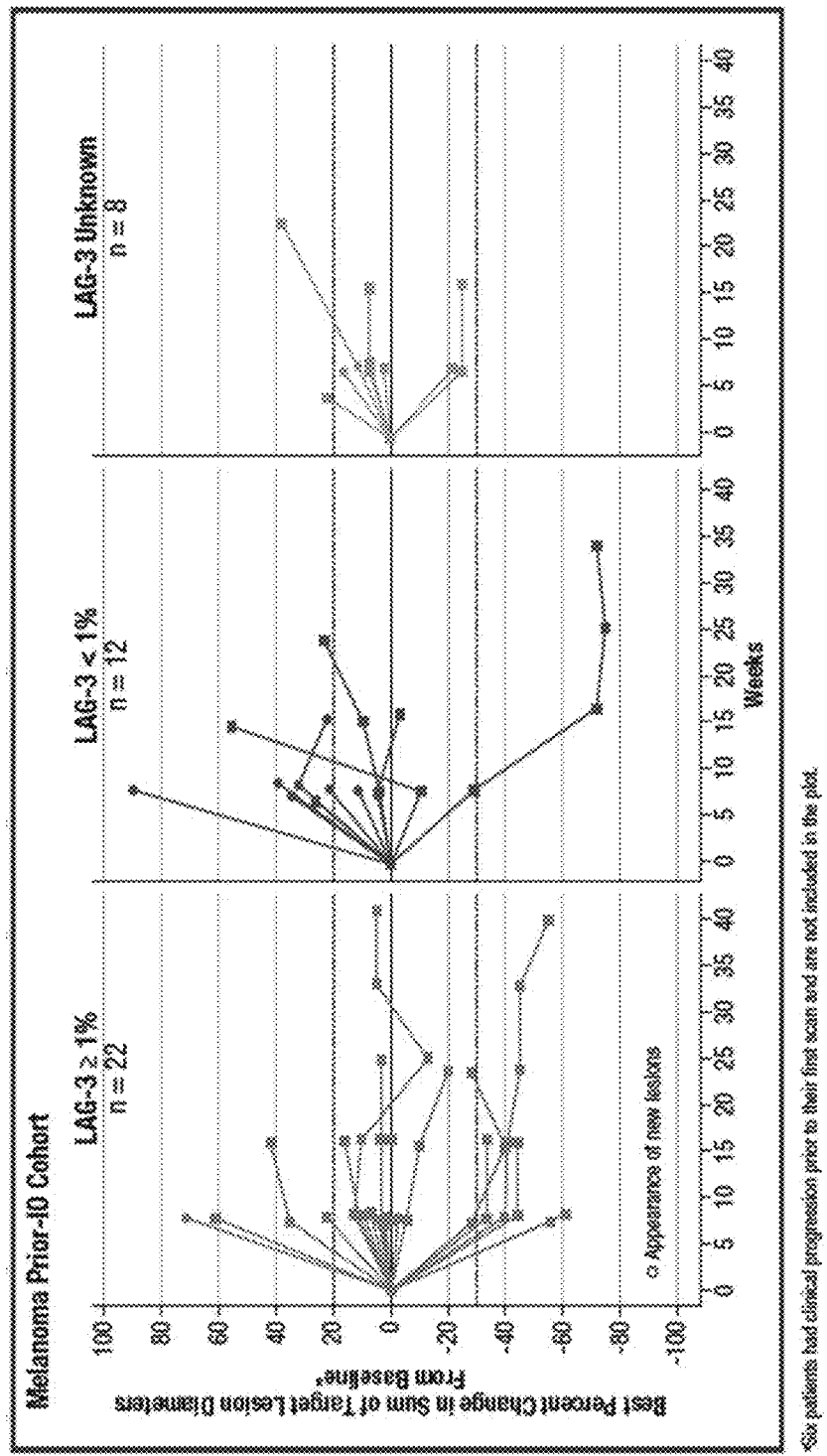
FIG. 9. Depth and duration of response by LAG-3 expression.

Efficacy in the melanoma prior IO cohort. Median duration of follow-up for all efficacy-evaluable patients (n=48; all progressed on prior anti-PD-1/PD-L1 therapy) was 14 weeks (range, 4.1-41 weeks). Response by investigator assessment is shown in FIG. 7. Overall response rate (ORR) was 13% and 6 patients had PR (2 of who had PD as best response to prior anti-PD1/PD-L1 therapy). 15 patients had reduction in tumor burden from baseline; reduction>30% was observed in 7 patients (FIG. 8). As shown in FIG. 8, LAG-3 expression enriches for response. FIG. 9 shows the depth and duration of response LEG-3≥1%, LAG-3<1%, and LAG-3 unknown patients.

Figure 10:
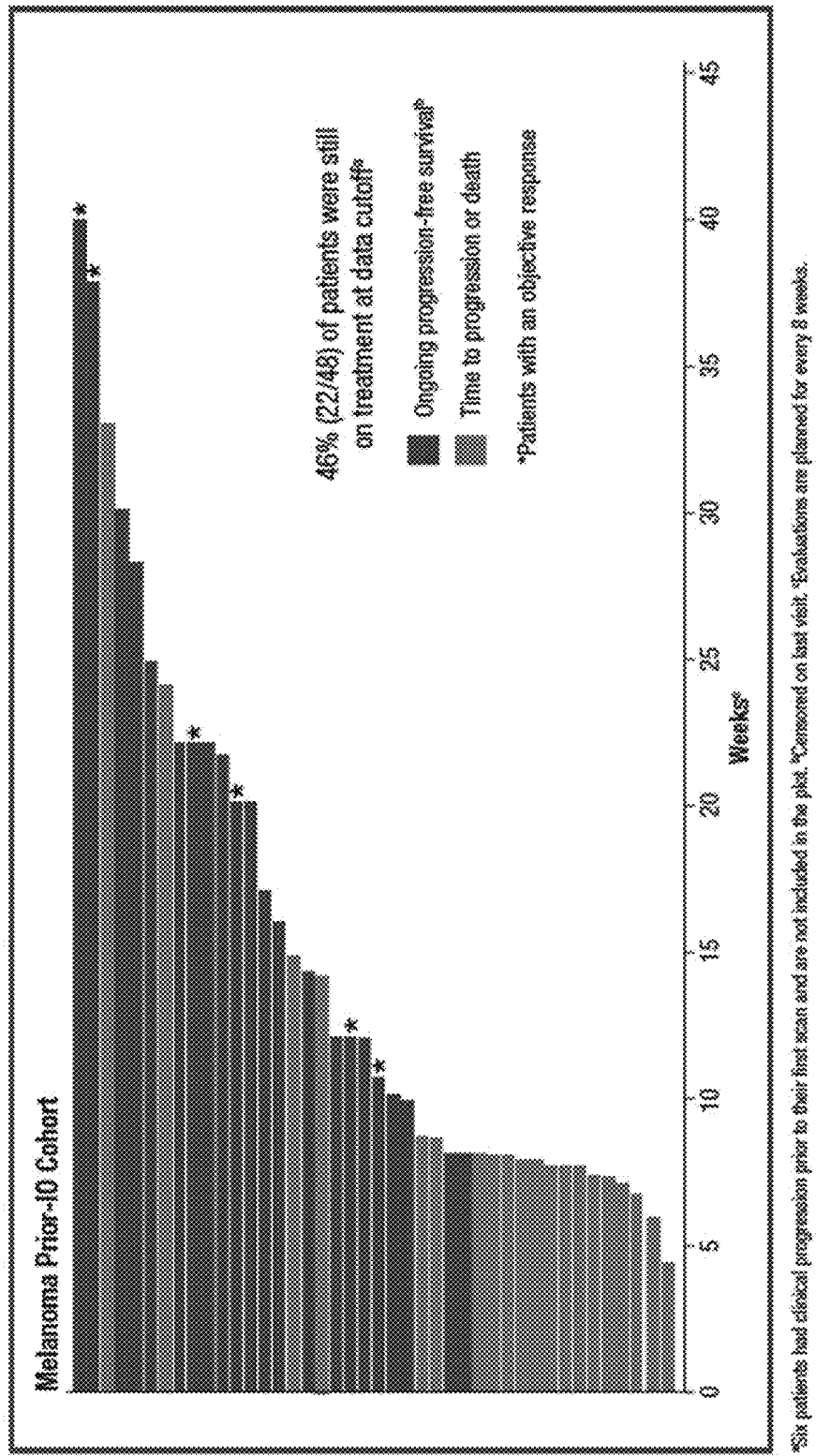
FIG. 10. Duration of progression-free survival.

FIG. 10 shows the duration of progression-free survival. Of 48 evaluable patients, 46% (22/48) of patients remain on treatment without progression at data cutoff.

As shown in FIG. 11, there was nearly a 3-fold increase in ORR for patients with LAG-3 expression ≥1% (20%) vs LAG-3 expression <1% (7.1%). PD-L1 expression did not appear to enrich for response.

Updated results from the clinical trial are shown in FIGS. 16-23. As of August 2017, 262 patients were treated, including 68 patients with melanoma who progressed on prior anti-PD1/PD-L1 therapy (mel prior IO). Updated baseline demographics and disease characteristics are shown in FIG. 17. Of the mel prior IO cohort, 68% of patients had M1C disease without brain metastasis, 13% had lactate dehydrogenase (LDH)≥2×upper limit of normal (ULN), and 25% had liver metastasis.

FIG. 18 shows the updated prior treatment history of the mel prior IO cohort. Of 68 patients, 77% had ≥2 prior therapies; 46% of patients had progressive disease (PD) as best response to prior anti-PD1/PD-L1 therapy. Most patients (57%) also received prior anti-CTLA-4 therapy. 46% of patients had a best response of PD to prior anti-PD-1/PD-L1 therapy.

FIG. 19 shows the updated efficacy data for the mel prior IO cohort. ORR was 11.5% and DCR was 49%. LAG-3 expression (≥1%) appeared to enrich for response. Median duration of response was not reached (range, 0.1+–39.3+).

FIG. 20 shows the response by baseline characteristics and LAG-3 expression observed in the mel prior IO cohort. LAG-3 expression (≥1%) enriched for response irrespective of PD-L1 expression.

Figure 21:
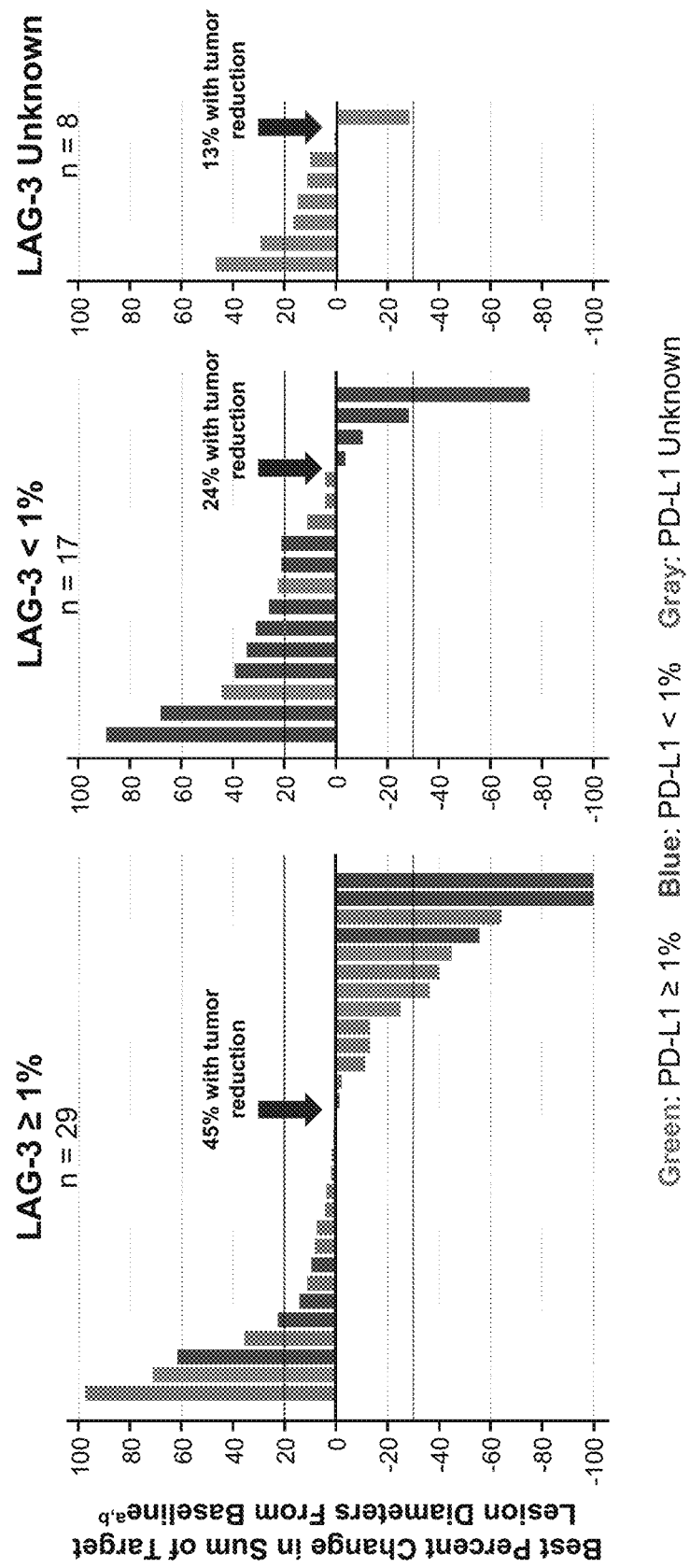
FIG. 21. Updated best change in target lesion size by LAG-3 and PD-L1 expression.
Figure 22:
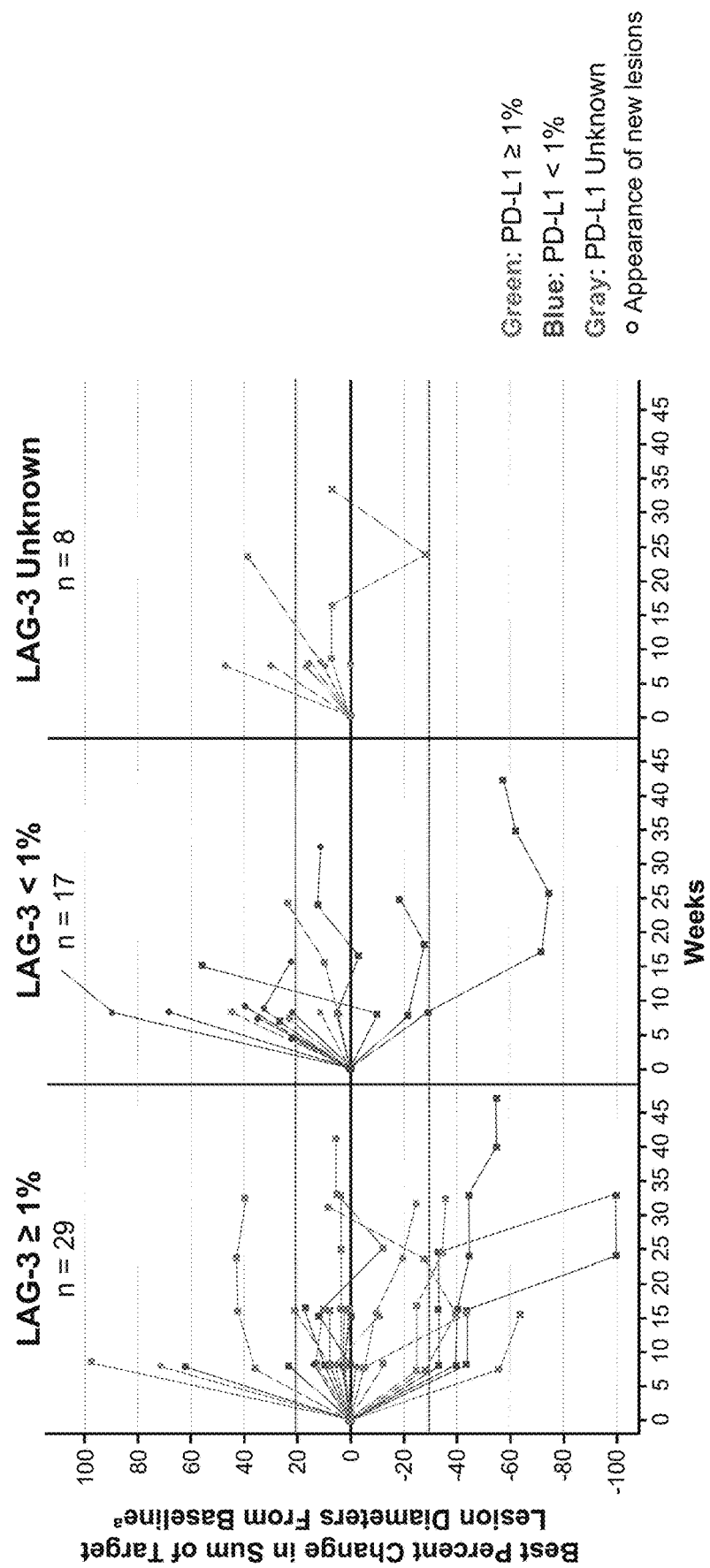
FIG. 22. Updated depth and duration of response by LAG-3 and PD-L1 expression.

FIGS. 21 and 22 show the best change in target lesion size by LAG-3 and PD-L1 expression and the depth and duration of response by LAG-3 and PD-L1 expression, respectively, observed in the mel prior IO cohort. Responses were more likely in patients with LAG-3 expression ≥1%. PD-L1 expression did not appear to enrich for response.

Figure 23:
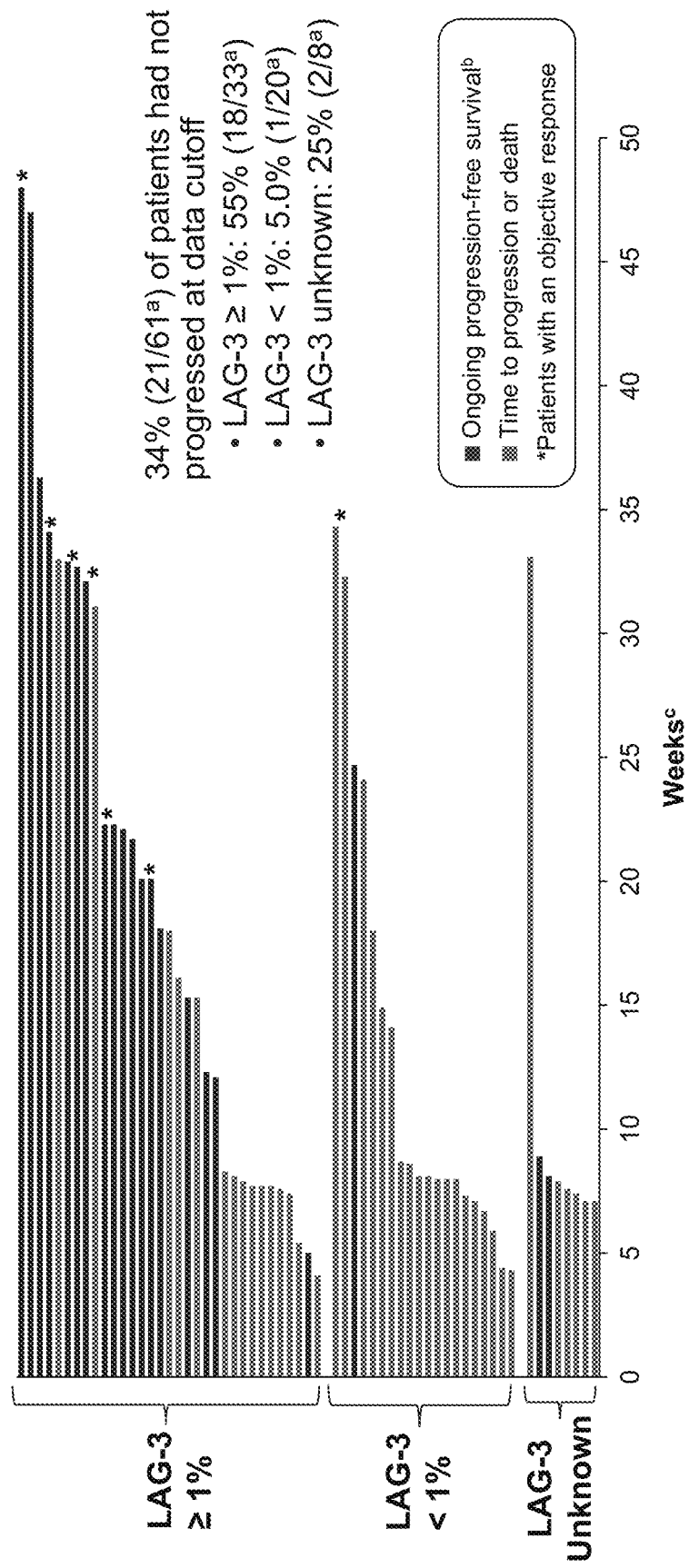
FIG. 23. Updated ongoing clinical follow-up.

FIG. 23 shows the duration of progression-free survival. Of 61 evaluable patients, 34% (21/61) of patients had not progressed at data cutoff. Of 33 evaluable LAG-3≥1% patients, 55% (18/33) of patients had not progressed at data cutoff. Of 20 evaluable LAG-3<1% patients, 5% (1/20) of patients had not progressed at data cutoff.

Example 3

Preliminary Efficacy and Biomarker Enrichment Across Several Advanced Solid Tumors in a Phase 1/2a Study of a Combination of Anti-LAG-3 and Anti-PD-1 Monoclonal Antibody LAG-3 is a transmembrane receptor that negatively regulates T-cell activation. Signaling through LAG-3 and other T-cell inhibitory receptors, including programmed death-1 (PD-1), can lead to T-cell exhaustion and is a mechanism of immune escape for tumors. Simultaneous blockade of LAG-3 and PD-1 may function synergistically to restore T-cell activation and enhance antitumor immunity. In a phase 1/2a study, BMS-986016 (IgG4 mAb targeting LAG-3)±nivolumab (IgG4 mAb targeting PD-1) demonstrated tolerability, peripheral T-cell activation, and preliminary clinical activity (NCT01968109; Lipson et al. *J Immunother Cancer.* 2016; 4(suppl):173 [abstract P232]). Efficacy of BMS-986016+ nivolumab across several advanced solid tumor expansion cohorts was evaluated in both all-comer and biomarker-enriched populations.

All patients (n=204 as of Apr. 7, 2017) were treated with BMS-986016 80 mg+nivolumab 240 mg Q2W in 56-day cycles until disease progression, confirmed complete response, completion of 12 cycles, or prohibitive toxicity. Most cohorts focused on immuno-oncology-naive patients with progression on/after at least 1 other prior therapy and included patients with advanced gastric/gastroesophageal junction cancer, squamous cell carcinoma of the head and neck, hepatocellular carcinoma, renal cell carcinoma, and NSCLC. One other cohort included patients with NSCLC who progressed on/after prior anti-PD-1/PD-L1 as their most recent therapy. Biomarker-defined patient subsets were described based on PD-L1 and LAG-3 immunohistochemical scoring in tumor biopsies.

Figure 12:
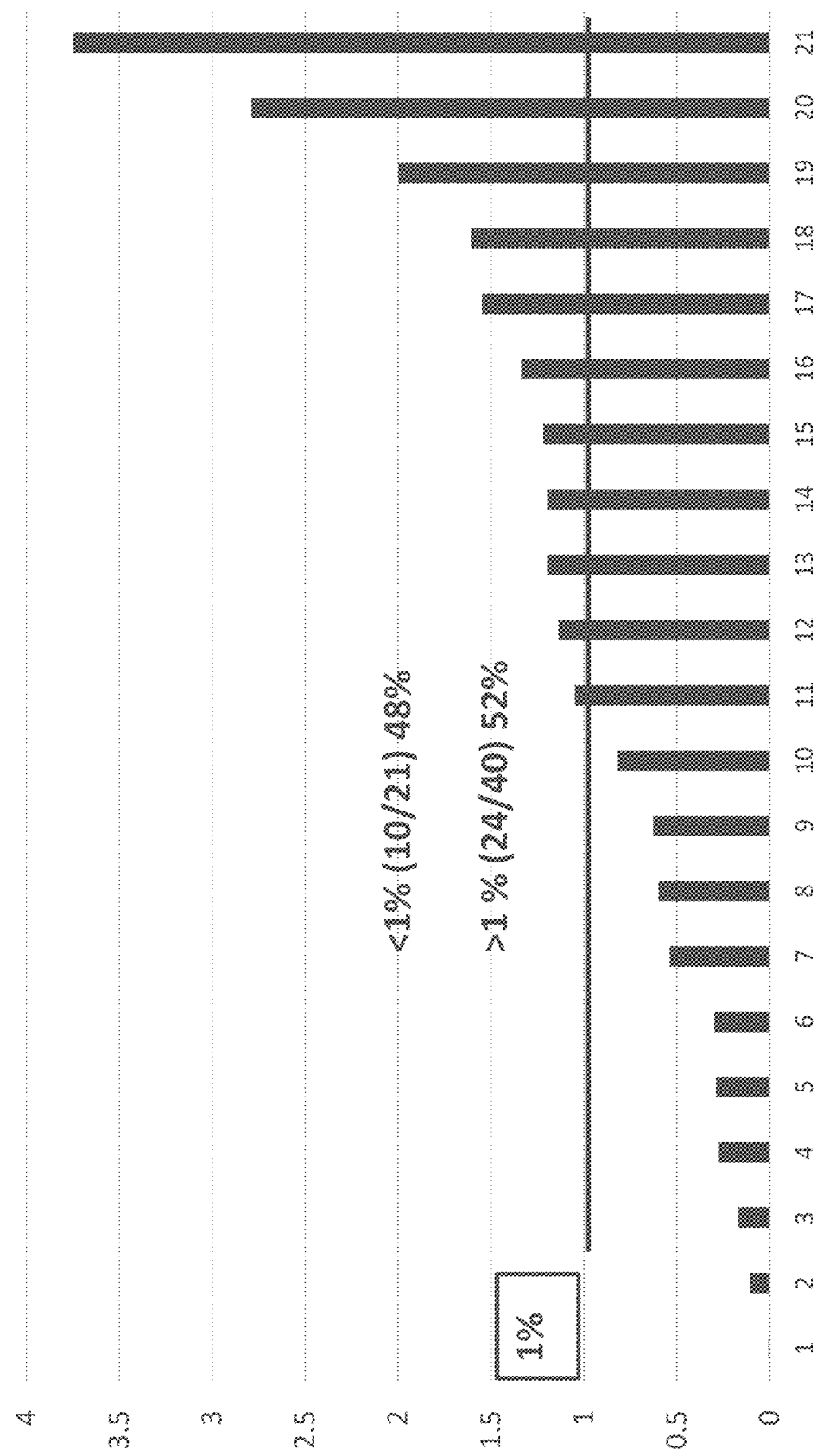
FIG. 12. LAG-3 expression status of gastric tumor samples. 48% (10/21) of the samples were scored as LAG-3 positive using a 1% cut-off in a monoplex RIC assay.

FIG. 12 shows LAG-3 expression status of immuno-oncology-naive gastric tumor samples. 48% (10/21) of the samples were scored as LAG-3 positive using a ≥1% cut-off in a monoplex IHC assay.

Figure 13:
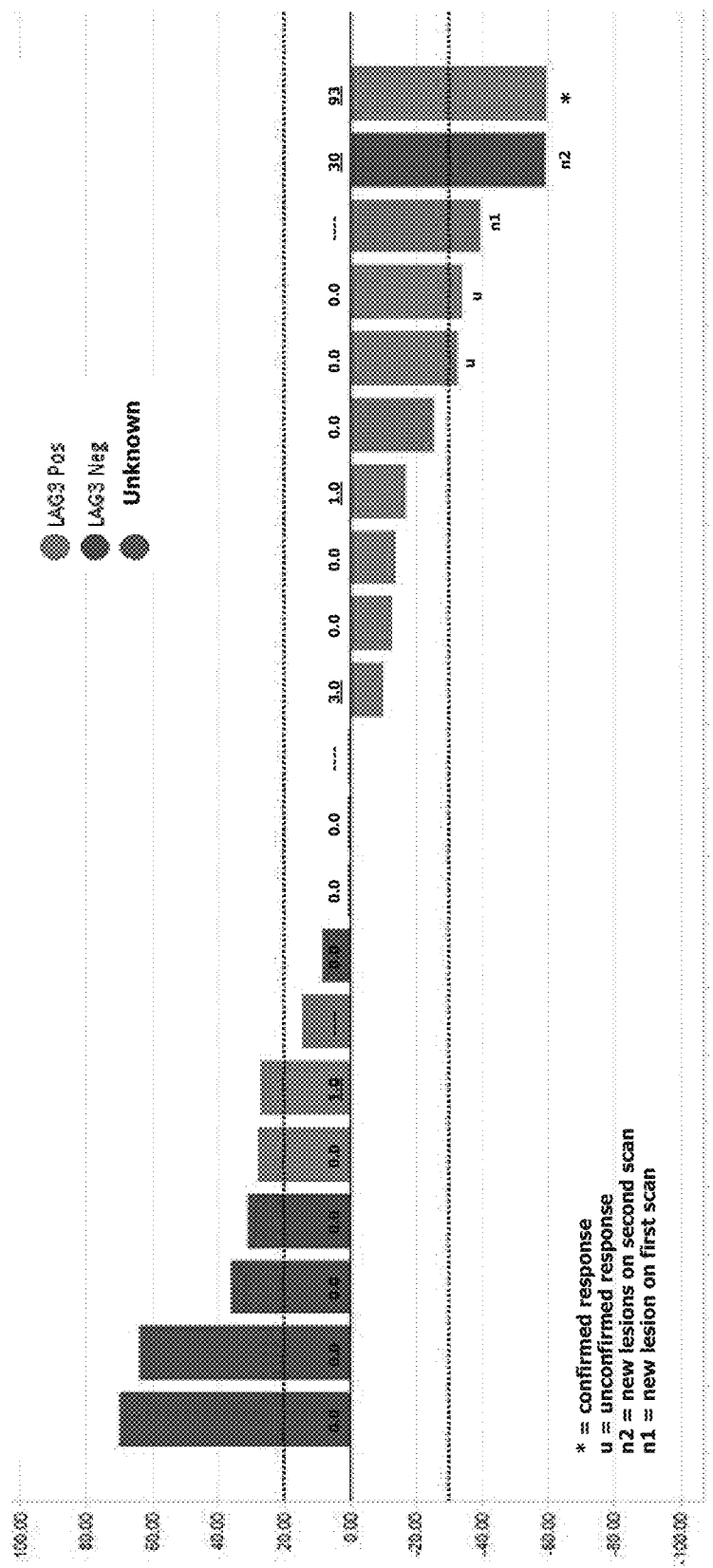
FIG. 13. Change in target lesion size in gastric cancer patients in response to treatment with a combination of anti-LAG-3 and anti-PD-1 antibody. LAG-3 positive tumors were enriched among the patients that were responsive to the treatment. Tumor response was determined according to RECIST. The patients in this study have not been previously exposed to anti-PD-1/PD-L1 treatment.

FIG. 13 shows change in target lesion size in immuno-oncology-naive gastric cancer patients in response to treatment with a combination of anti-LAG-3 and anti-PD-1 antibody. LAG-3 positive tumors were enriched among the patients that were responsive to the treatment. Tumor response was determined according to RECIST. The group of patients shown have not been previously exposed to anti-PD-1/PD-L1 treatment.

Figure 14:
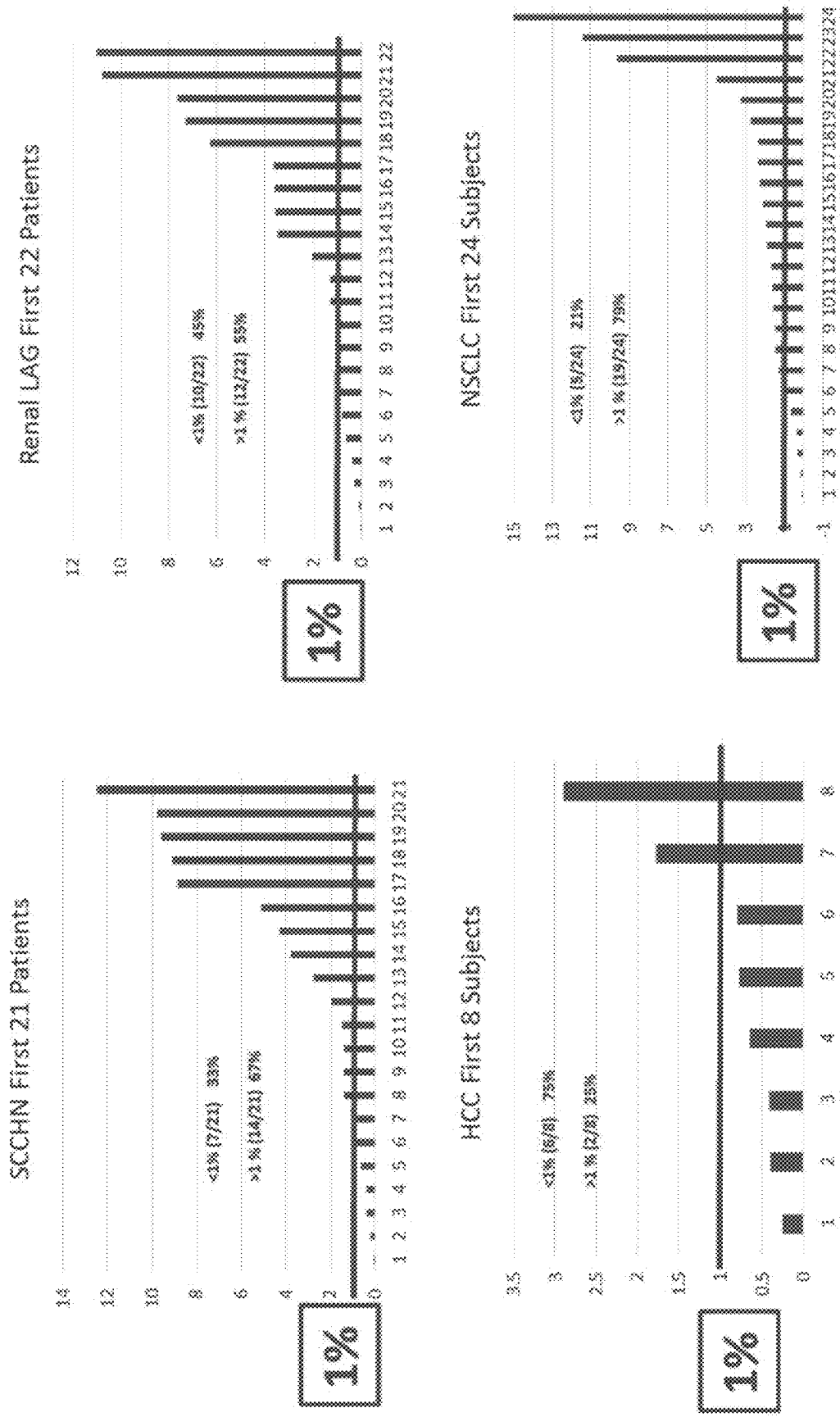
FIG. 14. LAG-3 expression status of squamous cell cancer of the head and neck (SCCHN), renal carcinoma, hepatocellular carcinoma (HCC), and NSCLC tumor samples as determined by a monoplex IHC assay.
Figure 16:
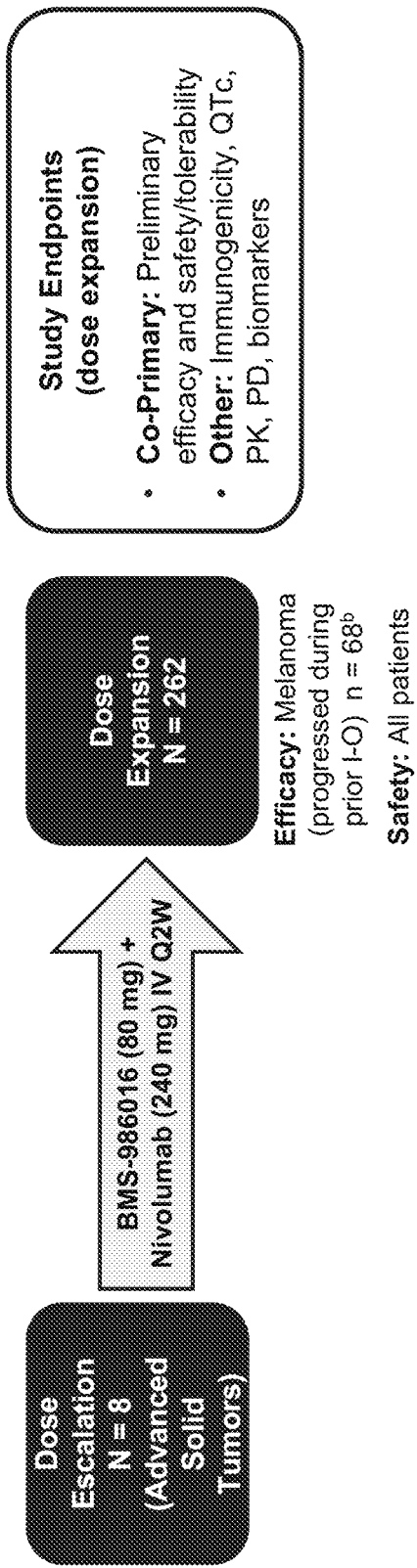
FIG. 16. Updated study design and endpoints.

FIG. 14 shows LAG-3 expression status of immuno-oncology-naive SCCHN, renal carcinoma, HCC, and NSCLC tumor samples as determined by a monoplex IHC assay.

Example 4

Multitumor Profiling of LAG-3 and Association With Immune Cell Phenotypes

Figure 24:
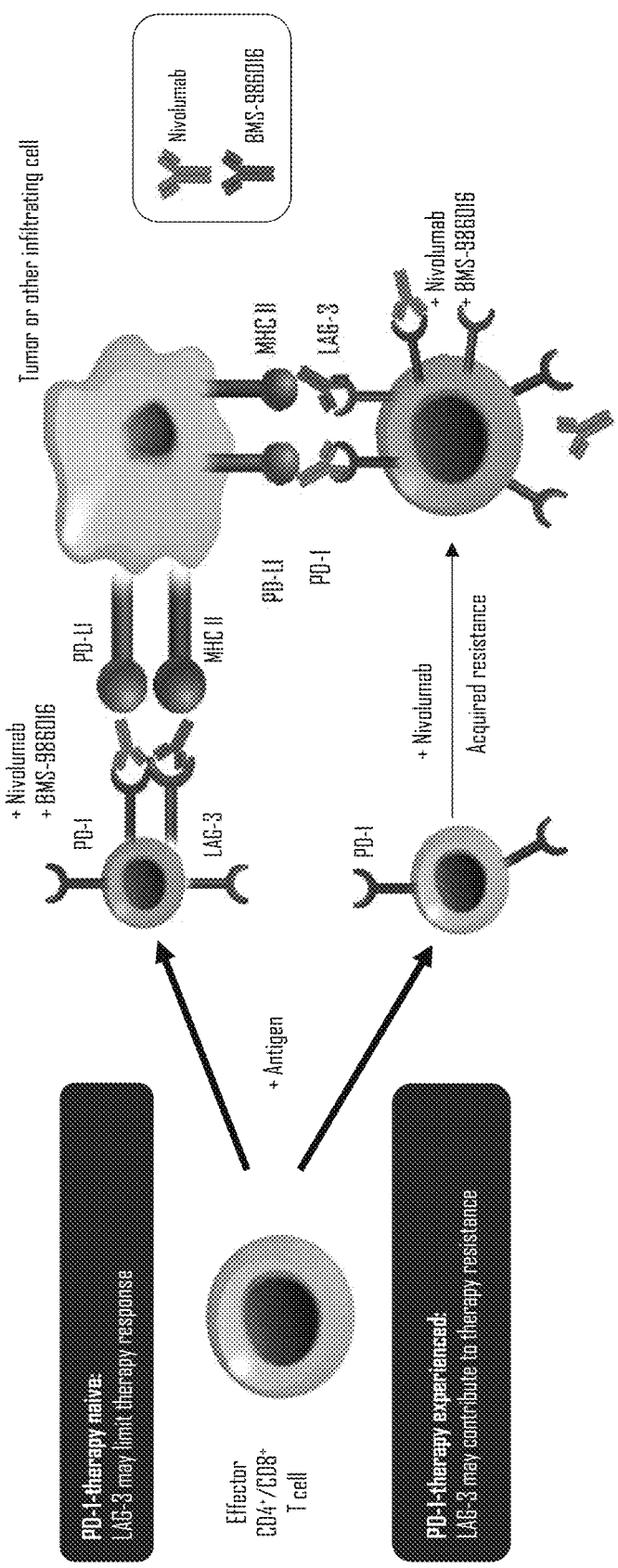
FIG. 24. Role of LAG-3 and PD-1 in T-cell exhaustion and proposed clinical utility of combined with nivolumab.

LAG-3 negatively regulates T-cell activation. Sierro S et al. *Expert Opin Ther Targets.* 15:91-101 (2011); Grosso J F et al. *J Clin Invest.* 117:3383-3392 (2007). LAG-3 and programmed death-1 (PD-1) receptors are overexpressed and co-expressed on tumor-infiltrating lymphocytes (TILs). Goding S R et al. *J Immunol.* 190:4899-4909 (2013). LAG-3 and PD-1 overexpression may limit treatment response to anti-PD-1 therapy and lead to tumor progression. Ascierto P et al. Poster 9520 presented at the 53rd Annual Meeting of the American Society of Clinical Oncology; Jun. 2-6, 2017; Chicago, IL; Wherry, *Nat Immunol.* 12(6):492-9 (2011); Woo S R et al. Cancer Res. 72:917-927 (2012); Huang C T et al. Immunity. 21:503-513 (2004). BMS-986016 is a fully human IgG4 antibody that targets LAG-3, blocking binding to its ligand, major histocompatibility complex class II (MHC II) (FIG. 24). Huard B et al. *Proc Natl Acad Sci USA.* 94:5744-5749 (1997). BMS-986016 combined with nivolumab (anti-PD-1) may restore T-cell activation and tumor response in patients whose disease progressed on anti-PD-1 monotherapy. Ascierto P et al. Poster 9520 presented at the 53rd Annual Meeting of the American Society of Clinical Oncology; Jun. 2-6, 2017; Chicago, IL. This dual inhibition may also enhance the durability of response in patients not previously treated with anti-PD-1 therapy. Simultaneous blockade of LAG-3 and PD-1 by BMS-986016 and nivolumab, respectively, produced peripheral T-cell activation and showed clinical activity and manageable safety in patients with advanced solid tumors. Ascierto P et al. Poster 9520 presented at the 53rd Annual Meeting of the American Society of Clinical Oncology; Jun. 2-6, 2017; Chicago, IL; Lipson E et al. J Immunother Cancer. 4(suppl 1):173 (2016). To further understand the association between LAG-3 and markers of resistance across tumors, a comprehensive profiling of commercially sourced tumor specimens to investigate and characterize expression of LAG-3 and MHC II in the context of inflammatory biomarkers has been performed.

Methods

Quantitative Immunohistochemistry (IHC) Solid tumor specimens were profiled from patients with renal cell carcinoma (RCC), gastric carcinoma, non-small cell lung carcinoma (NSCLC), melanoma, squamous cell carcinoma of the head and neck (SCCHN), and urothelial carcinoma. Slide sections were stained by IHC for LAG-3, CD8, FOXP3, CD68, CD163, PD-L1, and MHC II using the Leica Bond Rx or Dako Link 48 platforms. For immune cell markers (LAG-3, CD8, FOXP3, CD68, CD163), the percent positivity was determined using Aperio image analysis software by defining the proportion of total nucleated cells expressing the biomarker in the tumor microenvironment. MHC II and PD-L1 expression by IHC on tumor cells were scored manually. Unsupervised clustering (Ward's method) was performed on the IHC data to identify associations between LAG-3 and other immune biomarkers. To determine MHC II+ and LAG-3+ colocalization, MHC II-high (>70% MHC II+) or MHC II-low (<10% MHC II+) tumor cell regions were assessed for the number of LAG-3 stained cells (average of three 20× fields of view each for positive and negative regions).

mRNA Analysis In patients with RCC and melanoma, changes in LAG-3 mRNA levels were determined by differential gene expression analyses of Affymetrix (RCC) or RNA-sequencing (melanoma) data from tumor biopsy samples collected at screening and 2-4 weeks post-immunotherapy initiation.

Statistical Analyses Correlations between LAG-3 expression and other immune biomarkers were assessed by Spearman's correlation, r. Mann-Whitney test was conducted to assess statistical differences. Differential gene expression analyses were performed using generalized linear models that included treatment group and time as factors.

Results

Figure 25:
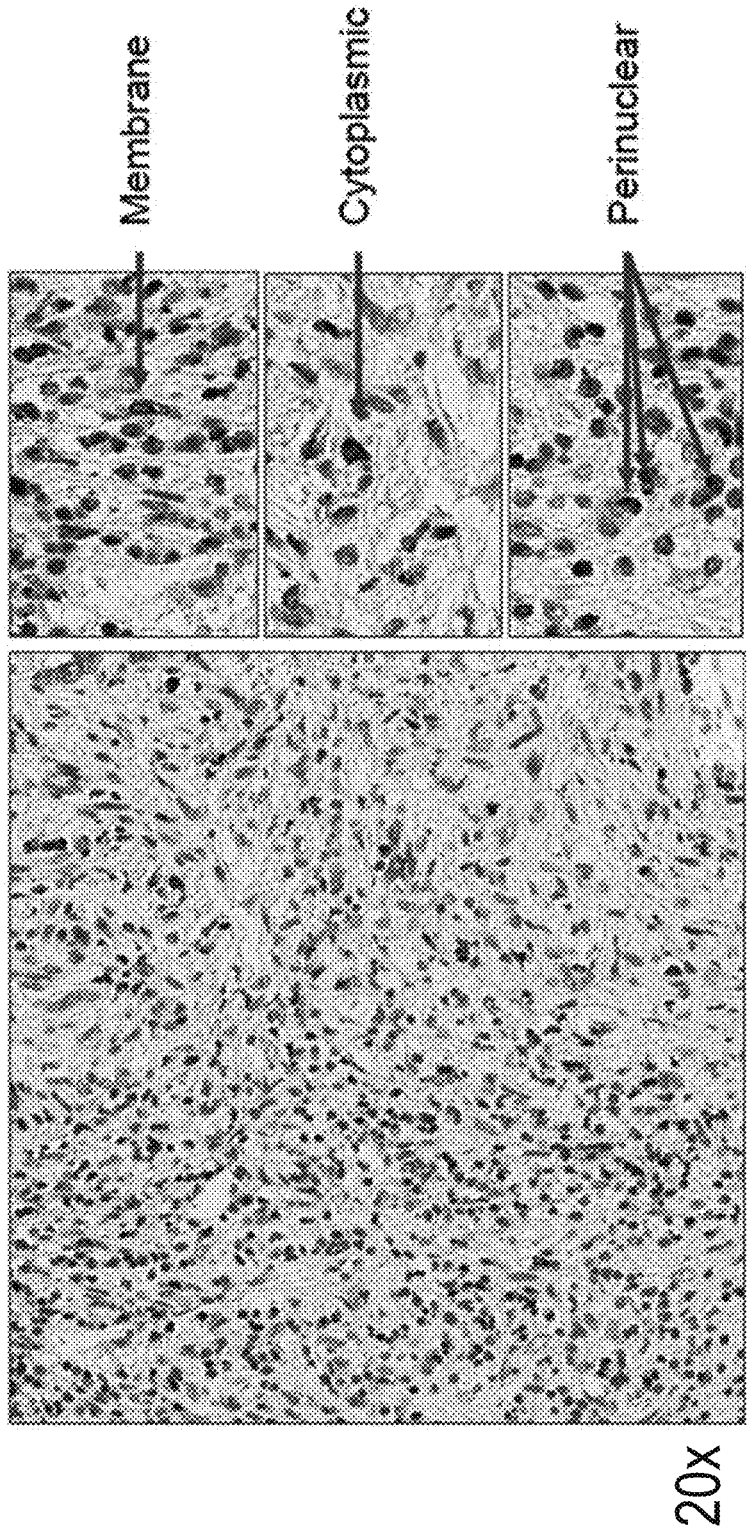
FIG. 25. LAG-3 patterns of expression by IHC staining of total nucleated cells in a melanoma tumor specimen.

LAG-3 Expression in Tumors. For tumor specimens analyzed across 6 different solid tumor types (n=245: RCC, 43; gastric, 41; NSCLC, 41; melanoma, 40; SCCHN, 40; urothelial, 40) a range of low to high LAG-3 expression was observed (0.01% to 33% of total nucleated cells). LAG-3 expression may be localized to the perinuclear, membrane, or cytoplasmic regions of lymphocytes, as shown by IHC staining (FIG. 25).

Figure 26:
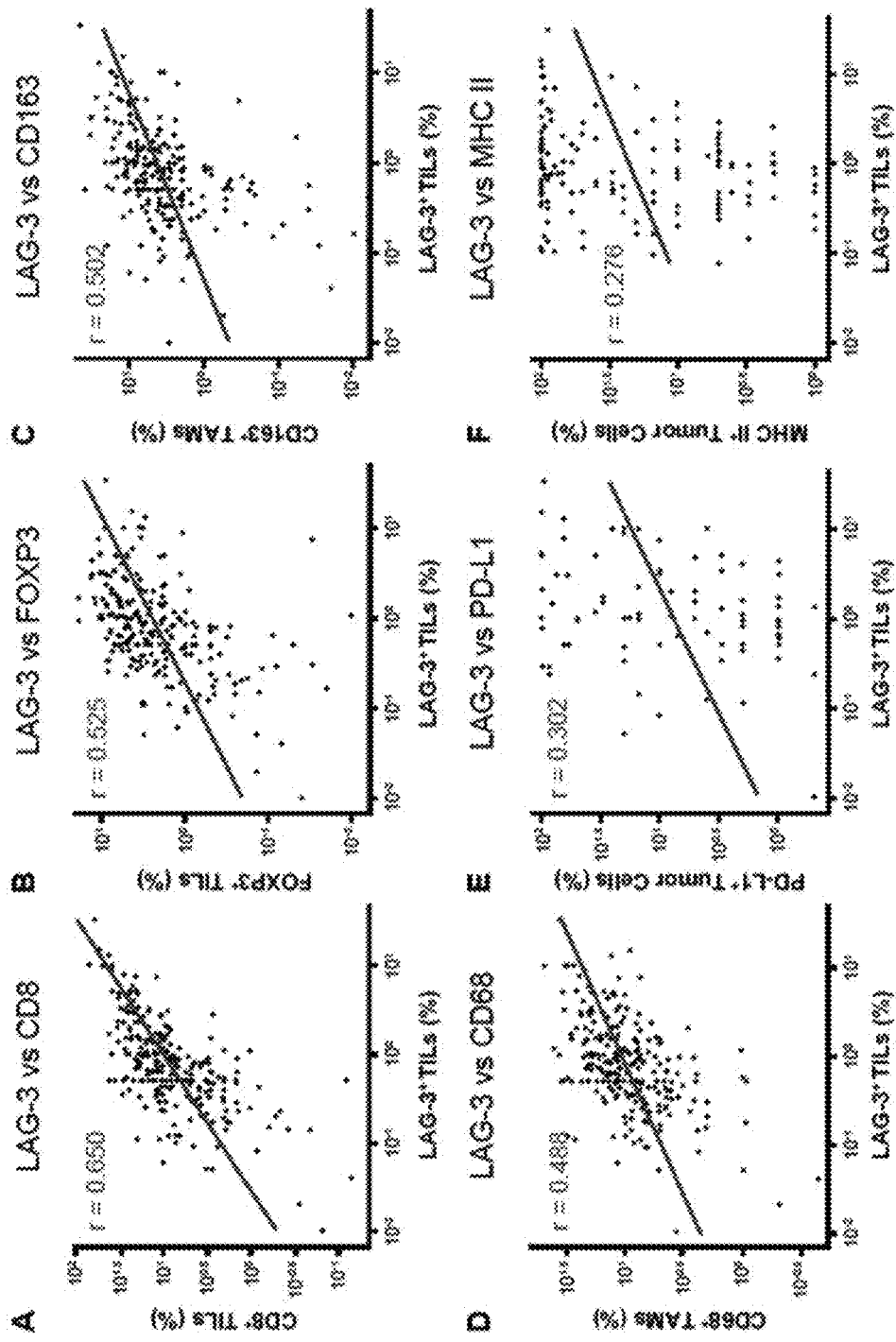
FIGS. 26A-F. Association of LAG-3 with immune and inflammatory biomarkers: (A) LAG-3 vs CD8, (B) LAG-3 vs FOXP3, (C) LAG-3 vs CD163, (D) LAG-3 vs CD68, (E) LAG-3 vs PD-L1, (F) LAG-3 vs MHC II.

LAG-3 Association With Immune and Inflammatory Biomarkers. A moderate correlation of LAG-3 expression with CD8, FOXP3, CD163, and CD68 (n=237: RCC, 43; gastric, 39; NSCLC, 39; melanoma, 39; SCCHN, 40; urothelial, 37) was observed (FIG. 26A-D, r=0.49-0.65); no correlation of LAG-3 with PD-L1 and MHC II tumor expression was observed (FIGS. 26E and 26F, r=0.28-0.30). MHC II expression in tumor cells (≥1%) was frequently observed, ranging from a low of 55% (melanoma) to a high of 82% (gastric carcinoma).

Figure 27:
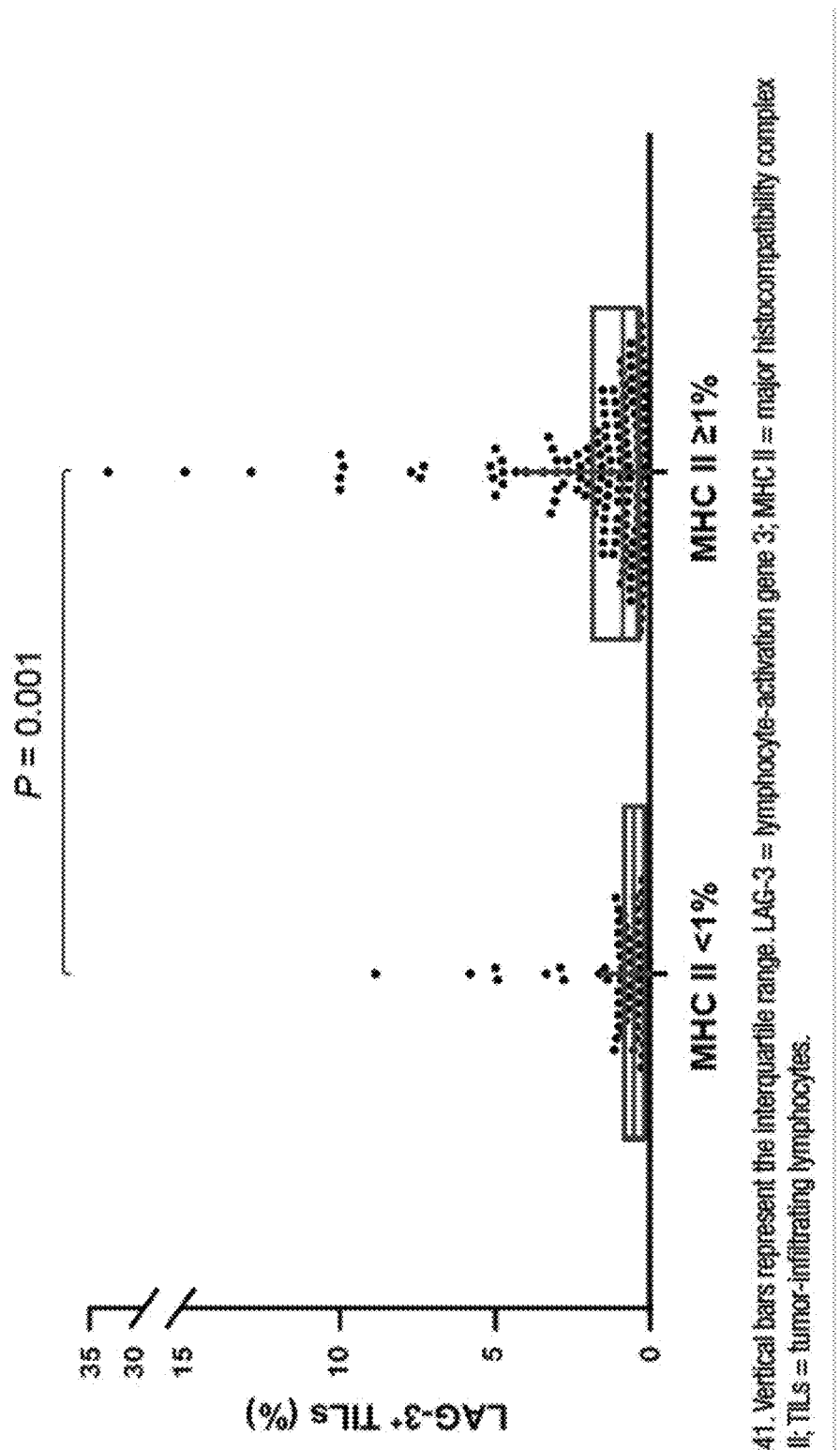
FIG. 27. Ratio of LAG-3 positive tumor infiltrating lymphocytes (TILs) in tumors comprising <1% or ≤1% MHC II positive tumor cells.

Tumors with ≥1% MHC II expression in tumor cells showed a significant increase in the frequency of LAG-3+ TILs (FIG. 27, n=241: RCC, 43; gastric, 40; NSCLC, 40; melanoma, 38; SCCHN, 40; urothelial, 40).

Unsupervised clustering of samples by tumor type revealed clusters of tumors with a range of inflammation from low to high in the 6 tumor types analyzed (examples in FIG. 28A, urothelial carcinoma, n=37; and 28B, gastric carcinoma, n=39).

Figure 28C:
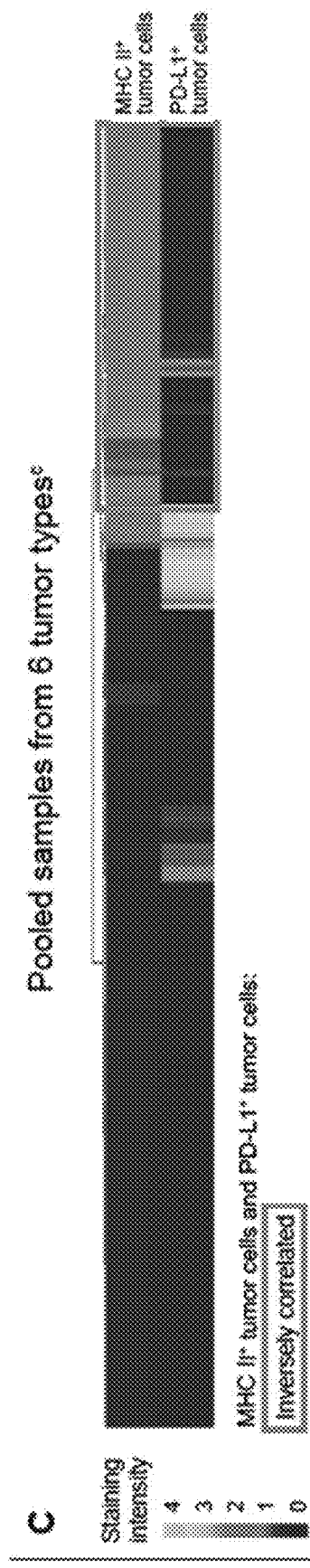

Increased MHC II tumor expression was frequently observed in inflammation high tumors, but was also observed in tumors with lower levels of inflammation (example in FIG. 28A, urothelial carcinoma). Of those specimens that stained positively for tumor-cell MHC II expression, the level of MHC II expression was correlated with the level of LAG-3+ TILs in some tumor types (examples in FIGS. 28A and 28B, urothelial and gastric carcinoma). The majority of tumors with high MHC II expression had low PD-L1 expression (FIG. 28C, n=229: RCC, 43; gastric, 39; NSCLC, 38; melanoma, 33; SCCHN, 39; urothelial, 37).

Heterogeneous MHC II Tumor Cell Expression and LAG-3+ TILs. In a subset of tumor specimens tested (n=6), heterogeneous MHC II tumor cell expression was observed, ranging from low (<10%) to high (>70%) (FIG. 29A, urothelial carcinoma, n=4; gastric carcinoma, n=2). In this subset, a significant increase in the number of LAG-3+ TILs was observed in tumor regions with high MHC II expression vs low MHC II expression (FIG. 29A-C).

Figure 30A:
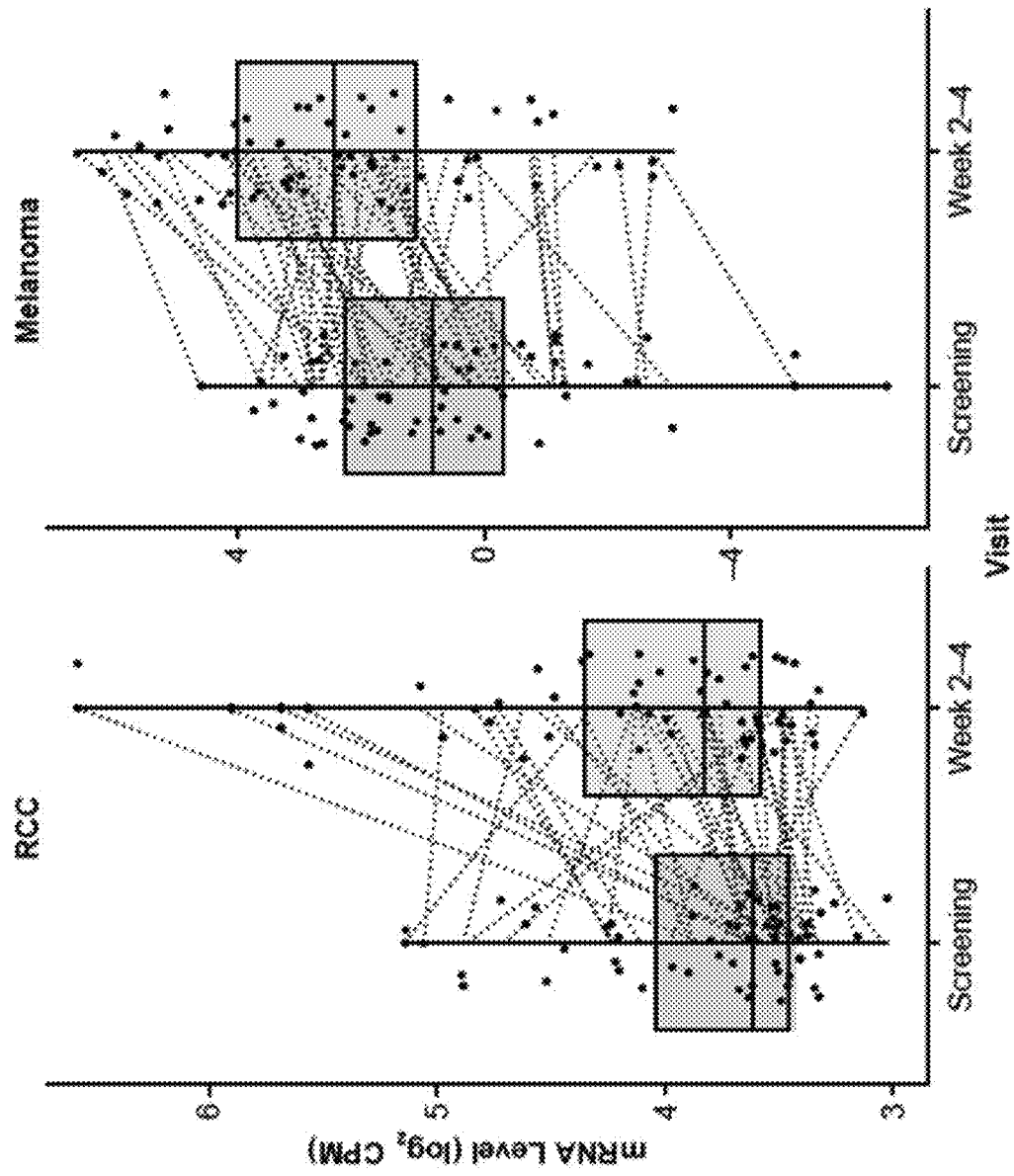
FIGS. 30A and B. LAG-3 mRNA levels at screening and at week 2-4 of nivolumab monotherapy.

Changes in LAG-3 mRNA Level During Anti-PD-1 Monotherapy. In an analysis of tissue samples from patients with metastatic melanoma (NCT01621490/CheckMate 038) or metastatic RCC (NCT01358721/CheckMate 009), a significant increase in LAG-3 mRNA levels between screening and week 2-4 of treatment with nivolumab was observed (FIG. 30).

LAG-3 expression was associated with cellular inflammation in the tumor microenvironment, as shown by IHC. MHC II tumor cell expression was frequently observed across the 6 tumor types analyzed; LAG-3 expression in immune cells was enriched in tumors with expression of MHC II in tumor cells. Higher frequency of LAG-3+ TILs was observed in MHC II high/positive tumor regions vs MHC II low/negative tumor regions within individual tumor specimens, raising the possibility that co-localization of LAG-3 and MHC II expression in tumor cells may serve as a mechanism of LAG-3 checkpoint activation in certain tumors. These findings, and the observation that nivolumab may induce LAG-3 expression, support the use of LAG-3 as a predictive biomarker for BMS-986016 therapy in patients whose disease progressed following treatment with anti-PD-1 therapy.

```
                                SEQUENCES

SEQ ID NO: 1 Heavy Chain Amino Acid Sequence; Anti-LAG-3 mAb (BMS-986016)
QVQLQQWGAGLLKPSETLSLTCAVYGGSFSDYYWNWIRQPPGKGLEWIGEINHRGSTNSNPSLKS
RVTLSLDTSKNQFSLKLRSVTAADTAVYCAFGYSDYEYNWFDPWGQGTLVTVSSASTKGPSVFP
LAPCSRSTSESTAALGCLVKDYFPEPVTVSWNSGALTSGVHTFPAVLQSSGLYSLSSVVTVPSSS
LGTKTYTCNVDHKPSNTKVDKRVESKYGPPCPPCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSN
KGLPSSIEKTISKAKGQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKSLSLSLGK SEQ ID NO: 2 Light Chain Amino Acid Sequence; Anti-LAG-3 mAb (BMS-986016)
EIVLTQSPATLSLSPGERATLSCRASQSISSYLAWYQQKPGQAPRLLIYDASNRATGIPARFSGS
GSGTDFTLTISSLEPEDFAVYYCQQRSNWPLTFGQGTNLEIKRTVAAPSVFIFPPSDEQLKSGTA
SVVCLLNNFYPREAKVQWKVDNALQSGNSQESVTEQDSKDSTYSLSSTLTLSKADYEKHKVYACE
VTHQGLSSPVTKSFNRGEC SEQ ID NO: 3 Heavy Chain Variable Region (VH) Amino Acid Sequence; Anti-
LAG-3 mAb (BMS-986016)
QVQLQQWGAGLLKPSETLSLTCAVYGGSFSDYYWNWIRQPPGKGLEWIGEINHRGSTN
SNPSLKSRVTLSLDTSKNQFSLKLRSVTAADTAVYYCAFGYSDYEYNWFDPWGQGTLV
TVSS SEQ ID NO: 4 Heavy Chain Variable Region (VH) Nucleotide Sequence; Anti-
LAG-3 mAb (BMS-986016)
caggtgcagctacagcagtggggcgcaggactgttgaagccttcggagaccctgtccctcacctg
cgctgtctatggtgggtccttcagtgattactactggaactggatccgccagccccagggaagg
ggctggagtggattggggaaatcaatcatcgtggaagcaccaactccaacccgtccctcaagagt
cgagtcaccctatcactagacacgtccaagaaccagttctccctgaagctgaggtctgtgaccgc
cgcggacacggctgtgtattactgtgcgtttggatatagtgactacgagtacaactggttcgacc
cctggggccagggaaccctggtcaccgtctcctca SEQ ID NO: 5 Light Chain Variable Region (VL) Amino Acid Sequence; Anti-
LAG-3 mAb (BMS-986016)
EIVLTQSPATLSLSPGERATLSCRASQSISSYLAWYQQKPGQAPRLLIYDASNRATGIPARFSGS
GSGTDFTLTISSLEPEDFAVYYCQQRSNWPLTFGQGTNLEIK SEQ ID NO: 6 Light Chain Variable Region (VL) Nucleotide Sequence; Anti-
LAG-3 mAb (BMS-986016)
gaaattgtgttgacacagtctccagccaccctgtctttgtctccaggggaaagagccaccctctc
ctgcagggccagtcagagtattagcagctacttagcctggtaccaacagaaacctggccaggctc
ccaggctcctcatctatgatgcatccaacagggccactggcatcccagccaggttcagtggcagt
gggtctgggacagacttcactctcaccatcagcagcctagagcctgaagattttgcagtttatta
ctgtcagcagcgtagcaactggcctctcacttttggccaggggaccaacctggagatcaaa SEQ ID NO: 7 Heavy Chain CDR1 Amino Acid Sequence; Anti-LAG-3 mAb (BMS-
986016)
DYYWN SEQ ID NO: 8 Heavy Chain CDR2 Amino Acid Sequence; Anti-LAG-3 mAb (BMS-
986016)
EINHRGSTNSNPSLKS
```

SEQUENCES

SEQ ID NO: 9 Heavy Chain CDR3 Amino Acid Sequence; Anti-LAG-3 mAb (BMS-986016)
GYSDYEYNWFDP SEQ ID NO: 10 Light Chain CDR1 Amino Acid Sequence; Anti-LAG-3 mAb (BMS-986016)
RASQSISSYLA SEQ ID NO: 11 Light Chain CDR2 Amino Acid Sequence; Anti-LAG-3 mAb (BMS-986016)
DASNRAT SEQ ID NO: 12 Light Chain CDR3 Amino Acid Sequence; Anti-LAG-3 mAb (BMS-986016)
QQRSNWPLT SEQ ID NO: 13 Human LAG-3 Amino Acid Sequence
MWEAQFLGLLFLQPLWVAPVKPLQPGAEVPVVWAQEGAPAQLPCSPTIPLQDLSLLRRAGVTWQH
QPDSGPPAAAPGHPLAPGPHPAAPSSWGPRPRRYTVLSVGPGGLRSGRLPLQPRVQLDERGRQRG
DFSLWLRPARRADAGEYRAAVHLRDRALSCRLRLRLGQASMTASPPGSLRASDWVILNCSFSRPD
RPASVHWFRNRGQGRVPVRESPHHHLAESFLFLPQVSPMDSGPWGCILTYRDGFNVSIMYNLTVL
GLEPPTPLTVYAGAGSRVGLPCRLPAGVGTRSFLTAKWTPPGGGPDLLVTGDNGDFTLRLEDVSQ
AQAGTYTCHIHLQEQQLNATVTLAIITVTPKSFGSPGSLGKLLCEVTPVSGQERFVWSSLDTPSQ
RSFSGPWLEAQEAQLLSQPWQCQLYQGERLLGAAVYFTELSSPGAQRSGRAPGALPAGHLLLFLT
LGVLSLLLLVTGAFGFHLWRRQWRPRRFSALEQGIHPPQAQSKIEELEQEPEPEPEPEPEPEPEP
EPEQL SEQ ID NO: 14 LAG-3 Epitope
PGHPLAPG SEQ ID NO: 15 LAG-3 Epitope
HPAAPSSW SEQ ID NO: 16 LAG-3 Epitope
PAAPSSWG SEQ ID NO: 17 Heavy Chain Amino Acid Sequence; Anti-PD-1 mAb (BMS936558)
QVQLVESGGGVVQPGRSLRLDCKASGITFSNSGMHWVRQAPGKGLEWVAVIWYDGSKRYYADSVK
GRFTISRDNSKNTLFLQMNSLRAEDTAVYYCATNDDYWGQGTLVTVSSASTKGPSVFPLAPCSRS
TSESTAALGCLVKDYFPEPVTVSWNSGALTSGVHTFPAVLQSSGLYSLSSVVTVPSSSLGTKTYT
CNVDHKPSNTKVDKRVESKYGPPCPPCPAPEFLGGPSVFLFPPKPKDTLMISRTPEVTCVVVDVS
QEDPEVQFNWYVDGVEVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK SEQ ID NO: 18 Light Chain Amino Acid Sequence; Anti-PD-1 mAb (BMS936558)
EIVLTQSPATLSLSPGERATLSCRASQSVSSYLAWYQQKPGQAPRLLIYDASNRATGIPARFSGS
GSGTDFTLTISSLEPEDFAVYYCQQSSNWPRTFGQGTKVEIKRTVAAPSVFIFPPSDEQLKSGTA
SVVCLLNNFYPREAKVQWKVDNALQSGNSQESVTEQDSKDSTYSLSSTLLSKADYEKHKVYACEV
THQGLSSPVTKSFNRGEC SEQ ID NO: 19 Heavy Chain Variable Region (VH) Amino Acid Sequence; Anti-PD-1 mAb (BMS936558)
QVQLVESGGGVVQPGRSLRLDCKASGITFSNSGMHWVRQAPGKGLEWVAVIWYDGSKRYYADSVK
GRFTISRDNSKNTLFLQMNSLRAEDTAVYYCATNDDYWGQGTLVTVSS SEQ ID NO: 20 Heavy Chain Variable Region (VH) Nucleotide Sequence; Anti-PD-1 mAb (BMS936558)
caggtgcagctggtggagtctgggggaggcgtggtccagcctgggaggtccctgagactcgactg
taaagcgtctggaatcaccttcagtaactctggcatgcactgggtccgccaggctccaggcaagg
ggctggagtgggtggcagttatttggtatgatggaagtaaaagatactatgcagactccgtgaag
ggccgattcaccatctccagagacaattccaagaacacgctgtttctgcaaatgaacagcctgag
agccgaggacacggctgtgtattactgtgcgacaaacgacgactactggggccagggaaccctgg
tcaccgtctcctca SEQ ID NO: 21 Light Chain Variable Region (VL) Amino Acid Sequence; Anti-PD-1 mAb (BMS936558)
EIVLTQSPATLSLSPGERATLSCRASQSVSSYLAWYQQKPGQAPRLLIYDASNRATGIPARFSGS
GSGTDFTLTISSLEPEDFAVYYCQQSSNWPRTFGQGTKVEIK SEQ ID NO: 22 Light Chain Variable Region (VL) Nucleotide Sequence; Anti-PD-1 mAb (BMS936558)
gaaattgtgttgacacagtctccagccaccctgtctttgtctccaggggaaagagccaccctctc
ctgcagggccagtcagagtgttagtagttacttagcctggtaccaacagaaacctggccaggctc
ccaggctcctcatctatgatgcatccaacagggccactggcatcccagccaggttcagtggcagt -continued

SEQUENCES gggtctgggacagacttcactctcaccatcagcagcctagagcctgaagattttgcagtttatta
ctgtcagcagagtagcaactggcctcggacgttcggccaagggaccaaggtggaaatcaaa SEQ ID NO: 23 Heavy Chain CDR1 Amino Acid Sequence; Anti-PD-1 mAb
(BMS936558)
NSGMH SEQ ID NO: 24 Heavy Chain CDR2 Amino Acid Sequence; Anti-PD-1 mAb
(BMS936558)
VIWYDGSKRYYADSVKG SEQ ID NO: 25 Heavy Chain CDR3 Amino Acid Sequence; Anti-PD-1 mAb
(BMS936558)
NDDY SEQ ID NO: 26 Light Chain CDR1 Amino Acid Sequence; Anti-PD-1 mAb
(BMS936558)
RASQSVSSYLA SEQ ID NO: 27 Light Chain CDR2 Amino Acid Sequence; Anti-PD-1 mAb
(BMS936558)
DASNRAT SEQ ID NO: 28 Light Chain CDR3 Amino Acid Sequence; Anti-PD-1 mAb
(BMS936558)
QQSSNWPRT SEQ ID NO: 29 Complete Homo sapiens PD-1 sequence
agtttcccttccgctcacctccgcctgagcagtggagaaggcggcactctggtggggctgctcca
ggcatgcagatcccacaggcgccctggccagtcgtctgggcggtgctacaactgggctggggcc
aggatggttcttagactccccagacaggccctggaaccccccaccttcttcccagccctgctcg
tggtgaccgaaggggacaacgccaccttcacctgcagcttctccaacacatcggagagcttcgtg
ctaaactggtaccgcatgagcccccagcaaccagacggacaagctggccgccttccccgaggaccg
cagccagcccggccaggactgccgcttccgtgtcacacaactgcccaacgggcgtgacttccaca
tgagcgtggtcagggcccggcgcaatgacagcggcacctacctctgtggggccatctccctggcc
cccaaggcgcagatcaaagagagcctgcgggcagagctcagggtgacagagagaagggcagaagt
gcccacagcccaccccagccctcacccaggcagccggccagttccaaaccctggtggttggtg
tcgtgggcggcctgctgggcagcctggtgctgctagtctgggtcctggccgtcatctgctcccgg
gccgcacgagggacaataggagccaggcgcaccggccagcccctgaaggaggacccctcagccgt
gcctgtgttctctgtggactatggggagctggatttccagtggcgagagaagaccccggagcccc
ccgtgccctgtgtccctgagcagacggagtatgccaccattgtctttcctagcggaatgggcacc
tcatccccgcccgcagggggctcagccgacggccctcggagtgcccagccactgaggcctgagga
tggacactgctcttggcccctctgaccggcttccttggccaccagtgttctgcagaccctccacc
atgagcccgggtcagcgcatttcctcaggagaagcaggcagggtgcaggccattgcaggccgtcc
agggctgagctgcctgggggcgaccggggctccagcctgcacctgcaccaggcacagcccacc
acaggactcatgtctcaatgcccacagtgagcccaggcagcaggtgtcaccgtcccctacaggga
gggcagatgcagtcactgcttcaggtcctgccagcacagagctgcctgcgtccagctccctgaa
tctctgctgctgctgctgctgctgctgcctgcggcccggggctgaaggcgccgtggccc
tgcctgacgcccggagcctcctgcctgaacttgggggctggttggagatggccttggagcagcc
aaggtgcccctggcagtggcatcccgaaacgccctggacgcagggccccaagactgggcacaggag
tgggaggtacatggggctggggactccccaggagttatctgctccctgcaggcctagagaagttt
cagggaaggtcagaagagctcctggctgtggtgggcagggcaggaaaccctcccacctttacac
atgcccaggcagcacctcaggccctttgtggggcagggaagctgaggcagtaagcgggcaggcag
agctggaggcctttcaggccagccagcactctggcctctgccgccgcattccaccccagcccct
cacaccactcgggagggacatcctacggtcccaaggtcaggagggcagggctggggttgactc
aggcccctcccagctgtggccacctgggtgttgggagggcagaagtgcaggcacctagggccccc
catgtgcccaccctgggagctctccttggaacccattcctgaaattatttaaagggggttggccgg
gctcccaccagggcctgggtgggaaggtacaggcgttccccgggcctagtacccccgcgtggc
ctatccactcctcacatccacacactgcaccccactcctggggcagggccaccagcatccaggc
ggccagcaggcacctgagtggctgggacaagggatccccttccctgtggttctattatattata
attataattaaatatgagagcatgct SEQ ID NO: 30 Heavy Chain Nucleotide Sequence; Anti-LAG-3 mAb (BMS-
986016)
caggtgcagctacagcagtggggcgcaggactgttgaagccttcggagaccctgtccctcacctg
cgctgtctatggtgggtccttcagtgattactactggaactggatccgccagcccccagggaagg
ggctggagtggattgggaaatcaatcatcgtggaagcaccaactccaacccgtccctcaagagt
cgagtcaccctatcactagacacgtccaagaaccagttctccctgaagctgagctctgtgaccgc
cgcggacacggctgtgtattactgtgcgtttggatatagtgactacgagtacaactggttcgacc
cctggggccagggaaccctggtcaccgtctcctcagctagcaccaagggcccatccgtcttcccc
ctggcgccctgctcaggagcacctccgagagcacagccgccctgggctgcctggtcaaggacta
cttcccgaaccggtgacggtgtcgtggaactcaggcgccctgaccagcggcgtgcacaccttccc
cggctgcctacagtcctcaggactctactccctcagcagcgtggtgaccgtgccctccagcagc
ttgggcacgaagacctacacctgcaacgtagatcacaagcccagcaacaccaaggtggacaagag
agttgagtccaaatatggtcccccatgcccaccatgcccagcacctgagttcctggggggaccat
cagtcttcctgttccccccaaaacccaaggacactctcatgatctcccgacccctgaggtcacg
tgcgtggtggtggacgtgagccaggaagaccccgaggtccagttcaactggtacgtggatggcgt -continued

| SEQUENCES |
|---|
| ggaggtgcataatgccaagacaaagccgcgggaggagcagttcaacagcacgtaccgtgtggtca<br>gcgtcctcaccgtcctgcaccaggactggctgaacggcaaggagtacaagtgcaaggtctccaac<br>aaaggcctcccgtcctccatcgagaaaaccatctccaaagccaaagggcagccccgagagccaca<br>ggtgtacaccctgcccccatcccaggaggagatgaccaagaaccaggtcagcctgacctgcctgg<br>tcaaaggcttctacccccagcgacatcgccgtggagtgggagagcaatgggcagccggagaacaac<br>tacaagaccacgcctcccgtgctggactccgacggctccttcttcctctacagcaggctaaccgt<br>ggacaagagcaggtggcaggaggggaatgtcttctcatgctccgtgatgcatgaggctctgcaca<br>accactacacacagaagagcctctccctgtctctgggtaaatga<br><br>SEQ ID NO: 31 Light Chain Nucleotide Sequence; Anti-LAG-3 mAb (BMS-986016)<br>gaaattgtgttgacacagtctccagccacccctgtctttgtctcaggggaaagagccaccctctc<br>ctgcagggccagtcagagtattagcagctacttagcctggtaccaacagaaacctggccaggctc<br>ccaggctcctcatctatgatgcatccaacagggccactggcatcccagccaggttcagtggcagt<br>gggtctgggacagacttcactctcaccatcagcagcctagagcctgaagattttgcagtttatta<br>ctgtcagcagcgtagcaactggcctctcacttttggccaggggaccaacctggagatcaaacgta<br>cggtggctgcaccatctgtcttcatcttcccgccatctgatgagcagttgaaatctggaactgcc<br>tctgttgtgtgcctgctgaataacttctatcccagagaggccaaagtacagtggaaggtggataa<br>cgccctccaatcgggtaactcccaggagagtgtcacagagcaggacagcaaggacagcacctaca<br>gcctcagcagcaccctgacgctgagcaaagcagactacgagaaacacaaagtctacgcctgcgaa<br>gtcacccatcagggcctgagctcgcccgtcacaaagagcttcaacaggggagagtgttag<br><br>SEQ ID NO: 32 Motif<br>MYPPPY |

SEQUENCE LISTING

```
Sequence total quantity: 32
SEQ ID NO: 1              moltype = AA   length = 447
FEATURE                   Location/Qualifiers
REGION                    1..447
                          note = Heavy Chain Amino Acid Sequence; Anti-LAG-3 mAb
                            (BMS-986016)
source                    1..447
                          mol_type = protein
                          organism = synthetic construct
SEQUENCE: 1
QVQLQQWGAG LLKPSETLSL TCAVYGGSFS DYYWNWIRQP PGKGLEWIGE INHRGSTNSN   60
PSLKSRVTLS LDTSKNQFSL KLRSVTAADT AVYYCAFGYS DYEYNWFDPW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 2              moltype = AA   length = 214
FEATURE                   Location/Qualifiers
REGION                    1..214
                          note = Light Chain Amino Acid Sequence; Anti-LAG-3 mAb
                            (BMS-986016)
source                    1..214
                          mol_type = protein
                          organism = synthetic construct
SEQUENCE: 2
EIVLTQSPAT LSLSPGERAT LSCRASQSIS SYLAWYQQKP GQAPRLLIYD ASNRATGIPA   60
RFSGSGSGTD FTLTISSLEP EDFAVYYCQQ RSNWPLTFGQ GTNLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 3              moltype = AA   length = 120
FEATURE                   Location/Qualifiers
REGION                    1..120
                          note = Heavy Chain Variable Region (VH) Amino Acid
                            Sequence; Anti-LAG-3 mAb (BMS-986016)
source                    1..120
                          mol_type = protein
                          organism = synthetic construct
SEQUENCE: 3
QVQLQQWGAG LLKPSETLSL TCAVYGGSFS DYYWNWIRQP PGKGLEWIGE INHRGSTNSN   60
PSLKSRVTLS LDTSKNQFSL KLRSVTAADT AVYYCAFGYS DYEYNWFDPW GQGTLVTVSS   120

SEQ ID NO: 4              moltype = DNA   length = 360
```

```
FEATURE                     Location/Qualifiers
misc_feature                1..360
                            note = Heavy Chain Variable Region (VH) Nucleotide
                              Sequence; Anti-LAG-3 mAb (BMS-986016)
source                      1..360
                            mol_type = other DNA
                            organism = synthetic construct
SEQUENCE: 4
caggtgcagc tacagcagtg gggcgcagga ctgttgaagc cttcggagac cctgtccctc    60
acctgcgctg tctatggtgg gtccttcagt gattactact ggaactggat ccgccagccc   120
ccagggaagg ggctggagtg gattgggaa atcaatcatc gtggaagcac caactccaac    180
ccgtccctca agagtcgagt caccctatca ctagacacgt ccaagaacca gttctccctg   240
aagctgaggt ctgtgaccgc cgcggacacg gctgtgtatt actgtgcgtt tggatatagt   300
gactacgagt acaactggtt cgaccccctgg ggccagggaa ccctggtcac cgtctcctca  360

SEQ ID NO: 5                moltype = AA   length = 107
FEATURE                     Location/Qualifiers
REGION                      1..107
                            note = Light Chain Variable Region (VL) Amino Acid
                              Sequence; Anti-LAG-3 mAb (BMS-986016)
source                      1..107
                            mol_type = protein
                            organism = synthetic construct
SEQUENCE: 5
EIVLTQSPAT LSLSPGERAT LSCRASQSIS SYLAWYQQKP GQAPRLLIYD ASNRATGIPA    60
RFSGSGSGTD FTLTISSLEP EDFAVYYCQQ RSNWPLTFGQ GTNLEIK                 107

SEQ ID NO: 6                moltype = DNA   length = 321
FEATURE                     Location/Qualifiers
misc_feature                1..321
                            note = Light Chain Variable Region (VL) Nucleotide
                              Sequence; Anti-LAG-3 mAb (BMS-986016)
source                      1..321
                            mol_type = other DNA
                            organism = synthetic construct
SEQUENCE: 6
gaaattgtgt tgacacagtc tccagccacc ctgtctttgt ctccagggga aagagccacc    60
ctctcctgca gggccagtca gagtattagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctctcac ttttggccag   300
gggaccaacc tggagatcaa a                                             321

SEQ ID NO: 7                moltype = AA   length = 5
FEATURE                     Location/Qualifiers
REGION                      1..5
                            note = Heavy Chain CDR1 Amino Acid Sequence; Anti-LAG-3 mAb
                              (BMS-986016)
source                      1..5
                            mol_type = protein
                            organism = synthetic construct
SEQUENCE: 7
DYYWN                                                                 5

SEQ ID NO: 8                moltype = AA   length = 16
FEATURE                     Location/Qualifiers
REGION                      1..16
                            note = Heavy Chain CDR2 Amino Acid Sequence; Anti-LAG-3 mAb
                              (BMS-986016)
source                      1..16
                            mol_type = protein
                            organism = synthetic construct
SEQUENCE: 8
EINHRGSTNS NPSLKS                                                    16

SEQ ID NO: 9                moltype = AA   length = 12
FEATURE                     Location/Qualifiers
REGION                      1..12
                            note = Heavy Chain CDR3 Amino Acid Sequence; Anti-LAG-3 mAb
                              (BMS-986016)
source                      1..12
                            mol_type = protein
                            organism = synthetic construct
SEQUENCE: 9
GYSDYEYNWF DP                                                        12

SEQ ID NO: 10               moltype = AA   length = 11
FEATURE                     Location/Qualifiers
REGION                      1..11
```

```
                         note = Light Chain CDR1 Amino Acid Sequence; Anti-LAG-3 mAb
                           (BMS-986016)
source                   1..11
                         mol_type = protein
                         organism = synthetic construct
SEQUENCE: 10
RASQSISSYL A                                                              11

SEQ ID NO: 11            moltype = AA   length = 7
FEATURE                  Location/Qualifiers
REGION                   1..7
                         note = Light Chain CDR2 Amino Acid Sequence; Anti-LAG-3 mAb
                           (BMS-986016)
source                   1..7
                         mol_type = protein
                         organism = synthetic construct
SEQUENCE: 11
DASNRAT                                                                   7

SEQ ID NO: 12            moltype = AA   length = 9
FEATURE                  Location/Qualifiers
REGION                   1..9
                         note = Light Chain CDR3 Amino Acid Sequence; Anti-LAG-3 mAb
                           (BMS-986016)
source                   1..9
                         mol_type = protein
                         organism = synthetic construct
SEQUENCE: 12
QQRSNWPLT                                                                 9

SEQ ID NO: 13            moltype = AA   length = 525
FEATURE                  Location/Qualifiers
REGION                   1..525
                         note = Human LAG-3 Amino Acid Sequence
source                   1..525
                         mol_type = protein
                         organism = synthetic construct
SEQUENCE: 13
MWEAQFLGLL FLQPLWVAPV KPLQPGAEVP VVWAQEGAPA QLPCSPTIPL QDLSLLRRAG    60
VTWQHQPDSG PPAAAPGHPL APGPHPAAPS SWGPRPRRYT VLSVGPGGLR SGRLPLQPRV   120
QLDERGRQRG DFSLWLRPAR RADAGEYRAA VHLRDRALSC RLRLRLGQAS MTASPPGSLR   180
ASDWVILNCS FSRPDRPASV HWFRNRGQGR VPVRESPHHH LAESFLFLPQ VSPMDSGPWG   240
CILTYRDGFN VSIMYNLTVL GLEPPTPLTV YAGAGSRVGL PCRLPAGVGT RSFLTAKWTP   300
PGGGPDLLVT GDNGDFTLRL EDVSQAQAGT YTCHIHLQEQ QLNATVTLAI ITVTPKSFGS   360
PGSLGKLLCE VTPVSGQERF VWSSLDTPSQ RSFSGPWLEA QEAQLLSQPW QCQLYQGERL   420
LGAAVYFTEL SSPGAQRSGR APGALPAGHL LLFLTLGVLS LLLLVTGAFG FHLWRRQWRP   480
RRFSALEQGI HPPQAQSKIE ELEQEPEPEP EPEPEPEPEP EPEQL                   525

SEQ ID NO: 14            moltype = AA   length = 8
FEATURE                  Location/Qualifiers
REGION                   1..8
                         note = LAG-3 Epitope
source                   1..8
                         mol_type = protein
                         organism = synthetic construct
SEQUENCE: 14
PGHPLAPG                                                                  8

SEQ ID NO: 15            moltype = AA   length = 8
FEATURE                  Location/Qualifiers
REGION                   1..8
                         note = LAG-3 Epitope
source                   1..8
                         mol_type = protein
                         organism = synthetic construct
SEQUENCE: 15
HPAAPSSW                                                                  8

SEQ ID NO: 16            moltype = AA   length = 8
FEATURE                  Location/Qualifiers
REGION                   1..8
                         note = LAG-3 Epitope
source                   1..8
                         mol_type = protein
                         organism = synthetic construct
SEQUENCE: 16
PAAPSSWG                                                                  8

SEQ ID NO: 17            moltype = AA   length = 440
```

```
FEATURE                 Location/Qualifiers
REGION                  1..440
                        note = Heavy Chain Amino Acid Sequence; Anti-PD-1 mAb
                           (BMS936558)
source                  1..440
                        mol_type = protein
                        organism = synthetic construct
SEQUENCE: 17
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSSASTKGPS   120
VFPLAPCSRS TSESTAALGC LVKDYFPEPV TVSWNSGALT SGVHTFPAVL QSSGLYSLSS   180
VVTVPSSSLG TKTYTCNVDH KPSNTKVDKR VESKYGPPCP PCPAPEFLGG PSVFLFPPKP   240
KDTLMISRTP EVTCVVVDVS QEDPEVQFNW YVDGVEVHNA KTKPREEQFN STYRVVSVLT   300
VLHQDWLNGK EYKCKVSNKG LPSSIEKTIS KAKGQPREPQ VYTLPPSQEE MTKNQVSLTC   360
LVKGFYPSDI AVEWESNGQP ENNYKTTPPV LDSDGSFFLY SRLTVDKSRW QEGNVFSCSV   420
MHEALHNHYT QKSLSLSLGK                                               440

SEQ ID NO: 18           moltype = AA  length = 213
FEATURE                 Location/Qualifiers
REGION                  1..213
                        note = Light Chain Amino Acid Sequence; Anti-PD-1 mAb
                           (BMS936558)
source                  1..213
                        mol_type = protein
                        organism = synthetic construct
SEQUENCE: 18
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ SSNWPRTFGQ GTKVEIKRTV AAPSVFIFPP   120
SDEQLKSGTA SVVCLLNNFY PREAKVQWKV DNALQSGNSQ ESVTEQDSKD STYSLSSTLL   180
SKADYEKHKV YACEVTHQGL SSPVTKSFNR GEC                                213

SEQ ID NO: 19           moltype = AA  length = 113
FEATURE                 Location/Qualifiers
REGION                  1..113
                        note = Heavy Chain Variable Region (VH) Amino Acid
                           Sequence; Anti-PD-1 mAb (BMS936558)
source                  1..113
                        mol_type = protein
                        organism = synthetic construct
SEQUENCE: 19
QVQLVESGGG VVQPGRSLRL DCKASGITFS NSGMHWVRQA PGKGLEWVAV IWYDGSKRYY    60
ADSVKGRFTI SRDNSKNTLF LQMNSLRAED TAVYYCATND DYWGQGTLVT VSS          113

SEQ ID NO: 20           moltype = DNA  length = 339
FEATURE                 Location/Qualifiers
misc_feature            1..339
                        note = Heavy Chain Variable Region (VH) Nucleotide
                           Sequence; Anti-PD-1 mAb (BMS936558)
source                  1..339
                        mol_type = other DNA
                        organism = synthetic construct
SEQUENCE: 20
caggtgcagc tggtggagtc tgggggaggc gtggtccagc ctgggaggtc cctgagactc    60
gactgtaaag cgtctggaat caccttcagt aactctggca tgcactgggt ccgccaggct   120
ccaggcaagg ggctggagtg ggtggcagtt atttggtatg atggaagtaa aagatactat   180
gcagactccg tgaagggccg attcaccatc tccagagaca attccaagaa cacgctgttt   240
ctgcaaatga acagcctgag agccgaggac acggctgtgt attactgtgc gacaaacgac   300
gactactggg gccagggaac cctggtcacc gtctcctca                          339

SEQ ID NO: 21           moltype = AA  length = 107
FEATURE                 Location/Qualifiers
REGION                  1..107
                        note = Light Chain Variable Region (VL) Amino Acid
                           Sequence; Anti-PD-1 mAb (BMS936558)
source                  1..107
                        mol_type = protein
                        organism = synthetic construct
SEQUENCE: 21
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ SSNWPRTFGQ GTKVEIK                 107

SEQ ID NO: 22           moltype = DNA  length = 321
FEATURE                 Location/Qualifiers
misc_feature            1..321
                        note = Light Chain Variable Region (VL) Nucleotide
                           Sequence; Anti-PD-1 mAb (BMS936558)
source                  1..321
                        mol_type = other DNA
                        organism = synthetic construct
```

-continued

```
SEQUENCE: 22
gaaattgtgt tgacacagtc tccagccacc ctgtctttgt ctccagggga aagagccacc    60
ctctcctgca gggccagtca gagtgttagt agttacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag agtagcaact ggcctcggac gttcggccaa   300
gggaccaagg tggaaatcaa a                                             321

SEQ ID NO: 23           moltype = AA  length = 5
FEATURE                 Location/Qualifiers
REGION                  1..5
                        note = Heavy Chain CDR1 Amino Acid Sequence; Anti-PD-1 mAb
                          (BMS936558)
source                  1..5
                        mol_type = protein
                        organism = synthetic construct
SEQUENCE: 23
NSGMH                                                                 5

SEQ ID NO: 24           moltype = AA  length = 17
FEATURE                 Location/Qualifiers
REGION                  1..17
                        note = Heavy Chain CDR2 Amino Acid Sequence; Anti-PD-1 mAb
                          (BMS936558)
source                  1..17
                        mol_type = protein
                        organism = synthetic construct
SEQUENCE: 24
VIWYDGSKRY YADSVKG                                                   17

SEQ ID NO: 25           moltype = AA  length = 4
FEATURE                 Location/Qualifiers
REGION                  1..4
                        note = Heavy Chain CDR3 Amino Acid Sequence; Anti-PD-1 mAb
                          (BMS936558)
source                  1..4
                        mol_type = protein
                        organism = synthetic construct
SEQUENCE: 25
NDDY                                                                  4

SEQ ID NO: 26           moltype = AA  length = 11
FEATURE                 Location/Qualifiers
REGION                  1..11
                        note = Light Chain CDR1 Amino Acid Sequence; Anti-PD-1 mAb
                          (BMS936558)
source                  1..11
                        mol_type = protein
                        organism = synthetic construct
SEQUENCE: 26
RASQSVSSYL A                                                         11

SEQ ID NO: 27           moltype = AA  length = 7
FEATURE                 Location/Qualifiers
REGION                  1..7
                        note = Light Chain CDR2 Amino Acid Sequence; Anti-PD-1 mAb
                          (BMS936558)
source                  1..7
                        mol_type = protein
                        organism = synthetic construct
SEQUENCE: 27
DASNRAT                                                               7

SEQ ID NO: 28           moltype = AA  length = 9
FEATURE                 Location/Qualifiers
REGION                  1..9
                        note = Light Chain CDR3 Amino Acid Sequence; Anti-PD-1 mAb
                          (BMS936558)
source                  1..9
                        mol_type = protein
                        organism = synthetic construct
SEQUENCE: 28
QQSSNWPRT                                                             9

SEQ ID NO: 29           moltype = DNA  length = 2106
FEATURE                 Location/Qualifiers
misc_feature            1..2106
                        note = Complete Homo sapiens PD-1 sequence
source                  1..2106
```

```
                        mol_type = other DNA
                        organism = synthetic construct
SEQUENCE: 29
agtttccctt ccgctcacct ccgcctgagc agtggagaag gcggcactct ggtggggctg    60
ctccaggcat gcagatccca caggcgccct ggccagtcgt ctgggcggtg ctacaactgg   120
gctggcggcc aggatggttc ttagactccc cagacaggcc ctggaacccc cccaccttct   180
tcccagcccg gctcgtggtg accgaagggg acaacgccac cttcacctgc agcttctcca   240
acacatcgga gagcttcgtg ctaaactggt accgcatgag ccccagcaac cagacggaca   300
agctggccgc cttccccgag gaccgcagcc agcccggcca ggactgccgc ttccgtgtca   360
cacaactgcc caacgggcgt gacttccaca tgaccgtggt caggggccgg cgcaatgaca   420
gcggcaccta cctctgtggg gccatctccc tggcccccaa ggcgcagatc aaagagagcc   480
tgcgggcaga gctcagggtg acagagagaa gggcagaagt gcccacagcc caccccagcc   540
cctcacccag gccagccggc cagttccaaa ccctggtggt tggtgtcgtg ggcggcctgc   600
tgggcagcct ggtgctgcta gtctgggtcc tggccgtcat ctgctcccgg ccgcacgag   660
ggacaatagg agccaggcgc accggccagc ccctgaagga gacccctca gccgtgcctg   720
tgttctctgt ggactatggg gagctggatt tccagtggcg agagaagacc ccggagcccc   780
ccgtgccctg tgtccctgag cagacggagt atgccaccat tgtctttcct agcggaatgg   840
gcacctcatc ccccgcccgc aggggctcag ccgacgcgtc tcggagtgcc cagccactga   900
ggcctgagga tggacactgc tcttggcccc tctgaccggc ttccttggcc accagtgttc   960
tgcagaccct ccaccatgag cccgggtcag cgcatttcct caggagaagc aggcagggtg   1020
caggccattg caggccgtcc aggggctgag ctgcctgggg cgaccggggg ctccagcctg   1080
cacctgcacc aggcacagcc ccaccacagg actcatgtct caatgcccac agtgagccca   1140
ggcagcaggt gtcaccgtcc cctacaggga gggccagatg cagtcactgc ttcaggtcct   1200
gccagcacag agctgcctgc gtccagctcc ctgaatctct gctgctgctg ctgctgctgc   1260
tgctgctgcc tgcggcccgg ggctgaaggc gccgtggccc tgcctgacgc cccggagcct   1320
cctgcctgaa cttgggggct ggttggagat ggccttggag cagccaaggt gccccctggca   1380
gtggcatccc gaaacgccct ggacgcaggg cccaagactg gcacaggag tggaggtac    1440
atggggctgg ggactcccca ggagttatct gctccctgca ggcctagaga agtttcaggg    1500
aaggtcagaa gagctcctgg ctgtggtggg cagggcagga aacccctccc acctttacac    1560
atgcccaggc agcacctcag gcccttttgtg gggcagggaa gctgaggcag taagcgggca   1620
ggcagagctg gaggcctttc aggccagcca gcactctggc ctcctgccgc cgcattccac   1680
cccagcccct cacaccactc gggagaggga catcctacgg tcccaaggtc aggagggcag   1740
ggctgggggtt gactcaggcc cctcccagct gtggccacct gggtgttggg agggcagaag   1800
tgcaggcacc tagggcccc catgtgccca ccctgggagc tctccttgga acccattcct    1860
gaaattattt aaaggggttg gccgggctcc caccagggca tgggtgggaa ggtacaggcg   1920
ttcccccggg gcctagtacc cccgcgtggc ctatccactc ctcacatcca cacactgcac   1980
ccccactcct ggggcagggc caccagcatc caggcggcca gcaggcacct gagtggctgg   2040
gacaagggat ccccccttccc tgtggttcta ttatattata attataatta aatatgagag   2100
catgct                                                              2106

SEQ ID NO: 30           moltype = DNA  length = 1344
FEATURE                 Location/Qualifiers
misc_feature            1..1344
                        note = Heavy Chain Nucleotide Sequence; Anti-LAG-3 mAb
                        (BMS-986016)
source                  1..1344
                        mol_type = other DNA
                        organism = synthetic construct
SEQUENCE: 30
caggtgcagc tacagcagtg gggcgcagga ctgttgaagc cttcggagac cctgtccctc     60
acctgcgctg tctatggtgg gtccttcagt gattactact ggaactggat ccgccagccc    120
ccagggaagg ggctggagtg gattgggaa atcaatcatc gtggaagcac caactccaac    180
ccgtccctca agagtcgagt caccctatca ctagacacgt ccaagaacca gttctccctg    240
aagctgaggt ctgtgaccgc cgcggacacg gctgtgtatt actgtgcgtt tggatatagt    300
gactacgagt acaactggtt cgaccctggg ggccagggaa ccctggtcac cgtctcctca    360
gctagcacca agggcccatc cgtcttcccc ctggcgccct gctccaggag cacctccgag    420
agcacagccg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacgaagacc    600
tacacctgca acgtagatca caagcccagc aacaccaagg tggacaagag agttgagtcc    660
aaatatggtc cccatgccc accatgccca gcacctgagt tcctgggggg accatcagtc    720
ttcctgttcc ccccaaaacc caaggacact ctcatgatct cccggacccc tgaggtcacg    780
tgcgtggtgg tggacgtgag ccaggaagac cccgaggtcc agttcaactg gtacgtggat    840
ggcgtggagg tgcataatgc caagacaaag ccgcgggagg agcagttcaa cagcacgtac    900
cgtgtggtca gcgtcctcac cgtcctgcac caggactggc tgaacggcaa ggagtacaag    960
tgcaaggtct ccaacaaagg cctcccgtcc tccatcgaga aaaccatctc aaagccaaa   1020
gggcagcccc gagagccaca ggtgtacacc ctgcccccat cccaggagga gatgaccaag   1080
aaccaggtca gcctgacctg cctggtcaaa ggcttctacc ccagcgacat cgccgtggag   1140
tgggagagca atgggcagcc ggagaacaac tacaagacca cgcctcccgt gctggactcc   1200
gacggctcct tcttcctcta cagcaggcta accgtggaca agagcaggtg gcaggagggg   1260
aatgtcttct catgctccgt gatgcatgag gctctgcaca accactacac acagaagagc   1320
ctctccctgt ctctgggtaa atga                                          1344

SEQ ID NO: 31           moltype = DNA  length = 645
FEATURE                 Location/Qualifiers
misc_feature            1..645
                        note = Light Chain Nucleotide Sequence; Anti-LAG-3 mAb
                        (BMS-986016)
source                  1..645
```

```
                    mol_type = other DNA
                    organism = synthetic construct
SEQUENCE: 31
gaaattgtgt tgacacagtc tccagccacc ctgtctttgt ctccagggga aagagccacc    60
ctctcctgca gggccagtca gagtattagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctctcac ttttggccag   300
gggaccaacc tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645

SEQ ID NO: 32           moltype = AA  length = 6
FEATURE                 Location/Qualifiers
REGION                  1..6
                        note = Motif
source                  1..6
                        mol_type = protein
                        organism = synthetic construct
SEQUENCE: 32
MYPPPY                                                                 6
```

What is claimed is:

1. A method of treating a malignant tumor in a human patient, comprising administering an immunotherapy to the patient, wherein the immunotherapy comprises (i) an anti-LAG-3 antibody or antigen-binding fragment thereof and (ii) an anti-PD-1 antibody or antigen-binding fragment thereof or an anti-PD-L1 antibody or antigen-binding fragment thereof, and wherein about 1% to about 5% of nucleated cells in a sample of the patient's tumor are tumor-infiltrating lymphocytes expressing LAG-3.

2. The method of claim 1, further comprising determining the level of LAG-3 expression in the sample prior to administering the immunotherapy.

3. The method of claim 1, wherein the sample of the patient's tumor is PD-L1 negative.

4. The method of claim 3, further comprising determining the level of LAG-3 expression and PD-L1 expression in the sample prior to administering the immunotherapy.

5. The method of claim 1, wherein the malignant tumor is a liver cancer, bone cancer, pancreatic cancer, skin cancer, oral cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, cancers of the childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers, hematologic malignancies, viral-related cancer, or a combination thereof.

6. The method of claim 1, wherein the malignant tumor is a melanoma, small cell lung cancer, non-small cell lung cancer (NSCLC), human papilloma virus (HPV)-related tumor, gastric adenocarcinoma, multiple myeloma, B-cell lymphoma, Hodgkin lymphoma/primary mediastinal B-cell lymphoma, non-Hodgkin's lymphoma, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, precursor T-lymphoblastic lymphoma, gastroesophageal junction cancer, head and neck squamous cell carcinoma, renal cell cancer, or hepatocellular carcinoma.

7. The method of claim 1, wherein the malignant tumor is refractory to treatment with an immune checkpoint inhibitor.

8. The method of claim 1, wherein the anti-PD-1 and anti-LAG-3 antibodies or antigen-binding fragments thereof are formulated together.

9. The method of claim 1, wherein the anti-PD-1 and anti-LAG-3 antibodies or antigen-binding fragments thereof are formulated separately.

10. The method of claim 1, wherein the anti-PD-1 antibody or antigen-binding fragment thereof is administered concurrently with the anti-LAG-3 antibody or antigen-binding fragment thereof.

11. The method of claim 1, wherein the anti-LAG-3 antibody or antigen-binding fragment thereof and anti-PD-1 antibody or antigen-binding fragment thereof are administered as a first or second line of treatment.

12. The method of claim 1, wherein the anti-LAG-3 antibody or antigen-binding fragment thereof comprises (a) a heavy chain variable region CDR1 comprising the sequence set forth in SEQ ID NO:7; (b) a heavy chain variable region CDR2 comprising the sequence set forth in SEQ ID NO:8; (c) a heavy chain variable region CDR3 comprising the sequence set forth in SEQ ID NO:9; (d) a light chain variable region CDR1 comprising the sequence set forth in SEQ ID NO: 10; (e) a light chain variable region CDR2 comprising the sequence set forth in SEQ ID NO: 11; and (f) a light chain variable region CDR3 comprising the sequence set forth in SEQ ID NO: 12.

13. The method of claim 1, wherein the anti-LAG-3 antibody or antigen-binding fragment thereof comprises heavy and light chain variable regions comprising the sequences set forth in SEQ ID NOs:3 and 5, respectively.

14. The method of claim 1, wherein the anti-LAG-3 antibody or antigen-binding fragment thereof comprises BMS-986016, MK-4280 (28G-10), REGN3767, IMP731 (H5L7BW), BAP050, IMP-701 (LAG-525), Sym022, TSR-033, MGD013, FS118, or GSK2831781, or an antigen-binding fragment thereof.

15. The method of claim 1, wherein the anti-PD-1 antibody or antigen-binding fragment thereof comprises (a) a heavy chain variable region CDR1 comprising the sequence set forth in SEQ ID NO:23; (b) a heavy chain variable region CDR2 comprising the sequence set forth in SEQ ID NO:24; (c) a heavy chain variable region CDR3 comprising the sequence set forth in SEQ ID NO:25; (d) a light chain variable region CDR1 comprising the sequence set forth in SEQ ID NO:26; (e) a light chain variable region CDR2 comprising the sequence set forth in SEQ ID NO:27; and (f) a light chain variable region CDR3 comprising the sequence set forth in SEQ ID NO:28.

16. The method of claim 1, wherein the anti-PD-1 antibody or antigen-binding fragment thereof comprises heavy and light chain variable regions comprising the sequences set forth in SEQ ID NOs: 19 and 21, respectively.

17. The method of claim 1, wherein the anti-PD-1 antibody or antigen-binding fragment thereof comprises pembrolizumab, pidilizumab, or nivolumab, or an antigen-binding fragment thereof.

18. The method of claim 1, wherein the anti-PD-L1 antibody or antigen-binding fragment thereof comprises atezolizumab, durvalumab, avelumab, or BMS-936559, or an antigen-binding fragment thereof.

19. A method of treating a malignant tumor in a human patient, comprising administering an immunotherapy to the patient, wherein the immunotherapy comprises (i) an anti-LAG-3 antibody or antigen-binding fragment thereof and (ii) an anti-PD-1 antibody or antigen-binding fragment thereof or an anti-PD-L1 antibody or antigen-binding fragment thereof, and wherein about 1% to about 20% of nucleated cells in a sample of the patient's tumor are tumor-infiltrating lymphocytes expressing LAG-3.

20. The method of claim 19, wherein the sample of the patient's tumor is PD-L1 negative.

21. The method of claim 19, wherein about 1% to about 10% of nucleated cells in a sample of the patient's tumor are tumor-infiltrating lymphocytes expressing LAG-3.

22. The method of claim 19, wherein the anti-LAG-3 antibody or antigen-binding fragment thereof comprises (a) a heavy chain variable region CDR1 comprising the sequence set forth in SEQ ID NO:7; (b) a heavy chain variable region CDR2 comprising the sequence set forth in SEQ ID NO:8; (c) a heavy chain variable region CDR3 comprising the sequence set forth in SEQ ID NO:9; (d) a light chain variable region CDR1 comprising the sequence set forth in SEQ ID NO: 10; (e) a light chain variable region CDR2 comprising the sequence set forth in SEQ ID NO: 11; and (f) a light chain variable region CDR3 comprising the sequence set forth in SEQ ID NO: 12.

23. The method of claim 19, wherein the anti-LAG-3 antibody or antigen-binding fragment thereof comprises heavy and light chain variable regions comprising the sequences set forth in SEQ ID NOs:3 and 5, respectively.

24. The method of claim 19, wherein the anti-LAG-3 antibody or antigen-binding fragment thereof comprises MK-4280 (28G-10), REGN3767, IMP731 (H5L7BW), BAP050, IMP-701 (LAG-525), Sym022, TSR-033, MGD013, FS118, or GSK2831781, or an antigen-binding fragment thereof.

25. The method of claim 19, wherein the anti-PD-1 antibody or antigen-binding fragment thereof comprises (a) a heavy chain variable region CDR1 comprising the sequence set forth in SEQ ID NO:23; (b) a heavy chain variable region CDR2 comprising the sequence set forth in SEQ ID NO:24; (c) a heavy chain variable region CDR3 comprising the sequence set forth in SEQ ID NO:25; (d) a light chain variable region CDR1 comprising the sequence set forth in SEQ ID NO:26; (e) a light chain variable region CDR2 comprising the sequence set forth in SEQ ID NO:27; and (f) a light chain variable region CDR3 comprising the sequence set forth in SEQ ID NO:28.

26. The method of claim 19, wherein the anti-PD-1 antibody or antigen-binding fragment thereof comprises heavy and light chain variable regions comprising the sequences set forth in SEQ ID NOs: 19 and 21, respectively.

27. The method of claim 19, wherein the anti-PD-1 antibody or antigen-binding fragment thereof comprises pembrolizumab, pidilizumab, or nivolumab, or an antigen-binding fragment thereof, or the anti-PD-L1 antibody or antigen-binding fragment thereof comprises atezolizumab, durvalumab, avelumab, or BMS-936559, or an antigen-binding fragment thereof.

28. A method of treating a malignant tumor in a human patient, comprising administering an immunotherapy to the patient, wherein the immunotherapy comprises (i) an anti-LAG-3 antibody or antigen-binding fragment thereof and (ii) an anti-PD-1 antibody or antigen-binding fragment thereof or an anti-PD-L1 antibody or antigen-binding fragment thereof, and wherein at least about 1% of nucleated cells in a sample of the patient's tumor are tumor-infiltrating lymphocytes expressing LAG-3, wherein the anti-LAG-3 antibody or antigen-binding fragment thereof comprises BMS-986016, MK-4280 (28G-10), REGN3767, IMP731 (H5L7BW), BAP050, IMP-701 (LAG-525), Sym022, TSR-033, MGD013, FS118, or GSK2831781, or an antigen-binding fragment thereof.

29. The method of claim 28, wherein the anti-PD-1 antibody or antigen-binding fragment thereof comprises pembrolizumab, pidilizumab, or nivolumab, or an antigen-binding fragment thereof, or the anti-PD-L1 antibody or antigen-binding fragment thereof comprises atezolizumab, durvalumab, avelumab, or BMS-936559, or an antigen-binding fragment thereof.

30. The method of claim 28, wherein the anti-LAG-3 antibody or antigen-binding fragment thereof comprises BMS-986016 or an antigen binding fragment thereof, and the anti-PD-1 antibody or antigen-binding fragment thereof comprises nivolumab or an antigen-binding fragment thereof.

* * * * *